US011845939B2

(12) United States Patent
Kamrud et al.

(10) Patent No.: US 11,845,939 B2
(45) Date of Patent: Dec. 19, 2023

(54) COMPOSITIONS AND METHODS FOR ENHANCING GENE EXPRESSION

(71) Applicant: Janssen Pharmaceuticals, Inc., Titusville, NJ (US)

(72) Inventors: Kurt Iver Kamrud, San Diego, CA (US); Maung Nyan Win, San Diego, CA (US); Nathaniel Stephen Wang, San Diego, CA (US); Jason L. DeHart, San Diego, CA (US)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 890 days.

(21) Appl. No.: 15/831,230

(22) Filed: Dec. 4, 2017

(65) Prior Publication Data

US 2018/0171340 A1 Jun. 21, 2018

Related U.S. Application Data

(60) Provisional application No. 62/587,954, filed on Nov. 17, 2017, provisional application No. 62/486,361, filed on Apr. 17, 2017, provisional application No. 62/430,250, filed on Dec. 5, 2016.

(51) Int. Cl.

| | |
|---|---|
| ***C12N 15/63*** | (2006.01) |
| ***C12N 15/86*** | (2006.01) |
| ***A61K 48/00*** | (2006.01) |
| ***C12N 15/113*** | (2010.01) |
| ***C12N 15/85*** | (2006.01) |

(52) U.S. Cl.

CPC ............ *C12N 15/63* (2013.01); *A61K 48/005* (2013.01); *C12N 15/113* (2013.01); *C12N 15/86* (2013.01); *C07K 2319/50* (2013.01); *C12N 2015/8518* (2013.01); *C12N 2310/531* (2013.01); *C12N 2770/00042* (2013.01); *C12N 2770/36062* (2013.01); *C12N 2770/36111* (2013.01); *C12N 2770/36143* (2013.01); *C12N 2830/30* (2013.01); *C12N 2840/105* (2013.01)

(58) Field of Classification Search

CPC .............................. C12N 15/63; A61K 48/005

See application file for complete search history.

(56) References Cited

U.S. PATENT DOCUMENTS

| | | | | |
|---|---|---|---|---|
| 4,727,138 | A | 2/1988 | Goeddel et al. | |
| 4,738,927 | A | 4/1988 | Taniguchi et al. | |
| 4,762,791 | A | 4/1988 | Goeddel et al. | |
| 4,810,643 | A | 3/1989 | Souza | |
| 4,892,743 | A | 1/1990 | Leibowitz et al. | |
| 4,966,843 | A | 10/1990 | McCormick et al. | |
| 4,999,291 | A | 3/1991 | Souza | |
| 5,017,691 | A | 5/1991 | Lee et al. | |
| 5,116,742 | A | 5/1992 | Cech et al. | |
| 5,225,337 | A | 7/1993 | Robertson et al. | |
| 5,246,921 | A | 9/1993 | Reddy et al. | |
| 5,780,036 | A | 7/1998 | Chisari | |
| 5,958,060 | A | 9/1999 | Premerlani | |
| 6,041,252 | A | 3/2000 | Walker | |
| 6,110,161 | A | 8/2000 | Mathiesen | |
| 6,117,660 | A | 9/2000 | Walters | |
| 6,224,879 | B1 | 5/2001 | Sjoberg et al. | |
| 6,261,281 | B1 | 7/2001 | Mathiesen | |
| 6,273,525 | B1 | 8/2001 | Erban | |
| 6,278,895 | B1 | 8/2001 | Bernard | |
| 6,319,901 | B1 | 11/2001 | Bernard | |
| 6,697,669 | B2 | 2/2004 | Dev | |
| 6,873,549 | B2 | 3/2005 | Khalid | |
| 6,873,849 | B2 | 3/2005 | De La Red | |
| 6,912,417 | B1 | 6/2005 | Bernard | |
| 6,939,862 | B2 | 9/2005 | Bureau | |
| 6,958,060 | B2 | 10/2005 | Mathiesen | |
| 6,982,087 | B2 | 1/2006 | Johnston et al. | |
| 7,328,064 | B2 | 2/2008 | Mathiesen | |
| 7,419,674 | B2 | 9/2008 | Chulay et al. | |
| 7,664,545 | B2 | 2/2010 | Westersten | |
| 7,850,977 | B2 * | 12/2010 | Kamrud | A61K 39/12 424/199.1 |
| 8,080,255 | B2 | 12/2011 | Smith | |
| 8,187,249 | B2 | 5/2012 | Bernard | |
| 8,209,006 | B2 | 6/2012 | Smith | |
| 8,216,589 | B2 | 7/2012 | Yum | |

(Continued)

FOREIGN PATENT DOCUMENTS

| | | | |
|---|---|---|---|
| JP | 2007537761 | A | 12/2007 |
| WO | WO 1985/02862 | | 7/1985 |
| WO | WO 1985/04188 | | 9/1985 |
| WO | WO 1990/06370 | | 6/1990 |
| WO | 9503777 | A1 | 2/1995 |
| WO | WO 1995/31565 | A1 | 11/1995 |
| WO | WO 1996/37616 | A1 | 11/1996 |
| WO | 200224224 | A2 | 3/2002 |
| WO | 2002042480 | A2 | 5/2002 |
| WO | 02095040 | | 11/2002 |
| WO | WO 2004/055161 | A2 | 7/2004 |
| WO | 2005087311 | A1 | 9/2005 |

(Continued)

OTHER PUBLICATIONS

Kim et. al. Enhancement of protein expression by alphavirus replicons by designing self-replicating subgenomic RNAs 2014 PNAS 111(29), pp. 10708-10713 (Year: 2014).*

(Continued)

*Primary Examiner* — Samuel C Woolwine

*Assistant Examiner* — Tiffany Nicole Grooms

(74) *Attorney, Agent, or Firm* — ICE MILLER LLP

(57) ABSTRACT

The present disclosure generally relates to nucleic acid molecules for use in regulating gene expression. Disclosed herein include nucleic acid molecules containing one or more structural elements of the viral capsid enhancer operably linked to a coding sequence of a gene of interest. In some embodiments, the viral capsid enhancer comprises a Downstream Loop (DLP) from a viral capsid protein, or a variant of the DLP.

50 Claims, 35 Drawing Sheets

Specification includes a Sequence Listing.

(56) References Cited

U.S. PATENT DOCUMENTS

| | | | | |
|---|---|---|---|---|
| 8,859,198 | B2 | 10/2014 | Bartholomeusz | |
| 8,961,995 | B2 | 2/2015 | Frolov | |
| 9,364,664 | B2 | 6/2016 | Masterson | |
| 9,452,285 | B2 | 9/2016 | Draghia-Akli | |
| 9,801,897 | B2 | 10/2017 | Geall et al. | |
| 9,802,035 | B2 | 10/2017 | Masterson | |
| 10,538,786 | B2 | 1/2020 | Kamrud | |
| 11,021,692 | B2 | 6/2021 | Boden | |
| 11,185,688 | B2 | 11/2021 | Hannaman | |
| 2004/0213805 | A1 | 10/2004 | Verheije | |
| 2004/0235133 | A1* | 11/2004 | Frolov | C07K 14/005 435/235.1 |
| 2005/0070700 | A1 | 3/2005 | Giese | |
| 2005/0277605 | A1 | 12/2005 | Wu | |
| 2008/0279891 | A1* | 11/2008 | Johnston | A61K 39/12 424/205.1 |
| 2009/0018031 | A1 | 1/2009 | Trinklein et al. | |
| 2009/0075384 | A1 | 3/2009 | Kamrud | |
| 2011/0110974 | A1 | 5/2011 | Depla | |
| 2011/0300205 | A1 | 12/2011 | Geall | |
| 2012/0078161 | A1 | 3/2012 | Masterson | |
| 2012/0121650 | A1 | 5/2012 | Johnston | |
| 2014/0079734 | A1* | 3/2014 | Frolov | C12N 15/86 424/204.1 |
| 2014/0222105 | A1 | 8/2014 | Broderick | |
| 2015/0328404 | A1 | 11/2015 | Murakami | |
| 2016/0074500 | A1* | 3/2016 | Pushko | A61P 37/04 424/186.1 |
| 2016/0166678 | A1 | 6/2016 | Kallen et al. | |
| 2016/0362472 | A1* | 12/2016 | Bitter | C07K 16/2803 |
| 2017/0314043 | A1 | 11/2017 | Kamrud et al. | |
| 2018/0104359 | A1 | 4/2018 | Kamrud | |
| 2018/0171340 | A1 | 6/2018 | Kamrud | |
| 2020/0164062 | A1 | 5/2020 | Goh | |

FOREIGN PATENT DOCUMENTS

| | | | |
|---|---|---|---|
| WO | 2005113782 | A1 | 12/2005 |
| WO | 2007047749 | | 4/2007 |
| WO | 2008093976 | A1 | 8/2008 |
| WO | 2011015656 | A2 | 2/2011 |
| WO | WO 2012/087983 | A1 | 6/2012 |
| WO | 2012109668 | A1 | 8/2012 |
| WO | 2013007772 | A1 | 1/2013 |
| WO | WO 2014/170493 | A2 | 10/2014 |
| WO | 2016020538 | A1 | 2/2016 |
| WO | 2016054003 | A1 | 4/2016 |
| WO | WO 2016/184822 | A1 | 9/2016 |
| WO | WO 2017/024000 | A1 | 2/2017 |
| WO | 2017172838 | A1 | 10/2017 |
| WO | 2017176319 | A1 | 10/2017 |
| WO | WO 2017/180770 | A1 | 10/2017 |
| WO | WO 2018/075235 | A1 | 4/2018 |
| WO | WO 2018/106615 | A1 | 6/2018 |
| WO | 2018225731 | A1 | 12/2018 |
| WO | 2019099624 | A1 | 5/2019 |
| WO | 2019123252 | A1 | 6/2019 |

OTHER PUBLICATIONS

Yin et. al. Similarities and Differences in Antagonism of Neuron Alpha/Beta and Sindbis Alphaviruses 2009. Journal of Virology. 83 (19) p. 10036-10047 (Year: 2009).*

Mir et. al. A Multicistronic DNA Vaccine Induces Significant Protection against Tuberculosis in Mice and Offers Flexibility in the Expressed Antigen Repertoire. 2009. Clinical and Vaccine Immunology. vol. 16, No. 10. p. 1467-1475 (Year: 2009).*

GenBank: L01443.1. Accession No. L01443, 2004, Venezuelan equine encephalitis virus strain TC-83, complete genome (Year: 2004).*

GenBank: KT121715.1: Accession KT121715, Version KT121715. 1, 2015, Sindbis virus isolate Treatment1_population9, complete genome (Year: 2015).*

Frolov et al. 1994 Translation of Sindbis Virus mRNA: Effects of Sequences Downstream of the Initiating Codon. Journal of Virology, (68)12, p. 8111-8117 (Year: 1994).*

Hernandez et al.Structural Differences Observed in Arboviruses of the Alphavirus and Flavivirus Genera 2014. Advances in Virology. vol. 2014, Article ID 259382 (Year: 2014).*

Gebhard et al. Functional RNA Elements in the Dengue Virus Genome. 2011 Viruses 2011, 3, 1739-1756 (Year: 2011).*

Agapov et al., Noncytopathic Sindbis Virus RNA Vectors for Heterologous Gene Expression, Proc. Natl. Acad. Sci., 1998, pp. 12989-12994, vol. 95.

Altmann et al., Cotransfection of ICAM-1 and HLA-DR Reconstitutes Human Antigen-Presenting Cell Function in Mouse L Cells, Nature, 1989, pp. 512-514, vol. 338.

Altschul SF et al., "Basic Local Alignment Search Tool"; J. Mol. Biol. 215:403-410, 1990.

Atkins, G, et al. Theraputic and Prophylatic Applications of Alphavurus Vectors, Expert Reviews in Molecular Medi, Cambridge University Press, vol. 10, No. 1, pp. 1-18, (2008).

Attwood, T. The Abel of Bionofrmatics, vol. 290, No. 5491, pp. 471-473, (2000).

Baker et al, Proten Structure Prediction and Structual Genomics, Science, vol. 294, pp. 93-93, (2011).

Barbieri et al., Purification and partial characterization of another form of the antiviral protein from the seeds of *Phytolacca americana* L. (pokeweed), Biochem. J., 1982, pp. 55-59, vol. 203.

Barrette-Ng et al., Structure of Arterivirus nsp-4, J. Biol. Chem., 2002, pp. 39960-39966, vol. 277, Issue 42.

Beerens & Snijder, An RNA Pseudoknot in the 3' End of the Arterivirus Genome Has a Critical Role in Regulating Viral RNA Synthesis, J. Virol., 2007, pp. 9426-9436, vol. 81, Issue 17.

Berglund, P. et al., Enhancing Immune Response Using Suicidal DNA Vaccines,, Nature Biotechnology, vol. 16, pp. 562-565, (1998).

Besnard et al., Selection against expression of the *Escherichia coli* gene gpt in hprt+ mouse teratocarcinoma and hybrid cells, Mol. Cell. Biol., 1987, pp. 4139-4141, vol. 7.

Brakenhof et al., Molecular cloning and expression of hybridoma growth factor in *Escherichia coli*, J. Immunol., Dec. 15, 1987, pp. 4116-4121, vol. 139, Issue 12.

Bzik et al., Molecular cloning and sequence analysis of the Plasmodium falciparum dihydrofolate reductase-thymidylate synthase gene, Proc. Natl. Acad. Sci. USA, Dec. 1987, pp. 8360-8364, vol. 84.

Calderwood et al., Nucleotide sequence of the Shiga-like toxin genes of *Escherichia coli*, Proc. Natl. Acad. Sci. USA, Jul. 1987, pp. 4364-4368, vol. 84.

Carroll and Collier, Active Site of Pseudomonas aeruginosa Exotoxin A, J. Biol. Chem., 1987, pp. 8707-8711, vol. 262.

Castillo-Olivares et al., Generation of a Candidate Live Marker Vaccine for Equine Arteritis Virus by Deletion of the Major Virus Neutralization Domain, J. Virol., 2003, pp. 8470-8480, vol. 77, Issue 15.

Chen et al., The complete primary structure of abrin-a B chain. FEBS Letters, 1992, pp. 115-118, vol. 309.

Cheng, W. et al. Enhancement of Sindbis Virus Self-Replicating RNA Vaccine Potency by Linkage of *Mycobacterium tuberculosis* Heat Shock Protein 70 Gene to an Antigen Gene, Journal of Immunology, vol. 166, pp. 6218-6226, (2001).

Chin et al., Tissue-specific Expression of Hepatic Functions Genetic Aspects, Ann. N.Y. Acad. Sci., Oct. 1986, pp. 120-130, vol. 478.

Collins et al., Primary Amino Acid Sequence of α-Trichosanthin and Molecular Models for Abrin A-chain and α-Trichosanthin, J. Biol. Chem., 1990, pp. 8665-8669, vol. 265.

Coussens et al., Tyrosine kinase receptor with extensive homology to EGF receptor shares chromosomal location with neu oncogene, Science, 1985, pp. 1132-1139, vol. 230.

Davis, N. et al., In Vitro Synthesis of Infectious Venezuelan Equine Encephalitis Virus RNA from acDNA Clone: Analysis of a Viable Deletion Mutant Virology, vol. 171, pp. 189-204, (1989).

De Vries et al., Genetic Manipulation of Equine Arteritis Virus Using Full-Length cDNA Clones: Separation of Overlapping Genes and Expression of a Foreign Epitope. Virology, 2000, pp. 84-97, vol. 270.

(56) References Cited

OTHER PUBLICATIONS

De Vries et al., Recombinant Equine Arteritis Virus Expression Vector, Virology, Jun. 5, 2001, pp. 259-276, vol. 284, Issue 2.
De Wilde et al., Cyclophilin Inhibitors Block Arterivirus Replication by Interfering with Viral RNA Synthesis, J. Virol., 2013, pp. 1454-1464, vol. 87, Issue 3.
Den Boon et al., Equine Arteritis Virus Subgenomic RNA Transcription: UV Inactivation and Translation Inhibition Studies, Virology, 1995, pp. 364-372, vol. 213.
Deng et al., Structural Basis for the Regulatory Function of a Complex Zinc-binding Domain in a Replicative Arterivirus Helicase Resembling a Nonsense-Mediated mRNA Decay Helicase, Nucl. Acids Res., 2013, pp. 3464-3477, vol. 42, Issue 5.
Ding et al., In Vivo Genome-Wide Profiling of RNA Secondary Structure Reveals Novel Regulatory Features, Nature, 2014, pp. 696-700 (and Methods), vol. 505.
Dowdy et al., Efficient Generation of Human iPSCs by a Synthetic Self-Replicative RNA, Cell Stem Cell, 2013, pp. 246-254, vol. 13.
Dubensky, T. et al. Sindbis Virus DNA-Based Expression Vectors: Utility for In Vitro and In Vivo Gene Transfer, Journal of Virology, vol. 70, No. 1, pp. 508-519, (1996).
Evensen et al., Direct Molecular Cloning and Expression of Two Distinct Abrin A-chains, J. Biol. Chem., Apr. 15, 1991, pp. 6848-6852, vol. 266, Issue 11.
Fainstein et al., Nucleotide sequence analysis of human abl and bcr-abl cDNAs, Oncogene, Dec. 1, 1989, pp. 1477-1481, vol. 4. Issue 12.
Faktor et al., The identification of hepatitis B virus X gene responsive elements reveals functional similarity of X and HTLV-I tax, Oncogene, Jun. 1, 1990, pp. 867-872, vol. 5, Issue 6.
Familletti et al., A convenient and rapid cytopathic effect inhibition assay for interferon, Methods in Enz., 1981, pp. 387-394, vol. 78.
Fang et al., Efficient—2 Frameshifting by Mammalian Ribosomes to Synthesize an Additional Arterivirus Protein, PNAS, 2012, pp. E2920-E2928.
Field et al., Isolation and Characterization of Acyclovir-Resistant Mutants of Herpes Simplex Virus, J. Genl. Virol., 1980, pp. 115-124, vol. 49.
Finter et al., The Use of Interferon-α in Virus Infections, Drugs, 1991, pp. 749-765, vol. 42.
Firth et al., Discovery of a Small Arterivirus Gene that Overlaps the GP5 Coding Sequence and is Important for Virus Production, J. Genl. Virol., 2011, pp. 1097-1106, vol. 92.
Frolov, I. et al. Cis-acting RNA elements at the 5' end of Sindbis virus genome RNA regulate minus- and plus-strand RNA synthesis, RNO, vol. 7, pp. 1638-1651, (2001).
Frolov, I et al., Translation of Sindbis Virus mRNA: Effects of Sequences Downstream of the Initiating Codon Journal of Virology, Vo. 70, No. 2 , pp. 1182-1190 (1996).
Frolov, I et al.Translation of Sindbis Virus mRNA: Effects of Sequences Downstream of the Initiating Codon, Journal of Virology, vol. 68, No. 12, pp. 8111-8117, (1994).
Gansbacher et al., Retroviral Vector-mediated γ-Interferon Gene Transfer into Tumor Cells Generates Potent and Long Lasting Antitumor Immunity, Cancer Res., Dec. 15, 1999, pp. 7820-7825, vol. 50.
Gansbacher et al., Interleukin 2 Gene Transfer into Tumor Cells Abrogates Tumorigenicity and Includes Protective Immunity, J. Ex. Med., The Rockefeller University Press, Oct. 1990, pp. 1217-1224, vol. 172.
Gibson et al., Enzymatic Assembly of DNA Molecules up to Several Hundred Kilbases, Nature Methods 6:343-45, 2009.
Giulietta et al. 2013. Engineered alphavirus replicon vaccines based on known attenuated viral mutants show limited effects on immunogenicity. *Virology*, 447(1):254-264.
Glaser AL et al., An infectious cDNA clone of equine arteritis virus: a tool for future fundamental studies and vaccine development. Proceedings of the 8th International Conference on Equine Infectious Diseases, Dubai 1998; 1999, pp. 166-176.
Golumbek et al., Treatment of established renal cancer by tumor cells engineered to secrete interleukin-4, Science, Nov. 1, 1991, pp. 713-716, vol. 254.
Gorchakov, R. et al., Selection of Functional 5 cis-Acting Elements Promoting Efficient Sindbis Virus Genome Replication, Journal of Virology, vol. 78, No. 1, pp. 61-75, (2004).
Grabstein et al., Cloning of a T cell growth factor that interacts with the beta chain of the interleukin-2 receptor. Science, 1994, pp. 965-968, vol. 264.
Hardy, R. et al Requirements at the 3 End of the Sindbis Virus Genome for Efficient Synthesis of Minus-Strand RNA, Journal of Virology, pp. 4630-4639, (2005).
Hooper et al., Molecular Smallpox Vaccine Delivered by Alphavirus Replicons Elicits Protective Immunity in Mice and Non-Human Primates, Vaccine, 2009, pp. 494-511, vol. 28, Issue 2.
Horikawa et al., Molecular cloning and nucleotide sequence of cDNA encoding the human liver S-adenosylmethionine synthetase, Biochem. Intl., Sep. 1, 1991, pp. 81-90, vol. 25, Issue 1.
Hyde, J. et al., The 5' and 3' ends of alphavirus RNAs—non-coding is not non-functional, Virus Res., vol. 206, pp. 99-107, (2015).
Huang, Q. et a 1. Development of a Vaccine Vector Based on a Subgeonomic Replication of Porcine Reproductive and Respitory Syndrome Virus, Journal of Virological Methods, vol. 160, pp. 22-28, (2009).
Irvin JD, Purification and partial characterization of the antiviral protein from Phytolacca americana which inhibits eukaryotic protein synthesis, Arch. Biochem & Biophys, Aug. 1975, pp. 522-528, vol. 169, Issue 2.
Irvin JD, Pokeweed antiviral protein, Pharmac. Ther., 1983, pp. 371-387, vol. 21, Issue 3.
Irvin JD et al., Purification and properties of a second antiviral protein from Phytolacca americana which inactivates eukaryotic ribosomes, Arch. Biochem. & Biophys., Apr. 1, 1980, pp. 418-425, vol. 200, Issue 2.
Jackson et al., Nucleotide sequence analysis of the structural genes for Shiga-like toxin I encoded by bacteriophage 933J from *Escherichia coli*. Microb. Path., Feb. 1987, pp. 147-153, vol. 2, Issue 2.
Jayaraman et al., Enhancement of in vivo cell-mediated immune responses by three distinct cytokines, J. Immunol., 1990, pp. 942-951, vol. 144.
Kamrud et al., Alphavirus Replicon Approach to Promoterless Analysis of IRES Elements, Virology, 2007, pp. 376-387, vol. 360.
Karlin & Altschul, Applications and statistics for multiple high-scoring segments in molecular sequences Proc. Nat'l. Acad. Sci. USA 90:5873-87, 1993).
Karupiah et al., Elevated natural killer cell responses in mice infected with recombinant vaccinia virus encoding murine IL-2, J. Immunol., Jan. 1, 1990, pp. 290-298, vol. 144, Issue 1.
Kasteren PB et al., 2013. Deubiquitinase function of arterivirus papain-like protease 2 suppresses the innate immune response in infected host cells. Proc. Natl. Acad. Sci. USA, Feb. 2013, E838-E847.
Kelley, B. et al. Potential of Alphavirus Vecotrs in the Treament of Advanced Solid Tumors, Recent Patents on Anti-Drug Discovery, vol. 2, No. 2, pp. 159-166, (2007).
Kerr et al., Anti-penicillin-V-amidase conjugates kill antigen-positive tumor cells when combined with doxorubicin phenoxyacetamide, Cancer. Immunol. Immunother.,1990, pp. 202-206, vol. 31, Issue 4.
Kim et al. 2014. Enhancement of protein expression by alphavirus replicons by designing self-replicating subgenomic RNAs. *Proceedings National Academy of Sciences*, 111 (29):10708-10713.
Klimstra et al., Adaptation of Sindbis Virus to BHK Cells Selects for Use of Heparan Sulfate as an Attachment Receptor. J. Virol. 72: pp. 7357, 1988.
Kinney, R. et al., Attenuation of Venezuelan Equine Encephalitis Virus Strain TC-83 Is Encoded by the 5'-Noncoding Region and the E2 Envelope Glycoprotein, Journal of Virology, vol. 67, No. 3, pp. 1269-1277, (1993).
Knoops et al., Ultrastructural Characterization of Arterivirus Replication Structures: Reshaping the Endoplasmic Reticulum to Accommodate Viral RNA Synthesis, J. Virol., 2011, pp. 2474-2487, vol. 86, Issue 5.

(56) References Cited

OTHER PUBLICATIONS

Kofler R. et al., Mimicking live flavivirus immunization with a noninfectious RNA vaccine, PNAS, vol. 101, No. 7, pp. 1951-1956, (2004).
Kulasegaran-Shylini et al., Structural and Functional Elements of Promoter Encoded by the 5' Untranslated Region of the Venezuelan Equine Encephalitis Virus Genome J. Virol. 83:17 p. 8327-8339, 2009.
Kulasegaran-Shylini et al., The 5'UTR-specific mutation in VEEV TC-83 genome has a strong effect on RNA replication and subgenomic RNA synthesis, but not on translation of the encoded proteins. Virology. 2009, 387(1): 211-221.
Lamb et al., Nucleotide sequence of cloned cDNA coding for preproricin, Eur. J. Biochem.,1985, pp. 265-270, vol. 148.
Lee et al., Multiagent Vaccines Vectored by Venezuelan Equine Encephalitis Virus Replicon Elicits Immune Responses to Marburg Virus and Protection against Anthrax and Botulinum Neurotoxin in Mice, Vaccine, 2006, pp. 6886-6892, vol. 24.
Lehmann et al., Arterivirus nsp12 Versus the Coronavirus nsp16 2'-O-Methyltransferase: Comparison of the C-terminal Cleavage Products of Two Nidovirus pplab Polyproteins, J. Genl. Virol., 2015, pp. 2643-2655, vol. 96.
Lehmann et al., Arterivirus RNA-Dependent RNA Polymerase: Vital Enzymatic Activity remains Elusive, Virology, 2016, pp. 68-74, vol. 487.
Linsley et al., Binding of the B Cell activation antigen B7 to CD28 costimulates T cell proliferation and Interleukin 2 mRNA accumulation, J. Exp. Med., Mar. 1991, pp. 721-730, vol. 173.
Linsley et al., CTLA-4 Is a second receptor for the B Cell activation antigen B7, J. Exp. Med., Sep. 1991, pp. 561-570, vol. 174.
Luo, R., et al., Antiviral activity of type I and type III interferons against porcine reproductive and respiratory syndrome virus (PRRSV), Antiviral Resarch, vol. 91, pp. 99-101 (2011).
Maher and Dolinick, Specific hybridization arrest of dihydrofolate reductase mRNA in vitro using anti-sense RNA or anti-sense oligonucleotides, Arch. Biochem & Biophys., Feb. 15, 1987, pp. 214-220, vol. 253, Issue 1.
Maio, et al., Modulation by cytokines of HLA antigens, intercellular adhesion molecule 1 and high molecular weight melanoma associated antigen expression and of immune lysis of clones derived from the melanoma cell line MeM 50-10. Can. Immunol. Immunother., Jan. 1989, pp. 34-42, vol. 30, Issue 1.
Manolaridis, et al., Structure and Genetic Analysis of the Arterivirus Nonstructural Protein 7α, J. Virol., 2011, pp. 7449-7453, vol. 85, Issue 14.
McKnight et al., Deduced consensus sequence of Sindbis virus strain AR339: mutations contained in laboratory strains which affect cell culture and in vivo phenotypes. Virol. 70:1981, 1996.
McLoughlin, M. et al. Alphavirus infections in salmonids—a review, Journal of Fish Diseases, vol. 30, pp. 511-531, (2007).
Mekalanos et al., Cholera toxin genes: nucleotide sequence, deletion analysis and vaccine development, Nature, 1983, pp. 551-557, vol. 306.
Mogler, M. et al., RNA-based viral vectors, Expert Rev. Vaccines, pp. 1-30, (2014.
Molenkamp R et al., The arterivirus replicase is the only viral protein required for genome replication and subgenomic mRNA transcription, J. Genl. Virol., 2000, pp. 2491-2496, vol. 81.
Molenkamp et al., Isolation and Characterization of an Arterivirus Defective Interfering RNA Genome, J. Virol., 2000, pp. 3156-3165, vol. 74, Issue 7.
Molenkamp et al., Characterization of an Arterivirus Defective Interfering RNA, 2001, pp. 519-525. In the Nidoviruses (Coronaviruses and Arteriviruses), Ehud Lavi et al. (ed.), Kluwer Academic/Plenum Publishers.
Mullen, Transfer of the bacterial gene for cytosine deaminase to mammalian cells confers lethal sensitivity to 5-fluorocytosine: A negative selection system, Proc. Natl. Acad. Sci. USA, Jan. 1992, pp. 33-37, vol. 89.
Muraggi, G et al. Engineered Alphavirus Replicon Vaccines Based on Known Attenuated Viral Mutants Show Limited Effects on Immunogenicity, Virology, vol. 44, pp. 254-264, 2013.
Nagata, et al., Synthesis in *E. coli* of a polypeptide with human leukocyte interferon activity, Nature, 1980, pp. 316-320, vol. 284.
Nedialkova, et al., Biochemical Characterization of Arterivirus Nonstructural Protein 11 Reveals the Nidovirus-Wide Conservation of a Replicative Endoribonuclease, J. Virol., 2009, pp. 5671-5682, vol. 83, Issue 11.
Nedialkova et al., Arterivirus Nsp1 Modulates the Accumulation of Minus-Strand Templates to Control the Relative Abundance of Viral mRNAs, PLoS Pathogens, 2010, e1000772, pp. 1-15, vol. 6, Issue 2.
Needleman, S. et al., A general method applicable to the search for similarities in the amino acid sequence of two proteins J. Mol. Biol. 48:443-53, 1970.
Nolz, J et al. Strategies and Implications for Prime-Boost Vaccination to Generate Memory CD8 T Cells, Advances in Experimental Medicine and Biology, pp. 69-83, (2011).
Pasternak, Genetic Manipulation of Arterivirus Alternative mRNA Leader-Body Junction Sites Reveals Tight Regulation of Structural Protein Expression, J. Virol., Dec. 2000, pp. 11642-11653, vol. 74, Issue 24.
Pasternak, Sequence requirements for RNA strand transfer during nidovirus discontinuous subgenomic RNA synthesis, EMBO J., 2001, pp. 7220-7228, vol. 20, Issue 24.
Pasternak, The stability of the duplex between sense and antisense transcription-regulating sequences is a crucial factor in arterivirus subgenomic mRNA synthesis, J. Virol., 2003, pp. 1175-1183, vol. 77, Issue 2.
Pasternak, Regulation of Relative Abundance of Arterivirus Subgenomic mRNAs, J. Virol., Aug. 2004, pp. 8102-8113, vol. 78, Issue 15.
Pearson, W. et al., Improved tools for biological sequence comparison, Proc. Natl. Acad. Sci Us, vol. 85, pp. 2444-2448, (1988).
Pedersen et al., Open Reading Frame 1a-Encoded Subunits of the Arterivirus Replicase induce Endoplasmic Reticulum-Derived Double-Membrane Vesicles which carry the Viral Replication Complex, J. Virol., 1999, pp. 2016-2026, vol. 73, Issue 3.
Perri et al., Replicon Vectors Derived from Sindbis Virus and Semliki Forest Virus that Establish Persistent Replication in Host Cells, J. Virol., 2000, pp. 9802-9807, vol. 74, Issue 20.
Pijlman, G. et al., Kunjin virus replicons: an RNA-based, noncytopathic viral vector system for protein production, vaccine and gene therapy applications, Expert Opin. Biol. Ther, vol. 6, No. 2, pp. 135-145, (2006).
Posthuma et al., Site-Directed Mutagenesis of the Nidovirus Replicative Endoribonuclease NendoU Exerts Pleiotropic Effects on the Arterivirus Life Cycle, J. Virol., 2006, pp. 1653-1661, vol. 80, Issue 4.
Posthuma et al., Formation of the Arterivirus Replication/Transcription Complex: a Key Role for Nonstructural Protein 3 in the Remodeling of Intracellular Membranes, J. Virol., 2008, pp. 4480-4491, vol. 82, Issue 9.
Pushko et al., Individual and Bivalent Vaccines Based on Alphavirus Replicons Protect Guinea Pigs against Infection with Lassa and Ebola Viruses, J. Virol., 2001, pp. 11677-11685, vol. 75, Issue 23.
Pushko et al., Replicon-Helper Systems from Attenuated Venezuelan Equine Encephalitis Virus: Expression of Heterologous Genes In Vitro and Immunization against Heterologous Pathogens In Vivo, Virology, Dec. 22, 1997, pp. 389-401, vol. 239, Issue 2.
Radford et al., Cell-Type Specificity of Interferon-γ-Mediated HLA Class I Gene Transcription in Human Hematopoietic Tumor Cells. American Society of Hepatology, 1991, pp. 2008-2015.
Rice, C. et al., Production of Infectious RNA Transcripts from Sindbis Virus cDNA Clones: Mapping of Lethal Mutations, Rescue of a Temperature-Sensitive Marker, and In Vitro Mutagenesis to Generate Defined Mutants, Journal of Virology, vol. 61, No. 12, pp. 3809-3819, (1987).
Rogne et al., The isolation and characterisation of a cDNA clone for human lecithin:cholesterol acyl transferase and its use to analyze the genes in patients with LCAT deficiency and fish eye disease, Biochem, Biophys. Res. Commun., 1987, pp. 161-169, vol. 148, Issue 1.

(56) References Cited

OTHER PUBLICATIONS

Sanchez and Holmgren, Recombinant system for overexpression of cholera toxin B subunit in Vibrio cholerae as a basis for vaccine development, Proc. Natl. Acad. Sci. USA, Jan. 1989, pp. 481-485, vol. 86, Issue 2.
Seif et al., Stable Antiviral Expression in BALB/c 3T3 Cells Carrying a Beta Interferon Sequence behind a Major Histocompatibility Complex Promoter Fragment, J. Virol., Oct. 1991, pp. 664-671, vol. 65, Issue 2.
Seybert et al., Biochemical Characterization of the Equine Arteritis Virus Helicase Suggests a Close Functional Relationship Between Arterivirus and Coronavirus Helicases, J. Virol., 2000, pp. 9586-9593, vol. 74, Issue 20.
Shylini, R Structure-Function Studies of the Venezuelanequine Encephalitis Virus 5'utr Promoter Element And Its Role in Attenuation of the Virus, Dissertation for Doctor of Philosophy, The University of Texas Medical Branch (2009).
Sjoberg,E et al., ASignificantly Improved Semliki Forest Virus Expression System Based on Translation Enhancer Segments from the Viral Capsid Gene, Biotechnology, Vo,. 12, pp. 1127-1131, (1994).
Smith et all, "Comparison of Biosequences", Adv. Appl. Math., 2:482-89 (1981).
Snijder, E.J., The Arterivirus Replicase, The Road from RNA to Protein(s), and Back Again, 1998, pp. 97-108. In Coronaviruses and Arteriviruses, Enjuanes et al. (ed.), Plenum Press, NY.
Snijder, E.J., Arterivirus RNA Synthesis Dissected, 2001, pp. 241-253. In the Nidoviruses (Coronaviruses and Arteriviruses), Ehud Lavi et al. (ed.), Kluwer Academic/Plenum Publishers.
Snijder et al., Proteolytic Processing of the Arterivirus Replicase, 1995, pp. 443-451. In Corona- and Related Viruses, P.J. Talbot and G.A. Levy (ed.), Plenum Press, NY.
Snijder et al., The Arterivirus Nsp2 Protease, J. Biol. Chem., 1995, pp. 16671-16676, vol. 270, Issue 28.
Snijder et al., Heterodimerization of the Two Major Envelope Proteins is Essential for Arterivirus Infectivity, J. Virol., 2003, pp. 97-104, vol. 77, Issue 1.
Snijder et al., 2005. The order *Nidovirales*, pp. 390-404, In Topley and Wilson's microbiology and microbial infections, B. W. Mahy and V. ter Meulen (ed.), Hodder Arnold, London, United Kingdom.
Snijder EJ et al., "Identification of a Novel Structural Protein of Arteriviruses," J. Virol, Aug. 1999, pp. 6335-6345, vol. 37, Issue 8.
Stanton et al., Nucleotide sequence comparison of normal and translocated murine c-myc genes, Nature, Aug. 1984, pp. 423-425, vol. 310.
Strauss et al., The AlpahViruses: Gene Expression, Replication and Evolution, Microbiological Reviews, pp. 491-562, Sep. 1994.
Stirpe et al., Gelonin, a New Inhibitor of Protein Synthesis, Nontoxic to Intact Cells, J. Biol. Chem., Jul. 25, 1980, pp. 6947-6953, vol. 255.
Te Velthuis, et al., $Zn^{2+}$ Inhibits Coronavirus and Arterivirus RNA Polymerase Activity In Vitro and Zinc Ionophores Block the Replication of these Viruses in Cell Culture, PLoS Pathogens, 2010, e1001176, pp. 1-10, vol. 6, Issue 11.
Tepper et al., Murine interleukin-4 displays potent anti-tumor activity in vivo, Cell, May 5, 1989, pp. 503-512, vol. 57.
Thaa et al., Myristoylation of the Arterivirus E Protein: The Fatty Acid Modification is not Essential for Membrane Association but Contributes Significantly to Virus Infectivity, J. Genl. Virol., 2009, pp. 2704-2712, vol. 90.
Tian et al., Arterivirus Minor Envelope Proteins are a Major Determinant of Viral Tropism in Cell Culture, J. Virol., 2017, pp. 3701-3712, vol. 86, Issue 7.
Tijerina et al., DMS Footprinting of Structured RNAs and RNA-Protein Complexes, Nat. Protoc., 2007, pp. 2608-2623, vol. 2, Issue 10.
Tijms et al., A zinc finger-containing papain-like protease couples subgenomic mRNA synthesis to genome translation in a positive-stranded RNA virus, Proc. Natl. Acad. Sci. USA, 2001, pp. 1889-1894, vol. 98, Issue 4.
Tijms et al., Arterivirus Subgenomic mRNA Synthesis and Virion Biogenesis Depend on the Multifunctional nsp1 Autoprotease, J. Virol., Oct. 2007, pp. 10496-10505, vol. 81, Issue 19.
Toribio et al., IInhibition of host translation by virus infection in vivo, PNAS, vol. 107, No. 21, pp. 9837-9842, (2010).
Toribio et al., An RNA Trapping Mechanism in Alphavirus MRNA Promotes Translation and Initiation Nucleic Acids Res. 19; 44(9): pp. 4368-4380, (2016).
Tweten et al., Diphtheria toxin. Effect of substituting aspartic acid for glutamic acid 148 on ADP-ribosyltransferase activity., J. Biol. Chem., Jun. 3, 1985, pp. 10392-10394, vol. 260.
Twu et al., Hepatitis B virus X gene can transactivate heterologous viral sequences, Proc Natl. Acad. Sci. USA, Mar. 1989, pp. 2046-2050, vol. 86.
Van Aken et al., Expression, Purification, and In Vitro Activity of an Arterivirus Main Proteinase, Virus Res., 2006, pp. 97-106, vol. 120.
Van Aken et al., Mutagenesis Analysis of the nsp4 Main Proteinase Reveals Determinants of Arterivirus Replicase Polyprotein Autoprocessing, J. Virol., 2006, pp. 3428-3437, vol. 80, Issue 7.
Van Den Born et al., Discontinuous Subgenomic RNA Synthesis in Arteriviruses is Guided by an RNA Hairpin Structure Located in the Genomic Leader Region, J. Virol., 2005, pp. 6312-6324, vol. 79, Issue 10.
Van Den Born, Value of routine funduscopy in patients with hypertension: systematic review, BMJ, Jul. 9, 2005, pp. 1-5, vol. 331.
Van Den Born, et al., "An infectious recombinant equine arteritis virus expressing green fluorescent protein from its replicase gene," J. Genl. Virol., Apr. 2007, pp. 1196-1205, vol. 88.
Van Der Meer et al., ORF1a-Encoded Replicase Subunits are Involved in the Membrane Association of the Arterivirus Replication Complex, J. Virol., 1998, pp. 6689-6698, vol. 72, Issue 8.
Van Dinten, An infectious arterivirus cDNA clone: Identification of a replicase point mutation that abolishes discontinuous mRNA transcription, Proc. Natl. Acad. Sci. USA, Feb. 1997, pp. 991-996, vol. 94, Issue 3.
Van Dinten et al., Proteolytic Processing of the Open Reading Framer 1b-Encoded Part of Arterivirus Replicase is Mediated by nsp4 Serine Protease and is Essential for Virus Replication, J. Virol., 1999, pp. 2027-2037, vol. 73, Issue 3.
Van Dinten et al., The Predicted Metal-Binding Region of the Arterivirus Helicase Protein is Involved in Subgenomic mRNA Synthesis, Genome Replication, and Virion Biogenesis, J. Virol., 2000, pp. 5213-5223, vol. 74, Issue 11.
Van Hemert et al., The In Vitro RNA Synthesizing Activity of the Isolated Arterivirus Replication/Transcription Complex is Dependent on a Host Factor, J. Biol. Chem., 2008, pp. 16525-16536, vol. 283, Issue 24.
Van Kasteren et al., Arterivirus and Nairovirus Ovarian Tumor Domain-Containing Deubiquitinases Target Activated RIG-I to Control Innate Immune Signaling, J. Virol., 2011, pp. 773-785, vol. 82, Issue 2.
Van Kasteren et al., Deubiquitinase Function of Arterivirus Papain-Like Protease 2 Suppresses the Innate Immune Response in Infected Host Cells, PNAS, 2013, pp. E838-E847.
Van Marle, et al., Characterization of an Equine Arteritis Virus Replicase Mutant Defective in Subgenomic mRNA Synthesis, J. Virol., 1999, pp. 5274-5281, vol. 73, Issue 7.
Van Marle et al., Arterivirus discontinuous mRNA transcription is guided by base pairing between sense and antisense transcription-regulating sequences, Pro. Natl. Acad. Sci. USA, Aug. 6, 1999, pp. 12056-12061, vol. 96, Issue 21.
Ventoso, I., Adaptive Changes in Alphavirus mRNA Translation Allowed Colonization of Vertebrate Hosts, Journal of Virology, vol. 86, No. 17, pp. 9484-9494, (2012).
Ventoso, I. et al. Translational resistance of late alphavirus mRNA to eIF2 phosphorylation: a strategy to overcome the antiviral effect of protein kinase PKR, Genes and Development, vol. 20, pp. 87-100, (2006).
Vrudhula et al., Prodrugs of doxorubicin and melphalan and their activation by a monoclonal antibody-penicillin-G amidase conjugate, J. Med. Chem., 1993, pp. 919-923, vol. 36, Issue 7.

(56) References Cited

OTHER PUBLICATIONS

Ward, S. et al., Generation of CTL responses using Kunjin replicon RNA, Immunology and Cell Biology, vol. 81 , pp. 73-78, (2003).
Warner et al. Induction of the HIV-Specific and Antibody Responses in Mice Using Retroviral Vector-Transduced Cells, AIDS Res. and Human Retroviruses, vol. 7, No. 8, pp. 645-655 (1991).
Wassenaar, et al., Alternative Proteolytic Processing of the Arterivirus Replicase ORF1a Polyprotein: Evidence that NSP2 Acts as a Cofactor for the NSP4 Serine Protease, J. Virol., 1997, pp. 9313-9322, vol. 71, Issue 12.
Watanabe, et al., Exogenous expression of mouse interferon gamma cDNA in mouse neuroblastoma C1300 cells results in reduced tumorigenicity by augmented anti-tumor immunity, Proc. Natl. Acad. Sci. USA, Dec. 1989, pp. 9456-9460, vol. 86.
Weber et al., Immunotherapy of a murine tumor with interleukin 2. J. Exp. Med., 1987, pp. 1716-1733, vol. 166.
White, L. et al., Role of Alpha/Beta Interferon in Venezuelan Equine Encephalitis Virus Pathogenesis: Effect of an Attenuating Mutation in the 59 Untranslated Region, Journal of Virology, vol. 75, No. 8, pp. 3706-3718, (2001).
Wilson et al., Prospects for gene therapy of familial hypercholesterolemia, Mol. Biol. Med., Jun. 1, 1990, pp. 223-232, vol. 7, Issue 3.
Wood et al., Preproabrin: genomic cloning, characterisation and the expression of the A-chain in *Escherichia coli*, Eur. J. Biochem., 1991, pp. 723-732, vol. 198.
Yamamoto et al., The human LDL receptor: a cysteine-rich protein with multiple Alu sequences in its mRNA, Cell, Nov. 1984, pp. 27-38, vol. 39, Issue 1.
Zhou, X. et al. Self-replicating Semliki Forest virus RNA as recombinant vaccine, Vaccine, vol. 12, No. 16, pp. 1510-1514, (1994).
GenBank/NCBI accession No. J02363, dated Oct. 25, 2000; accessed Jul. 16, 2018.
GenBank accession # JX473847, dated Dec. 22, 2012; accessed Apr. 17, 2019.
GenBank/NCBI accession No. L01443.1., dated Nov. 17, 2014; accessed Oct. 3, 2016.
GenBank/NCBI accession No. L04653, dated Jun. 1, 2001; accessed Jul. 16, 2018.
GenBank/NCBI accession No. NC_001449, dated Feb. 10, 2015; accessed Jul. 16, 2018.
GenBank/NCBI accession No. NC_003215, dated Feb. 10, 2015; accessed Jul. 16, 2018.
GenBank/NCBI accession No. U38304; dated Feb. 10, 2015; accessed Jul. 16, 2018.
GenBank/NCBI accession No. U38305, dated Jan. 30, 2016, accessed Jul. 16, 2018.
GenBank/NCBI accession No. X04129, dated Mar. 13, 2001; accessed Jul. 16, 2018.
International Search Report and Written Opinion, dated Dec. 1, 2017, in International Application No. PCT/US2017/054928.
International Search Report and Written Opinion, dated Jul. 10, 2017, in International Patent Application No. PCT/US2017/027249, filed Apr. 12, 2017.
International Search Report and Written Opinion, dated Jul. 3, 2018, in International Application No. PCT/US2017/064561.
Boukhebza et al., "Comparative analysis of immunization schedules using a novel adenovirus-based immunotherapeutic targeting hepatitis B in naive and tolerant mouse models" Vaccine, 32(26), pp. 3258-3263, 2014.
Jones et al., "Hepatitis B virus reverse transcriptase: diverse functions as classical and emerging targets for antiviral intervention", Emerging Microbes and Infections, 2(9), e56, 9 pages, 2013.
Int'l Search Report and Written Opinion dated May 22, 2018 in Int'l Application No. PCT/IB2017/058142, 17 pages.
Obeng-Adjei et al. "DNA vaccine cocktail expressing genotype A and C HBV surface and consensus core antigens generates robust cytotoxic and antibody responses and mice and Rhesus macaques" Cancer Gene Therapy, 20, 352-662, 2013.
Cohen et al. "Is chronic hepatitis B being undertreated in the United States?" J. Viral Hepat., 18(6), 377-83,2011.
Belloni et al. "IFN-a inhibits HBV transcription and replication in cell culture and in humanized mice by targeting the epigenetic regulation of the nuclear cccDNA minichromosome" J. Clin. Invest., 122(2), 529-537, 2012.
World Health Organization, Hepatitis B: Fact sheet No. 204 [Internet] Mar. 2015. Available from https://www.who.int/news-room/fact-sheets/detail/hepatitis-b, 6 pages.
Michel et al. "Therapeutic vaccines and immune-based therapies for the treatment of chronic hepatitis B: perspectives and challenges." J. Hepatol., 54(6), 1286-1296, 2011.
Int'l Search Report and Written Opinion dated Apr. 17, 2019 in Int'l Application No. PCT/IB2018/060259, 16 pages.
Int'l Search Report and Written Opinion dated Jun. 25, 2018 in Int'l Application No. PCT/US2017/067269, 17 pages.
Int'l Search Report and Written Opinion dated Feb. 14, 2019 in Int'l Application No. PCT/US2018/066157, 19 pages.
Int'l Search Report and Written Opinion dated Mar. 26, 2018 in Int'l Application No. PCT/IB2017058148, 14 pages.
Int'l Search Report and Written Opinion dated Mar. 27, 2019 in Int'l Application No. PCT/IB2018/060257, 15 pages.
Kim, et al., "New World and Old World Alphaviruses Have Evolved to Exploit Different Components of Stress Granules, FXR and G3BP Proteins, for Assembly of Viral Replication Complexes", PLOS Pathogens, vol. 12, No. 8, p. 1-31, (Aug. 2016).
Foy, et al., "Hypervariable domains of nsP3 proteins of New World and Old World alphaviruses mediate formation of distinct, virus-specific protein complexes", J. Virol., vol. 87, No. 4, p. 1997-2010, (Dec. 2012).
Gotte, et al., "The Enigmatic Alphavirus Non-Structural Protein 3 (nsP3) Revealing Its Secrets at Last", Viruses, vol. 10, No. 3, p. 105, 1/26 to 26/26, (Feb. 2018).
Meshram, et al., "Multiple Host Factors Interact with the Hypervariable Domain of Chikungunya Virus nsP3 and Determine Viral Replication in Cell-Specific Mode", J. Virol., vol. 92, No. 16, p. 1-24, (Aug. 2018).
International Search Report and Written Opinion dated Dec. 13, 2019 in International Appl. No. PCT/US2019/055125, 15 pages.
Frolov et al, (Journal of Virology, 1999, p. 3854-3865).
Bolz et al.: "Use of Recombinant Virus Replicon Particles for Vaccination against *Mycobacterium ulcerans* Disease"; PLoS Negl Trop Dis,, Aug. 14, 2015, vol. 9(8):e0004011., PDF File: p. 1-18.
International Search Report dated Apr. 23, 2019, regarding PCT/US2019/014210, 13 pages.
Lundstrom, Kenneth L: "Replicon RNA Viral Vectors as Vaccines"; Vaccines, 2016, vol. 4(4). pii: E39. PDF File: p. 1-23.
Uematsu et al.: "Lack of Interference with Immunogenicity of a Chimeric Alphavirus Replicon Particle-Based Influenza Vaccine by Preexisting Antivector Immunity"; Clin Vaccine Immunol., Jul. 2012, vol. 19(7), p. 991-998.
Xu et al.: "Type-specific and cross-reactive antibodies induced by human papillomavirus 31 L1/L2 virus-like particle";, J Med Microbiol. 2007, vol. 56(Pt 7), p. 907-13.
Giese M, Bahr U, Jakob NJ, Kehm R, Handermann M, Müller H, Vahlenkamp TH, Spiess C, Schneider TH, Schusse G, Darai G. U Stable and long-lasting immune response in horses after DNA vaccination against equine arteritis virus. Virus Genes. Oct. 2002;25(2):159-67. (Year: 2002).
Reyes-Sandoval Arturo et al, "Prime-Boost Immunization with Adenoviral and Modified Vaccinia Virus Ankara Vectors Enhances the Durability and Polyfunctionality of Protective Malaria CD8(+) T-Cell Responses", Infection and Immunity, (Jan. 2010), vol. 78, No. 1, pp. 145-153, XP002778539.
Perrine Martin et al, "TG1050, an immunotherapeutic to treat chronic hepatitis B, induces robust T cells and exerts an antiviral effect in HBV-persistent mice", Gut, UK, (Nov. 26, 2014), vol. 64, No. 12, doi:10.1136/gutjnl-2014-308041, ISSN 0017-5749, pp. 1961-1971, XP055453477.
Barienschlager et al., "Expression of the P-protein of the human hepatitis B virus in a vaccinia virus system and detection of the

(56) References Cited

OTHER PUBLICATIONS nucleocapsid-associated P-gene product by radiolabelling at newly introduced phosphorylation sites", Nucleic Acids Research, vol. 20, No. 2, pp. 195-202,1992.
Ramirez et at., "Biology of Attenuated Modified Vaccinia Virus Ankara Recombinant Vector in Mice: Virus Fate and Activation of B- and T-Cell Immune Responses in Comparision with the Western Reserve Strain and advantages as a Vaccine", Journal of Virology, Vo. 74, No. 2, pp. 923-933, 2000.
Obeng-Adjei et al., "Synthetic DNA immunogen encoding hepatitis B core antigen drives immune response in liver," Cancer Gene Therapy, Nov. 5, 2012 Appleton & Lange, New York, vol. 19, Nr: 11, pp. 779-787.
Araujo et al, "Expression of Hepatitis B virus surface antigen (HBsAg) from genotypes A, D and F and influence of amino acid variations related or not to genotypes on HBsAg detection," Brazilian Journal of Infectious Diseases, Jan. 1, 2009, vol. 13, Nr: 4.
Jeeva S, Lee JA, Park SY, Song CS, Choi IS, Lee JB. Development of porcine respiratory and reproductive syndrome virus replicon vector for foot-and-mouth disease vaccine. Clin Exp Vaccine Res. Jan. 2014;3(1):100-9. doi: 10.7774/cevr.2014.3.1.100. Epub Dec. 18, 2013. PMID: 24427767; PMCID: PMC3890444. (Year: 2014).
Petrakova et al, Noncytopathic Replication of Venezuelan Equine Encephalitis Virus and Eastern Equine Encephalitis Virus Replicons in Mammalian Cells, Journal of Virology, Jun. 2005, p. 7597-7608.
Johansson et al, 2012, PLOS One, Intradermal Electroporation of Naked Replicon RNA Elicits Strong Immune Responses, 7(1):e29732.
Liang Qianqian, Construction of Porcine Reproductive and Respiratory Syndrome DNA Vaccine Based on Alpha-virus Replicon Vector and Evaluation of Its Immune Efficacy, May 2013, pp. 1-86, Chinese with English abstract.

* cited by examiner

Adapted from Strauss *et al.*, 1994

Adopted from Toribio *et al.* 2016

Adopted from Toribio *et al.* 2016

SEQUENCE LISTING

<160> NUMBER OF SEQ ID NOS: 52

<210> SEQ ID NO 1
<211> LENGTH: 145
<212> TYPE: DNA
<213> ORGANISM: Sindbis virus

<400> SEQUENCE: 1
atagtcagca tagtacattt catctgacta atactacaac accaccacca tgaatagagg 60
attctttaac atgctcggcc gccgcccctt cccggccccc actgccatgt ggaggccgcg 120
gagaaggagg caggcggccc cgatg 145

<210> SEQ ID NO 2
<211> LENGTH: 480
<212> TYPE: DNA
<213> ORGANISM: Artificial Sequence
<220> FEATURE:
<223> OTHER INFORMATION: Synthetic polynucleotide

<400> SEQUENCE: 2
gctcgaagtg tgtatggtgc catatacggc tcaccaccat atacactgca agaattacta 60
ttcttgtggg cccctctcgg taaatcctag agggctttcc tctcgttatt gcgagattcg 120
tcgttagata acggcaagtt ccctttctta ctatcctatt ttcatcttgt ggcttgacgg 180
gtcactgcct acgtcgtcga tctctatcaa ctacccttgc gacttaggca accttctccg 240
ctactggatt tggagggagt tttgttaggg actggtccct ggacttaccc gacgcttgtg 300
agcatagtca gcatagtaca tttcatctga ctaatactac aacaccacca ccatgaatag 360
aggattcttt aacatgctcg gccgccgccc cttcccggcc cccactgcca tgtggaggcc 420
gcggagaagg aggcaggcgg ccccgatgat ggcaaccttc tccgctactg gatttggagg 480

<210> SEQ ID NO 3
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: 2A proteolytic cleavage site

<400> SEQUENCE: 3
ggaagcggag ctactaactt cagcctgctg aagcaggctg gagacgtgga ggagaaccct 60
ggacct 66

<210> SEQ ID NO 4
<211> LENGTH: 1749
<212> TYPE: DNA
<213> ORGANISM: Artificial Sequence
<220> FEATURE:

<223> OTHER INFORMATION: Synthetic polynucleotide
<220> FEATURE:
<221> NAME/KEY: misc_feature
<223> OTHER INFORMATION: g-block for construction of rEx-DLP-rFF

<400> SEQUENCE: 4

```
cagaggcgca ggacttgatc catggcccac ctacagcatg ccacctgggc caagaaattg     60

acctttggtc caatgagggc ctcgaatatt acaaggaagt caacctgctg tacacacacg    120

tccccatcaa ggatggtgta atacacagtt accctaattg tggccctgcc tgtggctggg    180

aaaagcaatc caacaaaatt tcgtgcctcc cgagagtggc acaaaatttg ggctaccact    240

attccccaga cttaccagga ttttgcccca taccaaaaga actcgctgag cattggcccg    300

tagtgtccaa tgatagatac ccgaattgct tgcaaattac cttacagcaa gtatgtgaac    360

tcagtaaacc gtgctcagcg ggctatatgg ttggacaatc ggttttcgtg cagacgcctg    420

gtgtgacatc ttactggctt actgaatggg tcgacggcaa agcgcgtgct ctaccagatt    480

ccttattctc gtccggtagg ttcgagacta acagccgcgc tttcctcgat gaagccgagg    540

aaaagtttgc cgccgctcac cctcatgcct gtttgggaga aattaataag tccaccgtgg    600

gaggatccca cttcatcttt tcccaatatt taccaccatt gctacccgca gacgctgttg    660

ccctggtagg tgcttcattg gctgggaaag ctgctaaagc tgcttgcagc gttgttgatg    720

tctatgctcc atcatttgaa ccttatctac accctgagac actgagtcgc gtgtacaaga    780

ttatgatcga tttcaagccg tgtaggctta tggtgtggag aaacgcgacc ttttatgtcc    840

aagagggtgt tgatgcagtt acatcagcac tagcagctgt gtccaaactc atcaaagtgc    900

cggccaatga gcctgtttca ttccatgtgg catcagggta cagaaccaac gcgctggtag    960

cgccccaggc taaaatttca attggagcct acgccgccga gtgggcactg tcaactgaac   1020

cgccacctgc tggttatgcg atcgtgcggc gatatattgt aaagaggctc ctcagctcaa   1080

cagaagtgtt cttgtgccgc aggggtgttg tgtcttccac ctcagtgcag accatttgtg   1140

cactagaggg atgtaaacct ctgttcaact tcttacaaat tggttcagtc attgggcccg   1200

tgtgactcta gagtggacct gttcccatcc cccgctcaac tactcaggta gtggttcgcg   1260

gcaacgggta caccgcagtt ggtaacaagc ttgtcgatag tcagcatagt acatttcatc   1320

tgactaatac tacaacacca ccaccatgaa tagaggattc tttaacatgc tcggccgccg   1380

ccccttcccg gcccccactg ccatgtggag gccgcggaga aggaggcagg cggccccgat   1440

gatggaaaat atggaaaacg acgagaacat cgtggtgggc cccaagccct tctaccccat   1500

cgaggaaggc agcgccggca cccagctgcg gaagtacatg gaaagatacg ccaagctggg   1560

cgccattgcc ttcaccaacg ccgtgaccgg cgtggactac agctacgccg agtacctgga   1620

aaagagctgc tgcctgggca aggctctgca gaactacggc ctggtggtgg acggccggat   1680

cgccctgtgc agcgagaact gcgaggaatt cttcatcccc gtgatcgccg gcctgttcat   1740

cggcgtggg                                                           1749
```

<210> SEQ ID NO 5
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer pp1a-DLP-F
<220> FEATURE:
<221> NAME/KEY: misc_feature -continued

<223> OTHER INFORMATION: RP114

<400> SEQUENCE: 5
gccatgtgga ggccgcggag aaggaggcag gcggccccga tgatggcaac cttctccgct 60
actggat 67

<210> SEQ ID NO 6
<211> LENGTH: 25
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer pBR322-3'SrfI-R
<220> FEATURE:
<221> NAME/KEY: misc_feature
<223> OTHER INFORMATION: RP115

<400> SEQUENCE: 6
acaatgttgc ctcccacatc tgcaa 25

<210> SEQ ID NO 7
<211> LENGTH: 25
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer pBR322-3'SrfI-F
<220> FEATURE:
<221> NAME/KEY: misc_feature
<223> OTHER INFORMATION: RP116

<400> SEQUENCE: 7
gggtcacaag gtagtcgccg tggtt 25

<210> SEQ ID NO 8
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer pBR322-bla-R
<220> FEATURE:
<221> NAME/KEY: misc_feature
<223> OTHER INFORMATION: RP117

<400> SEQUENCE: 8
cgtcaggtgg cacttttcgg ggaa 24

<210> SEQ ID NO 9
<211> LENGTH: 70
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer pp1a-DLP-2A-F

<400> SEQUENCE: 9
agcctgctga agcaggctgg agacgtggag gagaaccctg gacctatggc aaccttctcc 60
gctactggat 70

<210> SEQ ID NO 10
<211> LENGTH: 589
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: g-block for rEx-DLP-pp1ab-rFF

<400> SEQUENCE: 10
aaacaaatag gggttccgcg cacatttccc cgaaaagtgc cacctgacgt ctaagaaacc 60
attattatca tgacattaag catccgcctt tcgttttatt tgaccatgtt ggtatgtaat 120
acgactcact atagctcgaa gtgtgtatgg tgccatatac ggctcaccac catatacact 180
gcaagaatta ctattcttgt gggcccctct cggtaaatcc tagagggctt tcctctcgtt 240
attgcgagat tcgtcgttag ataacggcaa gttccctttc ttactatcct attttcatct 300
tgtggcttga cgggtcactg cctacgtcgt cgatctctat caactaccct tgcgacttag 360
gcaaccttct ccgctactgg atttggaggg agttttgtta gggactggtc cctggactta 420
cccgacgctt gtgagcatag tcagcatagt acatttcatc tgactaatac tacaacacca 480
ccaccatgaa tagaggattc tttaacatgc tcggccgccg ccccttcccg gcccccactg 540
ccatgtggag gccgcggaga aggaggcagg cggccccgat gatggcaac 589

<210> SEQ ID NO 11
<211> LENGTH: 655
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: g-block for rEx-DLP-2A-pp1ab-rFF

<400> SEQUENCE: 11
aaacaaatag gggttccgcg cacatttccc cgaaaagtgc cacctgacgt ctaagaaacc 60
attattatca tgacattaag catccgcctt tcgttttatt tgaccatgtt ggtatgtaat 120
acgactcact atagctcgaa gtgtgtatgg tgccatatac ggctcaccac catatacact 180
gcaagaatta ctattcttgt gggcccctct cggtaaatcc tagagggctt tcctctcgtt 240
attgcgagat tcgtcgttag ataacggcaa gttccctttc ttactatcct attttcatct 300
tgtggcttga cgggtcactg cctacgtcgt cgatctctat caactaccct tgcgacttag 360
gcaaccttct ccgctactgg atttggaggg agttttgtta gggactggtc cctggactta 420
cccgacgctt gtgagcatag tcagcatagt acatttcatc tgactaatac tacaacacca 480
ccaccatgaa tagaggattc tttaacatgc tcggccgccg ccccttcccg gcccccactg 540
ccatgtggag gccgcggaga aggaggcagg cggccccgat gggaagcgga gctactaact 600
tcagcctgct gaagcaggct ggagacgtgg aggagaaccc tggacctatg gcaac 655

<210> SEQ ID NO 12
<211> LENGTH: 655
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: g-block for rEx-DLP-2A-pp1ab-DLP-rFF

<400> SEQUENCE: 12
aaacaaatag gggttccgcg cacatttccc cgaaaagtgc cacctgacgt ctaagaaacc 60
attattatca tgacattaag catccgcctt tcgttttatt tgaccatgtt ggtatgtaat 120
acgactcact atagctcgaa gtgtgtatgg tgccatatac ggctcaccac catatacact 180
gcaagaatta ctattcttgt gggcccctct cggtaaatcc tagagggctt tcctctcgtt 240
attgcgagat tcgtcgttag ataacggcaa gttccctttc ttactatcct attttcatct 300
tgtggcttga cgggtcactg cctacgtcgt cgatctctat caactaccct tgcgacttag 360
gcaaccttct ccgctactgg atttggaggg agttttgtta gggactggtc cctggactta 420
cccgacgctt gtgagcatag tcagcatagt acatttcatc tgactaatac tacaacacca 480
ccaccatgaa tagaggattc tttaacatgc tcggccgccg ccccttcccg gcccccactg 540
ccatgtggag gccgcggaga aggaggcagg cggccccgat gggaagcgga gctactaact 600
tcagcctgct gaagcaggct ggagacgtgg aggagaaccc tggacctatg gcaac 655

<210> SEQ ID NO 13
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer DLP-pp1ab-screen-F
<220> FEATURE:
<221> NAME/KEY: misc_feature
<223> OTHER INFORMATION: RP126

<400> SEQUENCE: 13
cagcatcttt tactttcacc agcgtttctg 30

<210> SEQ ID NO 14
<211> LENGTH: 25
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer DLP-pp1ab-screen-R
<220> FEATURE:
<221> NAME/KEY: misc_feature
<223> OTHER INFORMATION: RP127

<400> SEQUENCE: 14
ggaactggcg aagccagttt taaca 25

<210> SEQ ID NO 15
<211> LENGTH: 12529
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Construct rEx-DLP-rFF
<220> FEATURE:
<221> NAME/KEY: misc_feature
<222> LOCATION: (1)...(18)
<223> OTHER INFORMATION: T7 promoter

<400> SEQUENCE: 15
taatacgact cactatagct cgaagtgtgt atggtgccat atacggctca ccaccatata 60

-continued

```
cactgcaaga attactattc ttgtgggccc ctctcggtaa atcctagagg gctttcctct    120
cgttattgcg agattcgtcg ttagataacg gcaagttccc tttcttacta tcctattttc    180
atcttgtggc ttgacgggtc actgccatcg tcgtcgatct ctatcaacta cccttgcgac    240
tatggcaacc ttctccgcta ctggatttgg agggagtttt gttagggact ggtccctgga    300
cttacccgac gcttgtgagc atggcgcggg attgtgctgc gaagtggacg gctccacctt    360
atgcgccgag tgttttcgcg gttgcgaagg aatggagcaa tgtcctggct tgttcatggg    420
actgttaaaa ctggcttcgc cagttccagt gggacataag ttcctgattg gttggtatcg    480
agctgccaaa gtcaccgggc gttacaattt ccttgagctg ttgcaacacc ctgctttcgc    540
ccagctgcgt gtggttgatg ctaggttagc cattgaagag gcaagtgtgt ttatttccac    600
tgaccacgcg tctgctaagc gtttccctgg cgctagattt gcgctgacac cggtgtatgc    660
taacgcttgg gttgtgagcc cggctgctaa cagtttgata gtgaccactg accaggaaca    720
agatgggttc tgctggttaa aacttttgcc acctgaccgc cgtgaggctg gtttgcggtt    780
gtattacaac cattaccgcg aacaaaggac cgggtggctg tctaaaacag gacttcgctt    840
atggcttgga gacctgggtt tgggcatcaa tgcgagctct ggagggctga aattccacat    900
tatgaggggt tcgcctcagc gagcttggca tatcacaaca cgcagctgca agctgaagag    960
ctactacgtt tgtgacatct ctgaagcaga ctggtcctgt ttgcctgctg gcaactacgg   1020
cggctacaat ccaccagggg acggagcttg cggttacagg tgcttggcct tcatgaatgg   1080
cgccactgtt gtgtcggctg gttgcagttc tgacttgtgg tgtgatgatg agttggctta   1140
tcgagtcttt caattgtcac ccacgttcac ggttaccatc ccaggtgggc gagtttgtcc   1200
gaatgccaag tacgcaatga tttgtgacaa gcagcactgg cgcgtcaaac gtgcaaaggg   1260
cgtcggcctg tgtctcgatg aaagctgttt caggggcatc tgcaattgcc aacgcatgag   1320
tggaccacca cctgcacccg tgtcagccgc cgtgttagat cacatactgg aggcggcgac   1380
gtttggcaac gttcgcgtgg ttacacctga agggcagcca cgccccgtac cagcgccgcg   1440
agttcgtccc agcgccaact cttctggaga tgtcaaagat ccggcgcccg ttccgccagt   1500
accaaaacca aggaccaagc ttgccacacc gaacccaact caggcgccca tcccagcacc   1560
gcgcacgcga cttcaagggg cctcaacaca ggagccactg gcgagtgcag gagttgcttc   1620
tgactcggca cctaaatggc gtgtggccaa aactgtgtac agctccgcgg agcgctttcg   1680
gaccgaactg gtacaacgtg ctcggtccgt tggggacgtt cttgttcaag cgctaccgct   1740
caaaacccca gcagtgcagc ggtataccat gactctgaag atgatgcgtt cacgcttcag   1800
ttggcactgc gacgtgtggt accctttggc tgtaatcgct tgtttgctcc ctatatggcc   1860
atctcttgct ttgctcctta gctttgccat tgggttgata cccagtgtgg gcaataatgt   1920
tgttctgaca gcgcttctgg tttcatcagc taattatgtt gcgtcaatgg accatcaatg   1980
tgaaggtgcg gcttgcttag ccttgctgga agaagaacac tattatagag cggtccgttg   2040
gcgcccgatt acaggcgcgc tgtcgcttgt gctcaattta ctggggcagg taggctatgt   2100
agctcgttcc acctttgatg cagcttatgt tccttgcact gtgttcgatc tttgcagctt   2160
tgctattctg tacctctgcc gcaatcgttg ctggagatgc ttcggacgct gtgtgcgagt   2220
tgggcctgcc acgcatgttt tgggctccac cgggcaacga gtttccaaac tggcgctcat   2280
tgatttgtgt gaccactttt caaagcccac catcgatgtt gtgggcatgg caactggttg   2340
gagcggatgt tacacaggaa ccgccgcaat ggagcgtcag tgtgcctcta cggtggaccc   2400
tcactcgttc gaccagaaga aggcaggagc gactgtttac ctcacccccc ctgtcaacag   2460
```

-continued

```
cgggtcagcg ctgcagtgcc tcaatgtcat gtggaagcga ccaattgggt ccactgtcct   2520

tggggaacaa acaggagctg ttgtgacggc ggtcaagagt atctctttct cacctccctg   2580

ctgcgtctct accactttgc ccacccgacc cggtgtgacc gttgtcgacc atgctcttta   2640

caaccggttg actgcttcag ggtcgatcc cgctttattg cgtgttgggc aaggtgattt   2700

tctaaaactt aatccggggt tccggctgat aggtggatgg atttatggga tatgctattt   2760

tgtgttggtg gttgtgtcaa cttttacctg cttacctatc aaatgtggca ttggcacccg   2820

cgaccctttc tgccgcagag tgttttctgt acccgtcacc aagacccaag agcactgcca   2880

tgctggaatg tgtgctagcg ctgaaggcat ctctctggac tctctggggt taactcagtt   2940

acaaagttac tggatcgcag ccgtcactag cggattagtg atcttgttgg tctgccaccg   3000

cctggccatc agcgccttgg acttgttgac tctagcttcc cctttagtgt tgcttgtgtt   3060

cccttgggca tctgtggggc ttttacttgc ttgcagtctc gctggtgctg ctgtgaaaat   3120

acagttgttg gcgacgcttt ttgtgaatct attctttccc caagctaccc ttgtcactat   3180

gggatactgg gcgtgcgtgg cggctttggc cgtttacagt ttgatgggct tgcgagtgaa   3240

agtgaatgtg cccatgtgtg tgacacctgc ccattttctg ctgctggcga ggtcagctgg   3300

acagtcaaga gagcagatgc tccgggtcag cgctgctgcc cccaccaatt cactgcttgg   3360

agtggctcgt gattgttatg tcacaggcac aactcggctg tacataccca aggaaggcgg   3420

gatggtgttt gaagggctat tcaggtcacc gaaggcgcgc ggcaacgtcg gcttcgtggc   3480

tggtagcagc tacggcacag ggtcagtgtg gaccaggaac aacgaggtcg tcgtactgac   3540

agcgtcacac gtggttggcc gcgctaacat ggccactctg aagatcggtg acgcaatgct   3600

gactctgact ttcaaaaaga atggcgactt cgccgaggca gtgacgacac agtccgagct   3660

cccaggcaat tggccacagt tgcatttcgc ccaaccaaca accgggcccg cttcatggtg   3720

cactgccaca ggagatgaag aaggcttgct cagtggcgag gtttgtctgg cgtggactac   3780

tagtggcgac tctggatctg cagtggttca gggtgacgct gtggtagggg tccacaccgg   3840

ttcgaacaca agtggtgttg cctacgtgac caccccaagc ggaaaactcc ttggcgccga   3900

caccgtgact ttgtcatcac tgtcaaagca tttcacaggc cctttgacat caatcccgaa   3960

ggacatccct gacaacatta ttgccgatgt tgatgctgtt cctcgttctc tggccatgct   4020

gattgatggc ttatccaata gagagagcag cctttctgga cctcagttgt tgttaattgc   4080

ttgttttatg tggtcttatc ttaaccaacc tgcttacttg ccttatgtgc tgggcttctt   4140

tgccgctaac ttcttcctgc caaaaagtgt tggccgccct gtggtcactg ggcttctatg   4200

gttgtgctgc ctcttcacac cgctttccat gcgcttgtgc ttgttccatc tggtctgtgc   4260

taccgtcacg ggaaacgtga tatctttgtg gttctacatc actgccgctg gcacgtctta   4320

cctttctgag atgtggttcg gaggctatcc caccatgttg tttgtgccac ggttcctagt   4380

gtaccagttc cccggctggg ctattggcac agtactagcg gtatgcagca tcaccatgct   4440

ggctgctgcc ctcggtcaca ccctgttact ggatgtgttc tccgcctcag gtcgctttga   4500

caggactttc atgatgaaat acttcctgga gggaggagtg aaagagagtg tcaccgcctc   4560

agtcacccgc gcttatggca aaccaattac ccaggagagt ctcactgcaa cattagctgc   4620

cctcactgat gatgacttcc aattcctctc tgatgtgctt gactgtcggg ccgtccgatc   4680

ggcaatgaat ctgcgtgccg ctctcacaag ttttcaagtg gcgcagtatc gtaacatcct   4740

taatgcatcc ttgcaagtcg atcgtgacgc tgctcgtagt cgcagactaa tggcaaaact   4800
```

-continued

```
ggctgatttt gcggttgaac aagaagtaac agctggagac cgtgttgtgg ttatcgacgg   4860
tctggaccgc atggctcact tcaaagacga tttggtgctg gttcctttga ccaccaaagt   4920
agtaggcggt tctaggtgca ccatttgtga cgtcgttaag gaagaagcca atgacacccc   4980
agttaagcca atgcccagca ggagacgccg caagggcctg cctaaaggtg ctcagttgga   5040
gtgggaccgt caccaggaag agaagaggaa cgccggtgat gatgattttg cggtctcgaa   5100
tgattatgtc aagagagtgc caaagtactg ggatcccagc gacacccgag gcacgacagt   5160
gaaaatcgcc ggcactacct atcagaaagt ggttgactat tcaggcaatg tgcattacgt   5220
ggagcatcag gaagatctgc tagactacgt gctgggcaag gggagctatg aaggcctaga   5280
tcaggacaaa gtgttggacc tcacaaacat gcttaaagtg gaccccacgg agctctcctc   5340
caaagacaaa gccaaggcgc gtcagcttgc tcatctgctg ttggatctgg ctaacccagt   5400
tgaggcagtg aatcagttaa actgagagcg ccccacatct ttcccggcga tgtggggcgt   5460
cggacctttg ctgactctaa agacaagggt ttcgtggctc tacacagtcg cacaatgttt   5520
ttagctgccc gggacttttt atttaacatc aaatttgtgt gcgacgaaga gttcacaaag   5580
accccaaaag acacactgct tgggtacgta cgcgcctgcc ctggttactg gtttattttc   5640
cgtcgtacgc accggtcgct gattgatgca tactgggaca gtatggagtg cgtttacgcg   5700
cttcccacca tatctgattt tgatgtgagc ccaggtgacg tcgcagtgac gggcgagcga   5760
tgggattttg aatctcccgg aggaggccgt gcaaaacgtc tcacagctga tctggtgcac   5820
gcttttcaag ggttccacgg agcctcttat tcctatgatg acaaggtggc agctgctgtc   5880
agtggtgacc cgtatcggtc ggacggcgtc ttgtataaca cccgttgggg caacattcca   5940
tattctgtcc caaccaatgc tttggaagcc acagcttgct accgtgctgg atgtgaggcc   6000
gttaccgacg ggaccaacgt catcgcaaca attgggccct tcccggagca acaacccata   6060
ccggacatcc caaagagcgt gcttgacaac tgcgctgaca tcagctgtga cgctttcata   6120
gcgcccgctg cagagacagc cctgtgtgga gatttagaga aatacaacct atccacgcag   6180
ggttttgtgt tgcctagtgt tttctccatg gtgcgggcgt acttaaaaga ggagattgga   6240
gacgctccac cactctactt gccatctact gtaccatcta aaaattcaca agccggaatt   6300
aacggcgctg agtttcctac aaagtcttta cagagctact gtttgattga tgacatggtg   6360
tcacagtcca tgaaaagcaa tctacaaacc gccaccatgg cgacttgtaa acggcaatac   6420
tgttccaaat acaagattag gagcattctg ggcaccaaca attacattgg cctaggtttg   6480
cgtgcctgcc tttcgggggt tacggccgca ttccaaaaag ctggaaagga tgggtcaccg   6540
atttatttgg gcaagtcaaa attcgacccg ataccagctc ctgacaagta ctgccttgaa   6600
acagacctgg agagttgtga tcgctccacc ccggctttgg tgcgttggtt cgctactaat   6660
cttatttttg agctagctgg ccagcccgag ttggtgcaca gctacgtgtt gaattgctgt   6720
cacgatctag ttgtggcggg tagtgtagca ttcaccaaac gcgggggttt gtcatctgga   6780
gaccctatca cttccatttc caataccatc tattcattgg tgctgtacac ccagcacatg   6840
ttgctatgtg gacttgaagg ctatttccca gagattgcag aaaaatatct tgatggcagc   6900
ctggagctgc gggacatgtt caagtacgtt cgagtgtaca tctactcgga cgatgtggtt   6960
ctaaccacac ccaaccagca ttacgcggcc agctttgacc gctgggtccc ccacctgcag   7020
gcgctgctag gtttcaaggt tgacccaaag aaaactgtga acaccagctc cccttccttt   7080
ttgggctgcc ggttcaagca agtggacggc aagtgttatc tagccagtct tcaggaccgc   7140
gttacacgct ctctgttata ccacattggt gcaaagaatc cctcagagta ctatgaagct   7200
```

gctgtttcca tctttaagga ctccattatc tgctgtgatg aagactggtg gacggacctc 7260
catcgacgta tcagtggcgc tgcgcgtacc gacggagttg agttccccac cattgaaatg 7320
ttaacatcct tccgcaccaa gcagtatgag agtgccgtgt gcacagtttg tggggccgcc 7380
cccgtggcca agtctgcttg tggagggtgg ttctgtggca attgtgtccc gtaccacgcg 7440
ggtcattgtc acacaacctc gctcttcgcc aactgcgggc acgacatcat gtaccgctcc 7500
acttactgca caatgtgtga gggttcccca aaacagatgg taccaaaagt gcctcacccg 7560
atcctggatc atttgctgtg ccacattgat tacggcagta aagaggaact aactctggta 7620
gtggcggatg gtcgaacaac atcaccgccc gggcgctaca aagtgggtca caaggtagtc 7680
gccgtggttg cagatgtggg aggcaacatt gtgtttgggt gcggtcctgg atcacacatc 7740
gcagtaccac ttcaggatac gctcaagggc gtggtggtga ataaagctct gaagaacgcc 7800
gccgcctctg agtacgtgga aggacccccct gggagtggga agacttttca cctggtcaaa 7860
gatgtgctag ccgtggtcgg tagcgcgacc ttggttgtgc ccacccacgc gtccatgctg 7920
gactgcatca acaagctcaa acaagcgggc gccgatccat actttgtggt gcccaagtat 7980
acagttcttg actttccccg gcctggcagt ggaaacatca cagtgcgact gccacaggtc 8040
ggaaccagtg agggagaaac ctttgtggat gaggtggcct acttctcacc agtggatctg 8100
gcgcgcattt taacccaggg tcgagtcaag ggttacggtg atttaaatca gctcgggtgc 8160
gtcggacccg cgagcgtgcc acgtaacctt tggctccgac attttgtcag cctggagccc 8220
ttgcgagtgt gccatcgatt cggcgctgct gtgtgtgatt tgatcaaggg catttatcct 8280
tattatgagc cagctccaca taccactaaa gtggtgtttg tgccaaatcc agactttgag 8340
aaaggtgtag tcatcaccgc ctaccacaaa gatcgcggtc ttggtcaccg cacaattgat 8400
tcaattcaag gctgtacatt ccctgttgtg actcttcgac tgcccacacc ccaatcactg 8460
acgcgcccgc gcgcagttgt ggcggttact agggcgtctc aggaattata catctacgac 8520
ccctttgatc agcttagcgg gttgttgaag ttcaccaagg aagcagaggc gcaggacttg 8580
atccatggcc cacctacagc atgccacctg ggccaagaaa ttgacctttg gtccaatgag 8640
ggcctcgaat attacaagga agtcaacctg ctgtacacac acgtccccat caaggatggt 8700
gtaatacaca gttaccctaa ttgtggccct gcctgtggct gggaaaagca atccaacaaa 8760
atttcgtgcc tcccgagagt ggcacaaaat ttgggctacc actattcccc agacttacca 8820
ggattttgcc ccataccaaa agaactcgct gagcattggc ccgtagtgtc caatgataga 8880
tacccgaatt gcttgcaaat taccttacag caagtatgtg aactcagtaa accgtgctca 8940
gcgggctata tggttggaca atcggttttc gtgcagacgc ctggtgtgac atcttactgg 9000
cttactgaat gggtcgacgg caaagcgcgt gctctaccag attccttatt ctcgtccggt 9060
aggttcgaga ctaacagccg cgctttcctc gatgaagccg aggaaaagtt tgccgccgct 9120
caccctcatg cctgtttggg agaaattaat aagtccaccg tgggaggatc ccacttcatc 9180
ttttcccaat atttaccacc attgctaccc gcagacgctg ttgccctggt aggtgcttca 9240
ttggctggga aagctgctaa agctgcttgc agcgttgttg atgtctatgc tccatcattt 9300
gaaccttatc tacaccctga gacactgagt cgcgtgtaca agattatgat cgatttcaag 9360
ccgtgtaggc ttatggtgtg gagaaacgcg accttttatg tccaagaggg tgttgatgca 9420
gttacatcag cactagcagc tgtgtccaaa ctcatcaaag tgccggccaa tgagcctgtt 9480
tcattccatg tggcatcagg gtacagaacc aacgcgctgg tagcgcccca ggctaaaatt 9540

-continued tcaattggag cctacgccgc cgagtgggca ctgtcaactg aaccgccacc tgctggttat 9600
gcgatcgtgc ggcgatatat tgtaaagagg ctcctcagct caacagaagt gttcttgtgc 9660
cgcaggggtg ttgtgtcttc cacctcagtg cagaccattt gtgcactaga gggatgtaaa 9720
cctctgttca acttcttaca aattggttca gtcattgggc ccgtgtgact ctagagtgga 9780
cctgttccca tcccccgctc aactactcag gtagtggttc gcggcaacgg gtacaccgca 9840
gttggtaaca agcttgtcga tagtcagcat agtacatttc atctgactaa tactacaaca 9900
ccaccaccat gaatagagga ttctttaaca tgctcggccg ccgccccttc ccggccccca 9960
ctgccatgtg gaggccgcgg agaaggaggc aggcggcccc gatgatggaa aatatggaaa 10020
acgacgagaa catcgtggtg ggccccaagc ccttctaccc catcgaggaa ggcagcgccg 10080
gcacccagct gcggaagtac atggaaagat acgccaagct gggcgccatt gccttcacca 10140
acgccgtgac cggcgtggac tacagctacg ccgagtacct ggaaaagagc tgctgcctgg 10200
gcaaggctct gcagaactac ggcctggtgg tggacggccg gatcgccctg tgcagcgaga 10260
actgcgagga attcttcatc cccgtgatcg ccggcctgtt catcggcgtg ggcgtggctc 10320
ccaccaacga gatctacacc ctgcgggagc tggtgcacag cctgggcatc agcaagccca 10380
ccatcgtgtt cagcagcaag aagggcctgg acaaagtcat caccgtgcag aaaaccgtga 10440
ccaccatcaa gaccatcgtg atcctggaca gcaaggtgga ctaccggggc taccagtgcc 10500
tggacacctt catcaagcgg aacacccccc ctggcttcca ggccagcagc ttcaagaccg 10560
tggaggtgga ccggaaagaa caggtggccc tgatcatgaa cagcagcggc agcaccggcc 10620
tgcccaaggg cgtgcagctg acccacgaga acaccgtgac ccggttcagc cacgccaggg 10680
accccatcta cggcaaccag gtgtcccccg gcaccgccgt gctgaccgtg gtgcccttcc 10740
accacggctt cggcatgttc accaccctgg gctacctgat ctgcggcttc cgggtggtga 10800
tgctgaccaa gttcgacgag gaaaccttcc tgaaaaccct gcaggactac aagtgcacct 10860
acgtgattct ggtgcccacc ctgttcgcca tcctgaacaa gagcgagctg ctgaacaagt 10920
acgacctgag caacctggtg gagatcgcca gcggcggagc ccccctgagc aaagaagtgg 10980
gagaggccgt cgccaggcgg ttcaatctgc ccggcgtgcg gcagggctac ggcctgaccg 11040
agacaaccag cgccatcatc atcacccccg agggcgacga caagcctgga gccagcggca 11100
aggtggtgcc cctgttcaag gccaaagtga tcgacctgga caccaagaag agcctgggcc 11160
ccaacagacg gggcgaagtg tgcgtgaagg gccccatgct gatgaagggc tacgtgaaca 11220
accccgaggc caccaaagag ctgatcgacg aagagggctg gctgcacacc ggcgacatcg 11280
gctactacga cgaagagaag cacttcttca tcgtggaccg gctgaagagc ctgatcaagt 11340
acaagggcta tcaggtgccc cctgccgagc tggaaagcgt cctgctgcag caccccagca 11400
tcttcgacgc cggcgtggcc ggggtgccag atcctgtggc cggcgagctg cctggcgccg 11460
tggtggtgct ggaatccggc aagaacatga ccgagaaaga agtgatggac tacgtcgcca 11520
gccaggtgtc caacgccaag cggctgagag gcggcgtgag attcgtggac gaagtgccaa 11580
agggcctgac cggcaagatc gacggcaggg ccatccggga gatcctgaag aaacccgtgg 11640
ccaagatgtg attataactc gagggagcca tagattcatt ttgtggtgac gggattttag 11700
gtgagtatct agattacttt attctgtccg tcccactctt gctgttgctt actaggtatg 11760
tagcatctgg gttagtgtat gttttgactg ccttgttcta ttcctttgta ttagcagctt 11820
atatttggtt tgttatagtt ggaagagcct tttctactgc ttatgctttt gtgcttttgg 11880
ctgcttttct gttattagta atgaggatga ttgtgggtat gatgcctcgt cttcggtcca 11940

```
ttttcaacca tcgccaactg gtggtagctg attttgtgga cacacctagt ggacctgttc  12000

ccatcccccg cccaaccact caggtagtgg ttcgcggcaa cgggtacacc gcagttggta  12060

acaagcttgt cgatggcgtc aagacgatca cgtccgcagg ccgcctcttt tcgaaacgga  12120

cggcggcgac agcctacaag ctacaatgac ctactgcgca tgtttggtca gatgcgggtc  12180

cgcaaaccgc ccgcgcaacc cactcaggct attattgcag agcctggaga ccttaggcat  12240

gatttaaatc aacaggagcg cgccaccctt tcgtcgaacg tacaacggtt cttcatgatt  12300

gggcatggtt cactcactgc agatgccgga ggactcacgt acaccgtcag ttgggttcct  12360

accaaacaaa tccagcgcaa agttgcgcct ccagcagggc cgtaagacgt ggatattctc  12420

ctgtgtggcg tcatgttgaa gtagttatta gccacccagg aaccaaaaaa aaaaaaaaaa  12480

aaaaaaaaaa aaaaaaaaaa aaaaaaaaaa aaaaaaaaaa aaaaaaaaa             12529
```

```
<210> SEQ ID NO 16
<211> LENGTH: 12608
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Construct rEx-DLP-pp1ab-rFF
<220> FEATURE:
<221> NAME/KEY: misc_feature
<222> LOCATION: (1)...(18)
<223> OTHER INFORMATION: T7 promoter

<400> SEQUENCE: 16

taatacgact cactatagct cgaagtgtgt atggtgccat atacggctca ccaccatata     60

cactgcaaga attactattc ttgtgggccc ctctcggtaa atcctagagg gctttcctct    120

cgttattgcg agattcgtcg ttagataacg gcaagttccc tttcttacta tcctattttc    180

atcttgtggc ttgacgggtc actgcctacg tcgtcgatct ctatcaacta cccttgcgac    240

ttaggcaacc ttctccgcta ctggatttgg agggagtttt gttagggact ggtccctgga    300

cttacccgac gcttgtgagc atagtcagca tagtacattt catctgacta atactacaac    360

accaccacca tgaatagagg attctttaac atgctcggcc gccgcccctt cccggccccc    420

actgccatgt ggaggccgcg gagaaggagg caggcggccc cgatgatggc aaccttctcc    480

gctactggat ttggagggag ttttgttagg gactggtccc tggacttacc cgacgcttgt    540

gagcatggcg cgggattgtg ctgcgaagtg gacggctcca ccttatgcgc cgagtgtttt    600

cgcggttgcg aaggaatgga gcaatgtcct ggcttgttca tgggactgtt aaaactggct    660

tcgccagttc cagtgggaca taagttcctg attggttggt atcgagctgc caaagtcacc    720

gggcgttaca atttccttga gctgttgcaa caccctgctt tcgcccagct gcgtgtggtt    780

gatgctaggt tagccattga agaggcaagt gtgtttattt ccactgacca cgcgtctgct    840

aagcgtttcc ctggcgctag atttgcgctg acaccggtgt atgctaacgc ttgggttgtg    900

agcccggctg ctaacagttt gatagtgacc actgaccagg aacaagatgg gttctgctgg    960

ttaaaacttt tgccacctga ccgccgtgag gctggtttgc ggttgtatta caaccattac   1020

cgcgaacaaa ggaccgggtg gctgtctaaa acaggacttc gcttatggct tggagacctg   1080

ggtttgggca tcaatgcgag ctctggaggg ctgaaattcc acattatgag ggggttcgcct  1140

cagcgagctt ggcatatcac aacacgcagc tgcaagctga agagctacta cgtttgtgac   1200

atctctgaag cagactggtc ctgtttgcct gctggcaact acggcggcta caatccacca   1260
```

-continued

```
ggggacggag cttgcggtta caggtgcttg gccttcatga atggcgccac tgttgtgtcg   1320
gctggttgca gttctgactt gtggtgtgat gatgagttgg cttatcgagt ctttcaattg   1380
tcacccacgt tcacggttac catcccaggt gggcgagttt gtccgaatgc caagtacgca   1440
atgatttgtg acaagcagca ctggcgcgtc aaacgtgcaa agggcgtcgg cctgtgtctc   1500
gatgaaagct gtttcagggg catctgcaat tgccaacgca tgagtggacc accacctgca   1560
cccgtgtcag ccgccgtgtt agatcacata ctggaggcgg cgacgtttgg caacgttcgc   1620
gtggttacac ctgaagggca gccacgcccc gtaccagcgc cgcgagttcg tcccagcgcc   1680
aactcttctg gagatgtcaa agatccggcg cccgttccgc cagtaccaaa accaaggacc   1740
aagcttgcca caccgaaccc aactcaggcg cccatcccag caccgcgcac gcgacttcaa   1800
ggggcctcaa cacaggagcc actggcgagt gcaggagttg cttctgactc ggcacctaaa   1860
tggcgtgtgg ccaaaactgt gtacagctcc gcggagcgct ttcggaccga actggtacaa   1920
cgtgctcggt ccgttgggga cgttcttgtt caagcgctac cgctcaaaac cccagcagtg   1980
cagcggtata ccatgactct gaagatgatg cgttcacgct tcagttggca ctgcgacgtg   2040
tggtaccctt tggctgtaat cgcttgtttg ctccctatat ggccatctct tgctttgctc   2100
cttagctttg ccattgggtt gatacccagt gtgggcaata atgttgttct gacagcgctt   2160
ctggtttcat cagctaatta tgttgcgtca atggaccatc aatgtgaagg tgcggcttgc   2220
ttagccttgc tggaagaaga acactattat agagcggtcc gttggcgccc gattacaggc   2280
gcgctgtcgc ttgtgctcaa tttactgggg caggtaggct atgtagctcg ttccaccttt   2340
gatgcagctt atgttccttg cactgtgttc gatctttgca gctttgctat tctgtacctc   2400
tgccgcaatc gttgctggag atgcttcgga cgctgtgtgc gagttgggcc tgccacgcat   2460
gttttgggct ccaccgggca acgagtttcc aaactggcgc tcattgattt gtgtgaccac   2520
ttttcaaagc ccaccatcga tgttgtgggc atggcaactg gttggagcgg atgttacaca   2580
ggaaccgccg caatggagcg tcagtgtgcc tctacggtgg accctcactc gttcgaccag   2640
aagaaggcag gagcgactgt ttacctcacc ccccctgtca acagcgggtc agcgctgcag   2700
tgcctcaatg tcatgtggaa gcgaccaatt gggtccactg tccttgggga acaaacagga   2760
gctgttgtga cggcggtcaa gagtatctct ttctcacctc cctgctgcgt ctctaccact   2820
ttgcccaccc gacccggtgt gaccgttgtc gaccatgctc tttacaaccg gttgactgct   2880
tcaggggtcg atcccgcttt attgcgtgtt gggcaaggtg attttctaaa acttaatccg   2940
gggttccggc tgataggtgg atggatttat gggatatgct attttgtgtt ggtggttgtg   3000
tcaactttta cctgcttacc tatcaaatgt ggcattggca cccgcgaccc tttctgccgc   3060
agagtgtttt ctgtacccgt caccaagacc caagagcact gccatgctgg aatgtgtgct   3120
agcgctgaag gcatctctct ggactctctg ggttaactc agttacaaag ttactggatc   3180
gcagccgtca ctagcggatt agtgatcttg ttggtctgcc accgcctggc catcagcgcc   3240
ttggacttgt tgactctagc ttccccttta gtgttgcttg tgttcccttg ggcatctgtg   3300
gggcttttac ttgcttgcag tctcgctggt gctgctgtga aaatacagtt gttggcgacg   3360
ctttttgtga atctattctt tccccaagct acccttgtca ctatgggata ctgggcgtgc   3420
gtggcggctt tggccgttta cagtttgatg ggcttgcgag tgaaagtgaa tgtgcccatg   3480
tgtgtgacac ctgcccattt tctgctgctg gcgaggtcag ctggacagtc aagagagcag   3540
atgctccggg tcagcgctgc tgcccccacc aattcactgc ttggagtggc tcgtgattgt   3600
```

-continued

```
tatgtcacag gcacaactcg gctgtacata cccaaggaag gcgggatggt gtttgaaggg   3660
ctattcaggt caccgaaggc gcgcggcaac gtcggcttcg tggctggtag cagctacggc   3720
acagggtcag tgtggaccag gaacaacgag gtcgtcgtac tgacagcgtc acacgtggtt   3780
ggccgcgcta acatggccac tctgaagatc ggtgacgcaa tgctgactct gactttcaaa   3840
aagaatggcg acttcgccga ggcagtgacg acacagtccg agctcccagg caattggcca   3900
cagttgcatt tcgcccaacc aacaaccggg cccgcttcat ggtgcactgc cacaggagat   3960
gaagaaggct tgctcagtgg cgaggtttgt ctggcgtgga ctactagtgg cgactctgga   4020
tctgcagtgg ttcagggtga cgctgtggta ggggtccaca ccggttcgaa cacaagtggt   4080
gttgcctacg tgaccacccc aagcggaaaa ctccttggcg ccgacaccgt gactttgtca   4140
tcactgtcaa agcatttcac aggccctttg acatcaatcc cgaaggacat ccctgacaac   4200
attattgccg atgttgatgc tgttcctcgt tctctggcca tgctgattga tggcttatcc   4260
aatagagaga gcagcctttc tggacctcag ttgttgttaa ttgcttgttt tatgtggtct   4320
tatcttaacc aacctgctta cttgccttat gtgctgggct tctttgccgc taacttcttc   4380
ctgccaaaaa gtgttggccg ccctgtggtc actgggcttc tatggttgtg ctgcctcttc   4440
acaccgcttt ccatgcgctt gtgcttgttc catctggtct gtgctaccgt cacgggaaac   4500
gtgatatctt tgtggttcta catcactgcc gctggcacgt cttacctttc tgagatgtgg   4560
ttcggaggct atcccaccat gttgtttgtg ccacggttcc tagtgtacca gttccccggc   4620
tgggctattg gcacagtact agcggtatgc agcatcacca tgctggctgc tgccctcggt   4680
cacaccctgt tactggatgt gttctccgcc tcaggtcgct ttgacaggac tttcatgatg   4740
aaatacttcc tggagggagg agtgaaagag agtgtcaccg cctcagtcac ccgcgcttat   4800
ggcaaaccaa ttacccagga gagtctcact gcaacattag ctgccctcac tgatgatgac   4860
ttccaattcc tctctgatgt gcttgactgt cgggccgtcc gatcggcaat gaatctgcgt   4920
gccgctctca caagttttca agtggcgcag tatcgtaaca tccttaatgc atccttgcaa   4980
gtcgatcgtg acgctgctcg tagtcgcaga ctaatggcaa aactggctga ttttgcggtt   5040
gaacaagaag taacagctgg agaccgtgtt gtggttatcg acggtctgga ccgcatggct   5100
cacttcaaag acgatttggt gctggttcct ttgaccacca aagtagtagg cggttctagg   5160
tgcaccattt gtgacgtcgt taaggaagaa gccaatgaca ccccagttaa gccaatgccc   5220
agcaggagac gccgcaaggg cctgcctaaa ggtgctcagt tggagtggga ccgtcaccag   5280
gaagagaaga ggaacgccgg tgatgatgat tttgcggtct cgaatgatta tgtcaagaga   5340
gtgccaaagt actgggatcc cagcgacacc cgaggcacga cagtgaaaat cgccggcact   5400
acctatcaga aagtggttga ctattcaggc aatgtgcatt acgtggagca tcaggaagat   5460
ctgctagact acgtgctggg caaggggagc tatgaaggcc tagatcagga caaagtgttg   5520
gacctcacaa acatgcttaa agtggacccc acggagctct cctccaaaga caaagccaag   5580
gcgcgtcagc ttgctcatct gctgttggat ctggctaacc cagttgaggc agtgaatcag   5640
ttaaactgag agcgccccac atctttcccg gcgatgtggg gcgtcggacc tttgctgact   5700
ctaaagacaa gggtttcgtg gctctacaca gtcgcacaat gtttttagct gcccgggact   5760
ttttatttaa catcaaattt gtgtgcgacg aagagttcac aaagaccccca aaagacacac   5820
tgcttgggta cgtacgcgcc tgccctggtt actggtttat tttccgtcgt acgcaccggt   5880
cgctgattga tgcatactgg gacagtatgg agtgcgttta cgcgcttccc accatatctg   5940
attttgatgt gagcccaggt gacgtcgcag tgacgggcga gcgatgggat tttgaatctc   6000
```

-continued ccggaggagg ccgtgcaaaa cgtctcacag ctgatctggt gcacgctttt caagggttcc 6060
acggagcctc ttattcctat gatgacaagg tggcagctgc tgtcagtggt gacccgtatc 6120
ggtcggacgg cgtcttgtat aacacccgtt ggggcaacat tccatattct gtcccaacca 6180
atgctttgga agccacagct tgctaccgtg ctggatgtga ggccgttacc gacgggacca 6240
acgtcatcgc aacaattggg cccttcccgg agcaacaacc cataccggac atcccaaaga 6300
gcgtgcttga caactgcgct gacatcagct gtgacgcttt catagcgccc gctgcagaga 6360
cagccctgtg tggagattta gagaaataca acctatccac gcagggtttt gtgttgccta 6420
gtgttttctc catggtgcgg gcgtacttaa aagaggagat tggagacgct ccaccactct 6480
acttgccatc tactgtacca tctaaaaatt cacaagccgg aattaacggc gctgagtttc 6540
ctacaaagtc tttacagagc tactgtttga ttgatgacat ggtgtcacag tccatgaaaa 6600
gcaatctaca aaccgccacc atggcgactt gtaaacggca atactgttcc aaatacaaga 6660
ttaggagcat tctgggcacc aacaattaca ttggcctagg tttgcgtgcc tgcctttcgg 6720
gggttacggc cgcattccaa aaagctggaa aggatgggtc accgatttat ttgggcaagt 6780
caaaattcga cccgatacca gctcctgaca agtactgcct tgaaacagac ctggagagtt 6840
gtgatcgctc caccccggct ttggtgcgtt ggttcgctac taatcttatt tttgagctag 6900
ctggccagcc cgagttggtg cacagctacg tgttgaattg ctgtcacgat ctagttgtgg 6960
cgggtagtgt agcattcacc aaacgcgggg gtttgtcatc tggagaccct atcacttcca 7020
tttccaatac catctattca ttggtgctgt acacccagca catgttgcta tgtggacttg 7080
aaggctattt cccagagatt gcagaaaaat atcttgatgg cagcctggag ctgcgggaca 7140
tgttcaagta cgttcgagtg tacatctact cggacgatgt ggttctaacc acacccaacc 7200
agcattacgc ggccagcttt gaccgctggg tcccccacct gcaggcgctg ctaggtttca 7260
aggttgaccc aaagaaaact gtgaacacca gctccccttc ctttttgggc tgccggttca 7320
agcaagtgga cggcaagtgt tatctagcca gtcttcagga ccgcgttaca cgctctctgt 7380
tataccacat tggtgcaaag aatccctcag agtactatga agctgctgtt tccatcttta 7440
aggactccat tatctgctgt gatgaagact ggtggacgga cctccatcga cgtatcagtg 7500
gcgctgcgcg taccgacgga gttgagttcc ccaccattga aatgttaaca tccttccgca 7560
ccaagcagta tgagagtgcc gtgtgcacag tttgtggggc cgcccccgtg gccaagtctg 7620
cttgtggagg gtggttctgt ggcaattgtg tcccgtacca cgcgggtcat tgtcacacaa 7680
cctcgctctt cgccaactgc gggcacgaca tcatgtaccg ctccacttac tgcacaatgt 7740
gtgagggttc cccaaaacag atggtaccaa aagtgcctca cccgatcctg gatcatttgc 7800
tgtgccacat tgattacggc agtaaagagg aactaactct ggtagtggcg gatggtcgaa 7860
caacatcacc gcccgggcgc tacaaagtgg gtcacaaggt agtcgccgtg gttgcagatg 7920
tgggaggcaa cattgtgttt gggtgcggtc ctggatcaca catcgcagta ccacttcagg 7980
atacgctcaa gggcgtggtg gtgaataaag ctctgaagaa cgccgccgcc tctgagtacg 8040
tggaaggacc ccctgggagt gggaagactt ttcacctggt caaagatgtg ctagccgtgg 8100
tcggtagcgc gaccttggtt gtgcccaccc acgcgtccat gctggactgc atcaacaagc 8160
tcaaacaagc gggcgccgat ccatactttg tggtgcccaa gtatacagtt cttgactttc 8220
cccggcctgg cagtggaaac atcacagtgc gactgccaca ggtcggaacc agtgagggag 8280
aaacctttgt ggatgaggtg gcctacttct caccagtgga tctggcgcgc attttaaccc 8340
agggtcgagt caagggttac ggtgatttaa atcagctcgg gtgcgtcgga cccgcgagcg 8400
tgccacgtaa cctttggctc cgacattttg tcagcctgga gcccttgcga gtgtgccatc 8460
gattcggcgc tgctgtgtgt gatttgatca agggcattta tccttattat gagccagctc 8520
cacataccac taaagtggtg tttgtgccaa atccagactt tgagaaaggt gtagtcatca 8580
ccgcctacca caaagatcgc ggtcttggtc accgcacaat tgattcaatt caaggctgta 8640
cattccctgt tgtgactctt cgactgccca caccccaatc actgacgcgc ccgcgcgcag 8700
ttgtggcggt tactagggcg tctcaggaat tatacatcta cgaccccttt gatcagctta 8760
gcgggttgtt gaagttcacc aaggaagcag aggcgcagga cttgatccat ggcccaccta 8820
cagcatgcca cctgggccaa gaaattgacc tttggtccaa tgagggcctc gaatattaca 8880
aggaagtcaa cctgctgtac acacacgtcc ccatcaagga tggtgtaata cacagttacc 8940
ctaattgtgg ccctgcctgt ggctgggaaa agcaatccaa caaaatttcg tgcctcccga 9000
gagtggcaca aaatttgggc taccactatt ccccagactt accaggattt tgccccatac 9060
caaaagaact cgctgagcat tggcccgtag tgtccaatga tagataccg aattgcttgc 9120 aaattacctt acagcaagta tgtgaactca gtaaaccgtg ctcagcgggc tatatggttg 9180
gacaatcggt tttcgtgcag acgcctggtg tgacatctta ctggcttact gaatgggtcg 9240
acggcaaagc gcgtgctcta ccagattcct tattctcgtc cggtaggttc gagactaaca 9300
gccgcgcttt cctcgatgaa gccgaggaaa agtttgccgc cgctcaccct catgcctgtt 9360
tgggagaaat taataagtcc accgtgggag gatcccactt catcttttcc caatatttac 9420
caccattgct acccgcagac gctgttgccc tggtaggtgc ttcattggct gggaaagctg 9480
ctaaagctgc ttgcagcgtt gttgatgtct atgctccatc atttgaacct tatctacacc 9540
ctgagacact gagtcgcgtg tacaagatta tgatcgattt caagccgtgt aggcttatgg 9600
tgtggagaaa cgcgaccttt tatgtccaag agggtgttga tgcagttaca tcagcactag 9660
cagctgtgtc caaactcatc aaagtgccgg ccaatgagcc tgtttcattc catgtggcat 9720
cagggtacag aaccaacgcg ctggtagcgc cccaggctaa aatttcaatt ggagcctacg 9780
ccgccgagtg ggcactgtca actgaaccgc cacctgctgg ttatgcgatc gtgcggcgat 9840
atattgtaaa gaggctcctc agctcaacag aagtgttctt gtgccgcagg ggtgttgtgt 9900
cttccacctc agtgcagacc atttgtgcac tagagggatg taaacctctg ttcaacttct 9960
tacaaattgg ttcagtcatt gggcccgtgt gactctagag tggacctgtt cccatccccc 10020
gctcaactac tcaggtagtg gttcgcggca acgggtacac cgcagttggt aacaagcttg 10080
tcgatggaaa atatggaaaa cgacgagaac atcgtggtgg gccccaagcc cttctacccc 10140
atcgaggaag gcagcgccgg cacccagctg cggaagtaca tggaaagata cgccaagctg 10200
ggcgccattg ccttcaccaa cgccgtgacc ggcgtggact acagctacgc cgagtacctg 10260
gaaaagagct gctgcctggg caaggctctg cagaactacg gcctggtggt ggacggccgg 10320
atcgccctgt gcagcgagaa ctgcgaggaa ttcttcatcc ccgtgatcgc cggcctgttc 10380
atcggcgtgg gcgtggctcc caccaacgag atctacaccc tgcgggagct ggtgcacagc 10440
ctgggcatca gcaagcccac catcgtgttc agcagcaaga agggcctgga caaagtcatc 10500
accgtgcaga aaaccgtgac caccatcaag accatcgtga tcctggacag caaggtggac 10560
taccggggct accagtgcct ggacaccttc atcaagcgga acaccccccc tggcttccag 10620
gccagcagct tcaagaccgt ggaggtggac cggaaagaac aggtggccct gatcatgaac 10680
agcagcggca gcaccggcct gcccaagggc gtgcagctga cccacgagaa caccgtgacc 10740

```
cggttcagcc acgccaggga ccccatctac ggcaaccagg tgtcccccgg caccgccgtg  10800
ctgaccgtgg tgcccttcca ccacggcttc ggcatgttca ccaccctggg ctacctgatc  10860
tgcggcttcc gggtggtgat gctgaccaag ttcgacgagg aaaccttcct gaaaaccctg  10920
caggactaca agtgcaccta cgtgattctg gtgcccaccc tgttcgccat cctgaacaag  10980
agcgagctgc tgaacaagta cgacctgagc aacctggtgg agatcgccag cggcggagcc  11040
cccctgagca aagaagtggg agaggccgtc gccaggcggt tcaatctgcc cggcgtgcgg  11100
cagggctacg gcctgaccga gacaaccagc gccatcatca tcacccccga gggcgacgac  11160
aagcctggag ccagcggcaa ggtggtgccc ctgttcaagg ccaaagtgat cgacctggac  11220
accaagaaga gcctgggccc caacagacgg ggcgaagtgt gcgtgaaggg ccccatgctg  11280
atgaagggct acgtgaacaa ccccgaggcc accaaagagc tgatcgacga agagggctgg  11340
ctgcacaccg gcgacatcgg ctactacgac gaagagaagc acttcttcat cgtggaccgg  11400
ctgaagagcc tgatcaagta caagggctat caggtgcccc ctgccgagct ggaaagcgtc  11460
ctgctgcagc accccagcat cttcgacgcc ggcgtggccg gggtgccaga tcctgtggcc  11520
ggcgagctgc ctggcgccgt ggtggtgctg gaatccggca agaacatgac cgagaaagaa  11580
gtgatggact acgtcgccag ccaggtgtcc aacgccaagc ggctgagagg cggcgtgaga  11640
ttcgtggacg aagtgccaaa gggcctgacc ggcaagatcg acggcagggc catccgggag  11700
atcctgaaga aacccgtggc caagatgtga ttataactcg agggagccat agattcattt  11760
tgtggtgacg ggattttagg tgagtatcta gattacttta ttctgtccgt cccactcttg  11820
ctgttgctta ctaggtatgt agcatctggg ttagtgtatg ttttgactgc cttgttctat  11880
tcctttgtat tagcagctta tatttggttt gttatagttg gaagagcctt ttctactgct  11940
tatgcttttg tgcttttggc tgcttttctg ttattagtaa tgaggatgat tgtgggtatg  12000
atgcctcgtc ttcggtccat tttcaaccat cgccaactgg tggtagctga ttttgtggac  12060
acacctagtg gacctgttcc catcccccgc ccaaccactc aggtagtggt tcgcggcaac  12120
gggtacaccg cagttggtaa caagcttgtc gatggcgtca agacgatcac gtccgcaggc  12180
cgcctctttt cgaaacggac ggcggcgaca gcctacaagc tacaatgacc tactgcgcat  12240
gtttggtcag atgcgggtcc gcaaaccgcc cgcgcaaccc actcaggcta ttattgcaga  12300
gcctggagac cttaggcatg atttaaatca acaggagcgc gccacccttt cgtcgaacgt  12360
acaacggttc ttcatgattg ggcatggttc actcactgca gatgccggag gactcacgta  12420
caccgtcagt tgggttccta ccaaacaaat ccagcgcaaa gttgcgcctc cagcagggcc  12480
gtaagacgtg gatattctcc tgtgtggcgt catgttgaag tagttattag ccacccagga  12540
accaaaaaaa aaaaaaaaaa aaaaaaaaaa aaaaaaaaaa aaaaaaaaaa aaaaaaaaaa  12600
aaaaaaaa                                                           12608
```

<210> SEQ ID NO 17
<211> LENGTH: 12674
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Construct rEx-DLP-2A-pp1ab-rFF
<220> FEATURE:
<221> NAME/KEY: misc_feature
<222> LOCATION: (1)...(18)
<223> OTHER INFORMATION: T7 promoter

<400> SEQUENCE: 17
taatacgact cactatagct cgaagtgtgt atggtgccat atacggctca ccaccatata 60
cactgcaaga attactattc ttgtgggccc ctctcggtaa atcctagagg gctttcctct 120
cgttattgcg agattcgtcg ttagataacg gcaagttccc tttcttacta tcctattttc 180
atcttgtggc ttgacgggtc actgcctacg tcgtcgatct ctatcaacta cccttgcgac 240
ttaggcaacc ttctccgcta ctggatttgg agggagtttt gttagggact ggtccctgga 300
cttacccgac gcttgtgagc atagtcagca tagtacattt catctgacta atactacaac 360
accaccacca tgaatagagg attctttaac atgctcggcc gccgcccctt cccggccccc 420
actgccatgt ggaggccgcg gagaaggagg caggcggccc cgatgggaag cggagctact 480
aacttcagcc tgctgaagca ggctggagac gtggaggaga accctggacc tatggcaacc 540
ttctccgcta ctggatttgg agggagtttt gttagggact ggtccctgga cttacccgac 600
gcttgtgagc atggcgcggg attgtgctgc gaagtggacg gctccacctt atgcgccgag 660
tgttttcgcg gttgcgaagg aatggagcaa tgtcctggct tgttcatggg actgttaaaa 720
ctggcttcgc cagttccagt gggacataag ttcctgattg gttggtatcg agctgccaaa 780
gtcaccgggc gttacaattt ccttgagctg ttgcaacacc ctgctttcgc ccagctgcgt 840
gtggttgatg ctaggttagc cattgaagag gcaagtgtgt ttatttccac tgaccacgcg 900
tctgctaagc gtttccctgg cgctagattt gcgctgacac cggtgtatgc taacgcttgg 960
gttgtgagcc cggctgctaa cagtttgata gtgaccactg accaggaaca agatgggttc 1020
tgctggttaa aacttttgcc acctgaccgc cgtgaggctg gtttgcggtt gtattacaac 1080
cattaccgcg aacaaaggac cgggtggctg tctaaaacag gacttcgctt atggcttgga 1140
gacctgggtt tgggcatcaa tgcgagctct ggagggctga aattccacat tatgaggggt 1200
tcgcctcagc gagcttggca tatcacaaca cgcagctgca agctgaagag ctactacgtt 1260
tgtgacatct ctgaagcaga ctggtcctgt ttgcctgctg gcaactacgg cggctacaat 1320
ccaccagggg acggagcttg cggttacagg tgcttggcct tcatgaatgg cgccactgtt 1380
gtgtcggctg gttgcagttc tgacttgtgg tgtgatgatg agttggctta tcgagtcttt 1440
caattgtcac ccacgttcac ggttaccatc ccaggtgggc gagtttgtcc gaatgccaag 1500
tacgcaatga tttgtgacaa gcagcactgg cgcgtcaaac gtgcaaaggg cgtcggcctg 1560
tgtctcgatg aaagctgttt caggggcatc tgcaattgcc aacgcatgag tggaccacca 1620
cctgcacccg tgtcagccgc cgtgttagat cacatactgg aggcggcgac gtttggcaac 1680
gttcgcgtgg ttacacctga agggcagcca cgccccgtac cagcgccgcg agttcgtccc 1740
agcgccaact cttctggaga tgtcaaagat ccggcgcccg ttccgccagt accaaaacca 1800
aggaccaagc ttgccacacc gaacccaact caggcgccca tcccagcacc gcgcacgcga 1860
cttcaagggg cctcaacaca ggagccactg gcgagtgcag gagttgcttc tgactcggca 1920
cctaaatggc gtgtggccaa aactgtgtac agctccgcgg agcgctttcg gaccgaactg 1980
gtacaacgtg ctcggtccgt tggggacgtt cttgttcaag cgctaccgct caaaacccca 2040
gcagtgcagc ggtataccat gactctgaag atgatgcgtt cacgcttcag ttggcactgc 2100
gacgtgtggt accctttggc tgtaatcgct tgtttgctcc ctatatggcc atctcttgct 2160
ttgctcctta gctttgccat tgggttgata cccagtgtgg gcaataatgt tgttctgaca 2220
gcgcttctgg tttcatcagc taattatgtt gcgtcaatgg accatcaatg tgaaggtgcg 2280

-continued

```
gcttgcttag ccttgctgga agaagaacac tattatagag cggtccgttg gcgcccgatt   2340
acaggcgcgc tgtcgcttgt gctcaattta ctggggcagg taggctatgt agctcgttcc   2400
acctttgatg cagcttatgt tccttgcact gtgttcgatc tttgcagctt tgctattctg   2460
tacctctgcc gcaatcgttg ctggagatgc ttcggacgct gtgtgcgagt tgggcctgcc   2520
acgcatgttt tgggctccac cgggcaacga gtttccaaac tggcgctcat tgatttgtgt   2580
gaccactttt caaagcccac catcgatgtt gtgggcatgg caactggttg gagcggatgt   2640
tacacaggaa ccgccgcaat ggagcgtcag tgtgcctcta cggtggaccc tcactcgttc   2700
gaccagaaga aggcaggagc gactgtttac ctcacccccc ctgtcaacag cgggtcagcg   2760
ctgcagtgcc tcaatgtcat gtggaagcga ccaattgggt ccactgtcct tggggaacaa   2820
acaggagctg ttgtgacggc ggtcaagagt atctctttct cacctccctg ctgcgtctct   2880
accactttgc ccacccgacc cggtgtgacc gttgtcgacc atgctcttta caaccggttg   2940
actgcttcag gggtcgatcc cgctttattg cgtgttgggc aaggtgattt tctaaaactt   3000
aatccggggt tccggctgat aggtggatgg atttatggga tatgctattt tgtgttggtg   3060
gttgtgtcaa cttttacctg cttacctatc aaatgtggca ttggcacccg cgaccctttc   3120
tgccgcagag tgtttttctgt acccgtcacc aagacccaag agcactgcca tgctggaatg   3180
tgtgctagcg ctgaaggcat ctctctggac tctctggggt taactcagtt acaaagttac   3240
tggatcgcag ccgtcactag cggattagtg atcttgttgg tctgccaccg cctggccatc   3300
agcgccttgg acttgttgac tctagcttcc cctttagtgt tgcttgtgtt cccttgggca   3360
tctgtggggc ttttacttgc ttgcagtctc gctggtgctg ctgtgaaaat acagttgttg   3420
gcgacgcttt ttgtgaatct attctttccc caagctaccc ttgtcactat gggatactgg   3480
gcgtgcgtgg cggctttggc cgtttacagt ttgatgggct tgcgagtgaa agtgaatgtg   3540
cccatgtgtg tgacacctgc ccattttctg ctgctggcga ggtcagctgg acagtcaaga   3600
gagcagatgc tccgggtcag cgctgctgcc cccaccaatt cactgcttgg agtggctcgt   3660
gattgttatg tcacaggcac aactcggctg tacataccca aggaaggcgg gatggtgttt   3720
gaagggctat tcaggtcacc gaaggcgcgc ggcaacgtcg gcttcgtggc tggtagcagc   3780
tacggcacag ggtcagtgtg gaccaggaac aacgaggtcg tcgtactgac agcgtcacac   3840
gtggttggcc gcgctaacat ggccactctg aagatcggtg acgcaatgct gactctgact   3900
ttcaaaaaga atggcgactt cgccgaggca gtgacgacac agtccgagct cccaggcaat   3960
tggccacagt tgcatttcgc ccaaccaaca accgggcccg cttcatggtg cactgccaca   4020
ggagatgaag aaggcttgct cagtggcgag gtttgtctgg cgtggactac tagtggcgac   4080
tctggatctg cagtggttca gggtgacgct gtggtagggg tccacaccgg ttcgaacaca   4140
agtggtgttg cctacgtgac caccccaagc ggaaaactcc ttggcgccga caccgtgact   4200
ttgtcatcac tgtcaaagca tttcacaggc cctttgacat caatcccgaa ggacatccct   4260
gacaacatta ttgccgatgt tgatgctgtt cctcgttctc tggccatgct gattgatggc   4320
ttatccaata gagagagcag cctttctgga cctcagttgt tgttaattgc ttgttttatg   4380
tggtcttatc ttaaccaacc tgcttacttg ccttatgtgc tgggcttctt tgccgctaac   4440
ttcttcctgc caaaaagtgt tggccgccct gtggtcactg ggcttctatg gttgtgctgc   4500
ctcttcacac cgctttccat gcgcttgtgc ttgttccatc tggtctgtgc taccgtcacg   4560
ggaaacgtga tatctttgtg gttctacatc actgccgctg gcacgtctta cctttctgag   4620
atgtggttcg gaggctatcc caccatgttg tttgtgccac ggttcctagt gtaccagttc   4680
```

cccggctggg ctattggcac agtactagcg gtatgcagca tcaccatgct ggctgctgcc 4740
ctcggtcaca ccctgttact ggatgtgttc tccgcctcag gtcgctttga caggactttc 4800
atgatgaaat acttcctgga gggaggagtg aaagagagtg tcaccgcctc agtcacccgc 4860
gcttatggca aaccaattac ccaggagagt ctcactgcaa cattagctgc cctcactgat 4920
gatgacttcc aattcctctc tgatgtgctt gactgtcggg ccgtccgatc ggcaatgaat 4980
ctgcgtgccg ctctcacaag ttttcaagtg gcgcagtatc gtaacatcct taatgcatcc 5040
ttgcaagtcg atcgtgacgc tgctcgtagt cgcagactaa tggcaaaact ggctgatttt 5100
gcggttgaac aagaagtaac agctggagac cgtgttgtgg ttatcgacgg tctggaccgc 5160
atggctcact tcaaagacga tttggtgctg gttcctttga ccaccaaagt agtaggcggt 5220
tctaggtgca ccatttgtga cgtcgttaag gaagaagcca atgacacccc agttaagcca 5280
atgcccagca ggagacgccg caagggcctg cctaaaggtg ctcagttgga gtgggaccgt 5340
caccaggaag agaagaggaa cgccggtgat gatgattttg cggtctcgaa tgattatgtc 5400
aagagagtgc caaagtactg ggatcccagc gacacccgag gcacgacagt gaaaatcgcc 5460
ggcactacct atcagaaagt ggttgactat tcaggcaatg tgcattacgt ggagcatcag 5520
gaagatctgc tagactacgt gctgggcaag gggagctatg aaggcctaga tcaggacaaa 5580
gtgttggacc tcacaaacat gcttaaagtg gaccccacgg agctctcctc caaagacaaa 5640
gccaaggcgc gtcagcttgc tcatctgctg ttggatctgg ctaacccagt tgaggcagtg 5700
aatcagttaa actgagagcg ccccacatct ttcccggcga tgtggggcgt cggacctttg 5760
ctgactctaa agacaagggt ttcgtggctc tacacagtcg cacaatgttt ttagctgccc 5820
gggacttttt atttaacatc aaatttgtgt gcgacgaaga gttcacaaag accccaaaag 5880
acacactgct tgggtacgta cgcgcctgcc ctggttactg gtttattttc cgtcgtacgc 5940
accggtcgct gattgatgca tactgggaca gtatggagtg cgtttacgcg cttcccacca 6000
tatctgattt tgatgtgagc ccaggtgacg tcgcagtgac gggcgagcga tgggattttg 6060
aatctcccgg aggaggccgt gcaaaacgtc tcacagctga tctggtgcac gcttttcaag 6120
ggttccacgg agcctcttat tcctatgatg acaaggtggc agctgctgtc agtggtgacc 6180
cgtatcggtc ggacggcgtc ttgtataaca cccgttgggg caacattcca tattctgtcc 6240
caaccaatgc tttggaagcc acagcttgct accgtgctgg atgtgaggcc gttaccgacg 6300
ggaccaacgt catcgcaaca attgggccct tcccggagca acaacccata ccggacatcc 6360
caaagagcgt gcttgacaac tgcgctgaca tcagctgtga cgctttcata gcgcccgctg 6420
cagagacagc cctgtgtgga gatttagaga aatacaacct atccacgcag ggttttgtgt 6480
tgcctagtgt tttctccatg gtgcgggcgt acttaaaaga ggagattgga gacgctccac 6540
cactctactt gccatctact gtaccatcta aaaattcaca agccggaatt aacggcgctg 6600
agtttcctac aaagtcttta cagagctact gtttgattga tgacatggtg tcacagtcca 6660
tgaaaagcaa tctacaaacc gccaccatgg cgacttgtaa acggcaatac tgttccaaat 6720
acaagattag gagcattctg ggcaccaaca attacattgg cctaggtttg cgtgcctgcc 6780
tttcgggggt tacggccgca ttccaaaaag ctggaaagga tgggtcaccg atttatttgg 6840
gcaagtcaaa attcgacccg ataccagctc ctgacaagta ctgccttgaa acagacctgg 6900
agagttgtga tcgctccacc ccggctttgg tgcgttggtt cgctactaat cttatttttg 6960
agctagctgg ccagcccgag ttggtgcaca gctacgtgtt gaattgctgt cacgatctag 7020

-continued

```
ttgtggcggg tagtgtagca ttcaccaaac gcgggggttt gtcatctgga gaccctatca   7080
cttccatttc caataccatc tattcattgg tgctgtacac ccagcacatg ttgctatgtg   7140
gacttgaagg ctatttccca gagattgcag aaaaatatct tgatggcagc ctggagctgc   7200
gggacatgtt caagtacgtt cgagtgtaca tctactcgga cgatgtggtt ctaaccacac   7260
ccaaccagca ttacgcggcc agctttgacc gctgggtccc ccacctgcag gcgctgctag   7320
gtttcaaggt tgacccaaag aaaactgtga acaccagctc cccttccttt ttgggctgcc   7380
ggttcaagca agtggacggc aagtgttatc tagccagtct tcaggaccgc gttacacgct   7440
ctctgttata ccacattggt gcaaagaatc cctcagagta ctatgaagct gctgtttcca   7500
tctttaagga ctccattatc tgctgtgatg aagactggtg gacggacctc catcgacgta   7560
tcagtggcgc tgcgcgtacc gacggagttg agttccccac cattgaaatg ttaacatcct   7620
tccgcaccaa gcagtatgag agtgccgtgt gcacagtttg tggggccgcc cccgtggcca   7680
agtctgcttg tggagggtgg ttctgtggca attgtgtccc gtaccacgcg ggtcattgtc   7740
acacaacctc gctcttcgcc aactgcgggc acgacatcat gtaccgctcc acttactgca   7800
caatgtgtga gggttcccca aaacagatgg taccaaaagt gcctcacccg atcctggatc   7860
atttgctgtg ccacattgat tacggcagta aagaggaact aactctggta gtggcggatg   7920
gtcgaacaac atcaccgccc gggcgctaca aagtgggtca caaggtagtc gccgtggttg   7980
cagatgtggg aggcaacatt gtgtttgggt gcggtcctgg atcacacatc gcagtaccac   8040
ttcaggatac gctcaagggc gtggtggtga ataaagctct gaagaacgcc gccgcctctg   8100
agtacgtgga aggaccccct gggagtggga agacttttca cctggtcaaa gatgtgctag   8160
ccgtggtcgg tagcgcgacc ttggttgtgc ccacccacgc gtccatgctg gactgcatca   8220
acaagctcaa acaagcgggc gccgatccat actttgtggt gcccaagtat acagttcttg   8280
actttccccg gcctggcagt ggaaacatca cagtgcgact gccacaggtc ggaaccagtg   8340
agggagaaac ctttgtggat gaggtggcct acttctcacc agtggatctg gcgcgcattt   8400
taacccaggg tcgagtcaag ggttacggtg atttaaatca gctcgggtgc gtcggacccg   8460
cgagcgtgcc acgtaacctt tggctccgac attttgtcag cctggagccc ttgcgagtgt   8520
gccatcgatt cggcgctgct gtgtgtgatt tgatcaaggg catttatcct tattatgagc   8580
cagctccaca taccactaaa gtggtgtttg tgccaaatcc agactttgag aaaggtgtag   8640
tcatcaccgc ctaccacaaa gatcgcggtc ttggtcaccg cacaattgat tcaattcaag   8700
gctgtacatt ccctgttgtg actcttcgac tgcccacacc ccaatcactg acgcgcccgc   8760
gcgcagttgt ggcggttact agggcgtctc aggaattata catctacgac ccctttgatc   8820
agcttagcgg gttgttgaag ttcaccaagg aagcagaggc gcaggacttg atccatggcc   8880
cacctacagc atgccacctg ggccaagaaa ttgacctttg gtccaatgag ggcctcgaat   8940
attacaagga agtcaacctg ctgtacacac acgtccccat caaggatggt gtaatacaca   9000
gttaccctaa ttgtggccct gcctgtggct gggaaaagca atccaacaaa atttcgtgcc   9060
tcccgagagt ggcacaaaat ttgggctacc actattcccc agacttacca ggattttgcc   9120
ccataccaaa agaactcgct gagcattggc ccgtagtgtc caatgataga tacccgaatt   9180
gcttgcaaat taccttacag caagtatgtg aactcagtaa accgtgctca gcgggctata   9240
tggttggaca atcggttttc gtgcagacgc ctggtgtgac atcttactgg cttactgaat   9300
gggtcgacgg caaagcgcgt gctctaccag attccttatt ctcgtccggt aggttcgaga   9360
ctaacagccg cgctttcctc gatgaagccg aggaaaagtt tgccgccgct caccctcatg   9420
```

```
cctgtttggg agaaattaat aagtccaccg tgggaggatc ccacttcatc ttttcccaat   9480
atttaccacc attgctaccc gcagacgctg ttgccctggt aggtgcttca ttggctggga   9540
aagctgctaa agctgcttgc agcgttgttg atgtctatgc tccatcattt gaaccttatc   9600
tacaccctga gacactgagt cgcgtgtaca agattatgat cgatttcaag ccgtgtaggc   9660
ttatggtgtg gagaaacgcg acctttatg tccaagaggg tgttgatgca gttacatcag   9720
cactagcagc tgtgtccaaa ctcatcaaag tgccggccaa tgagcctgtt tcattccatg   9780
tggcatcagg gtacagaacc aacgcgctgg tagcgcccca ggctaaaatt tcaattggag   9840
cctacgccgc cgagtgggca ctgtcaactg aaccgccacc tgctggttat gcgatcgtgc   9900
ggcgatatat tgtaaagagg ctcctcagct caacagaagt gttcttgtgc cgcaggggtg   9960
ttgtgtcttc cacctcagtg cagaccattt gtgcactaga gggatgtaaa cctctgttca  10020
acttcttaca aattggttca gtcattgggc ccgtgtgact ctagagtgga cctgttccca  10080
tcccccgctc aactactcag gtagtggttc gcggcaacgg gtacaccgca gttggtaaca  10140
agcttgtcga tggaaaatat ggaaaacgac gagaacatcg tggtgggccc caagcccttc  10200
taccccatcg aggaaggcag cgccggcacc cagctgcgga agtacatgga aagatacgcc  10260
aagctgggcg ccattgcctt caccaacgcc gtgaccggcg tggactacag ctacgccgag  10320
tacctggaaa agagctgctg cctgggcaag gctctgcaga actacggcct ggtggtggac  10380
ggccggatcg ccctgtgcag cgagaactgc gaggaattct tcatccccgt gatcgccggc  10440
ctgttcatcg gcgtgggcgt ggctcccacc aacgagatct acaccctgcg ggagctggtg  10500
cacagcctgg gcatcagcaa gcccaccatc gtgttcagca gcaagaaggg cctggacaaa  10560
gtcatcaccg tgcagaaaac cgtgaccacc atcaagacca tcgtgatcct ggacagcaag  10620
gtggactacc ggggctacca gtgcctggac accttcatca agcggaacac ccccccctggc  10680
ttccaggcca gcagcttcaa gaccgtggag gtggaccgga aagaacaggt ggccctgatc  10740
atgaacagca gcggcagcac cggcctgccc aagggcgtgc agctgaccca cgagaacacc  10800
gtgacccggt tcagccacgc cagggacccc atctacggca accaggtgtc ccccggcacc  10860
gccgtgctga ccgtggtgcc cttccaccac ggcttcggca tgttcaccac cctgggctac  10920
ctgatctgcg gcttccgggt ggtgatgctg accaagttcg acgaggaaac cttcctgaaa  10980
accctgcagg actacaagtg cacctacgtg attctggtgc ccaccctgtt cgccatcctg  11040
aacaagagcg agctgctgaa caagtacgac ctgagcaacc tggtggagat cgccagcggc  11100
ggagcccccc tgagcaaaga agtgggagag gccgtcgcca ggcggttcaa tctgcccggc  11160
gtgcggcagg gctacggcct gaccgagaca accagcgcca tcatcatcac cccccgaggggc  11220
gacgacaagc ctggagccag cggcaaggtg gtgcccctgt tcaaggccaa agtgatcgac  11280
ctggacacca agaagagcct gggccccaac agacggggcg aagtgtgcgt gaagggcccc  11340
atgctgatga agggctacgt gaacaacccc gaggccacca aagagctgat cgacgaagag  11400
ggctggctgc acaccggcga catcggctac tacgacgaag agaagcactt cttcatcgtg  11460
gaccggctga agagcctgat caagtacaag ggctatcagg tgccccctgc cgagctggaa  11520
agcgtcctgc tgcagcaccc cagcatcttc gacgccggcg tggccggggt gccagatcct  11580
gtggccggcg agctgcctgg cgccgtggtg gtgctggaat ccggcaagaa catgaccgag  11640
aaagaagtga tggactacgt cgccagccag gtgtccaacg ccaagcggct gagaggcggc  11700
gtgagattcg tggacgaagt gccaaagggc ctgaccggca agatcgacgg cagggccatc  11760
```

```
cgggagatcc tgaagaaacc cgtggccaag atgtgattat aactcgaggg agccatagat  11820
tcattttgtg gtgacgggat tttaggtgag tatctagatt actttattct gtccgtccca  11880
ctcttgctgt tgcttactag gtatgtagca tctgggttag tgtatgtttt gactgccttg  11940
ttctattcct ttgtattagc agcttatatt tggtttgtta tagttggaag agccttttct  12000
actgcttatg cttttgtgct tttggctgct tttctgttat tagtaatgag gatgattgtg  12060
ggtatgatgc ctcgtcttcg gtccattttc aaccatcgcc aactggtggt agctgatttt  12120
gtggacacac ctagtggacc tgttcccatc ccccgcccaa ccactcaggt agtggttcgc  12180
ggcaacgggt acaccgcagt tggtaacaag cttgtcgatg gcgtcaagac gatcacgtcc  12240
gcaggccgcc tcttttcgaa acggacggcg gcgacagcct acaagctaca atgacctact  12300
gcgcatgttt ggtcagatgc gggtccgcaa accgcccgcg caacccactc aggctattat  12360
tgcagagcct ggagacctta ggcatgattt aaatcaacag gagcgcgcca ccctttcgtc  12420
gaacgtacaa cggttcttca tgattgggca tggttcactc actgcagatg ccggaggact  12480
cacgtacacc gtcagttggg ttcctaccaa acaaatccag cgcaaagttg cgcctccagc  12540
agggccgtaa gacgtggata ttctcctgtg tggcgtcatg ttgaagtagt tattagccac  12600
ccaggaacca aaaaaaaaaa aaaaaaaaaa aaaaaaaaaa aaaaaaaaaa aaaaaaaaaa  12660
aaaaaaaaaa aaaa                                                    12674
```

<210> SEQ ID NO 18
<211> LENGTH: 12819
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Construct rEx-DLP-2A-pp1ab-DLP-rFF
<220> FEATURE:
<221> NAME/KEY: misc_feature
<222> LOCATION: (1)...(18)
<223> OTHER INFORMATION: T7 promoter

<400> SEQUENCE: 18

```
taatacgact cactatagct cgaagtgtgt atggtgccat atacggctca ccaccatata     60
cactgcaaga attactattc ttgtgggccc ctctcggtaa atcctagagg gctttcctct    120
cgttattgcg agattcgtcg ttagataacg gcaagttccc tttcttacta tcctattttc    180
atcttgtggc ttgacgggtc actgcctacg tcgtcgatct ctatcaacta cccttgcgac    240
ttaggcaacc ttctccgcta ctggatttgg agggagtttt gttagggact ggtccctgga    300
cttacccgac gcttgtgagc atagtcagca tagtacattt catctgacta atactacaac    360
accaccacca tgaatagagg attctttaac atgctcggcc gccgcccctt cccggccccc    420
actgccatgt ggaggccgcg gagaaggagg caggcggccc cgatgggaag cggagctact    480
aacttcagcc tgctgaagca ggctggagac gtggaggaga accctggacc tatggcaacc    540
ttctccgcta ctggatttgg agggagtttt gttagggact ggtccctgga cttacccgac    600
gcttgtgagc atggcgcggg attgtgctgc gaagtggacg gctccacctt atgcgccgag    660
tgttttcgcg gttgcgaagg aatggagcaa tgtcctggct tgttcatggg actgttaaaa    720
ctggcttcgc cagttccagt gggacataag ttcctgattg gttggtatcg agctgccaaa    780
gtcaccgggc gttacaattt ccttgagctg ttgcaacacc ctgctttcgc ccagctgcgt    840
gtggttgatg ctaggttagc cattgaagag gcaagtgtgt ttatttccac tgaccacgcg    900
```

-continued

```
tctgctaagc gtttccctgg cgctagattt gcgctgacac cggtgtatgc taacgcttgg    960
gttgtgagcc cggctgctaa cagtttgata gtgaccactg accaggaaca agatgggttc   1020
tgctggttaa aacttttgcc acctgaccgc cgtgaggctg gtttgcggtt gtattacaac   1080
cattaccgcg aacaaaggac cgggtggctg tctaaaacag gacttcgctt atggcttgga   1140
gacctgggtt tgggcatcaa tgcgagctct ggagggctga aattccacat tatgaggggt   1200
tcgcctcagc gagcttggca tatcacaaca cgcagctgca agctgaagag ctactacgtt   1260
tgtgacatct ctgaagcaga ctggtcctgt ttgcctgctg gcaactacgg cggctacaat   1320
ccaccagggg acggagcttg cggttacagg tgcttggcct tcatgaatgg cgccactgtt   1380
gtgtcggctg gttgcagttc tgacttgtgg tgtgatgatg agttggctta tcgagtcttt   1440
caattgtcac ccacgttcac ggttaccatc ccaggtgggc gagtttgtcc gaatgccaag   1500
tacgcaatga tttgtgacaa gcagcactgg cgcgtcaaac gtgcaaaggg cgtcggcctg   1560
tgtctcgatg aaagctgttt caggggcatc tgcaattgcc aacgcatgag tggaccacca   1620
cctgcacccg tgtcagccgc cgtgttagat cacatactgg aggcggcgac gtttggcaac   1680
gttcgcgtgg ttacacctga agggcagcca cgccccgtac cagcgccgcg agttcgtccc   1740
agcgccaact cttctggaga tgtcaaagat ccggcgcccg ttccgccagt accaaaacca   1800
aggaccaagc ttgccacacc gaacccaact caggcgccca tcccagcacc gcgcacgcga   1860
cttcaagggg cctcaacaca ggagccactg gcgagtgcag gagttgcttc tgactcggca   1920
cctaaatggc gtgtggccaa aactgtgtac agctccgcgg agcgctttcg gaccgaactg   1980
gtacaacgtg ctcggtccgt tggggacgtt cttgttcaag cgctaccgct caaaacccca   2040
gcagtgcagc ggtataccat gactctgaag atgatgcgtt cacgcttcag ttggcactgc   2100
gacgtgtggt accctttggc tgtaatcgct tgtttgctcc ctatatggcc atctcttgct   2160
ttgctcctta gctttgccat tgggttgata cccagtgtgg gcaataatgt tgttctgaca   2220
gcgcttctgg tttcatcagc taattatgtt gcgtcaatgg accatcaatg tgaaggtgcg   2280
gcttgcttag ccttgctgga agaagaacac tattatagag cggtccgttg gcgcccgatt   2340
acaggcgcgc tgtcgcttgt gctcaattta ctggggcagg taggctatgt agctcgttcc   2400
acctttgatg cagcttatgt tccttgcact gtgttcgatc tttgcagctt tgctattctg   2460
tacctctgcc gcaatcgttg ctggagatgc ttcggacgct gtgtgcgagt tgggcctgcc   2520
acgcatgttt tgggctccac cgggcaacga gtttccaaac tggcgctcat tgatttgtgt   2580
gaccactttt caaagcccac catcgatgtt gtgggcatgg caactggttg gagcggatgt   2640
tacacaggaa ccgccgcaat ggagcgtcag tgtgcctcta cggtggaccc tcactcgttc   2700
gaccagaaga aggcaggagc gactgtttac ctcacccccc ctgtcaacag cgggtcagcg   2760
ctgcagtgcc tcaatgtcat gtggaagcga ccaattgggt ccactgtcct tggggaacaa   2820
acaggagctg ttgtgacggc ggtcaagagt atctctttct cacctccctg ctgcgtctct   2880
accactttgc ccacccgacc cggtgtgacc gttgtcgacc atgctcttta caaccggttg   2940
actgcttcag ggtcgatcc cgctttattg cgtgttgggc aaggtgattt tctaaaactt    3000
aatccggggt tccggctgat aggtggatgg atttatggga tatgctattt tgtgttggtg   3060
gttgtgtcaa cttttacctg cttacctatc aaatgtggca ttggcacccg cgaccctttc   3120
tgccgcagag tgttttctgt acccgtcacc aagacccaag agcactgcca tgctggaatg   3180
tgtgctagcg ctgaaggcat ctctctggac tctctggggt taactcagtt acaaagttac   3240
tggatcgcag ccgtcactag cggattagtg atcttgttgg tctgccaccg cctggccatc   3300
```

agcgccttgg acttgttgac tctagcttcc cctttagtgt tgcttgtgtt cccttgggca 3360
tctgtggggc ttttacttgc ttgcagtctc gctggtgctg ctgtgaaaat acagttgttg 3420
gcgacgcttt ttgtgaatct attctttccc caagctaccc ttgtcactat gggatactgg 3480
gcgtgcgtgg cggctttggc cgtttacagt ttgatgggct tgcgagtgaa agtgaatgtg 3540
cccatgtgtg tgacacctgc ccattttctg ctgctggcga ggtcagctgg acagtcaaga 3600
gagcagatgc tccgggtcag cgctgctgcc cccaccaatt cactgcttgg agtggctcgt 3660
gattgttatg tcacaggcac aactcggctg tacataccca aggaaggcgg gatggtgttt 3720
gaagggctat tcaggtcacc gaaggcgcgc ggcaacgtcg gcttcgtggc tggtagcagc 3780
tacggcacag ggtcagtgtg gaccaggaac aacgaggtcg tcgtactgac agcgtcacac 3840
gtggttggcc gcgctaacat ggccactctg aagatcggtg acgcaatgct gactctgact 3900
ttcaaaaaga atggcgactt cgccgaggca gtgacgacac agtccgagct cccaggcaat 3960
tggccacagt tgcatttcgc ccaaccaaca accgggcccg cttcatggtg cactgccaca 4020
ggagatgaag aaggcttgct cagtggcgag gtttgtctgg cgtggactac tagtggcgac 4080
tctggatctg cagtggttca gggtgacgct gtggtagggg tccacaccgg ttcgaacaca 4140
agtggtgttg cctacgtgac caccccaagc ggaaaactcc ttggcgccga caccgtgact 4200
ttgtcatcac tgtcaaagca tttcacaggc cctttgacat caatcccgaa ggacatccct 4260
gacaacatta ttgccgatgt tgatgctgtt cctcgttctc tggccatgct gattgatggc 4320
ttatccaata gagagagcag cctttctgga cctcagttgt tgttaattgc ttgttttatg 4380
tggtcttatc ttaaccaacc tgcttacttg ccttatgtgc tgggcttctt tgccgctaac 4440
ttcttcctgc caaaaagtgt tggccgccct gtggtcactg ggcttctatg gttgtgctgc 4500
ctcttcacac cgctttccat gcgcttgtgc ttgttccatc tggtctgtgc taccgtcacg 4560
ggaaacgtga tatctttgtg gttctacatc actgccgctg gcacgtctta cctttctgag 4620
atgtggttcg gaggctatcc caccatgttg tttgtgccac ggttcctagt gtaccagttc 4680
cccggctggg ctattggcac agtactagcg gtatgcagca tcaccatgct ggctgctgcc 4740
ctcggtcaca ccctgttact ggatgtgttc tccgcctcag gtcgctttga caggactttc 4800
atgatgaaat acttcctgga gggaggagtg aaagagagtg tcaccgcctc agtcacccgc 4860
gcttatggca aaccaattac ccaggagagt ctcactgcaa cattagctgc cctcactgat 4920
gatgacttcc aattcctctc tgatgtgctt gactgtcggg ccgtccgatc ggcaatgaat 4980
ctgcgtgccg ctctcacaag ttttcaagtg gcgcagtatc gtaacatcct taatgcatcc 5040
ttgcaagtcg atcgtgacgc tgctcgtagt cgcagactaa tggcaaaact ggctgatttt 5100
gcggttgaac aagaagtaac agctggagac cgtgttgtgg ttatcgacgg tctggaccgc 5160
atggctcact tcaaagacga tttggtgctg gttcctttga ccaccaaagt agtaggcggt 5220
tctaggtgca ccatttgtga cgtcgttaag gaagaagcca atgacacccc agttaagcca 5280
atgcccagca ggagacgccg caagggcctg cctaaaggtg ctcagttgga gtgggaccgt 5340
caccaggaag agaagaggaa cgccggtgat gatgattttg cggtctcgaa tgattatgtc 5400
aagagagtgc caaagtactg ggatcccagc gacacccgag gcacgacagt gaaaatcgcc 5460
ggcactacct atcagaaagt ggttgactat tcaggcaatg tgcattacgt ggagcatcag 5520
gaagatctgc tagactacgt gctgggcaag gggagctatg aaggcctaga tcaggacaaa 5580
gtgttggacc tcacaaacat gcttaaagtg gaccccacgg agctctcctc caaagacaaa 5640

-continued

```
gccaaggcgc gtcagcttgc tcatctgctg ttggatctgg ctaacccagt tgaggcagtg   5700
aatcagttaa actgagagcg ccccacatct ttcccggcga tgtggggcgt cggacctttg   5760
ctgactctaa agacaagggt ttcgtggctc tacacagtcg cacaatgttt ttagctgccc   5820
gggacttttt atttaacatc aaatttgtgt gcgacgaaga gttcacaaag accccaaaag   5880
acacactgct tgggtacgta cgcgcctgcc ctggttactg gtttattttc cgtcgtacgc   5940
accggtcgct gattgatgca tactgggaca gtatggagtg cgtttacgcg cttcccacca   6000
tatctgattt tgatgtgagc ccaggtgacg tcgcagtgac gggcgagcga tgggattttg   6060
aatctcccgg aggaggccgt gcaaaacgtc tcacagctga tctggtgcac gcttttcaag   6120
ggttccacgg agcctcttat tcctatgatg acaaggtggc agctgctgtc agtggtgacc   6180
cgtatcggtc ggacggcgtc ttgtataaca cccgttgggg caacattcca tattctgtcc   6240
caaccaatgc tttggaagcc acagcttgct accgtgctgg atgtgaggcc gttaccgacg   6300
ggaccaacgt catcgcaaca attgggccct tcccggagca acaacccata ccggacatcc   6360
caaagagcgt gcttgacaac tgcgctgaca tcagctgtga cgctttcata gcgcccgctg   6420
cagagacagc cctgtgtgga gatttagaga aatacaacct atccacgcag ggttttgtgt   6480
tgcctagtgt tttctccatg gtgcgggcgt acttaaaaga ggagattgga gacgctccac   6540
cactctactt gccatctact gtaccatcta aaaattcaca agccggaatt aacggcgctg   6600
agtttcctac aaagtcttta cagagctact gtttgattga tgacatggtg tcacagtcca   6660
tgaaaagcaa tctacaaacc gccaccatgg cgacttgtaa acggcaatac tgttccaaat   6720
acaagattag gagcattctg ggcaccaaca attacattgg cctaggtttg cgtgcctgcc   6780
tttcgggggt tacggccgca ttccaaaaag ctggaaagga tgggtcaccg atttatttgg   6840
gcaagtcaaa attcgacccg ataccagctc ctgacaagta ctgccttgaa acagacctgg   6900
agagttgtga tcgctccacc ccggctttgg tgcgttggtt cgctactaat cttatttttg   6960
agctagctgg ccagcccgag ttggtgcaca gctacgtgtt gaattgctgt cacgatctag   7020
ttgtggcggg tagtgtagca ttcaccaaac gcgggggttt gtcatctgga gaccctatca   7080
cttccatttc caataccatc tattcattgg tgctgtacac ccagcacatg ttgctatgtg   7140
gacttgaagg ctatttccca gagattgcag aaaaatatct tgatggcagc ctggagctgc   7200
gggacatgtt caagtacgtt cgagtgtaca tctactcgga cgatgtggtt ctaaccacac   7260
ccaaccagca ttacgcggcc agctttgacc gctgggtccc ccacctgcag gcgctgctag   7320
gtttcaaggt tgacccaaag aaaactgtga acaccagctc cccttccttt ttgggctgcc   7380
ggttcaagca agtggacggc aagtgttatc tagccagtct tcaggaccgc gttacacgct   7440
ctctgttata ccacattggt gcaaagaatc cctcagagta ctatgaagct gctgtttcca   7500
tctttaagga ctccattatc tgctgtgatg aagactggtg gacggacctc catcgacgta   7560
tcagtggcgc tgcgcgtacc gacggagttg agttccccac cattgaaatg ttaacatcct   7620
tccgcaccaa gcagtatgag agtgccgtgt gcacagtttg tggggccgcc cccgtggcca   7680
agtctgcttg tggagggtgg ttctgtggca attgtgtccc gtaccacgcg ggtcattgtc   7740
acacaacctc gctcttcgcc aactgcgggc acgacatcat gtaccgctcc acttactgca   7800
caatgtgtga gggttcccca aaacagatgg taccaaaagt gcctcacccg atcctggatc   7860
atttgctgtg ccacattgat tacggcagta aagaggaact aactctggta gtggcggatg   7920
gtcgaacaac atcaccgccc gggcgctaca aagtgggtca caaggtagtc gccgtggttg   7980
cagatgtggg aggcaacatt gtgtttgggt gcggtcctgg atcacacatc gcagtaccac   8040
```

```
ttcaggatac gctcaagggc gtggtggtga ataaagctct gaagaacgcc gccgcctctg   8100
agtacgtgga aggacccct  gggagtggga agacttttca cctggtcaaa gatgtgctag   8160
ccgtggtcgg tagcgcgacc ttggttgtgc ccacccacgc gtccatgctg gactgcatca   8220
acaagctcaa acaagcgggc gccgatccat actttgtggt gcccaagtat acagttcttg   8280
actttccccg gcctggcagt ggaaacatca cagtgcgact gccacaggtc ggaaccagtg   8340
agggagaaac ctttgtggat gaggtggcct acttctcacc agtggatctg gcgcgcattt   8400
taacccaggg tcgagtcaag ggttacggtg atttaaatca gctcgggtgc gtcggacccg   8460
cgagcgtgcc acgtaacctt tggctccgac attttgtcag cctggagccc ttgcgagtgt   8520
gccatcgatt cggcgctgct gtgtgtgatt tgatcaaggg catttatcct tattatgagc   8580
cagctccaca taccactaaa gtggtgtttg tgccaaatcc agactttgag aaaggtgtag   8640
tcatcaccgc ctaccacaaa gatcgcggtc ttggtcaccg cacaattgat tcaattcaag   8700
gctgtacatt ccctgttgtg actcttcgac tgcccacacc ccaatcactg acgcgcccgc   8760
gcgcagttgt ggcggttact agggcgtctc aggaattata catctacgac ccctttgatc   8820
agcttagcgg gttgttgaag ttcaccaagg aagcagaggc gcaggacttg atccatggcc   8880
cacctacagc atgccacctg ggccaagaaa ttgacctttg gtccaatgag ggcctcgaat   8940
attacaagga agtcaacctg ctgtacacac acgtccccat caaggatggt gtaatacaca   9000
gttaccctaa ttgtggccct gcctgtggct gggaaaagca atccaacaaa atttcgtgcc   9060
tcccgagagt ggcacaaaat ttgggctacc actattcccc agacttacca ggattttgcc   9120
ccataccaaa agaactcgct gagcattggc ccgtagtgtc caatgataga tacccgaatt   9180
gcttgcaaat taccttacag caagtatgtg aactcagtaa accgtgctca gcgggctata   9240
tggttggaca atcggttttc gtgcagacgc ctggtgtgac atcttactgg cttactgaat   9300
gggtcgacgg caaagcgcgt gctctaccag attccttatt ctcgtccggt aggttcgaga   9360
ctaacagccg cgctttcctc gatgaagccg aggaaaagtt tgccgccgct caccctcatg   9420
cctgtttggg agaaattaat aagtccaccg tgggaggatc ccacttcatc ttttcccaat   9480
atttaccacc attgctaccc gcagacgctg ttgccctggt aggtgcttca ttggctggga   9540
aagctgctaa agctgcttgc agcgttgttg atgtctatgc tccatcattt gaaccttatc   9600
tacaccctga gacactgagt cgcgtgtaca agattatgat cgatttcaag ccgtgtaggc   9660
ttatggtgtg gagaaacgcg accttttatg tccaagaggg tgttgatgca gttacatcag   9720
cactagcagc tgtgtccaaa ctcatcaaag tgccggccaa tgagcctgtt tcattccatg   9780
tggcatcagg gtacagaacc aacgcgctgg tagcgcccca ggctaaaatt tcaattggag   9840
cctacgccgc cgagtgggca ctgtcaactg aaccgccacc tgctggttat gcgatcgtgc   9900
ggcgatatat tgtaaagagg ctcctcagct caacagaagt gttcttgtgc cgcaggggtg   9960
ttgtgtcttc cacctcagtg cagaccattt gtgcactaga gggatgtaaa cctctgttca  10020
acttcttaca aattggttca gtcattgggc ccgtgtgact ctagagtgga cctgttccca  10080
tcccccgctc aactactcag gtagtggttc gcggcaacgg gtacaccgca gttggtaaca  10140
agcttgtcga tagtcagcat agtacatttc atctgactaa tactacaaca ccaccaccat  10200
gaatagagga ttctttaaca tgctcggccg ccgccccttc ccggccccca ctgccatgtg  10260
gaggccgcgg agaaggaggc aggcggcccc gatgatggaa aatatggaaa acgacgagaa  10320
catcgtggtg ggccccaagc ccttctaccc catcgaggaa ggcagcgccg gcacccagct  10380
```

-continued gcggaagtac atggaaagat acgccaagct gggcgccatt gccttcacca acgccgtgac 10440
cggcgtggac tacagctacg ccgagtacct ggaaaagagc tgctgcctgg gcaaggctct 10500
gcagaactac ggcctggtgg tggacggccg gatcgccctg tgcagcgaga actgcgagga 10560
attcttcatc cccgtgatcg ccggcctgtt catcggcgtg ggcgtggctc ccaccaacga 10620
gatctacacc ctgcgggagc tggtgcacag cctgggcatc agcaagccca ccatcgtgtt 10680
cagcagcaag aagggcctgg acaaagtcat caccgtgcag aaaaccgtga ccaccatcaa 10740
gaccatcgtg atcctggaca gcaaggtgga ctaccggggc taccagtgcc tggacacctt 10800
catcaagcgg aacaccccc ctggcttcca ggccagcagc ttcaagaccg tggaggtgga 10860
ccggaaagaa caggtggccc tgatcatgaa cagcagcggc agcaccggcc tgcccaaggg 10920
cgtgcagctg acccacgaga acaccgtgac ccggttcagc cacgccaggg accccatcta 10980
cggcaaccag gtgtcccccg gcaccgccgt gctgaccgtg gtgcccttcc accacggctt 11040
cggcatgttc accaccctgg gctacctgat ctgcggcttc cgggtggtga tgctgaccaa 11100
gttcgacgag gaaaccttcc tgaaaaccct gcaggactac aagtgcacct acgtgattct 11160
ggtgcccacc ctgttcgcca tcctgaacaa gagcgagctg ctgaacaagt acgacctgag 11220
caacctggtg gagatcgcca gcggcggagc ccccctgagc aaagaagtgg gagaggccgt 11280
cgccaggcgg ttcaatctgc ccggcgtgcg gcagggctac ggcctgaccg agacaaccag 11340
cgccatcatc atcacccccg agggcgacga caagcctgga gccagcggca aggtggtgcc 11400
cctgttcaag gccaaagtga tcgacctgga caccaagaag agcctgggcc ccaacagacg 11460
gggcgaagtg tgcgtgaagg gccccatgct gatgaagggc tacgtgaaca accccgaggc 11520
caccaaagag ctgatcgacg aagagggctg gctgcacacc ggcgacatcg gctactacga 11580
cgaagagaag cacttcttca tcgtggaccg gctgaagagc ctgatcaagt acaagggcta 11640
tcaggtgccc cctgccgagc tggaaagcgt cctgctgcag caccccagca tcttcgacgc 11700
cggcgtggcc ggggtgccag atcctgtggc cggcgagctg cctggcgccg tggtggtgct 11760
ggaatccggc aagaacatga ccgagaaaga agtgatggac tacgtcgcca gccaggtgtc 11820
caacgccaag cggctgagag gcggcgtgag attcgtggac gaagtgccaa agggcctgac 11880
cggcaagatc gacggcaggg ccatccggga gatcctgaag aaacccgtgg ccaagatgtg 11940
attataactc gagggagcca tagattcatt ttgtggtgac gggattttag gtgagtatct 12000
agattacttt attctgtccg tcccactctt gctgttgctt actaggtatg tagcatctgg 12060
gttagtgtat gttttgactg ccttgttcta ttcctttgta ttagcagctt atatttggtt 12120
tgttatagtt ggaagagcct tttctactgc ttatgctttt gtgcttttgg ctgcttttct 12180
gttattagta atgaggatga ttgtgggtat gatgcctcgt cttcggtcca ttttcaacca 12240
tcgccaactg gtggtagctg attttgtgga cacacctagt ggacctgttc ccatcccccg 12300
cccaaccact caggtagtgg ttcgcggcaa cgggtacacc gcagttggta acaagcttgt 12360
cgatggcgtc aagacgatca cgtccgcagg ccgcctcttt tcgaaacgga cggcggcgac 12420
agcctacaag ctacaatgac ctactgcgca tgtttggtca gatgcgggtc cgcaaaccgc 12480
ccgcgcaacc cactcaggct attattgcag agcctggaga ccttaggcat gatttaaatc 12540
aacaggagcg cgccaccctt tcgtcgaacg tacaacggtt cttcatgatt gggcatggtt 12600
cactcactgc agatgccgga ggactcacgt acaccgtcag ttgggttcct accaaacaaa 12660
tccagcgcaa agttgcgcct ccagcagggc cgtaagacgt ggatattctc ctgtgtggcg 12720
tcatgttgaa gtagttatta gccacccagg aaccaaaaaa aaaaaaaaaa aaaaaaaaaa 12780
aaaaaaaaaa aaaaaaaaaa aaaaaaaaaa aaaaaaaaa 12819

<210> SEQ ID NO 19
<211> LENGTH: 464
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Construct Alpha-R-DLP-2A-nsp-rFF

<400> SEQUENCE: 19
gataggcggc gcatgagaga agcccagacc aattacctac ccaaatagga gaaagttcac 60
gttgacatcg aggaagacag cccattcctc agagctttgc agcggagctt cccgcagttt 120
gaggtagaag ccaagcaggt cactgataat gaccatgcta atgccagagc gttttcgcat 180
ctggcttcaa aactgatcga aacggaggtg gacccatccg acacgatcct tgacattgga 240
atagtcagca tagtacattt catctgacta atactacaac accaccacca tgaatagagg 300
attctttaac atgctcggcc gccgcccctt cccggccccc actgccatgt ggaggccgcg 360
gagaaggagg caggcggccc cgggaagcgg agctactaac ttcagcctgc tgaagcaggc 420
tggagacgtg gaggagaacc ctggacctat ggagaaagtt cacg 464

<210> SEQ ID NO 20
<211> LENGTH: 80
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer DLP-rFF-F
<220> FEATURE:
<221> NAME/KEY: misc_feature
<223> OTHER INFORMATION: RP112

<400> SEQUENCE: 20
cctgaatgga ctacgacata gtctagtccg ccaagatatc gcaccatagt cagcatagta 60
catttcatct gactaatact 80

<210> SEQ ID NO 21
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer DLP-rFF-R
<220> FEATURE:
<221> NAME/KEY: misc_feature
<223> OTHER INFORMATION: RP113

<400> SEQUENCE: 21
gcagcttgcc aattgctgct gtatcgatca attaatcaca tcttggccac gggtttcttc 60

<210> SEQ ID NO 22
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer 5'Alpha-P2A-F
<220> FEATURE:
<221> NAME/KEY: misc_feature
<223> OTHER INFORMATION: RP124

<400> SEQUENCE: 22
gaagcaggct ggagacgtgg aggagaaccc tggacctgag aaagttcacg ttgacatcga 60
ggaagac 67

<210> SEQ ID NO 23
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer 5'ScaI-R
<220> FEATURE:
<221> NAME/KEY: misc_feature
<223> OTHER INFORMATION: RP125

<400> SEQUENCE: 23
caccagtcac agaaaagcat cttacggatg 30

<210> SEQ ID NO 24
<211> LENGTH: 1014
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: g-block for Alpha-R-DLP-2A-nsp-rFF

<400> SEQUENCE: 24
tgtcatgcca tccgtaagat gcttttctgt gactggtgag tactcaacca agtcattctg 60
agaatagtgt atgcggcgac cgagttgctc ttgcccggcg tcaacacggg ataataccgc 120
gccacatagc agaactttaa aagtgctcat cattggaaaa cgttcttcgg ggcgaaaact 180
ctcaaggatc ttaccgctgt tgagatccag ttcgatgtaa cccactcgtg cacccaactg 240
atcttcagca tcttttactt tcaccagcgt ttctgggtga gcaaaaacag gaaggcaaaa 300
tgccgcaaaa aagggaataa gggcgacacg gaaatgttga atactcatac tcttcctttt 360
tcaatattat tgaagcattt atcagggtta ttgtctcatg agcggataca tatttgaatg 420
tatttagaaa aataaacaaa taggggttcc gcgcacattt ccccgaaaag tgccacctga 480
cgtctaagaa accattatta tcatgacatt aagcatccgc ctttcgtttt atttgaccat 540
gttggtatgt aatacgactc actatagata ggcggcgcat gagagaagcc cagaccaatt 600
acctacccaa ataggagaaa gttcacgttg acatcgagga agacagccca ttcctcagag 660
ctttgcagcg gagcttcccg cagtttgagg tagaagccaa gcaggtcact gataatgacc 720
atgctaatgc cagagcgttt tcgcatctgg cttcaaaact gatcgaaacg gaggtggacc 780
catccgacac gatccttgac attggaatag tcagcatagt acatttcatc tgactaatac 840
tacaacacca ccaccatgaa tagaggattc tttaacatgc tcggccgccg cccettcccg 900 gcccccactg ccatgtggag gccgcggaga aggaggcagg cggccccggg aagcggagct 960
actaacttca gcctgctgaa gcaggctgga gacgtggagg agaaccctgg acct 1014

<210> SEQ ID NO 25
<211> LENGTH: 1014

-continued

<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: g-block for Alpha-R-DLP-2A-nsp-DLP-rFF

<400> SEQUENCE: 25

```
tgtcatgcca tccgtaagat gcttttctgt gactggtgag tactcaacca agtcattctg      60

agaatagtgt atgcggcgac cgagttgctc ttgcccggcg tcaacacggg ataataccgc     120

gccacatagc agaactttaa aagtgctcat cattggaaaa cgttcttcgg ggcgaaaact     180

ctcaaggatc ttaccgctgt tgagatccag ttcgatgtaa cccactcgtg cacccaactg     240

atcttcagca tcttttactt tcaccagcgt ttctgggtga gcaaaaacag gaaggcaaaa     300

tgccgcaaaa aagggaataa gggcgacacg gaaatgttga atactcatac tcttcctttt     360

tcaatattat tgaagcattt atcagggtta ttgtctcatg agcggataca tatttgaatg     420

tatttagaaa aataaacaaa taggggttcc gcgcacattt ccccgaaaag tgccacctga     480

cgtctaagaa accattatta tcatgacatt aagcatccgc ctttcgtttt atttgaccat     540

gttggtatgt aatacgactc actatagata ggcggcgcat gagagaagcc cagaccaatt     600

acctacccaa ataggagaaa gttcacgttg acatcgagga agacagccca ttcctcagag     660

ctttgcagcg gagcttcccg cagtttgagg tagaagccaa gcaggtcact gataatgacc     720

atgctaatgc cagagcgttt tcgcatctgg cttcaaaact gatcgaaacg gaggtggacc     780

catccgacac gatccttgac attggaatag tcagcatagt acatttcatc tgactaatac     840

tacaacacca ccaccatgaa tagaggattc tttaacatgc tcggccgccg ccccttcccg     900

gcccccactg ccatgtggag gccgcggaga aggaggcagg cggccccggg aagcggagct     960

actaacttca gcctgctgaa gcaggctgga gacgtggagg agaaccctgg acct          1014
```

<210> SEQ ID NO 26
<211> LENGTH: 9476
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: construct Alpha-R-rFF
<220> FEATURE:
<221> NAME/KEY: misc_feature
<222> LOCATION: (1)...(18)
<223> OTHER INFORMATION: T7 promoter

<400> SEQUENCE: 26

```
taatacgact cactatagat aggcggcgca tgagagaagc ccagaccaat tacctaccca      60

aaatggagaa agttcacgtt gacatcgagg aagacagccc attcctcaga gctttgcagc     120

ggagcttccc gcagtttgag gtagaagcca agcaggtcac tgataatgac catgctaatg     180

ccagagcgtt ttcgcatctg gcttcaaaac tgatcgaaac ggaggtggac ccatccgaca     240

cgatccttga cattggaagt gcgcccgccc gcagaatgta ttctaagcac aagtatcatt     300

gtatctgtcc gatgagatgt gcggaagatc cggacagatt gtataagtat gcaactaagc     360

tgaagaaaaa ctgtaaggaa ataactgata aggaattgga caagaaaatg aaggagctcg     420

ccgccgtcat gagcgaccct gacctggaaa ctgagactat gtgcctccac gacgacgagt     480

cgtgtcgcta cgaagggcaa gtcgctgttt accaggatgt atacgcggtt gacggaccga     540
```

-continued

```
caagtctcta tcaccaagcc aataagggag ttagagtcgc ctactggata ggctttgaca    600
ccaccccttt tatgtttaag aacttggctg gagcatatcc atcatactct accaactggg    660
ccgacgaaac cgtgttaacg gctcgtaaca taggcctatg cagctctgac gttatggagc    720
ggtcacgtag agggatgtcc attcttagaa agaagtattt gaaaccatcc aacaatgttc    780
tattctctgt tggctcgacc atctaccacg agaagaggga cttactgagg agctggcacc    840
tgccgtctgt atttcactta cgtggcaagc aaaattacac atgtcggtgt gagactatag    900
ttagttgcga cgggtacgtc gttaaaagaa tagctatcag tccaggcctg tatgggaagc    960
cttcaggcta tgctgctacg atgcaccgcg agggattctt gtgctgcaaa gtgacagaca   1020
cattgaacgg ggagagggtc tcttttcccg tgtgcacgta tgtgccagct acattgtgtg   1080
accaaatgac tggcatactg gcaacagatg tcagtgcgga cgacgcgcaa aaactgctgg   1140
ttgggctcaa ccagcgtata gtcgtcaacg gtcgcaccca gagaaacacc aataccatga   1200
aaaattacct tttgcccgta gtggcccagg catttgctag gtgggcaaag gaatataagg   1260
aagatcaaga agatgaaagg ccactaggac tacgagatag acagttagtc atggggtgtt   1320
gttgggcttt tagaaggcac aagataacat ctatttataa gcgcccggat acccaaacca   1380
tcatcaaagt gaacagcgat ttccactcat tcgtgctgcc caggataggc agtaacacat   1440
tggagatcgg gctgagaaca agaatcagga aaatgttaga ggagcacaag gagccgtcac   1500
ctctcattac cgccgaggac gtacaagaag ctaagtgcgc agccgatgag gctaaggagg   1560
tgcgtgaagc cgaggagttg cgcgcagctc taccaccttt ggcagctgat gttgaggagc   1620
ccactctgga agccgatgtc gacttgatgt tacaagaggc tggggccggc tcagtggaga   1680
cacctcgtgg cttgataaag gttaccagct acgatggcga ggacaagatc ggctcttacg   1740
ctgtgctttc tccgcaggct gtactcaaga gtgaaaaatt atcttgcatc caccctctcg   1800
ctgaacaagt catagtgata acacactctg gccgaaaagg gcgttatgcc gtggaaccat   1860
accatggtaa agtagtggtg ccagagggac atgcaatacc cgtccaggac tttcaagctc   1920
tgagtgaaag tgccaccatt gtgtacaacg aacgtgagtt cgtaaacagg tacctgcacc   1980
atattgccac acatggagga gcgctgaaca ctgatgaaga atattacaaa actgtcaagc   2040
ccagcgagca cgacggcgaa tacctgtacg acatcgacag gaaacagtgc gtcaagaaag   2100
aactagtcac tgggctaggg ctcacaggcg agctggtgga tcctcccttc catgaattcg   2160
cctacgagag tctgagaaca cgaccagccg ctccttacca agtaccaacc ataggggtgt   2220
atggcgtgcc aggatcaggc aagtctggca tcattaaaag cgcagtcacc aaaaaagatc   2280
tagtggtgag cgccaagaaa gaaaactgtg cagaaattat aagggacgtc aagaaaatga   2340
aagggctgga cgtcaatgcc agaactgtgg actcagtgct cttgaatgga tgcaaacacc   2400
ccgtagagac cctgtatatt gacgaagctt ttgcttgtca tgcaggtact ctcagagcgc   2460
tcatagccat tataagacct aaaaaggcag tgctctgcgg ggatcccaaa cagtgcggtt   2520
tttttaacat gatgtgcctg aaagtgcatt ttaaccacga gatttgcaca caagtcttcc   2580
acaaaagcat ctctcgccgt tgcactaaat ctgtgacttc ggtcgtctca accttgtttt   2640
acgacaaaaa aatgagaacg acgaatccga aagagactaa gattgtgatt gacactaccg   2700
gcagtaccaa acctaagcag gacgatctca ttctcacttg tttcagaggg tgggtgaagc   2760
agttgcaaat agattacaaa ggcaacgaaa taatgacggc agctgcctct caagggctga   2820
cccgtaaagg tgtgtatgcc gttcggtaca aggtgaatga aaatcctctg tacgcaccca   2880
cctctgaaca tgtgaacgtc ctactgaccc gcacggagga ccgcatcgtg tggaaaacac   2940
```

```
tagccggcga cccatggata aaaacactga ctgccaagta ccctgggaat ttcactgcca   3000
cgatagagga gtggcaagca gagcatgatg ccatcatgag gcacatcttg gagagaccgg   3060
accctaccga cgtcttccag aataaggcaa acgtgtgttg ggccaaggct ttagtgccgg   3120
tgctgaagac cgctggcata gacatgacca ctgaacaatg gaacactgtg gattattttg   3180
aaacggacaa agctcactca gcagagatag tattgaacca actatgcgtg aggttctttg   3240
gactcgatct ggactccggt ctattttctg cacccactgt tccgttatcc attaggaata   3300
atcactggga taactccccg tcgcctaaca tgtacgggct gaataaagaa gtggtccgtc   3360
agctctctcg caggtaccca caactgcctc gggcagttgc cactggaaga gtctatgaca   3420
tgaacactgg tacactgcgc aattatgatc cgcgcataaa cctagtacct gtaaacagaa   3480
gactgcctca tgctttagtc ctccaccata atgaacaccc acagagtgac ttttcttcat   3540
tcgtcagcaa attgaagggc agaactgtcc tggtggtcgg ggaaaagttg tccgtcccag   3600
gcaaaatggt tgactggttg tcagaccggc ctgaggctac cttcagagct cggctggatt   3660
taggcatccc aggtgatgtg cccaaatatg acataatatt tgttaatgtg aggaccccat   3720
ataaatacca tcactatcag cagtgtgaag accatgccat taagcttagc atgttgacca   3780
agaaagcttg tctgcatctg aatcccggcg gaacctgtgt cagcataggt tatggttacg   3840
ctgacagggc cagcgaaagc atcattggtg ctatagcgcg gcagttcaag ttttcccggg   3900
tatgcaaacc gaaatcctca cttgaagaga cggaagttct gtttgtattc attgggtacg   3960
atcgcaaggc ccgtacgcac aatccttaca agctttcatc aaccttgacc aacatttata   4020
caggttccag actccacgaa gccggatgtg caccctcata tcatgtggtg cgaggggata   4080
ttgccacggc caccgaagga gtgattataa atgctgctaa cagcaaagga caacctggcg   4140
gaggggtgtg cggagcgctg tataagaaat tcccggaaag cttcgattta cagccgatcg   4200
aagtaggaaa agcgcgactg gtcaaaggtg cagctaaaca tatcattcat gccgtaggac   4260
caaacttcaa caaagtttcg gaggttgaag gtgacaaaca gttggcagag gcttatgagt   4320
ccatcgctaa gattgtcaac gataacaatt acaagtcagt agcgattcca ctgttgtcca   4380
ccggcatctt ttccgggaac aaagatcgac taacccaatc attgaaccat ttgctgacag   4440
ctttagacac cactgatgca gatgtagcca tatactgcag ggacaagaaa tgggaaatga   4500
ctctcaagga agcagtggct aggagagaag cagtggagga gatatgcata tccgacgact   4560
cttcagtgac agaacctgat gcagagctgg tgagggtgca tccgaagagt tctttggctg   4620
gaaggaaggg ctacagcaca agcgatggca aaactttctc atatttggaa gggaccaagt   4680
ttcaccaggc ggccaaggat atagcagaaa ttaatgccat gtggcccgtt gcaacggagg   4740
ccaatgagca ggtatgcatg tatatcctcg gagaaagcat gagcagtatt aggtcgaaat   4800
gccccgtcga agagtcggaa gcctccacac cacctagcac gctgccttgc ttgtgcatcc   4860
atgccatgac tccagaaaga gtacagcgcc taaaagcctc acgtccagaa caaattactg   4920
tgtgctcatc ctttccattg ccgaagtata gaatcactgg tgtgcagaag atccaatgct   4980
cccagcctat attgttctca ccgaaagtgc ctgcgtatat tcatccaagg aagtatctcg   5040
tggaaacacc accggtagac gagactccgg agccatcggc agagaaccaa tccacagagg   5100
ggacacctga acaaccacca cttataaccg aggatgagac caggactaga acgcctgagc   5160
cgatcatcat cgaagaggaa gaagaggata gcataagttt gctgtcagat ggcccgaccc   5220
accaggtgct gcaagtcgag gcagacattc acgggccgcc ctctgtatct agctcatcct   5280
```

-continued ggtccattcc tcatgcatcc gactttgatg tggacagttt atccatactt gacaccctgg 5340
agggagctag cgtgaccagc ggggcaacgt cagccgagac taactcttac ttcgcaaaga 5400
gtatggagtt tctggcgcga ccggtgcctg cgcctcgaac agtattcagg aaccctccac 5460
atcccgctcc gcgcacaaga acaccgtcac ttgcacccag cagggcctgc tcgagaacca 5520
gcctagtttc caccccgcca ggcgtgaata gggtgatcac tagagaggag ctcgaggcgc 5580
ttaccccgtc acgcactcct agcaggtcgg tctcgagaac cagcctggtc tccaacccgc 5640
caggcgtaaa tagggtgatt acaagagagg agtttgaggc gttcgtagca caacaacaat 5700
gacggtttga tgcgggtgca tacatctttt cctccgacac cggtcaaggg catttacaac 5760
aaaaatcagt aaggcaaacg gtgctatccg aagtggtgtt ggagaggacc gaattggaga 5820
tttcgtatgc cccgcgcctc gaccaagaaa aagaagaatt actacgcaag aaattacagt 5880
taaatcccac acctgctaac agaagcagat accagtccag gaaggtggag aacatgaaag 5940
ccataacagc tagacgtatt ctgcaaggcc tagggcatta tttgaaggca gaaggaaaag 6000
tggagtgcta ccgaaccctg catcctgttc ctttgtattc atctagtgtg aaccgtgcct 6060
tttcaagccc caaggtcgca gtggaagcct gtaacgccat gttgaaagag aactttccga 6120
ctgtggcttc ttactgtatt attccagagt acgatgccta tttggacatg gttgacggag 6180
cttcatgctg cttagacact gccagttttt gccctgcaaa gctgcgcagc tttccaaaga 6240
aacactccta tttggaaccc acaatacgat cggcagtgcc ttcagcgatc cagaacacgc 6300
tccagaacgt cctggcagct gccacaaaaa gaaattgcaa tgtcacgcaa atgagagaat 6360
tgcccgtatt ggattcggcg gcctttaatg tggaatgctt caagaaatat gcgtgtaata 6420
atgaatattg ggaaacgttt aaagaaaacc ccatcaggct tactgaagaa aacgtggtaa 6480
attacattac caaattaaaa ggaccaaaag ctgctgctct tttgcgaag acacataatt 6540 tgaatatgtt gcaggacata ccaatggaca ggtttgtaat ggacttaaag agagacgtga 6600
aagtgactcc aggaacaaaa catactgaag aacggcccaa ggtacaggtg atccaggctg 6660
ccgatccgct agcaacagcg tatctgtgcg gaatccaccg agagctggtt aggagattaa 6720
atgcggtcct gcttccgaac attcatacac tgtttgatat gtcggctgaa gactttgacg 6780
ctattatagc cgagcacttc cagcctgggg attgtgttct ggaaactgac atcgcgtcgt 6840
ttgataaaag tgaggacgac gccatggctc tgaccgcgtt aatgattctg gaagacttag 6900
gtgtggacgc agagctgttg acgctgattg aggcggcttt cggcgaaatt tcatcaatac 6960
atttgcccac taaaactaaa tttaaattcg gagccatgat gaaatctgga atgttcctca 7020
cactgtttgt gaacacagtc attaacattg taatcgcaag cagagtgttg agagaacggc 7080
taaccggatc accatgtgca gcattcattg gagatgacaa tatcgtgaaa ggagtcaaat 7140
cggacaaatt aatggcagac aggtgcgcca cctggttgaa tatggaagtc aagattatag 7200
atgctgtggt gggcgagaaa gcgccttatt tctgtggagg gtttattttg tgtgactccg 7260
tgaccggcac agcgtgccgt gtggcagacc ccctaaaaag gctgtttaag cttggcaaac 7320
ctctggcagc agacgatgaa catgatgatg acaggagaag ggcattgcat gaagagtcaa 7380
cacgctggaa ccgagtgggt attctttcag agctgtgcaa ggcagtagaa tcaaggtatg 7440
aaaccgtagg aacttccatc atagttatgg ccatgactac tctagctagc agtgttaaat 7500
cattcagcta cctgagaggg gcccctataa ctctctacgg ctaacctgaa tggactacga 7560
catagtctag tccgccaaga tatcgcacca tggaaaatat ggaaaacgac gagaacatcg 7620
tggtgggccc caagcccttc taccccatcg aggaaggcag cgccggcacc cagctgcgga 7680
agtacatgga aagatacgcc aagctgggcg ccattgcctt caccaacgcc gtgaccggcg 7740
tggactacag ctacgccgag tacctggaaa agagctgctg cctgggcaag gctctgcaga 7800
actacggcct ggtggtggac ggccggatcg ccctgtgcag cgagaactgc gaggaattct 7860
tcatccccgt gatcgccggc ctgttcatcg gcgtgggcgt ggctcccacc aacgagatct 7920
acaccctgcg ggagctggtg cacagcctgg gcatcagcaa gcccaccatc gtgttcagca 7980
gcaagaaggg cctggacaaa gtcatcaccg tgcagaaaac cgtgaccacc atcaagacca 8040
tcgtgatcct ggacagcaag gtggactacc ggggctacca gtgcctggac accttcatca 8100
agcggaacac ccccccctggc ttccaggcca gcagcttcaa gaccgtggag gtggaccgga 8160
aagaacaggt ggccctgatc atgaacagca gcggcagcac cggcctgccc aagggcgtgc 8220
agctgaccca cgagaacacc gtgacccggt tcagccacgc cagggacccc atctacggca 8280
accaggtgtc ccccggcacc gccgtgctga ccgtggtgcc cttccaccac ggcttcggca 8340
tgttcaccac cctgggctac ctgatctgcg gcttccgggt ggtgatgctg accaagttcg 8400
acgaggaaac cttcctgaaa accctgcagg actacaagtg cacctacgtg attctggtgc 8460
ccaccctgtt cgccatcctg aacaagagcg agctgctgaa caagtacgac ctgagcaacc 8520
tggtggagat cgccagcggc ggagcccccc tgagcaaaga agtgggagag gccgtcgcca 8580
ggcggttcaa tctgcccggc gtgcggcagg gctacggcct gaccgagaca accagcgcca 8640
tcatcatcac cccccgagggc gacgacaagc ctggagccag cggcaaggtg gtgcccctgt 8700
tcaaggccaa agtgatcgac ctggacacca agaagagcct gggccccaac agacggggcg 8760
aagtgtgcgt gaagggcccc atgctgatga agggctacgt gaacaacccc gaggccacca 8820
aagagctgat cgacgaagag ggctggctgc acaccggcga catcggctac tacgacgaag 8880
agaagcactt cttcatcgtg gaccggctga agagcctgat caagtacaag ggctatcagg 8940
tgccccctgc cgagctggaa agcgtcctgc tgcagcaccc cagcatcttc gacgccggcg 9000
tggccggggt gccagatcct gtggccggcg agctgcctgg cgccgtggtg gtgctggaat 9060
ccggcaagaa catgaccgag aaagaagtga tggactacgt cgccagccag gtgtccaacg 9120
ccaagcggct gagaggcggc gtgagattcg tggacgaagt gccaaagggc ctgaccggca 9180
agatcgacgg cagggccatc cgggagatcc tgaagaaacc cgtggccaag atgtgattaa 9240
ttgatcgata cagcagcaat tggcaagctg cttacataga aggcgcgccg tttaaacggc 9300
cggccttaat taagtaacga tacagcagca attggcaagc tgcttacata gaactcgcgg 9360
cgattggcat gccgctttaa aatttttatt ttattttttct tttcttttcc gaatcggatt 9420
ttgtttttaa tatttcaaaa aaaaaaaaaa aaaaaaaaaa aaaaaaaaaa aaaaaa 9476

<210> SEQ ID NO 27
<211> LENGTH: 9621
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: construct Alpha-R-DLP-rFF
<220> FEATURE:
<221> NAME/KEY: misc_feature
<222> LOCATION: (1)...(18)
<223> OTHER INFORMATION: T7 promoter

<400> SEQUENCE: 27
taatacgact cactatagat aggcggcgca tgagagaagc ccagaccaat tacctaccca 60

-continued

```
aaatggagaa agttcacgtt gacatcgagg aagacagccc attcctcaga gctttgcagc    120
ggagcttccc gcagtttgag gtagaagcca agcaggtcac tgataatgac catgctaatg    180
ccagagcgtt ttcgcatctg gcttcaaaac tgatcgaaac ggaggtggac ccatccgaca    240
cgatccttga cattggaagt gcgcccgccc gcagaatgta ttctaagcac aagtatcatt    300
gtatctgtcc gatgagatgt gcggaagatc cggacagatt gtataagtat gcaactaagc    360
tgaagaaaaa ctgtaaggaa ataactgata aggaattgga caagaaaatg aaggagctcg    420
ccgccgtcat gagcgaccct gacctggaaa ctgagactat gtgcctccac gacgacgagt    480
cgtgtcgcta cgaagggcaa gtcgctgttt accaggatgt atacgcggtt gacggaccga    540
caagtctcta tcaccaagcc aataagggag ttagagtcgc ctactggata ggctttgaca    600
ccaccccttt tatgtttaag aacttggctg gagcatatcc atcatactct accaactggg    660
ccgacgaaac cgtgttaacg gctcgtaaca taggcctatg cagctctgac gttatggagc    720
ggtcacgtag agggatgtcc attcttagaa agaagtattt gaaaccatcc aacaatgttc    780
tattctctgt tggctcgacc atctaccacg agaagaggga cttactgagg agctggcacc    840
tgccgtctgt atttcactta cgtggcaagc aaaattacac atgtcggtgt gagactatag    900
ttagttgcga cgggtacgtc gttaaaagaa tagctatcag tccaggcctg tatgggaagc    960
cttcaggcta tgctgctacg atgcaccgcg agggattctt gtgctgcaaa gtgacagaca   1020
cattgaacgg ggagagggtc tcttttcccg tgtgcacgta tgtgccagct acattgtgtg   1080
accaaatgac tggcatactg gcaacagatg tcagtgcgga cgacgcgcaa aaactgctgg   1140
ttgggctcaa ccagcgtata gtcgtcaacg gtcgcaccca gagaaacacc aataccatga   1200
aaaattacct tttgcccgta gtggcccagg catttgctag gtgggcaaag gaatataagg   1260
aagatcaaga agatgaaagg ccactaggac tacgagatag acagttagtc atggggtgtt   1320
gttgggcttt tagaaggcac aagataacat ctatttataa gcgcccggat acccaaacca   1380
tcatcaaagt gaacagcgat ttccactcat tcgtgctgcc caggataggc agtaacacat   1440
tggagatcgg gctgagaaca agaatcagga aaatgttaga ggagcacaag gagccgtcac   1500
ctctcattac cgccgaggac gtacaagaag ctaagtgcgc agccgatgag gctaaggagg   1560
tgcgtgaagc cgaggagttg cgcgcagctc taccaccttt ggcagctgat gttgaggagc   1620
ccactctgga agccgatgtc gacttgatgt tacaagaggc tggggccggc tcagtggaga   1680
cacctcgtgg cttgataaag gttaccagct acgatggcga ggacaagatc ggctcttacg   1740
ctgtgctttc tccgcaggct gtactcaaga gtgaaaaatt atcttgcatc caccctctcg   1800
ctgaacaagt catagtgata acacactctg gccgaaaagg gcgttatgcc gtggaaccat   1860
accatggtaa agtagtggtg ccagagggac atgcaatacc cgtccaggac tttcaagctc   1920
tgagtgaaag tgccaccatt gtgtacaacg aacgtgagtt cgtaaacagg tacctgcacc   1980
atattgccac acatggagga gcgctgaaca ctgatgaaga atattacaaa actgtcaagc   2040
ccagcgagca cgacggcgaa tacctgtacg acatcgacag gaaacagtgc gtcaagaaag   2100
aactagtcac tgggctaggg ctcacaggcg agctggtgga tcctcccttc catgaattcg   2160
cctacgagag tctgagaaca cgaccagccg ctccttacca agtaccaacc ataggggtgt   2220
atggcgtgcc aggatcaggc aagtctggca tcattaaaag cgcagtcacc aaaaaagatc   2280
tagtggtgag cgccaagaaa gaaaactgtg cagaaattat aagggacgtc aagaaaatga   2340
aagggctgga cgtcaatgcc agaactgtgg actcagtgct cttgaatgga tgcaaacacc   2400
```

-continued

```
ccgtagagac cctgtatatt gacgaagctt ttgcttgtca tgcaggtact ctcagagcgc   2460
tcatagccat tataagacct aaaaaggcag tgctctgcgg ggatcccaaa cagtgcggtt   2520
tttttaacat gatgtgcctg aaagtgcatt ttaaccacga gatttgcaca caagtcttcc   2580
acaaaagcat ctctcgccgt tgcactaaat ctgtgacttc ggtcgtctca accttgtttt   2640
acgacaaaaa aatgagaacg acgaatccga aagagactaa gattgtgatt gacactaccg   2700
gcagtaccaa acctaagcag gacgatctca ttctcacttg tttcagaggg tgggtgaagc   2760
agttgcaaat agattacaaa ggcaacgaaa taatgacggc agctgcctct caagggctga   2820
cccgtaaagg tgtgtatgcc gttcggtaca aggtgaatga aaatcctctg tacgcaccca   2880
cctctgaaca tgtgaacgtc ctactgaccc gcacggagga ccgcatcgtg tggaaaacac   2940
tagccggcga cccatggata aaaacactga ctgccaagta ccctgggaat ttcactgcca   3000
cgatagagga gtggcaagca gagcatgatg ccatcatgag gcacatcttg gagagaccgg   3060
accctaccga cgtcttccag aataaggcaa acgtgtgttg ggccaaggct ttagtgccgg   3120
tgctgaagac cgctggcata gacatgacca ctgaacaatg gaacactgtg gattattttg   3180
aaacggacaa agctcactca gcagagatag tattgaacca actatgcgtg aggttctttg   3240
gactcgatct ggactccggt ctattttctg cacccactgt tccgttatcc attaggaata   3300
atcactggga taactccccg tcgcctaaca tgtacgggct gaataaagaa gtggtccgtc   3360
agctctctcg caggtaccca caactgcctc gggcagttgc cactggaaga gtctatgaca   3420
tgaacactgg tacactgcgc aattatgatc cgcgcataaa cctagtacct gtaaacagaa   3480
gactgcctca tgctttagtc ctccaccata atgaacaccc acagagtgac ttttcttcat   3540
tcgtcagcaa attgaagggc agaactgtcc tggtggtcgg ggaaaagttg tccgtcccag   3600
gcaaaatggt tgactggttg tcagaccggc ctgaggctac cttcagagct cggctggatt   3660
taggcatccc aggtgatgtg cccaaatatg acataatatt tgttaatgtg aggaccccat   3720
ataaatacca tcactatcag cagtgtgaag accatgccat taagcttagc atgttgacca   3780
agaaagcttg tctgcatctg aatcccggcg gaacctgtgt cagcataggt tatggttacg   3840
ctgacagggc cagcgaaagc atcattggtg ctatagcgcg gcagttcaag ttttcccggg   3900
tatgcaaacc gaaatcctca cttgaagaga cggaagttct gtttgtattc attgggtacg   3960
atcgcaaggc ccgtacgcac aatccttaca agctttcatc aaccttgacc aacatttata   4020
caggttccag actccacgaa gccggatgtg caccctcata tcatgtggtg cgaggggata   4080
ttgccacggc caccgaagga gtgattataa atgctgctaa cagcaaagga caacctggcg   4140
gaggggtgtg cggagcgctg tataagaaat tcccggaaag cttcgattta cagccgatcg   4200
aagtaggaaa agcgcgactg gtcaaaggtg cagctaaaca tatcattcat gccgtaggac   4260
caaacttcaa caaagtttcg gaggttgaag gtgacaaaca gttggcagag gcttatgagt   4320
ccatcgctaa gattgtcaac gataacaatt acaagtcagt agcgattcca ctgttgtcca   4380
ccggcatctt ttccgggaac aaagatcgac taacccaatc attgaaccat ttgctgacag   4440
ctttagacac cactgatgca gatgtagcca tatactgcag ggacaagaaa tgggaaatga   4500
ctctcaagga agcagtggct aggagagaag cagtggagga gatatgcata tccgacgact   4560
cttcagtgac agaacctgat gcagagctgg tgagggtgca tccgaagagt tctttggctg   4620
gaaggaaggg ctacagcaca agcgatggca aaactttctc atatttggaa gggaccaagt   4680
ttcaccaggc ggccaaggat atagcagaaa ttaatgccat gtggcccgtt gcaacggagg   4740
ccaatgagca ggtatgcatg tatatcctcg gagaaagcat gagcagtatt aggtcgaaat   4800
```

-continued

```
gccccgtcga agagtcggaa gcctccacac cacctagcac gctgccttgc ttgtgcatcc   4860
atgccatgac tccagaaaga gtacagcgcc taaaagcctc acgtccagaa caaattactg   4920
tgtgctcatc ctttccattg ccgaagtata gaatcactgg tgtgcagaag atccaatgct   4980
cccagcctat attgttctca ccgaaagtgc ctgcgtatat tcatccaagg aagtatctcg   5040
tggaaacacc accggtagac gagactccgg agccatcggc agagaaccaa tccacagagg   5100
ggacacctga acaaccacca cttataaccg aggatgagac caggactaga acgcctgagc   5160
cgatcatcat cgaagaggaa gaagaggata gcataagttt gctgtcagat ggcccgaccc   5220
accaggtgct gcaagtcgag gcagacattc acgggccgcc ctctgtatct agctcatcct   5280
ggtccattcc tcatgcatcc gactttgatg tggacagttt atccatactt gacaccctgg   5340
agggagctag cgtgaccagc ggggcaacgt cagccgagac taactcttac ttcgcaaaga   5400
gtatggagtt tctggcgcga ccggtgcctg cgcctcgaac agtattcagg aaccctccac   5460
atcccgctcc gcgcacaaga acaccgtcac ttgcacccag cagggcctgc tcgagaacca   5520
gcctagtttc caccccgcca ggcgtgaata gggtgatcac tagagaggag ctcgaggcgc   5580
ttaccccgtc acgcactcct agcaggtcgg tctcgagaac cagcctggtc tccaacccgc   5640
caggcgtaaa tagggtgatt acaagagagg agtttgaggc gttcgtagca caacaacaat   5700
gacggtttga tgcgggtgca tacatctttt cctccgacac cggtcaaggg catttacaac   5760
aaaaatcagt aaggcaaacg gtgctatccg aagtggtgtt ggagaggacc gaattggaga   5820
tttcgtatgc cccgcgcctc gaccaagaaa aagaagaatt actacgcaag aaattacagt   5880
taaatcccac acctgctaac agaagcagat accagtccag gaaggtggag aacatgaaag   5940
ccataacagc tagacgtatt ctgcaaggcc tagggcatta tttgaaggca gaaggaaaag   6000
tggagtgcta ccgaaccctg catcctgttc ctttgtattc atctagtgtg aaccgtgcct   6060
tttcaagccc caaggtcgca gtggaagcct gtaacgccat gttgaaagag aactttccga   6120
ctgtggcttc ttactgtatt attccagagt acgatgccta tttggacatg gttgacggag   6180
cttcatgctg cttagacact gccagttttt gccctgcaaa gctgcgcagc tttccaaaga   6240
aacactccta tttggaaccc acaatacgat cggcagtgcc ttcagcgatc cagaacacgc   6300
tccagaacgt cctggcagct gccacaaaaa gaaattgcaa tgtcacgcaa atgagagaat   6360
tgcccgtatt ggattcggcg gcctttaatg tggaatgctt caagaaatat gcgtgtaata   6420
atgaatattg ggaaacgttt aaagaaaacc ccatcaggct tactgaagaa aacgtggtaa   6480
attacattac caaattaaaa ggaccaaaag ctgctgctct tttgcgaag acacataatt   6540
tgaatatgtt gcaggacata ccaatggaca ggtttgtaat ggacttaaag agagacgtga   6600
aagtgactcc aggaacaaaa catactgaag aacggcccaa ggtacaggtg atccaggctg   6660
ccgatccgct agcaacagcg tatctgtgcg gaatccaccg agagctggtt aggagattaa   6720
atgcggtcct gcttccgaac attcatacac tgtttgatat gtcggctgaa gactttgacg   6780
ctattatagc cgagcacttc cagcctgggg attgtgttct ggaaactgac atcgcgtcgt   6840
ttgataaaag tgaggacgac gccatggctc tgaccgcgtt aatgattctg gaagacttag   6900
gtgtggacgc agagctgttg acgctgattg aggcggcttt cggcgaaatt tcatcaatac   6960
atttgcccac taaaactaaa tttaaattcg gagccatgat gaaatctgga atgttcctca   7020
cactgtttgt gaacacagtc attaacattg taatcgcaag cagagtgttg agagaacggc   7080
taaccggatc accatgtgca gcattcattg gagatgacaa tatcgtgaaa ggagtcaaat   7140
```

-continued

```
cggacaaatt aatggcagac aggtgcgcca cctggttgaa tatggaagtc aagattatag   7200
atgctgtggt gggcgagaaa gcgccttatt tctgtggagg gtttattttg tgtgactccg   7260
tgaccggcac agcgtgccgt gtggcagacc ccctaaaaag gctgtttaag cttggcaaac   7320
ctctggcagc agacgatgaa catgatgatg acaggagaag ggcattgcat gaagagtcaa   7380
cacgctggaa ccgagtgggt attctttcag agctgtgcaa ggcagtagaa tcaaggtatg   7440
aaaccgtagg aacttccatc atagttatgg ccatgactac tctagctagc agtgttaaat   7500
cattcagcta cctgagaggg gcccctataa ctctctacgg ctaacctgaa tggactacga   7560
catagtctag tccgccaaga tatcgcacca tagtcagcat agtacatttc atctgactaa   7620
tactacaaca ccaccaccat gaatagagga ttctttaaca tgctcggccg ccgccccttc   7680
ccggccccca ctgccatgtg gaggccgcgg agaaggaggc aggcggcccc gatgatggaa   7740
aatatggaaa acgacgagaa catcgtggtg ggccccaagc ccttctaccc catcgaggaa   7800
ggcagcgccg gcacccagct gcggaagtac atggaaagat acgccaagct gggcgccatt   7860
gccttcacca acgccgtgac cggcgtggac tacagctacg ccgagtacct ggaaaagagc   7920
tgctgcctgg gcaaggctct gcagaactac ggcctggtgg tggacggccg gatcgccctg   7980
tgcagcgaga actgcgagga attcttcatc cccgtgatcg ccggcctgtt catcggcgtg   8040
ggcgtggctc ccaccaacga gatctacacc ctgcgggagc tggtgcacag cctgggcatc   8100
agcaagccca ccatcgtgtt cagcagcaag aagggcctgg acaaagtcat caccgtgcag   8160
aaaaccgtga ccaccatcaa gaccatcgtg atcctggaca gcaaggtgga ctaccggggc   8220
taccagtgcc tggacacctt catcaagcgg aacacccccc ctggcttcca ggccagcagc   8280
ttcaagaccg tggaggtgga ccggaaagaa caggtggccc tgatcatgaa cagcagcggc   8340
agcaccggcc tgcccaaggg cgtgcagctg acccacgaga acaccgtgac ccggttcagc   8400
cacgccaggg accccatcta cggcaaccag gtgtcccccg gcaccgccgt gctgaccgtg   8460
gtgcccttcc accacggctt cggcatgttc accaccctgg gctacctgat ctgcggcttc   8520
cgggtggtga tgctgaccaa gttcgacgag gaaaccttcc tgaaaaccct gcaggactac   8580
aagtgcacct acgtgattct ggtgcccacc ctgttcgcca tcctgaacaa gagcgagctg   8640
ctgaacaagt acgacctgag caacctggtg gagatcgcca gcggcggagc ccccctgagc   8700
aaagaagtgg gagaggccgt cgccaggcgg ttcaatctgc ccggcgtgcg gcagggctac   8760
ggcctgaccg agacaaccag cgccatcatc atcacccccg agggcgacga caagcctgga   8820
gccagcggca aggtggtgcc cctgttcaag gccaaagtga tcgacctgga caccaagaag   8880
agcctgggcc ccaacagacg gggcgaagtg tgcgtgaagg gccccatgct gatgaagggc   8940
tacgtgaaca accccgaggc caccaaagag ctgatcgacg aagagggctg gctgcacacc   9000
ggcgacatcg gctactacga cgaagagaag cacttcttca tcgtggaccg gctgaagagc   9060
ctgatcaagt acaagggcta tcaggtgccc cctgccgagc tggaaagcgt cctgctgcag   9120
caccccagca tcttcgacgc cggcgtggcc ggggtgccag atcctgtggc cggcgagctg   9180
cctggcgccg tggtggtgct ggaatccggc aagaacatga ccgagaaaga agtgatggac   9240
tacgtcgcca gccaggtgtc caacgccaag cggctgagag gcggcgtgag attcgtggac   9300
gaagtgccaa agggcctgac cggcaagatc gacggcaggg ccatccggga gatcctgaag   9360
aaacccgtgg ccaagatgtg attaattgat cgatacagca gcaattggca agctgcttac   9420
atagaaggcg cgccgtttaa acggccggcc ttaattaagt aacgatacag cagcaattgg   9480
caagctgctt acatagaact cgcggcgatt ggcatgccgc tttaaaattt ttattttatt   9540
```

tttcttttct tttccgaatc ggattttgtt tttaatattt caaaaaaaaa aaaaaaaaaa 9600
aaaaaaaaaa aaaaaaaaaa a 9621

<210> SEQ ID NO 28
<211> LENGTH: 9876
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: construct Alpha-R-DLP-2A-nsp-rFF
<220> FEATURE:
<221> NAME/KEY: misc_feature
<222> LOCATION: (1)...(18)
<223> OTHER INFORMATION: T7 promoter

<400> SEQUENCE: 28
taatacgact cactatagat aggcggcgca tgagagaagc ccagaccaat tacctaccca 60
aataggagaa agttcacgtt gacatcgagg aagacagccc attcctcaga gctttgcagc 120
ggagcttccc gcagtttgag gtagaagcca agcaggtcac tgataatgac catgctaatg 180
ccagagcgtt ttcgcatctg gcttcaaaac tgatcgaaac ggaggtggac ccatccgaca 240
cgatccttga cattggaata gtcagcatag tacatttcat ctgactaata ctacaacacc 300
accaccatga atagaggatt ctttaacatg ctcggccgcc gccccttccc ggcccccact 360
gccatgtgga ggccgcggag aaggaggcag gcggccccgg gaagcggagc tactaacttc 420
agcctgctga agcaggctgg agacgtggag gagaaccctg gacctgagaa agttcacgtt 480
gacatcgagg aagacagccc attcctcaga gctttgcagc ggagcttccc gcagtttgag 540
gtagaagcca agcaggtcac tgataatgac catgctaatg ccagagcgtt ttcgcatctg 600
gcttcaaaac tgatcgaaac ggaggtggac ccatccgaca cgatccttga cattggaagt 660
gcgcccgccc gcagaatgta ttctaagcac aagtatcatt gtatctgtcc gatgagatgt 720
gcggaagatc cggacagatt gtataagtat gcaactaagc tgaagaaaaa ctgtaaggaa 780
ataactgata aggaattgga caagaaaatg aaggagctcg ccgccgtcat gagcgaccct 840
gacctggaaa ctgagactat gtgcctccac gacgacgagt cgtgtcgcta cgaagggcaa 900
gtcgctgttt accaggatgt atacgcggtt gacggaccga caagtctcta tcaccaagcc 960
aataagggag ttagagtcgc ctactggata ggctttgaca ccaccccttt tatgtttaag 1020
aacttggctg gagcatatcc atcatactct accaactggg ccgacgaaac cgtgttaacg 1080
gctcgtaaca taggcctatg cagctctgac gttatggagc ggtcacgtag agggatgtcc 1140
attcttagaa agaagtattt gaaaccatcc aacaatgttc tattctctgt tggctcgacc 1200
atctaccacg agaagaggga cttactgagg agctggcacc tgccgtctgt atttcactta 1260
cgtggcaagc aaaattacac atgtcggtgt gagactatag ttagttgcga cgggtacgtc 1320
gttaaaagaa tagctatcag tccaggcctg tatgggaagc cttcaggcta tgctgctacg 1380
atgcaccgcg agggattctt gtgctgcaaa gtgacagaca cattgaacgg ggagagggtc 1440
tcttttcccg tgtgcacgta tgtgccagct acattgtgtg accaaatgac tggcatactg 1500
gcaacagatg tcagtgcgga cgacgcgcaa aaactgctgg ttgggctcaa ccagcgtata 1560
gtcgtcaacg gtcgcaccca gagaaacacc aataccatga aaaattacct tttgcccgta 1620
gtggcccagg catttgctag gtgggcaaag gaatataagg aagatcaaga agatgaaagg 1680
ccactaggac tacgagatag acagttagtc atggggtgtt gttgggcttt tagaaggcac 1740

-continued

```
aagataacat ctatttataa gcgcccggat acccaaacca tcatcaaagt gaacagcgat   1800
ttccactcat tcgtgctgcc caggataggc agtaacacat tggagatcgg gctgagaaca   1860
agaatcagga aaatgttaga ggagcacaag gagccgtcac ctctcattac cgccgaggac   1920
gtacaagaag ctaagtgcgc agccgatgag gctaaggagg tgcgtgaagc cgaggagttg   1980
cgcgcagctc taccaccttt ggcagctgat gttgaggagc ccactctgga agccgatgtc   2040
gacttgatgt tacaagaggc tggggccggc tcagtggaga cacctcgtgg cttgataaag   2100
gttaccagct acgatggcga ggacaagatc ggctcttacg ctgtgctttc tccgcaggct   2160
gtactcaaga gtgaaaaatt atcttgcatc caccctctcg ctgaacaagt catagtgata   2220
acacactctg gccgaaaagg gcgttatgcc gtggaaccat accatggtaa agtagtggtg   2280
ccagagggac atgcaatacc cgtccaggac tttcaagctc tgagtgaaag tgccaccatt   2340
gtgtacaacg aacgtgagtt cgtaaacagg tacctgcacc atattgccac acatggagga   2400
gcgctgaaca ctgatgaaga atattacaaa actgtcaagc ccagcgagca cgacggcgaa   2460
tacctgtacg acatcgacag gaaacagtgc gtcaagaaag aactagtcac tgggctaggg   2520
ctcacaggcg agctggtgga tcctcccttc catgaattcg cctacgagag tctgagaaca   2580
cgaccagccg ctccttacca agtaccaacc ataggggtgt atggcgtgcc aggatcaggc   2640
aagtctggca tcattaaaag cgcagtcacc aaaaaagatc tagtggtgag cgccaagaaa   2700
gaaaactgtg cagaaattat aagggacgtc aagaaaatga aagggctgga cgtcaatgcc   2760
agaactgtgg actcagtgct cttgaatgga tgcaaacacc ccgtagagac cctgtatatt   2820
gacgaagctt ttgcttgtca tgcaggtact ctcagagcgc tcatagccat tataagacct   2880
aaaaaggcag tgctctgcgg ggatcccaaa cagtgcggtt tttttaacat gatgtgcctg   2940
aaagtgcatt ttaaccacga gatttgcaca caagtcttcc acaaaagcat ctctcgccgt   3000
tgcactaaat ctgtgacttc ggtcgtctca accttgtttt acgacaaaaa aatgagaacg   3060
acgaatccga aagagactaa gattgtgatt gacactaccg gcagtaccaa acctaagcag   3120
gacgatctca ttctcacttg tttcagaggg tgggtgaagc agttgcaaat agattacaaa   3180
ggcaacgaaa taatgacggc agctgcctct caagggctga cccgtaaagg tgtgtatgcc   3240
gttcggtaca aggtgaatga aaatcctctg tacgcaccca cctctgaaca tgtgaacgtc   3300
ctactgaccc gcacggagga ccgcatcgtg tggaaaacac tagccggcga cccatggata   3360
aaaacactga ctgccaagta ccctgggaat ttcactgcca cgatagagga gtggcaagca   3420
gagcatgatg ccatcatgag gcacatcttg gagagaccgg accctaccga cgtcttccag   3480
aataaggcaa acgtgtgttg ggccaaggct ttagtgccgg tgctgaagac cgctggcata   3540
gacatgacca ctgaacaatg gaacactgtg gattattttg aaacggacaa agctcactca   3600
gcagagatag tattgaacca actatgcgtg aggttctttg gactcgatct ggactccggt   3660
ctattttctg cacccactgt tccgttatcc attaggaata atcactggga taactccccg   3720
tcgcctaaca tgtacgggct gaataaagaa gtggtccgtc agctctctcg caggtaccca   3780
caactgcctc gggcagttgc cactggaaga gtctatgaca tgaacactgg tacactgcgc   3840
aattatgatc cgcgcataaa cctagtacct gtaaacagaa gactgcctca tgctttagtc   3900
ctccaccata atgaacaccc acagagtgac ttttcttcat tcgtcagcaa attgaagggc   3960
agaactgtcc tggtggtcgg ggaaaagttg tccgtcccag gcaaaatggt tgactggttg   4020
tcagaccggc ctgaggctac cttcagagct cggctggatt taggcatccc aggtgatgtg   4080
```

-continued

```
cccaaatatg acataatatt tgttaatgtg aggaccccat ataaatacca tcactatcag   4140
cagtgtgaag accatgccat taagcttagc atgttgacca agaaagcttg tctgcatctg   4200
aatcccggcg gaacctgtgt cagcataggt tatggttacg ctgacagggc cagcgaaagc   4260
atcattggtg ctatagcgcg gcagttcaag ttttcccggg tatgcaaacc gaaatcctca   4320
cttgaagaga cggaagttct gtttgtattc attgggtacg atcgcaaggc ccgtacgcac   4380
aatccttaca agctttcatc aaccttgacc aacatttata caggttccag actccacgaa   4440
gccggatgtg caccctcata tcatgtggtg cgaggggata ttgccacggc caccgaagga   4500
gtgattataa atgctgctaa cagcaaagga caacctggcg gaggggtgtg cggagcgctg   4560
tataagaaat tcccggaaag cttcgattta cagccgatcg aagtaggaaa agcgcgactg   4620
gtcaaaggtg cagctaaaca tatcattcat gccgtaggac caaacttcaa caaagtttcg   4680
gaggttgaag gtgacaaaca gttggcagag gcttatgagt ccatcgctaa gattgtcaac   4740
gataacaatt acaagtcagt agcgattcca ctgttgtcca ccggcatctt ttccgggaac   4800
aaagatcgac taacccaatc attgaaccat ttgctgacag ctttagacac cactgatgca   4860
gatgtagcca tatactgcag ggacaagaaa tgggaaatga ctctcaagga agcagtggct   4920
aggagagaag cagtggagga gatatgcata tccgacgact cttcagtgac agaacctgat   4980
gcagagctgg tgagggtgca tccgaagagt tctttggctg gaaggaaggg ctacagcaca   5040
agcgatggca aaactttctc atatttggaa gggaccaagt ttcaccaggc ggccaaggat   5100
atagcagaaa ttaatgccat gtggcccgtt gcaacggagg ccaatgagca ggtatgcatg   5160
tatatcctcg gagaaagcat gagcagtatt aggtcgaaat gccccgtcga agagtcggaa   5220
gcctccacac cacctagcac gctgccttgc ttgtgcatcc atgccatgac tccagaaaga   5280
gtacagcgcc taaaagcctc acgtccagaa caaattactg tgtgctcatc ctttccattg   5340
ccgaagtata gaatcactgg tgtgcagaag atccaatgct cccagcctat attgttctca   5400
ccgaaagtgc ctgcgtatat tcatccaagg aagtatctcg tggaaacacc accggtagac   5460
gagactccgg agccatcggc agagaaccaa tccacagagg ggacacctga acaaccacca   5520
cttataaccg aggatgagac caggactaga acgcctgagc cgatcatcat cgaagaggaa   5580
gaagaggata gcataagttt gctgtcagat ggcccgaccc accaggtgct gcaagtcgag   5640
gcagacattc acgggccgcc ctctgtatct agctcatcct ggtccattcc tcatgcatcc   5700
gactttgatg tggacagttt atccatactt gacaccctgg agggagctag cgtgaccagc   5760
ggggcaacgt cagccgagac taactcttac ttcgcaaaga gtatggagtt tctggcgcga   5820
ccggtgcctg cgcctcgaac agtattcagg aaccctccac atcccgctcc gcgcacaaga   5880
acaccgtcac ttgcacccag cagggcctgc tcgagaacca gcctagtttc caccccgcca   5940
ggcgtgaata gggtgatcac tagagaggag ctcgaggcgc ttaccccgtc acgcactcct   6000
agcaggtcgg tctcgagaac cagcctggtc tccaacccgc caggcgtaaa tagggtgatt   6060
acaagagagg agtttgaggc gttcgtagca caacaacaat gacggtttga tgcgggtgca   6120
tacatctttt cctccgacac cggtcaaggg catttacaac aaaaatcagt aaggcaaacg   6180
gtgctatccg aagtggtgtt ggagaggacc gaattggaga tttcgtatgc cccgcgcctc   6240
gaccaagaaa aagaagaatt actacgcaag aaattacagt taaatcccac acctgctaac   6300
agaagcagat accagtccag gaaggtggag aacatgaaag ccataacagc tagacgtatt   6360
ctgcaaggcc tagggcatta tttgaaggca gaaggaaaag tggagtgcta ccgaaccctg   6420
catcctgttc ctttgtattc atctagtgtg aaccgtgcct tttcaagccc caaggtcgca   6480
```

gtggaagcct gtaacgccat gttgaaagag aactttccga ctgtggcttc ttactgtatt 6540
attccagagt acgatgccta tttggacatg gttgacggag cttcatgctg cttagacact 6600
gccagttttt gccctgcaaa gctgcgcagc tttccaaaga aacactccta tttggaaccc 6660
acaatacgat cggcagtgcc ttcagcgatc cagaacacgc tccagaacgt cctggcagct 6720
gccacaaaaa gaaattgcaa tgtcacgcaa atgagagaat tgcccgtatt ggattcggcg 6780
gcctttaatg tggaatgctt caagaaatat gcgtgtaata atgaatattg ggaaacgttt 6840
aaagaaaacc ccatcaggct tactgaagaa aacgtggtaa attacattac caaattaaaa 6900
ggaccaaaag ctgctgctct tttgcgaag acacataatt tgaatatgtt gcaggacata 6960
ccaatggaca ggtttgtaat ggacttaaag agagacgtga aagtgactcc aggaacaaaa 7020
catactgaag aacggcccaa ggtacaggtg atccaggctg ccgatccgct agcaacagcg 7080
tatctgtgcg gaatccaccg agagctggtt aggagattaa atgcggtcct gcttccgaac 7140
attcatacac tgtttgatat gtcggctgaa gactttgacg ctattatagc cgagcacttc 7200
cagcctgggg attgtgttct ggaaactgac atcgcgtcgt ttgataaaag tgaggacgac 7260
gccatggctc tgaccgcgtt aatgattctg gaagacttag gtgtggacgc agagctgttg 7320
acgctgattg aggcggcttt cggcgaaatt tcatcaatac atttgcccac taaaactaaa 7380
tttaaattcg gagccatgat gaaatctgga atgttcctca cactgtttgt gaacacagtc 7440
attaacattg taatcgcaag cagagtgttg agagaacggc taaccggatc accatgtgca 7500
gcattcattg gagatgacaa tatcgtgaaa ggagtcaaat cggacaaatt aatggcagac 7560
aggtgcgcca cctggttgaa tatggaagtc aagattatag atgctgtggt gggcgagaaa 7620
gcgccttatt tctgtggagg gtttattttg tgtgactccg tgaccggcac agcgtgccgt 7680
gtggcagacc ccctaaaaag gctgtttaag cttggcaaac ctctggcagc agacgatgaa 7740
catgatgatg acaggagaag ggcattgcat gaagagtcaa cacgctggaa ccgagtgggt 7800
attctttcag agctgtgcaa ggcagtagaa tcaaggtatg aaaccgtagg aacttccatc 7860
atagttatgg ccatgactac tctagctagc agtgttaaat cattcagcta cctgagaggg 7920
gcccctataa ctctctacgg ctaacctgaa tggactacga catagtctag tccgccaaga 7980
tatcgcacca tggaaaatat ggaaaacgac gagaacatcg tggtgggccc caagcccttc 8040
taccccatcg aggaaggcag cgccggcacc cagctgcgga agtacatgga aagatacgcc 8100
aagctgggcg ccattgcctt caccaacgcc gtgaccggcg tggactacag ctacgccgag 8160
tacctggaaa agagctgctg cctgggcaag gctctgcaga actacggcct ggtggtggac 8220
ggccggatcg ccctgtgcag cgagaactgc gaggaattct tcatccccgt gatcgccggc 8280
ctgttcatcg gcgtgggcgt ggctcccacc aacgagatct acaccctgcg ggagctggtg 8340
cacagcctgg gcatcagcaa gcccaccatc gtgttcagca gcaagaaggg cctggacaaa 8400
gtcatcaccg tgcagaaaac cgtgaccacc atcaagacca tcgtgatcct ggacagcaag 8460
gtggactacc ggggctacca gtgcctggac accttcatca agcggaacac ccccccctggc 8520
ttccaggcca gcagcttcaa gaccgtggag gtggaccgga aagaacaggt ggccctgatc 8580
atgaacagca gcggcagcac cggcctgccc aagggcgtgc agctgaccca cgagaacacc 8640
gtgacccggt tcagccacgc cagggacccc atctacggca accaggtgtc ccccggcacc 8700
gccgtgctga ccgtggtgcc cttccaccac ggcttcggca tgttcaccac cctgggctac 8760
ctgatctgcg gcttccgggt ggtgatgctg accaagttcg acgaggaaac cttcctgaaa 8820
accctgcagg actacaagtg cacctacgtg attctggtgc ccaccctgtt cgccatcctg 8880
aacaagagcg agctgctgaa caagtacgac ctgagcaacc tggtggagat cgccagcggc 8940
ggagcccccc tgagcaaaga agtgggagag gccgtcgcca ggcggttcaa tctgcccggc 9000
gtgcggcagg gctacggcct gaccgagaca accagcgcca tcatcatcac ccccgagggc 9060
gacgacaagc ctggagccag cggcaaggtg gtgcccctgt tcaaggccaa agtgatcgac 9120
ctggacacca agaagagcct gggccccaac agacggggcg aagtgtgcgt gaagggcccc 9180
atgctgatga agggctacgt gaacaacccc gaggccacca aagagctgat cgacgaagag 9240
ggctggctgc acaccggcga catcggctac tacgacgaag agaagcactt cttcatcgtg 9300
gaccggctga agagcctgat caagtacaag ggctatcagg tgccccctgc cgagctggaa 9360
agcgtcctgc tgcagcaccc cagcatcttc gacgccggcg tggccggggt gccagatcct 9420
gtggccggcg agctgcctgg cgccgtggtg gtgctggaat ccggcaagaa catgaccgag 9480
aaagaagtga tggactacgt cgccagccag gtgtccaacg ccaagcggct gagaggcggc 9540
gtgagattcg tggacgaagt gccaaagggc ctgaccggca agatcgacgg cagggccatc 9600
cgggagatcc tgaagaaacc cgtggccaag atgtgattaa ttgatcgata cagcagcaat 9660
tggcaagctg cttacataga aggcgcgccg tttaaacggc cggccttaat taagtaacga 9720
tacagcagca attggcaagc tgcttacata gaactcgcgg cgattggcat gccgctttaa 9780
aatttttatt ttattttttct tttcttttcc gaatcggatt ttgtttttaa tatttcaaaa 9840
aaaaaaaaaa aaaaaaaaaa aaaaaaaaaa aaaaaa 9876

<210> SEQ ID NO 29
<211> LENGTH: 10021
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: construct Alpha-R-DLP-2A-nsp-DLP-rFF
<220> FEATURE:
<221> NAME/KEY: misc_feature
<222> LOCATION: (1)...(18)
<223> OTHER INFORMATION: T7 promoter

<400> SEQUENCE: 29
taatacgact cactatagat aggcggcgca tgagagaagc ccagaccaat tacctaccca 60
aataggagaa agttcacgtt gacatcgagg aagacagccc attcctcaga gctttgcagc 120
ggagcttccc gcagtttgag gtagaagcca agcaggtcac tgataatgac catgctaatg 180
ccagagcgtt ttcgcatctg gcttcaaaac tgatcgaaac ggaggtggac ccatccgaca 240
cgatccttga cattggaata gtcagcatag tacatttcat ctgactaata ctacaacacc 300
accaccatga atagaggatt ctttaacatg ctcggccgcc gcccottccc ggccccccact 360 gccatgtgga ggccgcggag aaggaggcag gcggccccgg gaagcggagc tactaacttc 420
agcctgctga agcaggctgg agacgtggag gagaaccctg gacctgagaa agttcacgtt 480
gacatcgagg aagacagccc attcctcaga gctttgcagc ggagcttccc gcagtttgag 540
gtagaagcca agcaggtcac tgataatgac catgctaatg ccagagcgtt ttcgcatctg 600
gcttcaaaac tgatcgaaac ggaggtggac ccatccgaca cgatccttga cattggaagt 660
gcgcccgccc gcagaatgta ttctaagcac aagtatcatt gtatctgtcc gatgagatgt 720
gcggaagatc cggacagatt gtataagtat gcaactaagc tgaagaaaaa ctgtaaggaa 780

-continued

```
ataactgata aggaattgga caagaaaatg aaggagctcg ccgccgtcat gagcgaccct    840
gacctggaaa ctgagactat gtgcctccac gacgacgagt cgtgtcgcta cgaagggcaa    900
gtcgctgttt accaggatgt atacgcggtt gacggaccga caagtctcta tcaccaagcc    960
aataagggag ttagagtcgc ctactggata ggctttgaca ccaccccttt tatgtttaag   1020
aacttggctg gagcatatcc atcatactct accaactggg ccgacgaaac cgtgttaacg   1080
gctcgtaaca taggcctatg cagctctgac gttatggagc ggtcacgtag agggatgtcc   1140
attcttagaa agaagtattt gaaaccatcc aacaatgttc tattctctgt tggctcgacc   1200
atctaccacg agaagaggga cttactgagg agctggcacc tgccgtctgt atttcactta   1260
cgtggcaagc aaaattacac atgtcggtgt gagactatag ttagttgcga cgggtacgtc   1320
gttaaaagaa tagctatcag tccaggcctg tatgggaagc cttcaggcta tgctgctacg   1380
atgcaccgcg agggattctt gtgctgcaaa gtgacagaca cattgaacgg ggagagggtc   1440
tcttttcccg tgtgcacgta tgtgccagct acattgtgtg accaaatgac tggcatactg   1500
gcaacagatg tcagtgcgga cgacgcgcaa aaactgctgg ttgggctcaa ccagcgtata   1560
gtcgtcaacg gtcgcaccca gagaaacacc aataccatga aaaattacct tttgcccgta   1620
gtggcccagg catttgctag gtgggcaaag gaatataagg aagatcaaga agatgaaagg   1680
ccactaggac tacgagatag acagttagtc atggggtgtt gttgggcttt tagaaggcac   1740
aagataacat ctatttataa gcgcccggat acccaaacca tcatcaaagt gaacagcgat   1800
ttccactcat tcgtgctgcc caggataggc agtaacacat tggagatcgg gctgagaaca   1860
agaatcagga aaatgttaga ggagcacaag gagccgtcac ctctcattac cgccgaggac   1920
gtacaagaag ctaagtgcgc agccgatgag gctaaggagg tgcgtgaagc cgaggagttg   1980
cgcgcagctc taccaccttt ggcagctgat gttgaggagc ccactctgga agccgatgtc   2040
gacttgatgt tacaagaggc tggggccggc tcagtggaga cacctcgtgg cttgataaag   2100
gttaccagct acgatggcga ggacaagatc ggctcttacg ctgtgctttc tccgcaggct   2160
gtactcaaga gtgaaaaatt atcttgcatc caccctctcg ctgaacaagt catagtgata   2220
acacactctg gccgaaaagg gcgttatgcc gtggaaccat accatggtaa agtagtggtg   2280
ccagagggac atgcaatacc cgtccaggac tttcaagctc tgagtgaaag tgccaccatt   2340
gtgtacaacg aacgtgagtt cgtaaacagg tacctgcacc atattgccac acatggagga   2400
gcgctgaaca ctgatgaaga atattacaaa actgtcaagc ccagcgagca cgacggcgaa   2460
tacctgtacg acatcgacag gaaacagtgc gtcaagaaag aactagtcac tgggctaggg   2520
ctcacaggcg agctggtgga tcctcccttc catgaattcg cctacgagag tctgagaaca   2580
cgaccagccg ctccttacca agtaccaacc ataggggtgt atggcgtgcc aggatcaggc   2640
aagtctggca tcattaaaag cgcagtcacc aaaaaagatc tagtggtgag cgccaagaaa   2700
gaaaactgtg cagaaattat aagggacgtc aagaaaatga aagggctgga cgtcaatgcc   2760
agaactgtgg actcagtgct cttgaatgga tgcaaacacc ccgtagagac cctgtatatt   2820
gacgaagctt ttgcttgtca tgcaggtact ctcagagcgc tcatagccat tataagacct   2880
aaaaaggcag tgctctgcgg ggatcccaaa cagtgcggtt tttttaacat gatgtgcctg   2940
aaagtgcatt ttaaccacga gatttgcaca caagtcttcc acaaaagcat ctctcgccgt   3000
tgcactaaat ctgtgacttc ggtcgtctca accttgtttt acgacaaaaa aatgagaacg   3060
acgaatccga aagagactaa gattgtgatt gacactaccg gcagtaccaa acctaagcag   3120
gacgatctca ttctcacttg tttcagaggg tgggtgaagc agttgcaaat agattacaaa   3180
```

ggcaacgaaa taatgacggc agctgcctct caagggctga cccgtaaagg tgtgtatgcc 3240
gttcggtaca aggtgaatga aaatcctctg tacgcaccca cctctgaaca tgtgaacgtc 3300
ctactgaccc gcacggagga ccgcatcgtg tggaaaacac tagccggcga cccatggata 3360
aaaacactga ctgccaagta ccctgggaat ttcactgcca cgatagagga gtggcaagca 3420
gagcatgatg ccatcatgag gcacatcttg gagagaccgg accctaccga cgtcttccag 3480
aataaggcaa acgtgtgttg ggccaaggct ttagtgccgg tgctgaagac cgctggcata 3540
gacatgacca ctgaacaatg gaacactgtg gattattttg aaacggacaa agctcactca 3600
gcagagatag tattgaacca actatgcgtg aggttctttg gactcgatct ggactccggt 3660
ctattttctg cacccactgt tccgttatcc attaggaata atcactggga taactccccg 3720
tcgcctaaca tgtacgggct gaataaagaa gtggtccgtc agctctctcg caggtaccca 3780
caactgcctc gggcagttgc cactggaaga gtctatgaca tgaacactgg tacactgcgc 3840
aattatgatc cgcgcataaa cctagtacct gtaaacagaa gactgcctca tgctttagtc 3900
ctccaccata atgaacaccc acagagtgac ttttcttcat tcgtcagcaa attgaagggc 3960
agaactgtcc tggtggtcgg ggaaaagttg tccgtcccag gcaaaatggt tgactggttg 4020
tcagaccggc ctgaggctac cttcagagct cggctggatt taggcatccc aggtgatgtg 4080
cccaaatatg acataatatt tgttaatgtg aggaccccat ataaatacca tcactatcag 4140
cagtgtgaag accatgccat taagcttagc atgttgacca agaaagcttg tctgcatctg 4200
aatcccggcg gaacctgtgt cagcataggt tatggttacg ctgacagggc cagcgaaagc 4260
atcattggtg ctatagcgcg gcagttcaag ttttcccggg tatgcaaacc gaaatcctca 4320
cttgaagaga cggaagttct gtttgtattc attgggtacg atcgcaaggc ccgtacgcac 4380
aatccttaca agctttcatc aaccttgacc aacatttata caggttccag actccacgaa 4440
gccggatgtg caccctcata tcatgtggtg cgaggggata ttgccacggc caccgaagga 4500
gtgattataa atgctgctaa cagcaaagga caacctggcg gaggggtgtg cggagcgctg 4560
tataagaaat tcccggaaag cttcgattta cagccgatcg aagtaggaaa agcgcgactg 4620
gtcaaaggtg cagctaaaca tatcattcat gccgtaggac caaacttcaa caaagtttcg 4680
gaggttgaag gtgacaaaca gttggcagag gcttatgagt ccatcgctaa gattgtcaac 4740
gataacaatt acaagtcagt agcgattcca ctgttgtcca ccggcatctt ttccgggaac 4800
aaagatcgac taacccaatc attgaaccat ttgctgacag ctttagacac cactgatgca 4860
gatgtagcca tatactgcag ggacaagaaa tgggaaatga ctctcaagga agcagtggct 4920
aggagagaag cagtggagga gatatgcata tccgacgact cttcagtgac agaacctgat 4980
gcagagctgg tgagggtgca tccgaagagt tctttggctg gaaggaaggg ctacagcaca 5040
agcgatggca aaactttctc atatttggaa gggaccaagt ttcaccaggc ggccaaggat 5100
atagcagaaa ttaatgccat gtggcccgtt gcaacggagg ccaatgagca ggtatgcatg 5160
tatatcctcg gagaaagcat gagcagtatt aggtcgaaat gccccgtcga agagtcggaa 5220
gcctccacac cacctagcac gctgccttgc ttgtgcatcc atgccatgac tccagaaaga 5280
gtacagcgcc taaaagcctc acgtccagaa caaattactg tgtgctcatc ctttccattg 5340
ccgaagtata gaatcactgg tgtgcagaag atccaatgct cccagcctat attgttctca 5400
ccgaaagtgc ctgcgtatat tcatccaagg aagtatctcg tggaaacacc accggtagac 5460
gagactccgg agccatcggc agagaaccaa tccacagagg ggacacctga acaaccacca 5520

-continued

```
cttataaccg aggatgagac caggactaga acgcctgagc cgatcatcat cgaagaggaa   5580
gaagaggata gcataagttt gctgtcagat ggcccgaccc accaggtgct gcaagtcgag   5640
gcagacattc acgggccgcc ctctgtatct agctcatcct ggtccattcc tcatgcatcc   5700
gactttgatg tggacagttt atccatactt gacaccctgg agggagctag cgtgaccagc   5760
ggggcaacgt cagccgagac taactcttac ttcgcaaaga gtatggagtt tctggcgcga   5820
ccggtgcctg cgcctcgaac agtattcagg aaccctccac atcccgctcc gcgcacaaga   5880
acaccgtcac ttgcacccag cagggcctgc tcgagaacca gcctagtttc caccccgcca   5940
ggcgtgaata gggtgatcac tagagaggag ctcgaggcgc ttaccccgtc acgcactcct   6000
agcaggtcgg tctcgagaac cagcctggtc tccaacccgc caggcgtaaa tagggtgatt   6060
acaagagagg agtttgaggc gttcgtagca caacaacaat gacggtttga tgcgggtgca   6120
tacatctttt cctccgacac cggtcaaggg catttacaac aaaaatcagt aaggcaaacg   6180
gtgctatccg aagtggtgtt ggagaggacc gaattggaga tttcgtatgc cccgcgcctc   6240
gaccaagaaa aagaagaatt actacgcaag aaattacagt taaatcccac acctgctaac   6300
agaagcagat accagtccag gaaggtggag aacatgaaag ccataacagc tagacgtatt   6360
ctgcaaggcc tagggcatta tttgaaggca gaaggaaaag tggagtgcta ccgaaccctg   6420
catcctgttc ctttgtattc atctagtgtg aaccgtgcct tttcaagccc caaggtcgca   6480
gtggaagcct gtaacgccat gttgaaagag aactttccga ctgtggcttc ttactgtatt   6540
attccagagt acgatgccta tttggacatg gttgacggag cttcatgctg cttagacact   6600
gccagttttt gccctgcaaa gctgcgcagc tttccaaaga aacactccta tttggaaccc   6660
acaatacgat cggcagtgcc ttcagcgatc cagaacacgc tccagaacgt cctggcagct   6720
gccacaaaaa gaaattgcaa tgtcacgcaa atgagagaat tgcccgtatt ggattcggcg   6780
gcctttaatg tggaatgctt caagaaatat gcgtgtaata atgaatattg ggaaacgttt   6840
aaagaaaacc ccatcaggct tactgaagaa aacgtggtaa attacattac caaattaaaa   6900
ggaccaaaag ctgctgctct tttgcgaag acacataatt tgaatatgtt gcaggacata   6960
ccaatggaca ggtttgtaat ggacttaaag agagacgtga aagtgactcc aggaacaaaa   7020
catactgaag aacggcccaa ggtacaggtg atccaggctg ccgatccgct agcaacagcg   7080
tatctgtgcg gaatccaccg agagctggtt aggagattaa atgcggtcct gcttccgaac   7140
attcatacac tgtttgatat gtcggctgaa gactttgacg ctattatagc cgagcacttc   7200
cagcctgggg attgtgttct ggaaactgac atcgcgtcgt ttgataaaag tgaggacgac   7260
gccatggctc tgaccgcgtt aatgattctg gaagacttag gtgtggacgc agagctgttg   7320
acgctgattg aggcggcttt cggcgaaatt tcatcaatac atttgcccac taaaactaaa   7380
tttaaattcg gagccatgat gaaatctgga atgttcctca cactgtttgt gaacacagtc   7440
attaacattg taatcgcaag cagagtgttg agagaacggc taaccggatc caccatgtgca  7500
gcattcattg gagatgacaa tatcgtgaaa ggagtcaaat cggacaaatt aatggcagac   7560
aggtgcgcca cctggttgaa tatggaagtc aagattatag atgctgtggt gggcgagaaa   7620
gcgccttatt tctgtggagg gtttattttg tgtgactccg tgaccggcac agcgtgccgt   7680
gtggcagacc ccctaaaaag gctgtttaag cttggcaaac ctctggcagc agacgatgaa   7740
catgatgatg acaggagaag ggcattgcat gaagagtcaa cacgctggaa ccgagtgggt   7800
attctttcag agctgtgcaa ggcagtagaa tcaaggtatg aaaccgtagg aacttccatc   7860
atagttatgg ccatgactac tctagctagc agtgttaaat cattcagcta cctgagaggg   7920
```

```
gcccctataa ctctctacgg ctaacctgaa tggactacga catagtctag tccgccaaga   7980

tatcgcacca tagtcagcat agtacatttc atctgactaa tactacaaca ccaccaccat   8040

gaatagagga ttctttaaca tgctcggccg ccgccccttc ccggccccca ctgccatgtg   8100

gaggccgcgg agaaggaggc aggcggcccc gatgatggaa aatatggaaa acgacgagaa   8160

catcgtggtg ggccccaagc ccttctaccc catcgaggaa ggcagcgccg gcacccagct   8220

gcggaagtac atggaaagat acgccaagct gggcgccatt gccttcacca acgccgtgac   8280

cggcgtggac tacagctacg ccgagtacct ggaaaagagc tgctgcctgg gcaaggctct   8340

gcagaactac ggcctggtgg tggacggccg gatcgccctg tgcagcgaga actgcgagga   8400

attcttcatc cccgtgatcg ccggcctgtt catcggcgtg ggcgtggctc ccaccaacga   8460

gatctacacc ctgcgggagc tggtgcacag cctgggcatc agcaagccca ccatcgtgtt   8520

cagcagcaag aagggcctgg acaaagtcat caccgtgcag aaaaccgtga ccaccatcaa   8580

gaccatcgtg atcctggaca gcaaggtgga ctaccggggc taccagtgcc tggacacctt   8640

catcaagcgg aacacccccc ctggcttcca ggccagcagc ttcaagaccg tggaggtgga   8700

ccggaaagaa caggtggccc tgatcatgaa cagcagcggc agcaccggcc tgcccaaggg   8760

cgtgcagctg acccacgaga acaccgtgac ccggttcagc cacgccaggg accccatcta   8820

cggcaaccag gtgtcccccg gcaccgccgt gctgaccgtg gtgcccttcc accacggctt   8880

cggcatgttc accaccctgg gctacctgat ctgcggcttc cgggtggtga tgctgaccaa   8940

gttcgacgag gaaaccttcc tgaaaaccct gcaggactac aagtgcacct acgtgattct   9000

ggtgcccacc ctgttcgcca tcctgaacaa gagcgagctg ctgaacaagt acgacctgag   9060

caacctggtg gagatcgcca gcggcggagc ccccctgagc aaagaagtgg gagaggccgt   9120

cgccaggcgg ttcaatctgc ccggcgtgcg gcagggctac ggcctgaccg agacaaccag   9180

cgccatcatc atcacccccg agggcgacga caagcctgga gccagcggca aggtggtgcc   9240

cctgttcaag gccaaagtga tcgacctgga caccaagaag agcctgggcc ccaacagacg   9300

gggcgaagtg tgcgtgaagg gccccatgct gatgaagggc tacgtgaaca accccgaggc   9360

caccaaagag ctgatcgacg aagagggctg gctgcacacc ggcgacatcg gctactacga   9420

cgaagagaag cacttcttca tcgtggaccg gctgaagagc ctgatcaagt acaagggcta   9480

tcaggtgccc cctgccgagc tggaaagcgt cctgctgcag caccccagca tcttcgacgc   9540

cggcgtggcc ggggtgccag atcctgtggc cggcgagctg cctggcgccg tggtggtgct   9600

ggaatccggc aagaacatga ccgagaaaga agtgatggac tacgtcgcca gccaggtgtc   9660

caacgccaag cggctgagag gcggcgtgag attcgtggac gaagtgccaa agggcctgac   9720

cggcaagatc gacggcaggg ccatccggga gatcctgaag aaacccgtgg ccaagatgtg   9780

attaattgat cgatacagca gcaattggca agctgcttac atagaaggcg cgccgtttaa   9840

acggccggcc ttaattaagt aacgatacag cagcaattgg caagctgctt acatagaact   9900

cgcggcgatt ggcatgccgc tttaaaattt ttattttatt tttctttttct tttccgaatc   9960

ggattttgtt tttaatattt caaaaaaaaa aaaaaaaaaa aaaaaaaaaa aaaaaaaaaa  10020

a                                                                  10021
```

<210> SEQ ID NO 30
<211> LENGTH: 1150
<212> TYPE: DNA
<213> ORGANISM: Artificial Sequence
<220> FEATURE:

<223> OTHER INFORMATION: Synthetic polynucleotide
<220> FEATURE:
<221> NAME/KEY: misc_feature
<223> OTHER INFORMATION: g-block for Alpha-R-DLP-2A-rFF

<400> SEQUENCE: 30
tctacggcta acctgaatgg actacgacat agtctagtcc gccaagatat cgcaccatag 60
tcagcatagt acatttcatc tgactaatac tacaacacca ccaccatgaa tagaggattc 120
tttaacatgc tcggccgccg cccccttcccg gcccccactg ccatgtggag gccgcggaga 180
aggaggcagg cggccccggg aagcggagct actaacttca gcctgctgaa gcaggctgga 240
gacgtggagg agaaccctgg acctatggaa aatatggaaa acgacgagaa catcgtggtg 300
ggccccaagc ccttctaccc catcgaggaa ggcagcgccg gcacccagct gcggaagtac 360
atggaaagat acgccaagct gggcgccatt gccttcacca acgccgtgac cggcgtggac 420
tacagctacg ccgagtacct ggaaaagagc tgctgcctgg gcaaggctct gcagaactac 480
ggcctggtgg tggacggccg gatcgccctg tgcagcgaga actgcgagga attcttcatc 540
cccgtgatcg ccggcctgtt catcggcgtg ggcgtggctc ccaccaacga gatctacacc 600
ctgcgggagc tggtgcacag cctgggcatc agcaagccca ccatcgtgtt cagcagcaag 660
aagggcctgg acaaagtcat caccgtgcag aaaaccgtga ccaccatcaa gaccatcgtg 720
atcctggaca gcaaggtgga ctaccggggc taccagtgcc tggacacctt catcaagcgg 780
aacacccccc ctggcttcca ggccagcagc ttcaagaccg tggaggtgga ccggaaagaa 840
caggtggccc tgatcatgaa cagcagcggc agcaccggcc tgcccaaggg cgtgcagctg 900
acccacgaga acaccgtgac ccggttcagc cacgccaggg accccatcta cggcaaccag 960 gtgtccccccg gcaccgccgt gctgaccgtg gtgcccttcc accacggctt cggcatgttc 1020
accaccctgg gctacctgat ctgcggcttc cgggtggtga tgctgaccaa gttcgacgag 1080
gaaaccttcc tgaaaaccct gcaggactac aagtgcacct acgtgattct ggtgcccacc 1140
ctgttcgcca 1150

<210> SEQ ID NO 31
<211> LENGTH: 1150
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: g-block for Alpha-R-DLP-2A-nsp-DLP-2A-rFF

<400> SEQUENCE: 31
tctacggcta acctgaatgg actacgacat agtctagtcc gccaagatat cgcaccatag 60
tcagcatagt acatttcatc tgactaatac tacaacacca ccaccatgaa tagaggattc 120
tttaacatgc tcggccgccg ccccttcccg gcccccactg ccatgtggag gccgcggaga 180
aggaggcagg cggccccggg aagcggagct actaacttca gcctgctgaa gcaggctgga 240
gacgtggagg agaaccctgg acctatggaa aatatggaaa acgacgagaa catcgtggtg 300
ggccccaagc ccttctaccc catcgaggaa ggcagcgccg gcacccagct gcggaagtac 360
atggaaagat acgccaagct gggcgccatt gccttcacca acgccgtgac cggcgtggac 420
tacagctacg ccgagtacct ggaaaagagc tgctgcctgg gcaaggctct gcagaactac 480
ggcctggtgg tggacggccg gatcgccctg tgcagcgaga actgcgagga attcttcatc 540
cccgtgatcg ccggcctgtt catcggcgtg ggcgtggctc ccaccaacga gatctacacc 600
ctgcgggagc tggtgcacag cctgggcatc agcaagccca ccatcgtgtt cagcagcaag 660
aagggcctgg acaaagtcat caccgtgcag aaaaccgtga ccaccatcaa gaccatcgtg 720
atcctggaca gcaaggtgga ctaccggggc taccagtgcc tggacacctt catcaagcgg 780 aacaccccc ctggcttcca ggccagcagc ttcaagaccg tggaggtgga ccggaaagaa 840
caggtggccc tgatcatgaa cagcagcggc agcaccggcc tgcccaaggg cgtgcagctg 900
acccacgaga acaccgtgac ccggttcagc cacgccaggg accccatcta cggcaaccag 960
gtgtcccccg gcaccgccgt gctgaccgtg gtgcccttcc accacggctt cggcatgttc 1020
accaccctgg gctacctgat ctgcggcttc cgggtggtga tgctgaccaa gttcgacgag 1080
gaaaccttcc tgaaaaccct gcaggactac aagtgcacct acgtgattct ggtgcccacc 1140
ctgttcgcca 1150

<210> SEQ ID NO 32
<211> LENGTH: 25
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer Alpha-3'nsp4-F
<220> FEATURE:
<221> NAME/KEY: misc_feature
<223> OTHER INFORMATION: RP123

<400> SEQUENCE: 32
ggctgtttaa gcttggcaaa cctct 25

<210> SEQ ID NO 33
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: primer Alpha-3'nsp4-F
<220> FEATURE:
<221> NAME/KEY: misc_feature
<223> OTHER INFORMATION: rFF-seq1

<400> SEQUENCE: 33
agcgagaact gcgaggaatt ctt 23

<210> SEQ ID NO 34
<211> LENGTH: 12342
<212> TYPE: DNA
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Construct rEx-rFF

<400> SEQUENCE: 34
gctcgaagtg tgtatggtgc catatacggc tcaccaccat atacactgca agaattacta 60
ttcttgtggg cccctctcgg taaatcctag agggctttcc tctcgttatt gcgagattcg 120
tcgttagata acggcaagtt ccctttctta ctatcctatt ttcatcttgt ggcttgacgg 180
gtcactgcca tcgtcgtcga tctctatcaa ctacccttgc gactatggca accttctccg 240
ctactggatt tggagggagt tttgttaggg actggtccct ggacttaccc gacgcttgtg 300

-continued

```
agcatggcgc gggattgtgc tgcgaagtgg acggctccac cttatgcgcc gagtgttttc    360
gcggttgcga aggaatggag caatgtcctg gcttgttcat gggactgtta aaactggctt    420
cgccagttcc agtgggacat aagttcctga ttggttggta tcgagctgcc aaagtcaccg    480
ggcgttacaa tttccttgag ctgttgcaac accctgcttt cgcccagctg cgtgtggttg    540
atgctaggtt agccattgaa gaggcaagtg tgtttatttc cactgaccac gcgtctgcta    600
agcgtttccc tggcgctaga tttgcgctga caccggtgta tgctaacgct tgggttgtga    660
gcccggctgc taacagtttg atagtgacca ctgaccagga acaagatggg ttctgctggt    720
taaaactttt gccacctgac cgccgtgagg ctggtttgcg gttgtattac aaccattacc    780
gcgaacaaag gaccgggtgg ctgtctaaaa caggacttcg cttatggctt ggagacctgg    840
gtttgggcat caatgcgagc tctggagggc tgaaattcca cattatgagg ggttcgcctc    900
agcgagcttg gcatatcaca acacgcagct gcaagctgaa gagctactac gtttgtgaca    960
tctctgaagc agactggtcc tgtttgcctg ctggcaacta cggcggctac aatccaccag   1020
gggacggagc ttgcggttac aggtgcttgg ccttcatgaa tggcgccact gttgtgtcgg   1080
ctggttgcag ttctgacttg tggtgtgatg atgagttggc ttatcgagtc tttcaattgt   1140
cacccacgtt cacggttacc atcccaggtg ggcgagtttg tccgaatgcc aagtacgcaa   1200
tgatttgtga caagcagcac tggcgcgtca aacgtgcaaa gggcgtcggc ctgtgtctcg   1260
atgaaagctg tttcaggggc atctgcaatt gccaacgcat gagtggacca ccacctgcac   1320
ccgtgtcagc cgccgtgtta gatcacatac tggaggcggc gacgtttggc aacgttcgcg   1380
tggttacacc tgaagggcag ccacgccccg taccagcgcc gcgagttcgt cccagcgcca   1440
actcttctgg agatgtcaaa gatccggcgc ccgttccgcc agtaccaaaa ccaaggacca   1500
agcttgccac accgaaccca actcaggcgc ccatcccagc accgcgcacg cgacttcaag   1560
gggcctcaac acaggagcca ctggcgagtg caggagttgc ttctgactcg gcacctaaat   1620
ggcgtgtggc caaaactgtg tacagctccg cggagcgctt tcggaccgaa ctggtacaac   1680
gtgctcggtc cgttggggac gttcttgttc aagcgctacc gctcaaaacc ccagcagtgc   1740
agcggtatac catgactctg aagatgatgc gttcacgctt cagttggcac tgcgacgtgt   1800
ggtacccttt ggctgtaatc gcttgtttgc tccctatatg gccatctctt gctttgctcc   1860
ttagctttgc cattgggttg atacccagtg tgggcaataa tgttgttctg acagcgcttc   1920
tggtttcatc agctaattat gttgcgtcaa tggaccatca atgtgaaggt gcggcttgct   1980
tagccttgct ggaagaagaa cactattata gagcggtccg ttggcgcccg attacaggcg   2040
cgctgtcgct tgtgctcaat ttactggggc aggtaggcta tgtagctcgt tccacctttg   2100
atgcagctta tgttccttgc actgtgttcg atctttgcag ctttgctatt ctgtacctct   2160
gccgcaatcg ttgctggaga tgcttcggac gctgtgtgcg agttgggcct gccacgcatg   2220
ttttgggctc caccgggcaa cgagtttcca aactggcgct cattgatttg tgtgaccact   2280
tttcaaagcc caccatcgat gttgtgggca tggcaactgg ttggagcgga tgttacacag   2340
gaaccgccgc aatggagcgt cagtgtgcct ctacggtgga ccctcactcg ttcgaccaga   2400
agaaggcagg agcgactgtt tacctcaccc cccctgtcaa cagcgggtca gcgctgcagt   2460
gcctcaatgt catgtggaag cgaccaattg ggtccactgt ccttggggaa caaacaggag   2520
ctgttgtgac ggcggtcaag agtatctctt tctcacctcc ctgctgcgtc tctaccactt   2580
tgcccacccg acccggtgtg accgttgtcg accatgctct ttacaaccgg ttgactgctt   2640
```

-continued

```
caggggtcga tcccgcttta ttgcgtgttg ggcaaggtga ttttctaaaa cttaatccgg   2700
ggttccggct gataggtgga tggatttatg ggatatgcta ttttgtgttg gtggttgtgt   2760
caacttttac ctgcttacct atcaaatgtg gcattggcac ccgcgaccct ttctgccgca   2820
gagtgttttc tgtacccgtc accaagaccc aagagcactg ccatgctgga atgtgtgcta   2880
gcgctgaagg catctctctg gactctctgg ggttaactca gttacaaagt tactggatcg   2940
cagccgtcac tagcggatta gtgatcttgt tggtctgcca ccgcctggcc atcagcgcct   3000
tggacttgtt gactctagct tccccttttag tgttgcttgt gttcccttgg gcatctgtgg   3060
ggcttttact tgcttgcagt ctcgctggtg ctgctgtgaa aatacagttg ttggcgacgc   3120
tttttgtgaa tctattcttt ccccaagcta cccttgtcac tatgggatac tgggcgtgcg   3180
tggcggcttt ggccgtttac agtttgatgg gcttgcgagt gaaagtgaat gtgcccatgt   3240
gtgtgacacc tgcccatttt ctgctgctgg cgaggtcagc tggacagtca agagagcaga   3300
tgctccgggt cagcgctgct gcccccacca attcactgct tggagtggct cgtgattgtt   3360
atgtcacagg cacaactcgg ctgtacatac ccaaggaagg cgggatggtg tttgaagggc   3420
tattcaggtc accgaaggcg cgcggcaacg tcggcttcgt ggctggtagc agctacggca   3480
cagggtcagt gtggaccagg aacaacgagg tcgtcgtact gacagcgtca cacgtggttg   3540
gccgcgctaa catggccact ctgaagatcg gtgacgcaat gctgactctg actttcaaaa   3600
agaatggcga cttcgccgag gcagtgacga cacagtccga gctcccaggc aattggccac   3660
agttgcattt cgcccaacca acaaccgggc ccgcttcatg gtgcactgcc acaggagatg   3720
aagaaggctt gctcagtggc gaggtttgtc tggcgtggac tactagtggc gactctggat   3780
ctgcagtggt tcagggtgac gctgtggtag gggtccacac cggttcgaac acaagtggtg   3840
ttgcctacgt gaccacccca agcggaaaac tccttggcgc cgacaccgtg actttgtcat   3900
cactgtcaaa gcatttcaca ggccctttga catcaatccc gaaggacatc cctgacaaca   3960
ttattgccga tgttgatgct gttcctcgtt ctctggccat gctgattgat ggcttatcca   4020
atagagagag cagcctttct ggacctcagt tgttgttaat tgcttgtttt atgtggtctt   4080
atcttaacca acctgcttac ttgccttatg tgctgggctt ctttgccgct aacttcttcc   4140
tgccaaaaag tgttggccgc cctgtggtca ctgggcttct atggttgtgc tgcctcttca   4200
caccgctttc catgcgcttg tgcttgttcc atctggtctg tgctaccgtc acgggaaacg   4260
tgatatcttt gtggttctac atcactgccg ctggcacgtc ttacctttct gagatgtggt   4320
tcggaggcta tcccaccatg ttgtttgtgc cacggttcct agtgtaccag ttccccggct   4380
gggctattgg cacagtacta gcggtatgca gcatcaccat gctggctgct gccctcggtc   4440
acaccctgtt actggatgtg ttctccgcct caggtcgctt tgacaggact ttcatgatga   4500
aatacttcct ggagggagga gtgaaagaga gtgtcaccgc ctcagtcacc cgcgcttatg   4560
gcaaaccaat tacccaggag agtctcactg caacattagc tgccctcact gatgatgact   4620
tccaattcct ctctgatgtg cttgactgtc gggccgtccg atcggcaatg aatctgcgtg   4680
ccgctctcac aagttttcaa gtggcgcagt atcgtaacat ccttaatgca tccttgcaag   4740
tcgatcgtga cgctgctcgt agtcgcagac taatggcaaa actggctgat tttgcggttg   4800
aacaagaagt aacagctgga gaccgtgttg tggttatcga cggtctggac cgcatggctc   4860
acttcaaaga cgatttggtg ctggttcctt tgaccaccaa agtagtaggc ggttctaggt   4920
gcaccatttg tgacgtcgtt aaggaagaag ccaatgacac cccagttaag ccaatgccca   4980
gcaggagacg ccgcaagggc ctgcctaaag gtgctcagtt ggagtgggac cgtcaccagg   5040
```

-continued aagagaagag gaacgccggt gatgatgatt ttgcggtctc gaatgattat gtcaagagag 5100
tgccaaagta ctgggatccc agcgacaccc gaggcacgac agtgaaaatc gccggcacta 5160
cctatcagaa agtggttgac tattcaggca atgtgcatta cgtggagcat caggaagatc 5220
tgctagacta cgtgctgggc aaggggagct atgaaggcct agatcaggac aaagtgttgg 5280
acctcacaaa catgcttaaa gtggacccca cggagctctc ctccaaagac aaagccaagg 5340
cgcgtcagct tgctcatctg ctgttggatc tggctaaccc agttgaggca gtgaatcagt 5400
taaactgaga gcgccccaca tctttcccgg cgatgtgggg cgtcggacct ttgctgactc 5460
taaagacaag ggtttcgtgg ctctacacag tcgcacaatg tttttagctg cccgggactt 5520
tttatttaac atcaaatttg tgtgcgacga agagttcaca aagaccccaa aagacacact 5580
gcttgggtac gtacgcgcct gccctggtta ctggtttatt ttccgtcgta cgcaccggtc 5640
gctgattgat gcatactggg acagtatgga gtgcgtttac gcgcttccca ccatatctga 5700
ttttgatgtg agcccaggtg acgtcgcagt gacgggcgag cgatgggatt ttgaatctcc 5760
cggaggaggc cgtgcaaaac gtctcacagc tgatctggtg cacgcttttc aagggttcca 5820
cggagcctct tattcctatg atgacaaggt ggcagctgct gtcagtggtg acccgtatcg 5880
gtcggacggc gtcttgtata acacccgttg gggcaacatt ccatattctg tcccaaccaa 5940
tgctttggaa gccacagctt gctaccgtgc tggatgtgag gccgttaccg acgggaccaa 6000
cgtcatcgca acaattgggc ccttcccgga gcaacaaccc ataccggaca tcccaaagag 6060
cgtgcttgac aactgcgctg acatcagctg tgacgctttc atagcgcccg ctgcagagac 6120
agccctgtgt ggagatttag agaaatacaa cctatccacg cagggttttg tgttgcctag 6180
tgttttctcc atggtgcggg cgtacttaaa agaggagatt ggagacgctc caccactcta 6240
cttgccatct actgtaccat ctaaaaattc acaagccgga attaacggcg ctgagtttcc 6300
tacaaagtct ttacagagct actgtttgat tgatgacatg gtgtcacagt ccatgaaaag 6360
caatctacaa accgccacca tggcgacttg taaacggcaa tactgttcca aatacaagat 6420
taggagcatt ctgggcacca acaattacat tggcctaggt ttgcgtgcct gcctttcggg 6480
ggttacggcc gcattccaaa aagctggaaa ggatgggtca ccgatttatt tgggcaagtc 6540
aaaattcgac ccgataccag ctcctgacaa gtactgcctt gaaacagacc tggagagttg 6600
tgatcgctcc accccggctt tggtgcgttg gttcgctact aatcttattt ttgagctagc 6660
tggccagccc gagttggtgc acagctacgt gttgaattgc tgtcacgatc tagttgtggc 6720
gggtagtgta gcattcacca aacgcggggg tttgtcatct ggagacccta tcacttccat 6780
ttccaatacc atctattcat tggtgctgta cacccagcac atgttgctat gtggacttga 6840
aggctatttc ccagagattg cagaaaaata tcttgatggc agcctggagc tgcgggacat 6900
gttcaagtac gttcgagtgt acatctactc ggacgatgtg gttctaacca cacccaacca 6960
gcattacgcg gccagctttg accgctgggt cccccacctg caggcgctgc taggtttcaa 7020
ggttgaccca aagaaaactg tgaacaccag ctccccttcc tttttgggct gccggttcaa 7080
gcaagtggac ggcaagtgtt atctagccag tcttcaggac cgcgttacac gctctctgtt 7140
ataccacatt ggtgcaaaga atccctcaga gtactatgaa gctgctgttt ccatctttaa 7200
ggactccatt atctgctgtg atgaagactg gtggacggac ctccatcgac gtatcagtgg 7260
cgctgcgcgt accgacggag ttgagttccc caccattgaa atgttaacat ccttccgcac 7320
caagcagtat gagagtgccg tgtgcacagt ttgtggggcc gcccccgtgg ccaagtctgc 7380

-continued ttgtggaggg tggttctgtg gcaattgtgt cccgtaccac gcgggtcatt gtcacacaac 7440
ctcgctcttc gccaactgcg ggcacgacat catgtaccgc tccacttact gcacaatgtg 7500
tgagggttcc ccaaaacaga tggtaccaaa agtgcctcac ccgatcctgg atcatttgct 7560
gtgccacatt gattacggca gtaaagagga actaactctg gtagtggcgg atggtcgaac 7620
aacatcaccg cccgggcgct acaaagtggg tcacaaggta gtcgccgtgg ttgcagatgt 7680
gggaggcaac attgtgtttg ggtgcggtcc tggatcacac atcgcagtac cacttcagga 7740
tacgctcaag ggcgtggtgg tgaataaagc tctgaagaac gccgccgcct ctgagtacgt 7800
ggaaggaccc cctgggagtg ggaagacttt tcacctggtc aaagatgtgc tagccgtggt 7860
cggtagcgcg accttggttg tgcccaccca cgcgtccatg ctggactgca tcaacaagct 7920
caaacaagcg ggcgccgatc catactttgt ggtgcccaag tatacagttc ttgactttcc 7980
ccggcctggc agtggaaaca tcacagtgcg actgccacag gtcggaacca gtgagggaga 8040
aacctttgtg gatgaggtgg cctacttctc accagtggat ctggcgcgca ttttaaccca 8100
gggtcgagtc aagggttacg gtgatttaaa tcagctcggg tgcgtcggac ccgcgagcgt 8160
gccacgtaac ctttggctcc gacattttgt cagcctggag cccttgcgag tgtgccatcg 8220
attcggcgct gctgtgtgtg atttgatcaa gggcatttat ccttattatg agccagctcc 8280
acataccact aaagtggtgt ttgtgccaaa tccagacttt gagaaaggtg tagtcatcac 8340
cgcctaccac aaagatcgcg gtcttggtca ccgcacaatt gattcaattc aaggctgtac 8400
attccctgtt gtgactcttc gactgcccac accccaatca ctgacgcgcc cgcgcgcagt 8460
tgtggcggtt actagggcgt ctcaggaatt atacatctac gacccctttg atcagcttag 8520
cgggttgttg aagttcacca aggaagcaga ggcgcaggac ttgatccatg gcccacctac 8580
agcatgccac ctgggccaag aaattgacct ttggtccaat gagggcctcg aatattacaa 8640
ggaagtcaac ctgctgtaca cacacgtccc catcaaggat ggtgtaatac acagttaccc 8700
taattgtggc cctgcctgtg gctgggaaaa gcaatccaac aaaatttcgt gcctcccgag 8760
agtggcacaa aatttgggct accactattc cccagactta ccaggatttt gccccatacc 8820
aaaagaactc gctgagcatt ggcccgtagt gtccaatgat agatacccga attgcttgca 8880
aattacctta cagcaagtat gtgaactcag taaaccgtgc tcagcgggct atatggttgg 8940
acaatcggtt ttcgtgcaga cgcctggtgt gacatcttac tggcttactg aatgggtcga 9000
cggcaaagcg cgtgctctac cagattcctt attctcgtcc ggtaggttcg agactaacag 9060
ccgcgctttc ctcgatgaag ccgaggaaaa gtttgccgcc gctcaccctc atgcctgttt 9120
gggagaaatt aataagtcca ccgtgggagg atcccacttc atcttttccc aatatttacc 9180
accattgcta cccgcagacg ctgttgccct ggtaggtgct tcattggctg ggaaagctgc 9240
taaagctgct tgcagcgttg ttgatgtcta tgctccatca tttgaacctt atctacaccc 9300
tgagacactg agtcgcgtgt acaagattat gatcgatttc aagccgtgta ggcttatggt 9360
gtggagaaac gcgacctttt atgtccaaga gggtgttgat gcagttacat cagcactagc 9420
agctgtgtcc aaactcatca aagtgccggc caatgagcct gtttcattcc atgtggcatc 9480
agggtacaga accaacgcgc tggtagcgcc ccaggctaaa atttcaattg gagcctacgc 9540
cgccgagtgg gcactgtcaa ctgaaccgcc acctgctggt tatgcgatcg tgcggcgata 9600
tattgtaaag aggctcctca gctcaacaga agtgttcttg tgccgcaggg gtgttgtgtc 9660
ttccacctca gtgcagacca tttgtgcact agagggatgt aaacctctgt tcaacttctt 9720
acaaattggt tcagtcattg ggcccgtgtg actctagagt ggacctgttc ccatccccg 9780

-continued

```
ctcaactact caggtagtgg ttcgcggcaa cgggtacacc gcagttggta acaagcttgt   9840
cgatggaaaa tatggaaaac gacgagaaca tcgtggtggg ccccaagccc ttctacccca   9900
tcgaggaagg cagcgccggc acccagctgc ggaagtacat ggaaagatac gccaagctgg   9960
gcgccattgc cttcaccaac gccgtgaccg gcgtggacta cagctacgcc gagtacctgg  10020
aaaagagctg ctgcctgggc aaggctctgc agaactacgg cctggtggtg gacggccgga  10080
tcgccctgtg cagcgagaac tgcgaggaat tcttcatccc cgtgatcgcc ggcctgttca  10140
tcggcgtggg cgtggctccc accaacgaga tctacaccct gcgggagctg gtgcacagcc  10200
tgggcatcag caagcccacc atcgtgttca gcagcaagaa gggcctggac aaagtcatca  10260
ccgtgcagaa aaccgtgacc accatcaaga ccatcgtgat cctggacagc aaggtggact  10320
accggggcta ccagtgcctg gacaccttca tcaagcggaa caccccccct ggcttccagg  10380
ccagcagctt caagaccgtg gaggtggacc ggaaagaaca ggtggccctg atcatgaaca  10440
gcagcggcag caccggcctg cccaagggcg tgcagctgac ccacgagaac accgtgaccc  10500
ggttcagcca cgccagggac cccatctacg gcaaccaggt gtcccccggc accgccgtgc  10560
tgaccgtggt gcccttccac cacggcttcg gcatgttcac caccctgggc tacctgatct  10620
gcggcttccg ggtggtgatg ctgaccaagt tcgacgagga aaccttcctg aaaaccctgc  10680
aggactacaa gtgcacctac gtgattctgg tgcccaccct gttcgccatc ctgaacaaga  10740
gcgagctgct gaacaagtac gacctgagca acctggtgga gatcgccagc ggcggagccc  10800
ccctgagcaa agaagtggga gaggccgtcg ccaggcggtt caatctgccc ggcgtgcggc  10860
agggctacgg cctgaccgag acaaccagcg ccatcatcat caccccccgag ggcgacgaca  10920
agcctggagc cagcggcaag gtggtgcccc tgttcaaggc caaagtgatc gacctggaca  10980
ccaagaagag cctgggcccc aacagacggg gcgaagtgtg cgtgaagggc cccatgctga  11040
tgaagggcta cgtgaacaac cccgaggcca ccaaagagct gatcgacgaa gagggctggc  11100
tgcacaccgg cgacatcggc tactacgacg aagagaagca cttcttcatc gtggaccggc  11160
tgaagagcct gatcaagtac aagggctatc aggtgccccc tgccgagctg gaaagcgtcc  11220
tgctgcagca ccccagcatc ttcgacgccg gcgtggccgg ggtgccagat cctgtggccg  11280
gcgagctgcc tggcgccgtg gtggtgctgg aatccggcaa gaacatgacc gagaaagaag  11340
tgatggacta cgtcgccagc caggtgtcca acgccaagcg gctgagaggc ggcgtgagat  11400
tcgtggacga agtgccaaag ggcctgaccg gcaagatcga cggcagggcc atccgggaga  11460
tcctgaagaa acccgtggcc aagatgtgat tataactcga gggagccata gattcatttt  11520
gtggtgacgg gattttaggt gagtatctag attactttat tctgtccgtc ccactcttgc  11580
tgttgcttac taggtatgta gcatctgggt tagtgtatgt tttgactgcc ttgttctatt  11640
cctttgtatt agcagcttat atttggtttg ttatagttgg aagagccttt tctactgctt  11700
atgcttttgt gcttttggct gcttttctgt tattagtaat gaggatgatt gtgggtatga  11760
tgcctcgtct tcggtccatt ttcaaccatc gccaactggt ggtagctgat tttgtggaca  11820
cacctagtgg acctgttccc atcccccgcc caaccactca ggtagtggtt cgcggcaacg  11880
ggtacaccgc agttggtaac aagcttgtcg atggcgtcaa gacgatcacg tccgcaggcc  11940
gcctcttttc gaaacggacg gcggcgacag cctacaagct acaatgacct actgcgcatg  12000
tttggtcaga tgcgggtccg caaaccgccc gcgcaaccca ctcaggctat tattgcagag  12060
cctggagacc ttaggcatga tttaaatcaa caggagcgcg ccaccctttc gtcgaacgta  12120
```

-continued caacggttct tcatgattgg gcatggttca ctcactgcag atgccggagg actcacgtac 12180
accgtcagtt gggttcctac caaacaaatc cagcgcaaag ttgcgcctcc agcagggccg 12240
taagacgtgg atattctcct gtgtggcgtc atgttgaagt agttattagc cacccaggaa 12300
ccaaaaaaaa aaaaaaaaaa aaaaaaaaaa aaaaaaaaaa aa 12342

<210> SEQ ID NO 35
<211> LENGTH: 8554
<212> TYPE: DNA
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: Construct Alpha-R-eGFP

<400> SEQUENCE: 35
ataggcggcg catgagagaa gcccagacca attacctacc caaaatggag aaagttcacg 60
ttgacatcga ggaagacagc ccattcctca gagctttgca gcggagcttc ccgcagtttg 120
aggtagaagc caagcaggtc actgataatg accatgctaa tgccagagcg ttttcgcatc 180
tggcttcaaa actgatcgaa acggaggtgg acccatccga cacgatcctt gacattggaa 240
gtgcgcccgc ccgcagaatg tattctaagc acaagtatca ttgtatctgt ccgatgagat 300
gtgcggaaga tccggacaga ttgtataagt atgcaactaa gctgaagaaa aactgtaagg 360
aaataactga taaggaattg gacaagaaaa tgaaggagct cgccgccgtc atgagcgacc 420
ctgacctgga aactgagact atgtgcctcc acgacgacga gtcgtgtcgc tacgaagggc 480
aagtcgctgt ttaccaggat gtatacgcgg ttgacggacc gacaagtctc tatcaccaag 540
ccaataaggg agttagagtc gcctactgga taggctttga caccacccct tttatgttta 600
agaacttggc tggagcatat ccatcatact ctaccaactg ggccgacgaa accgtgttaa 660
cggctcgtaa cataggccta tgcagctctg acgttatgga gcggtcacgt agagggatgt 720
ccattcttag aaagaagtat ttgaaaccat ccaacaatgt tctattctct gttggctcga 780
ccatctacca cgagaagagg gacttactga ggagctggca cctgccgtct gtatttcact 840
tacgtggcaa gcaaaattac acatgtcggt gtgagactat agttagttgc gacgggtacg 900
tcgttaaaag aatagctatc agtccaggcc tgtatgggaa gccttcaggc tatgctgcta 960
cgatgcaccg cgagggattc ttgtgctgca aagtgacaga cacattgaac ggggagaggg 1020
tctcttttcc cgtgtgcacg tatgtgccag ctacattgtg tgaccaaatg actggcatac 1080
tggcaacaga tgtcagtgcg gacgacgcgc aaaaactgct ggttgggctc aaccagcgta 1140
tagtcgtcaa cggtcgcacc cagagaaaca ccaataccat gaaaaattac cttttgcccg 1200
tagtggccca ggcatttgct aggtgggcaa aggaatataa ggaagatcaa gaagatgaaa 1260
ggccactagg actacgagat agacagttag tcatggggtg ttgttgggct tttagaaggc 1320
acaagataac atctatttat aagcgcccgg atacccaaac catcatcaaa gtgaacagcg 1380
atttccactc attcgtgctg cccaggatag gcagtaacac attggagatc gggctgagaa 1440
caagaatcag gaaaatgtta gaggagcaca aggagccgtc acctctcatt accgccgagg 1500
acgtacaaga agctaagtgc gcagccgatg aggctaagga ggtgcgtgaa gccgaggagt 1560
tgcgcgcagc tctaccacct ttggcagctg atgttgagga gcccactctg gaagccgatg 1620
tcgacttgat gttacaagag gctggggccg gctcagtgga gacacctcgt ggcttgataa 1680
aggttaccag ctacgatggc gaggacaaga tcggctctta cgctgtgctt tctccgcagg 1740

-continued

```
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctctgaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag   4080
gagtgattat aaatgctgct aacagcaaag gacaacctgg cggaggggtg tgcggagcgc   4140
```

tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480

-continued

```
aaggaccaaa agctgctgct ctttttgcga agacacataa tttgaatatg ttgcaggaca   6540

taccaatgga caggtttgta atggacttaa agagagacgt gaaagtgact ccaggaacaa   6600

aacatactga agaacggccc aaggtacagg tgatccaggc tgccgatccg ctagcaacag   6660

cgtatctgtg cggaatccac cgagagctgg ttaggagatt aaatgcggtc ctgcttccga   6720

acattcatac actgtttgat atgtcggctg aagactttga cgctattata gccgagcact   6780

tccagcctgg ggattgtgtt ctggaaactg acatcgcgtc gtttgataaa agtgaggacg   6840

acgccatggc tctgaccgcg ttaatgattc tggaagactt aggtgtggac gcagagctgt   6900

tgacgctgat tgaggcggct ttcggcgaaa tttcatcaat acatttgccc actaaaacta   6960

aatttaaatt cggagccatg atgaaatctg gaatgttcct cacactgttt gtgaacacag   7020

tcattaacat tgtaatcgca agcagagtgt tgagagaacg gctaaccgga tcaccatgtg   7080

cagcattcat tggagatgac aatatcgtga aaggagtcaa atcggacaaa ttaatggcag   7140

acaggtgcgc cacctggttg aatatggaag tcaagattat agatgctgtg gtgggcgaga   7200

aagcgcctta tttctgtgga gggtttattt tgtgtgactc cgtgaccggc acagcgtgcc   7260

gtgtggcaga cccccctaaaa aggctgttta agcttggcaa acctctggca gcagacgatg   7320

aacatgatga tgacaggaga agggcattgc atgaagagtc aacacgctgg aaccgagtgg   7380

gtattctttc agagctgtgc aaggcagtag aatcaaggta tgaaaccgta ggaacttcca   7440

tcatagttat ggccatgact actctagcta gcagtgttaa atcattcagc tacctgagag   7500

gggcccctat aactctctac ggctaacctg aatggactac gacatagtct agtccgccaa   7560

gatatcgcac catgggaaga gccggcgtga gcaagggcga ggagctgttc accggggtgg   7620

tgcccatcct ggtcgagctg gacggcgacg taaacggcca caagttcagc gtgtccggcg   7680

agggcgaggg cgatgccacc tacggcaagc tgaccctgaa gctgatctgc accaccggca   7740

agctgcccgt gccctggccc accctcgtga ccaccctggg ctacggcctg cagtgcttcg   7800

cccgctaccc cgaccacatg aagcagcacg acttcttcaa gtccgccatg cccgaaggct   7860

acgtccagga gcgcaccatc ttcttcaagg acgacggcaa ctacaagacc cgcgccgagg   7920

tgaagttcga gggcgacacc ctggtgaacc gcatcgagct gaagggcatc gacttcaagg   7980

aggacggcaa catcctgggg cacaagctgg agtacaacta caacagccac aacgtctata   8040

tcaccgccga caagcagaag aacggcatca aggccaactt caagatccgc cacaacatcg   8100

aggacggcgg cgtgcagctc gccgaccact accagcagaa cacccccatc ggcgacggcc   8160

ccgtgctgct gcccgacaac cactacctga gctaccagtc cgccctgagc aaagacccca   8220

acgagaagcg cgatcacatg gtcctgctgg agttcgtgac cgccgccggg atcactctcg   8280

gcatggacga gctgtacaag taggctcttc gtaattaatt gatcgataca gcagcaattg   8340

gcaagctgct tacatagaag gcgcgccgtt taaacggccg gccttaatta agtaacgata   8400

cagcagcaat tggcaagctg cttacataga actcgcggcg attggcatgc cgctttaaaa   8460

tttttatttt atttttcttt tcttttccga atcggatttt gtttttaata tttcaaaaaa   8520

aaaaaaaaaa aaaaaaaaaa aaaaaaaaaa aaaa                              8554
```

<210> SEQ ID NO 36
<211> LENGTH: 59
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: 5 human beta globin UTR

<400> SEQUENCE: 36
acatttgctt ctgacacaac tgtgttcact agcaacctca aacagacacc gccgccacc 59

<210> SEQ ID NO 37
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: T7 Promoter

<400> SEQUENCE: 37
taatacgact cactatag 18

<210> SEQ ID NO 38
<211> LENGTH: 142
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: DLP

<400> SEQUENCE: 38
atagtcagca tagtacattt catctgacta atactacaac accaccacca tgaatagagg 60
attctttaac atgctcggcc gccgcccctt cccggccccc actgccatgt ggaggccgcg 120
gagaaggagg caggcggccc cg 142

<210> SEQ ID NO 39
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: P2A

<400> SEQUENCE: 39
ggaagcggag ctactaactt cagcctgctg aagcaggctg gagacgtgga ggagaaccct 60
ggacct 66

<210> SEQ ID NO 40
<211> LENGTH: 846
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: dsGFP

<400> SEQUENCE: 40
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagaag 720
cttagccatg gcttcccgcc ggaggtggag gagcaggatg atggcacgct gcccatgtct 780
tgtgcccagg agagcgggat ggaccgtcac cctgcagcct gtgcttctgc taggatcaat 840
gtgtag 846

<210> SEQ ID NO 41
<211> LENGTH: 134
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: 3 Human beta globin UTR

<400> SEQUENCE: 41
gctcgctttc ttgctgtcca atttctatta aaggttcctt tgttccctaa gtccaactac 60
taaactgggg gatattatga agggccttga gcatctggat tctgcctaat aaaaaacatt 120
tattttcatt gcaa 134

<210> SEQ ID NO 42
<211> LENGTH: 29
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: T7 Terminator

<400> SEQUENCE: 42
aacccctctc taaacggagg ggttttttt 29

<210> SEQ ID NO 43
<211> LENGTH: 1412
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Sequence of DLP dsGFP Mrna

<400> SEQUENCE: 43
taatacgact cactatagac atttgcttct gacacaactg tgttcactag caacctcaaa 60
cagacaccgc cgccaccata gtcagcatag tacatttcat ctgactaata ctacaacacc 120
accaccatga atagaggatt ctttaacatg ctcggccgcc gccccttccc ggcccccact 180
gccatgtgga ggccgcggag aaggaggcag gcggccccgg gaagcggagc tactaacttc 240
agcctgctga agcaggctgg agacgtggag gagaaccctg gacctatggt gagcaagggc 300
gaggagctgt tcaccggggt ggtgcccatc ctggtcgagc tggacggcga cgtaaacggc 360
cacaagttca gcgtgtccgg cgagggcgag ggcgatgcca cctacggcaa gctgaccctg 420
aagttcatct gcaccaccgg caagctgccc gtgccctggc ccaccctcgt gaccaccctg 480
acctacggcg tgcagtgctt cagccgctac cccgaccaca tgaagcagca cgacttcttc 540
aagtccgcca tgcccgaagg ctacgtccag gagcgcacca tcttcttcaa ggacgacggc 600
aactacaaga cccgcgccga ggtgaagttc gagggcgaca ccctggtgaa ccgcatcgag 660
ctgaagggca tcgacttcaa ggaggacggc aacatcctgg ggcacaagct ggagtacaac 720
tacaacagcc acaacgtcta tatcatggcc gacaagcaga agaacggcat caaggtgaac 780
ttcaagatcc gccacaacat cgaggacggc agcgtgcagc tcgccgacca ctaccagcag 840
aacaccccca tcggcgacgg ccccgtgctg ctgcccgaca accactacct gagcacccag 900
tccgccctga gcaaagaccc caacgagaag cgcgatcaca tggtcctgct ggagttcgtg 960
accgccgccg ggatcactct cggcatggac gagctgtaca agaagcttag ccatggcttc 1020
ccgccggagg tggaggagca ggatgatggc acgctgccca tgtcttgtgc ccaggagagc 1080
gggatggacc gtcaccctgc agcctgtgct tctgctagga tcaatgtgta ggctcgcttt 1140
cttgctgtcc aatttctatt aaaggttcct ttgttcccta agtccaacta ctaaactggg 1200
ggatattatg aagggccttg agcatctgga ttctgcctaa taaaaaacat ttattttcat 1260
tgcaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaacccct ctctaaacgg aggggttttt tt 1412

<210> SEQ ID NO 44
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: H-2 Kd peptide

<400> SEQUENCE: 44

Ile Tyr Ser Thr Val Ala Ser Ser Leu
1 5

<210> SEQ ID NO 45
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: CD4 T cell epitope

<400> SEQUENCE: 45

Lys Ser Ser Phe Phe Arg Asn Val Val Trp Leu Ile Lys Lys Asn
1 5 10 15

<210> SEQ ID NO 46
<211> LENGTH: 104
<212> TYPE: DNA
<213> ORGANISM: Sindbis virus

<400> SEQUENCE: 46
atgaatagag gattctttaa catgctcggc cgccgcccct tcccggcccc cactgccatg 60

-continued

```
tggaggccgc ggagaaggag gcaggcggcc ccgatgcctg cccg                     104


<210> SEQ ID NO 47
<211> LENGTH: 120
<212> TYPE: DNA
<213> ORGANISM: Aura virus

<400> SEQUENCE: 47

atgaactctg tcttttacaa tccgtttggc cgaggtgcct acgctcaacc tccaatagca     60

tggaggccaa gacgtagggc tgcacctgcg cctcgaccat ccgggttgac tacccagatc    120


<210> SEQ ID NO 48
<211> LENGTH: 71
<212> TYPE: DNA
<213> ORGANISM: Eastern Equine Encephalitis virus SA

<400> SEQUENCE: 48

atgtttccgt atccaacatt gaactacccg cctatggcac cggttaatcc gatggcatac     60

agggacccca a                                                          71


<210> SEQ ID NO 49
<211> LENGTH: 91
<212> TYPE: DNA
<213> ORGANISM: O'Nyong-Nyong virus

<400> SEQUENCE: 49

atggagttca taccagcaca aacttactac aatagaagat accagcctag accctggact     60

caacgcccta ctatccaggt gatcaggcca a                                    91


<210> SEQ ID NO 50
<211> LENGTH: 67
<212> TYPE: DNA
<213> ORGANISM: Semliki Forest virus

<400> SEQUENCE: 50

atgaattaca tccctacgca aacgttttac ggccgccggt ggcgcccgcg cccggcggcc     60

cgtcctt                                                               67


<210> SEQ ID NO 51
<211> LENGTH: 69
<212> TYPE: DNA
<213> ORGANISM: Ross River virus

<400> SEQUENCE: 51

atgaattaca taccaaccca gactttttac ggacgccgtt ggcggcctcg cccggcgttc     60

cgtccatgg                                                             69


<210> SEQ ID NO 52
<211> LENGTH: 91
<212> TYPE: DNA
<213> ORGANISM: Mayaro virus

<400> SEQUENCE: 52

atggatttcc taccaacaca agtgttttat ggcaggcgat ggagaccacg aatgccgcca     60

cgcccttgga ggccacgccc acctacaatt c                                    91
```

COMPOSITIONS AND METHODS FOR ENHANCING GENE EXPRESSION

RELATED APPLICATIONS

The present application claims priority to U.S. Provisional Application Ser. No. 62/430,250, filed on Dec. 5, 2016; U.S. Provisional Application Ser. No. 62/486,361, filed on Apr. 17, 2017; and U.S. Provisional Application Ser. No. 62/587,954, filed on Nov. 17, 2017. The contents of the above-referenced applications are hereby expressly incorporated by reference in their entireties.

INCORPORATION OF THE SEQUENCE LISTING

The material in the accompanying sequence listing is hereby incorporated by reference into this application. The accompanying sequence listing text file, named SGI012A_SeqListing.txt, was created on Dec. 4, 2017 and is 169 KB.

FIELD

The present disclosure relates to the field of molecular biology and genetic engineering, including nucleic acid molecules useful for regulating gene expression, and the use of the nucleic acid molecules for, for example, production of desired products in suitable host cells in cell culture or in a subject, and for conferring beneficial characteristics to the host cells or subjects.

BACKGROUND

Advances in biotechnology and molecular biology have offered many opportunities to develop recombinant cells and organisms with commercially desirable characteristics or traits. In particular, modern genetic engineering techniques have greatly accelerated the introduction of genes and hence new traits into recombinant cells and organisms. Proper expression level of a desirable gene in, for example, a host cell or a transgenic organism is helpful to achieve this goal.

However, despite the availability of many molecular tools, genetic modifications of host cells and organisms are often constrained by insufficient expression level or uncontrolled expression of the gene of interest. Thus, there is still a need for regulatory elements capable of enhancing transgene expression in host cells and organisms. The identification of novel molecular tools including regulatory elements, expression vector, and expression systems that function in various types of organisms can be useful in developing genetically enhanced cells and organisms.

SUMMARY

This section provides a general summary of the present application, and is not comprehensive of its full scope or all of its features.

The present disclosure relates generally to methods and compositions useful for regulating, for example increasing, gene expression in vitro, ex vivo, or in vivo. The gene expression can be, for example, in animal cells and other eukaryotic cells. The gene can be, for example, a heterologous gene encoding a protein of interest.

In one aspect, some embodiments disclosed herein relate to a nucleic acid molecule, including (i) a first nucleic acid sequence encoding one or more RNA stem-loops of a viral capsid enhancer or a variant thereof; and (ii) a second nucleic acid sequence operably linked to the first nucleic acid sequence, wherein the second nucleic acid sequence comprises a coding sequence for a gene of interest (GOI).

Implementations of embodiments of the nucleic acid molecule according to the present disclosure can include one or more of the following features. In some embodiments, the first nucleic acid sequence is operably linked upstream to the coding sequence for the GOI. In some embodiments, the nucleic acid molecule further includes a promoter operably linked upstream to the first nucleic acid sequence. In some embodiments, the nucleic acid molecule further includes a 5' UTR sequence operably linked upstream to the first nucleic acid sequence. In some embodiments, the 5' UTR sequence is operably linked downstream to the promoter and upstream to the first nucleic acid sequence. In some embodiments, the nucleic acid molecule further includes a coding sequence for an autoprotease peptide operably linked upstream to the second nucleic acid sequence. In some embodiments, the coding sequence for the autoprotease peptide is operably linked downstream to the first nucleic acid sequence and upstream to the second nucleic acid sequence. In some embodiments, the autoprotease peptide comprises a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof. In some embodiments, the nucleic acid molecule further includes a 3' UTR sequence operably linked downstream to the second sequence nucleic acid sequence.

In some embodiments, the viral capsid enhancer is derived from a capsid gene of a virus species belonging to the Togaviridae family. In some embodiments, the virus species belongs to the Alphavirus genus of the Togaviridae family. In some embodiments, the alphavirus species is Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), Salmonid alphavirus (SAV), or Buggy Creek virus. In some embodiments, the viral capsid enhancer comprises a downstream loop (DLP) motif of the virus species, and wherein the DLP motif comprises at least one of the one or more RNA stem-loops. In some embodiments, the viral capsid enhancer comprises a nucleic acid sequence exhibiting at least 80% sequence identity to at least one of SEQ ID NOs: 1 and 46-52. In some embodiments, the nucleic acid sequence exhibits at least 95% sequence identity to at least one of SEQ ID NOs: 1 and 46-52.

In some embodiments, the coding sequence for the GOI encodes a polypeptide. In some embodiments, the polypeptide is a therapeutic polypeptide, a prophylactic polypeptide, a diagnostic polypeptide, a nutraceutical polypeptide, an industrial enzyme, a reporter polypeptide, or a combination thereof. In some embodiments, the polypeptide is an antibody, an antigen, an immune modulator, a cytokine, an enzyme, or a combination thereof.

In some embodiments, the nucleic acid molecule of the disclosure further includes a third nucleic acid sequence encoding one or more RNA stem-loops of a second viral capsid enhancer or a variant thereof and a fourth nucleic acid sequence operably linked to the third nucleic acid sequence, wherein the fourth nucleic acid sequence comprises a coding sequence for a second gene of interest (GOI). In some embodiments, the nucleic acid molecule further includes a coding sequence for a second autoprotease peptide operably linked downstream to the third nucleic acid sequence and upstream to the fourth nucleic acid sequence.

In some embodiments, the nucleic acid molecule of the disclosure is an mRNA molecule or an RNA replicon. In some embodiments, the nucleic acid molecule is an expression vector or a transcription vector. In some embodiments, the expression vector or a transcription vector further includes one or more additional transcription regulatory sequences. In some embodiments, the expression vector or a transcription vector further includes one or more additional transcription regulatory sequences. In some embodiments, the expression vector or a transcription vector further includes one or more additional translation regulatory sequences. In some embodiments, the nucleic acid molecule is a plasmid, a bacteriophage vector, a cosmid, a fosmid, a viral replicon, a shuttle vector, or a combination thereof. In some embodiments, the nucleic acid molecule is a prokaryotic vector or a eukaryotic vector. In some embodiments, the nucleic acid molecule is produced via de novo synthesis.

Also disclosed in some embodiments include a method for producing a polypeptide of interest in a cell, which includes introducing a nucleic acid molecule of according to the present disclosure into a cell, thereby producing a polypeptide encoded by the GOI in the cell. In yet another related aspect, some embodiments disclosed herein related to a method for producing a polypeptide of interest in a cell, which includes introducing a RNA molecule into the cell, wherein the RNA molecule comprises one or more RNA stem-loops of a viral capsid enhancer or a variant thereof, and a coding sequence for the polypeptide of interest, thereby producing the polypeptide of interest in the cell.

In some embodiments, the RNA molecule is a messenger RNA (mRNA) molecule or a replicion RNA molecule. In some embodiments, the RNA molecule is produced via de novo synthesis and/or in vitro transcription before being introduced into the cell. In some embodiments, the RNA molecule comprises a downstream loop (DLP) motif of a virus species, and wherein the DLP motif comprises at least one of the one or more RNA stem-loops of the viral capsid enhancer. In some embodiments, the RNA molecule further comprises a coding sequence for an autoprotease peptide downstream to at least one of the one or more RNA stem-loops and upstream to the coding sequence for the polypeptide of interest. In some embodiments, the autoprotease peptide comprises a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof. In some embodiments, the polypeptide is a therapeutic polypeptide, a prophylactic polypeptide, a diagnostic polypeptide, a nutraceutical polypeptide, an industrial enzyme, a reporter polypeptide, or a combination thereof. In some embodiments, the polypeptide is an antibody, an antigen, an immune modulator, a cytokine, an enzyme, or a combination thereof. In some embodiments, the cell is present in a tissue, an organ, or a subject. In some embodiments, the subject is human, horse, pig, primate, mouse, ferret, rat, cotton rat, cattle, swine, sheep, rabbit, cat, dog, bird, fish, goat, donkey, hamster, or buffalo.

Some embodiments disclose a method for producing a messenger RNA (mRNA) in a cell. The method, in some embodiments, includes administering to the cell a nucleic acid molecule comprising a first nucleic acid sequence encoding one or more RNA stem-loops of a viral capsid enhancer or a variant thereof, and a second nucleic acid sequence operably linked to the first nucleic acid sequence, wherein the second nucleic acid sequence comprises a coding sequence for a gene of interest (GOI), thereby producing a mRNA of the GOI.

In some embodiments, the first nucleic acid sequence is operably linked upstream to the coding sequence for the GOI. In some embodiments, the nucleic acid molecule further includes a promoter operably linked upstream to the first nucleic acid sequence. In some embodiments, the nucleic acid molecule further includes a 5' UTR sequence operably linked upstream to the first nucleic acid sequence. In some embodiments, the 5' UTR sequence is operably linked downstream to the promoter and upstream to the first nucleic acid sequence. In some embodiments, the nucleic acid molecule further includes a coding sequence for an autoprotease peptide operably linked upstream to the second nucleic acid sequence. In some embodiments, the coding sequence for the autoprotease peptide is operably linked downstream to the first nucleic acid sequence and upstream to the second nucleic acid sequence. In some embodiments, the autoprotease peptide comprises a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof. In some embodiments, the nucleic acid molecule further includes a 3' UTR sequence operably linked downstream to the second sequence nucleic acid sequence.

In some embodiments disclosed herein, the viral capsid enhancer is derived from a capsid gene of a virus species belonging to the Togaviridae family. In some embodiments, the virus species belongs to the Alphavirus genus of the Togaviridae family. In some embodiments, the alphavirus species is Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), Salmonid alphavirus (SAV), or Buggy Creek virus. In some embodiments, the viral capsid enhancer comprises a downstream loop (DLP) motif of the virus species, and wherein the DLP motif comprises at least one of the one or more RNA stem-loops. In some embodiments, the viral capsid enhancer comprises a nucleic acid sequence exhibiting at least 80% sequence identity to at least one of SEQ ID NOs: 1 and 46-52. In some embodiments, the nucleic acid sequence exhibits at least 95% sequence identity to at least one of SEQ ID NOs: 1 and 46-52.

In some embodiments disclosed herein, the coding sequence for the GOI encodes a polypeptide. In some embodiments, the polypeptide is selected from the group consisting of a therapeutic polypeptide, a prophylactic polypeptide, a diagnostic polypeptide, a nutraceutical polypeptide, an industrial enzyme, a reporter polypeptide, and a combination thereof. In some embodiments, the polypeptide is an antibody, an antigen, an immune modulator, a cytokine, an enzyme, or a combination thereof. In some embodiments of the method for producing a messenger RNA (mRNA) according to the present disclosure, the nucleic acid molecule further includes a third nucleic acid sequence encoding one or more RNA stem-loops of a second viral capsid enhancer or a variant thereof and a fourth nucleic acid sequence operably linked to the third nucleic acid sequence, wherein the fourth nucleic acid sequence comprises a coding sequence for a second gene of interest (GOI). In some embodiments, the nucleic acid molecule further includes a coding sequence for a second autoprotease peptide operably linked downstream to the third nucleic acid sequence and upstream to the fourth nucleic acid sequence.

The nucleic acid molecule of the present disclosure can be, in some embodiments, an RNA replicon. In some embodiments, the nucleic acid molecule is an expression vector or a transcription vector. In some embodiments, the nucleic acid molecule further comprises one or more additional transcription regulatory sequences. In some embodiments, the nucleic acid molecule further comprises. In some embodiments, one or more additional translation regulatory sequences. In some embodiments, the nucleic acid molecule is an expression vector selected from the group consisting of a plasmid, a bacteriophage vector, a cosmid, a fosmid, a viral replicon, a shuttle vector, and a combination thereof. In some embodiments, the nucleic acid molecule is a prokaryotic expression vector or a eukaryotic expression vector. In some embodiments, the cell is present in a tissue, an organ, or a subject. In some embodiments, the subject is human, horse, pig, primate, mouse, ferret, rat, cotton rat, cattle, swine, sheep, rabbit, cat, dog, bird, fish, goat, donkey, hamster, or buffalo. In some embodiments of the method for producing a messenger RNA (mRNA) according to the present disclosure further includes producing a polypeptide encoded by the mRNA of the GOI in the cell. In some embodiments, the method further includes obtaining the produced mRNA of the GOI and introducing the obtained mRNA into a second cell for expression of a polypeptide encoded by the mRNA of the GOI in the second cell.

In one aspect, some embodiments of the disclosure relate to nucleic acid molecule comprising a nucleic acid sequence encoding a modified viral RNA replicon, wherein the modified viral RNA replicon comprises (i) a first nucleic acid sequence encoding one or more structural elements of a viral capsid enhancer or a variant thereof, wherein the viral capsid enhancer is heterologous to the viral RNA replicon, and (ii) a second nucleic acid sequence encoding at least one nonstructural viral protein or a portion thereof, wherein the first nucleic acid sequence is operably linked upstream to the second nucleic acid sequence.

In some embodiments, at least one of the one or more structural elements of the viral capsid enhancer comprises one or more RNA stem-loops. In some embodiments, the viral capsid enhancer is derived from a capsid gene of a virus species belonging to the Togaviridae family. In some embodiments, the virus species belongs to the Alphavirus genus of the Togaviridae family. In some embodiments, the alphavirus species Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), or Buggy Creek virus. In some embodiments, the viral capsid enhancer comprises a downstream loop (DLP) motif of the virus species, and wherein the DLP motif comprises at least one of the one or more RNA stem-loops. In some embodiments, the viral capsid enhancer comprises a nucleic acid sequence exhibiting at least 80% sequence identity to at least one of SEQ ID NOs: 1 and 46-52. In some embodiments, the nucleic acid sequence exhibits at least 95% sequence identity to at least one of SEQ ID NOs: 1 and 46-52.

In some embodiments, the nucleic acid sequence encoding the modified viral RNA replicon further comprising a coding sequence for an autoprotease peptide operably linked downstream to the first nucleic acid sequence and upstream to the second nucleic acid sequence. In some embodiments, the autoprotease peptide comprises a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof. In some embodiments, the first nucleic acid sequence is operably positioned within a region of about 1 to 1000 nucleotides downstream of the 5'-terminus of the modified viral RNA replicon. the second nucleic acid sequence comprises substantially all the coding sequence for the native viral nonstructural proteins of the corresponding unmodified viral RNA replicon.

In some embodiments disclosed herein, the modified viral RNA replicon comprises a modified RNA replicon derived from a virus species belonging to the Alphavirus genus of the Togaviridae family or to the Arterivirus genus of the Arteriviridae family.

In some embodiments, the arterivirus virus species is Equine arteritis virus (EAV), Porcine respiratory and reproductive syndrome virus (PRRSV), Lactate dehydrogenase elevating virus (LDV), or Simian hemorrhagic fever virus (SHFV). In some embodiments, the first nucleic acid sequence is operably positioned upstream to a second nucleic acid sequence encoding a portion or the entire pp1ab nonstructural protein of the modified arterivirus RNA replicon. In some embodiments, the nucleic acid sequence encoding the modified arterivirus RNA replicon further comprising one or more expression cassettes, wherein at least one of the one or more expression cassettes comprises a promoter operably linked to a coding sequence for a gene of interest (GOI). In some embodiments, the modified arterivirus RNA replicon comprises at least two, three, four, five, or six expression cassettes. In some embodiments, at least one of the one or more expression cassettes is operably linked downstream of the second nucleic acid sequence encoding a portion or the entire pp1ab nonstructural protein of the modified arterivirus RNA replicon. In some embodiments, at least one of the one or more expression cassettes is operably positioned downstream to a transcriptional regulatory sequence (TRS) of the modified arterivirus RNA replicon, wherein the TRS is TRS1, TRS2, TRS3, TRS4, TRS5, TRS6, or TRS7. In some embodiments, at least one of the one or more expression cassettes further comprises a third nucleic acid sequence encoding one or more structural elements of a viral capsid enhancer, wherein the third nucleic acid sequence is operably linked upstream to the coding sequence for the GOI.

In some embodiments, the nucleic acid sequence encoding the modified arterivirus RNA replicon further comprises a coding sequence for an autoprotease peptide operably linked downstream to the third nucleic acid sequence and upstream to the coding sequence for the GOI. In some embodiments, the coding sequence for the GOI encodes a therapeutic polypeptide, a prophylactic polypeptide, a diagnostic polypeptide, a nutraceutical polypeptide, an industrial enzyme, a reporter polypeptide, or any combination thereof. In some embodiments, the coding sequence for the GOI encodes an antibody, an antigen, an immune modulator, a cytokine, an enzyme, or any combination thereof.

In some embodiments, the modified viral RNA replicon comprises a modified RNA replicon derived from an alphavirus virus species selected from the group consisting of Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), Salmonid alphavirus (SAV), and Buggy Creek virus. In some embodiments, the first nucleic acid sequence is operably positioned upstream to a second nucleic acid sequence encoding one or more nonstructural proteins nsp1-4 or a portion thereof of the modified alphavirus RNA replicon. In some embodiments, the nucleic acid sequence encoding the modified alphavirus RNA replicon further comprises one or more expression cassettes, wherein each of the expression cassettes comprises a promoter operably linked to a coding sequence for a gene of interest (GOI). In some embodiments, the modified alphavirus RNA replicon comprises at least two, three, four, five, or six expression cassettes. In some embodiments, t least one of the one or more expression cassettes is operably linked downstream of a nucleic acid sequence encoding one or more nonstructural proteins nsp1-4 or a portion thereof of the modified alphavirus RNA replicon. In some embodiments, at least one of the one or more expression cassettes further comprises a third nucleic acid sequence encoding one or more structural elements of a viral capsid enhancer, wherein the third nucleic acid sequence is operably linked upstream of the coding sequence for the GOI. In some embodiments, the nucleic acid sequence encoding the modified alphavirus RNA replicon further comprises a coding sequence for an autoprotease peptide operably linked downstream to the third nucleic acid sequence and upstream to the coding sequence for the GOI. In some embodiments, the coding sequence for the GOI encodes a therapeutic polypeptide, a prophylactic polypeptide, a diagnostic polypeptide, a nutraceutical polypeptide, an industrial enzyme, a reporter polypeptide, or a combination thereof. In some embodiments, the coding sequence for the GOI encodes an antibody, an antigen, an immune modulator, an enzyme, a cytokine, or a combination thereof.

In one aspect, some embodiments of the disclosure relate to nucleic acid molecule comprising a nucleic acid sequence encoding a modified non-alphavirus RNA replicon, wherein the modified non-alphavirus RNA replicon comprising a first nucleic acid sequence encoding one or more structural elements of a viral capsid enhancer or a variant thereof. In some embodiments, the nucleic acid sequence encoding the modified non-alphavirus RNA replicon further comprises a second nucleic acid sequence encoding at least one nonstructural viral protein or a portion thereof, wherein the first nucleic acid sequence is operably linked upstream to the second nucleic acid sequence. In some embodiments, nucleic acid sequence encoding the modified non-alphavirus RNA replicon further comprises a coding sequence for an autoprotease peptide operably linked downstream to the first nucleic acid sequence and upstream to the second nucleic acid sequence. In some embodiments, the autoprotease peptide comprises a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof. In some embodiments, the nucleic acid sequence encoding the modified non-alphavirus RNA replicon comprises a modified RNA replicon derived from a positive-strand RNA virus. In some embodiments, the positive-strand RNA virus is a virus species belonging to a family selected from the group consisting of Togaviridae family, Flaviviridae family, Orthomyxoviridae family, Rhabdoviridae family, and Paramyxoviridae family. In some embodiments, the positive-strand RNA virus is a virus species belonging to the Arterivirus genus of the Arteriviridae family.

In some embodiments disclosed herein, the nucleic acid sequence encoding the modified non-alphavirus RNA replicon further comprising one or more expression cassettes, wherein each of the expression cassettes comprises a promoter operably linked to a coding sequence for a gene of interest (GOI). In some embodiments, the modified non-alphavirus RNA replicon comprises at least two, three, four, five, or six expression cassettes. In some embodiments, at least one of the one or more expression cassettes is operably linked downstream of the second nucleic acid sequence encoding the at least one nonstructural viral protein or a portion thereof. In some embodiments, at least one of the one or more expression cassettes further comprises a third nucleic acid sequence encoding one or more structural elements of a viral capsid enhancer, wherein the third nucleic acid sequence is operably linked upstream to the coding sequence for the GOI. In some embodiments, the nucleic acid sequence encoding the modified non-alphavirus RNA replicon further comprising a coding sequence for an autoprotease peptide operably linked downstream to the third nucleic acid sequence and upstream to the coding sequence for the GOI. In some embodiments, the nucleic acid molecule is produced via de novo synthesis.

In one aspect, some embodiments disclosed herein relate to a recombinant cell including a nucleic acid molecule as disclosed herein. In some embodiments, the recombinant cell is a prokaryotic cell or a eukaryotic cell. In some embodiments, the recombinant cell is an animal cell. In some embodiments, the nucleic acid molecule comprises a nucleic acid sequence encoding a modified RNA replicon, and wherein expression of the modified replicon RNA confers a resistance to innate immune response in the recombinant cell. In a related aspect, some embodiments disclosed herein relate to a cell culture which includes at least one recombinant cell as disclosed herein.

In some aspects, some embodiments disclosed herein relate to a method for conferring a resistance to the innate immune system in a subject which includes administering to the subject a nucleic acid molecule comprising a nucleic acid sequence which encodes a modified viral RNA replicon, wherein the modified viral RNA replicon comprises (i) a first nucleic acid sequence encoding one or more structural elements of a viral capsid enhancer or a variant thereof, wherein the viral capsid enhancer is heterologous to the viral RNA replicon, and (ii) a second nucleic acid sequence encoding at least one nonstructural protein or a portion thereof, wherein the first nucleic acid sequence is operably linked upstream to the second nucleic acid sequence, and wherein expression of the modified replicon RNA encoded by the nucleic acid molecule confers a resistance to innate immune response in the subject. In some embodiments, the subject is selected from the group consisting of human, horse, pig, primate, mouse, ferret, rat, cotton rat, cattle, swine, sheep, rabbit, cat, dog, bird, fish, goat, donkey, hamster, and buffalo In some aspect, some embodiments disclosed herein relate to a method for producing a polypeptide of interest in a subject which includes administering to the subject a nucleic acid molecule comprising a nucleic acid sequence which encodes a modified viral RNA replicon, wherein the modified viral RNA replicon comprises (i) a first nucleic acid sequence encoding one or more structural elements of a viral capsid enhancer or a variant thereof, wherein the viral capsid enhancer is heterologous to the viral RNA replicon, and (ii) a second nucleic acid sequence encoding at least one nonstructural protein or a portion thereof, wherein the first nucleic acid sequence is operably linked upstream to the second nucleic acid sequence. In some embodiments, the subject is human, horse, pig, primate, mouse, ferret, rat, cotton rat, cattle, swine, sheep, rabbit, cat, dog, bird, fish, goat, donkey, hamster, or buffalo.

In some aspect, some embodiments disclosed herein relate to a method for producing a polypeptide of interest, which includes culturing a host cell comprising a nucleic acid molecule which comprises a nucleic acid sequence encoding a modified viral RNA replicon, wherein the modified viral RNA replicon comprises (i) a first nucleic acid sequence encoding one or more structural elements of a viral capsid enhancer or a variant thereof, wherein the viral capsid enhancer is heterologous to the viral RNA replicon, and (ii) a second nucleic acid sequence encoding at least one nonstructural protein or a portion thereof, wherein the first nucleic acid sequence is operably linked upstream to the second nucleic acid sequence.

In some embodiments of the method for producing a polypeptide of interest according to the present disclosure, the subject is selected from the group consisting of human, horse, pig, primate, mouse, ferret, rat, cotton rat, cattle, swine, sheep, rabbit, cat, dog, bird, fish, goat, donkey, hamster, and buffalo. In some embodiments, at least one of the one or more structural elements of the viral capsid enhancer comprises one or more RNA stem-loops. In some embodiments, the viral capsid enhancer is derived from a capsid gene of a virus species belonging to the Togaviridae family. In some embodiments, the virus species belongs to the Alphavirus genus of the Togaviridae family. In some embodiments, the alphavirus species is Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), or Buggy Creek virus. In some embodiments, the viral capsid enhancer comprises a downstream loop (DLP) motif of the virus species, and wherein the DLP motif comprises at least one of the one or more RNA stem-loops. In some embodiments, the viral capsid enhancer comprises a nucleic acid sequence exhibiting at least 80% sequence identity to at least one of SEQ ID NOs: 1 and 46-52. In some embodiments, the nucleic acid sequence exhibits at least 95% sequence identity to at least one of SEQ ID NOs: 1 and 46-52.

In some embodiments disclosed herein, the nucleic acid sequence encoding the modified viral RNA replicon further comprising a coding sequence for an autoprotease peptide operably linked downstream to the first nucleic acid sequence and upstream to the second nucleic acid sequence. In some embodiments, the autoprotease peptide comprises a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof. In some embodiments, the first nucleic acid sequence is operably positioned within a region of about 1 to 1000 nucleotides downstream of the 5'-terminus of the modified viral RNA replicon. the second nucleic acid sequence comprises substantially all the coding sequence for the native viral nonstructural proteins of the corresponding unmodified viral RNA replicon.

In some embodiments, the modified viral RNA replicon comprises a modified RNA replicon derived from a virus species belonging to the Alphavirus genus of the Togaviridae family or to the Arterivirus genus of the Arteriviridae family. In some embodiments, the arterivirus virus species is Equine arteritis virus (EAV), Porcine respiratory and reproductive syndrome virus (PRRSV), Lactate dehydrogenase elevating virus (LDV), or Simian hemorrhagic fever virus (SHFV).

In some embodiments disclosed herein, the nucleic acid sequence encoding the modified arterivirus RNA replicon further comprises one or more expression cassettes, and wherein at least one of the expression cassettes comprises a promoter operably linked to a coding sequence for a gene of interest (GOI). In some embodiments, the virus species is an arterivirus, and wherein the first nucleic acid sequence is operably positioned upstream to a nucleic acid sequence encoding a portion or the entire pp1ab nonstructural protein of the modified arterivirus RNA replicon. In some embodiments, the modified arterivirus RNA replicon further comprises at least two, three, four, five, or six expression cassettes. In some embodiments, at least one of the one or more expression cassettes is operably linked downstream of the second nucleic acid sequence encoding a portion or the entire pp1ab nonstructural protein of the modified arterivirus RNA replicon. In some embodiments, at least one of the one or more expression cassettes is operably positioned downstream to a transcriptional regulatory sequence (TRS) of the modified arterivirus RNA replicon, wherein the TRS is TRS1, TRS2, TRS3, TRS4, TRS5, TRS6, or TRS7. In some embodiments, at least one of the one or more expression cassettes further comprises a third nucleic acid sequence encoding one or more structural elements of a viral capsid enhancer, wherein the third nucleic acid sequence is operably linked upstream to the coding sequence for the GOI. In some embodiments, the nucleic acid sequence encoding the modified arterivirus RNA replicon further comprising a coding sequence for an autoprotease peptide operably linked downstream to the third nucleic acid sequence and upstream to the coding sequence for the GOI. In some embodiments, the coding sequence for the GOI encodes a therapeutic polypeptide, a prophylactic polypeptide, a diagnostic polypeptide, a nutraceutical polypeptide, an industrial enzyme, a reporter polypeptide, or any combination thereof. In some embodiments, the coding sequence for the GOI encodes an antibody, an antigen, an immune modulator, a cytokine, an enzyme, or any combination thereof.

In some embodiments, the modified viral RNA replicon comprises a modified RNA replicon derived from an alphavirus virus species selected from the group consisting of Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), Salmonid alphavirus (SAV), and Buggy Creek virus. In some embodiments, the first nucleic acid sequence is operably positioned upstream to a nucleic acid sequence encoding one or more nonstructural proteins nsp1-4 or a portion thereof of the modified alphavirus RNA replicon.

In some embodiments, the nucleic acid sequence encoding the modified alphavirus RNA replicon further comprises one or more expression cassettes, wherein each of the expression cassettes comprises a promoter operably linked to a coding sequence for a gene of interest (GOI). In some embodiments, the modified alphavirus RNA replicon comprises at least two, three, four, five, or six expression cassettes. In some embodiments, at least one of the one or more expression cassettes is operably linked downstream of a nucleic acid sequence encoding one or more nonstructural proteins nsp1-4 or a portion thereof of the modified alphavirus RNA replicon. In some embodiments, at least one of the one or more expression cassettes further comprises a third nucleic acid sequence encoding one or more structural elements of a viral capsid enhancer, wherein the third nucleic acid sequence is operably linked upstream of the coding sequence for the GOI. In some embodiments, the modified alphavirus RNA replicon further comprising a coding sequence for an autoprotease peptide operably linked downstream to the third nucleic acid sequence and upstream to the coding sequence for the GOI. In some embodiments, the coding sequence for the GOI encodes a therapeutic polypeptide, a prophylactic polypeptide, a diagnostic polypeptide, a nutraceutical polypeptide, an industrial enzyme, a reporter polypeptide, or any combination thereof. In some embodiments, the coding sequence for the GOI encodes an antibody, an antigen, an immune modulator, a cytokine, an enzyme, or any combination thereof.

In another aspect, some embodiments disclosed herein relate to a method for conferring a resistance to the innate immune system in a subject, comprising administering to the subject a nucleic acid molecule comprising a nucleic acid sequence encoding a modified non-alphavirus RNA replicon, wherein the modified non-alphavirus RNA replicon comprises a first nucleic acid sequence encoding one or more structural elements of an alphavirus capsid enhancer and wherein expression of the modified non-alphavirus RNA replicon encoded by the nucleic acid molecule confers a resistance to innate immune response in the subject. In some embodiments, the subject is selected from the group consisting of human, horse, pig, primate, mouse, ferret, rat, cotton rat, cattle, swine, sheep, rabbit, cat, dog, bird, fish, goat, donkey, hamster, and buffalo.

Also disclosed herein include a method for producing a polypeptide of interest in a subject, where the method comprises administering to the subject a nucleic acid molecule comprising a nucleic acid sequence encoding a modified non-alphavirus RNA replicon, wherein the modified non-alphavirus RNA replicon comprises a first nucleic acid sequence encoding one or more structural elements of an alphavirus capsid enhancer. In some embodiments, the subject is human, horse, pig, primate, mouse, ferret, rat, cotton rat, cattle, swine, sheep, rabbit, cat, dog, bird, fish, goat, donkey, hamster, or buffalo.

Some embodiments disclosed herein relate to a method for producing a polypeptide of interest, where the method comprises culturing a host cell comprising a nucleic acid molecule which comprises a nucleic acid sequence encoding a modified non-alphavirus RNA replicon, wherein the modified non-alphavirus RNA replicon comprises a first nucleic acid sequence encoding one or more structural elements of an alphavirus capsid enhancer.

In some embodiments according to the above aspects of the disclosure, the modified non-alphavirus RNA replicon further comprising a second nucleic acid sequence encoding at least one nonstructural viral protein or a portion thereof, wherein the first nucleic acid sequence is operably linked upstream to the second nucleic acid sequence. In some embodiments, the modified non-alphavirus RNA replicon further comprises a coding sequence for an autoprotease peptide operably linked downstream to the first nucleic acid sequence and upstream to the second nucleic acid sequence. In some embodiments the autoprotease peptide comprises a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof. In some embodiments, the modified non-alphavirus RNA replicon comprises a modified RNA replicon derived from a positive-strand RNA virus. In some embodiments, the modified non-alphavirus RNA replicon comprises a modified RNA replicon derived from a virus species belonging to Togaviridae family, Flaviviridae family, Orthomyxoviridae family, Rhabdoviridae family, or Paramyxoviridae family. In some embodiments, the modified non-alphavirus RNA replicon comprises a modified RNA replicon derived from a virus species belonging to the Arterivirus genus of the Arteriviridae family. In some embodiments, the sequence encoding the non-alphavirus modified RNA replicon further comprising one or more expression cassettes, wherein each of the expression cassettes comprises a promoter operably linked to a coding sequence for a gene of interest (GOI). In some embodiments, the modified non-alphavirus RNA replicon comprises at least two, three, four, five, or six expression cassettes. In some embodiments, at least one of the one or more expression cassettes is operably linked downstream of the second nucleic acid sequence encoding the at least one nonstructural viral protein or a portion thereof of the modified non-alphavirus RNA replicon. In some embodiments, at least one of the one or more expression cassettes further comprises a third nucleic acid sequence encoding one or more structural elements of an alphavirus capsid enhancer, wherein the third nucleic acid sequence is operably linked upstream to the coding sequence for the GOI. In some embodiments, the modified non-alphavirus RNA replicon further comprises a coding sequence for an autoprotease peptide operably linked downstream to the third nucleic acid sequence and upstream to the coding sequence for the GOI.

In some aspects, some embodiments disclosed herein relate to recombinant polypeptides produced by a method in accordance with one or more embodiments described herein.

Some embodiments disclosed herein relate to a composition including a recombinant polypeptide as described herein and a pharmaceutically acceptable carrier.

Some embodiments disclosed herein relate to a composition including a nucleic acid molecule as disclosed herein and a pharmaceutically acceptable carrier.

In some embodiments, one or more of the compositions and/or molecules of the present application, e.g. nucleic acid molecules, RNA replicons, and polypeptides, is further formulated into a pharmaceutical formulation. In some embodiments, one or more of the compositions and/or molecules of the present application is formulated into a pharmaceutical formulation with covalent compounds, non-covalent compounds, physical compositions, or pharmaceutically acceptable buffers.

In some embodiments disclosed herein, one or more of the compositions and/or molecules of the present application, e.g. nucleic acid molecules, RNA replicons, and polypeptides, is further formulated for use as a protective composition (e.g., vaccine) or therapeutic composition. In particular, protective compositions made in accordance with the present disclosure have a variety of uses including, but not limited to, use as vaccines and other therapeutic agents, use as diagnostic agents and use as antigens in the production of polyclonal or monoclonal antibodies.

The foregoing summary is illustrative only and is not intended to be in any way limiting. In addition to the illustrative embodiments and features described herein, further aspects, embodiments, objects and features of the application will become fully apparent from the drawings and the detailed description and the claims.

BRIEF DESCRIPTION OF THE DRAWINGS

FIG. 2A: rEx-DLP-rFF; FIG. 2B: rEx-DLP-pp1ab-rFF; FIG. 2C: rEx-DLP-2A-pp1ab-rFF; and FIG. 2D: rEx-DLP-2A-pp1ab-DLP-rFF. DLP: Downstream Loop sequence; 2A: autoprotease peptide; pp1ab: nonstructural polypeptide sequence; and rFF: coding sequence for red Firefly reporter gene.

FIG. 3A: Alpha-R-rFF; FIG. 3B: Alpha-R-DLP-rFF; FIG. 3C: Alpha-R-DLP-2A-nsp-rFF; and FIG. 3D: Alpha-R-DLP-2A-nsp-DLP-rFF. DLP: Downstream Loop sequence; 2A: autoprotease peptide; nsp1-4: nonstructural polypeptide sequence; and rFF: coding sequence for red Firefly reporter gene.

FIG. 4A: Alpha-R-DLP-2A-rFF; and FIG. 4B: Alpha-R-DLP-2A-nsp-DLP-2A-rFF. DLP: Downstream Loop sequence; 2A: autoprotease peptide; nsp1-4: nonstructural polypeptide sequence; and rFF: coding sequence for red Firefly reporter gene.

FIG. 7A: α-rFF versus alpha-R-rFF construct; FIG. 7B: α-rFF versus α-DLP-2A-nsp-rFF; and FIG. 7C: α-rFF versus alpha-R-DLP-2A-nsp-rFF construct.

FIG. 12A: A significant increase in memory precursor effector cells (MPECs) was observed in constructs containing the DLP motif compared with each comparable dose of unmodified replicon. FIG. 12B: Effector T cell responses were measured by the number of antigen-specific HA cells that were secreting IFN-γ following stimulation with a CD8+ T cell peptide. FIG. 12C: Effector T cell responses were measured by the number of antigen-specific HA cells that were secreting IFN-γ following stimulation with a CD4+ T cell peptide.

FIG. 14A: HA-specific antibodies were measured in the serum. Serum antibody titer is the inverse of the EC20% and was calculated by interpolation of dilution versus optical density on a four-parametric logistic regression. FIG. 14B: IFN-γ ELISpot used to quantify CD8+ cell effector responses. For detection of antigen-specific CD8+ T cells, splenocytes were incubated with the H-2 Kd (IYSTVASSL; SEQ ID NO: 44) peptide. FIG. 14C: IFN-γ ELISpot used to quantify CD4+ T cell effector responses. For detection of antigen-specific CD4+ T cells, splenocytes were incubated with H2-D restricted CD4 T cell epitope KSSFFRNVVWLIKKN (SEQ ID NO: 45). Statistics between individual groups were conducted using a Mann-Whitney (non-parametric) test.

FIG. 16A:

inclusion of DLP in mRNA results in a statistically significant increase in the frequency of GFP positive cells in the presence of IFN. Mean with 95% confidence intervals in Kruskai-Wallist test (non-parametric). FIG. 16B: unmodified mRNA is sensitive to IFN treatment (mean with 95% confidence intervals in 2-way ANOVA. Interaction: p=0.0083. Row: p=<0.0001. Column: p=0.0273. Sidak's multiple comparison test with *p=0.0217 and # p=<0.0241). FIG. 16C: DLP modified mRNA yields a statistically significant 30% increase in protein production per cell compared to unmodified mRNA in the presence of IFN (mean with 95% confidence intervals in 2-way ANOVA: p=<0.0001. Sidak's multiple comparison test with *p=<0.0002 and p=<0.0001). FIG. 16D: DLP modified mRNA in the presence of IFN produces an equivalent amount of protein compared to unmodified mRNA in the absence of IFN treatment (mean with 95% confidence intervals in 2-way ANOVA. Interaction: p=<0.0001. Row: p=<0.0001. Column: p=0.0023. Sidak's multiple comparison test with p=<0.0001 and p=<0.0023).

Figure 1:
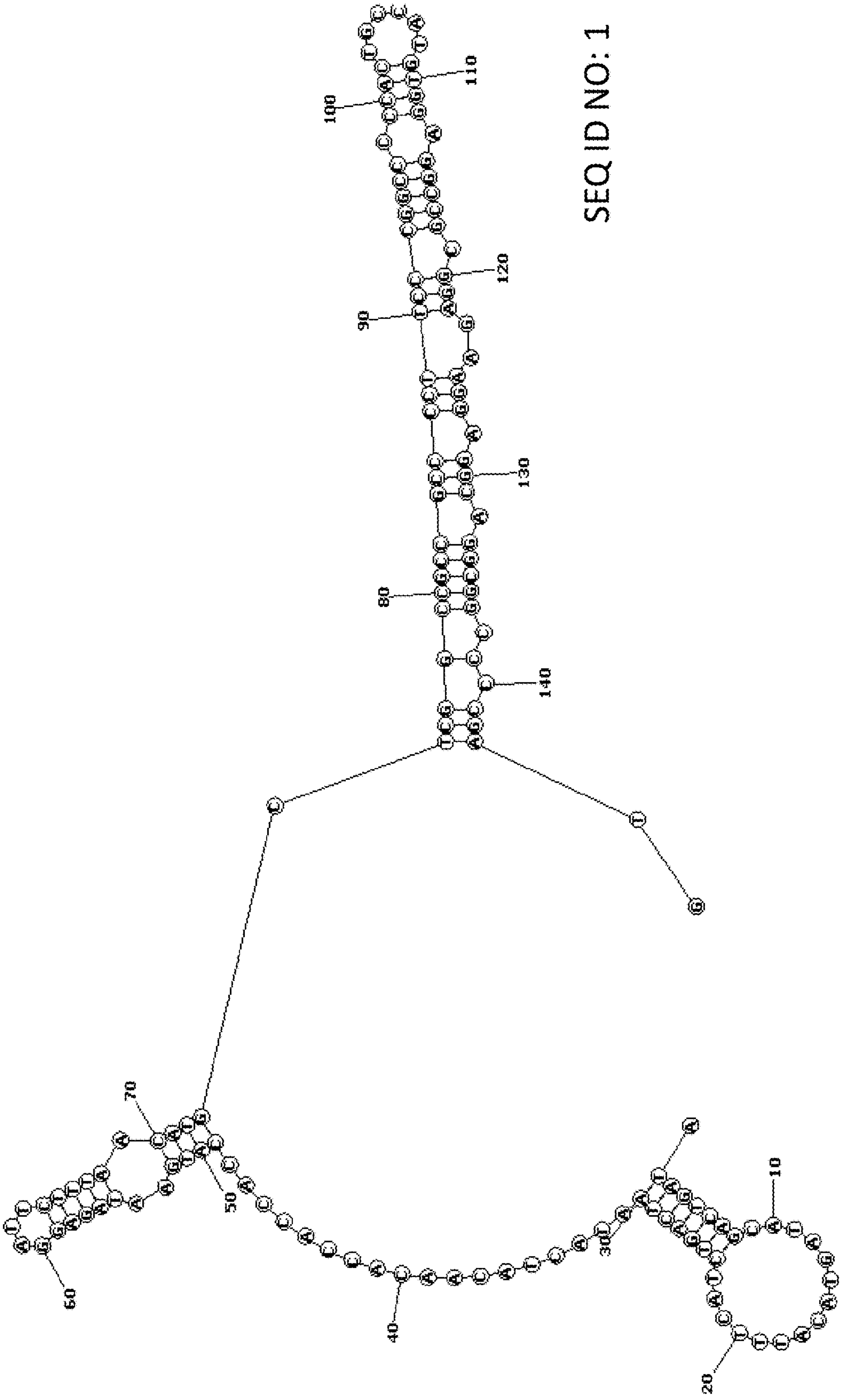
FIG. 1 is a graphical illustration of a non-limiting exemplary stem-loop RNA structure of an alphavirus capsid enhancer.
Figure 2A:
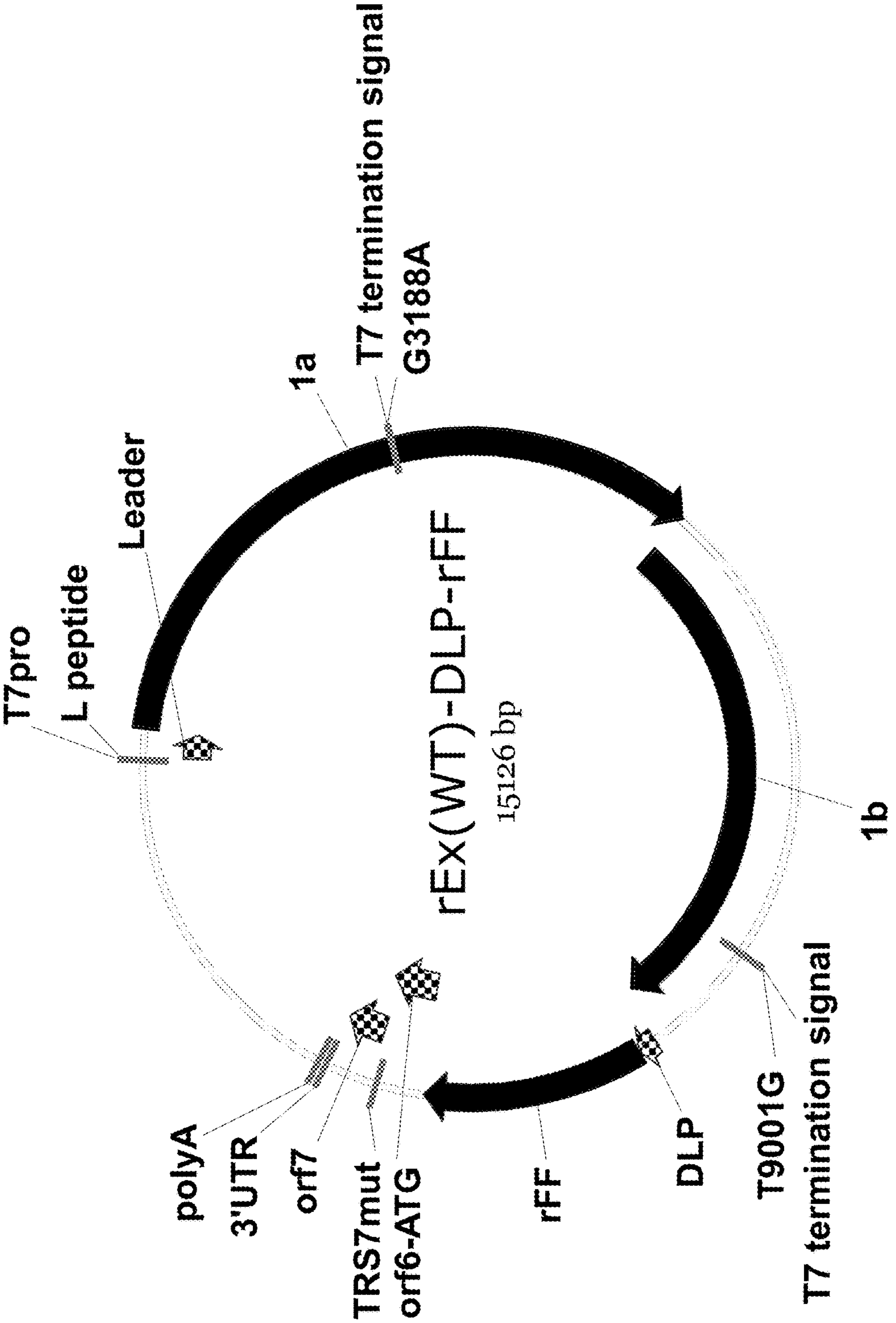
FIGS. 2A-2D are graphical representations of four non-limiting exemplary nucleic acid molecules of the present disclosure, where each of the nucleic acid molecules comprises a coding sequence for an alphavirus capsid enhancer (e.g., DLP motif) and a coding sequence for a gene of interest (GOI), e.g., a red Firefly (rFF) reporter gene.
Figure 2B:
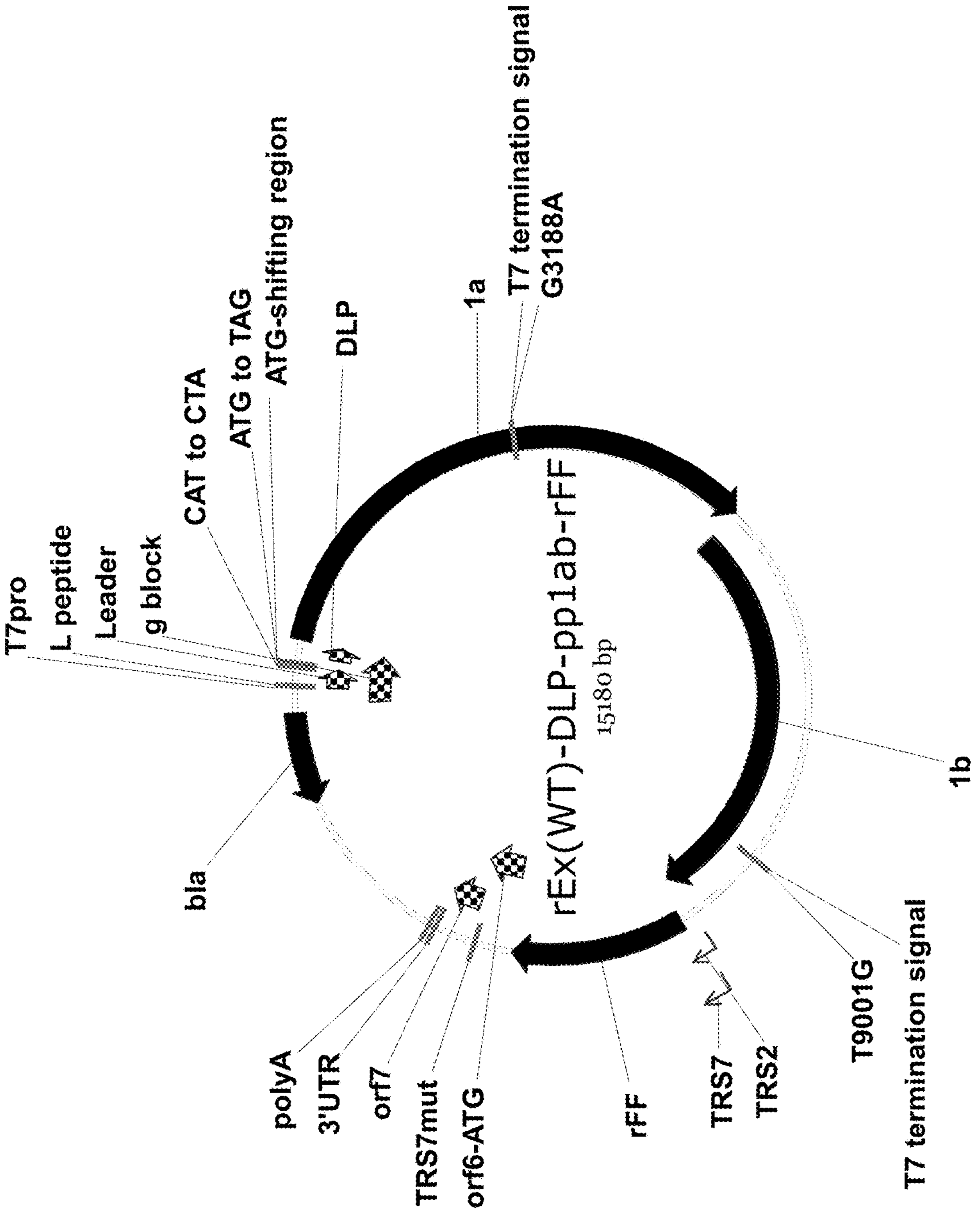
Figure 2C:
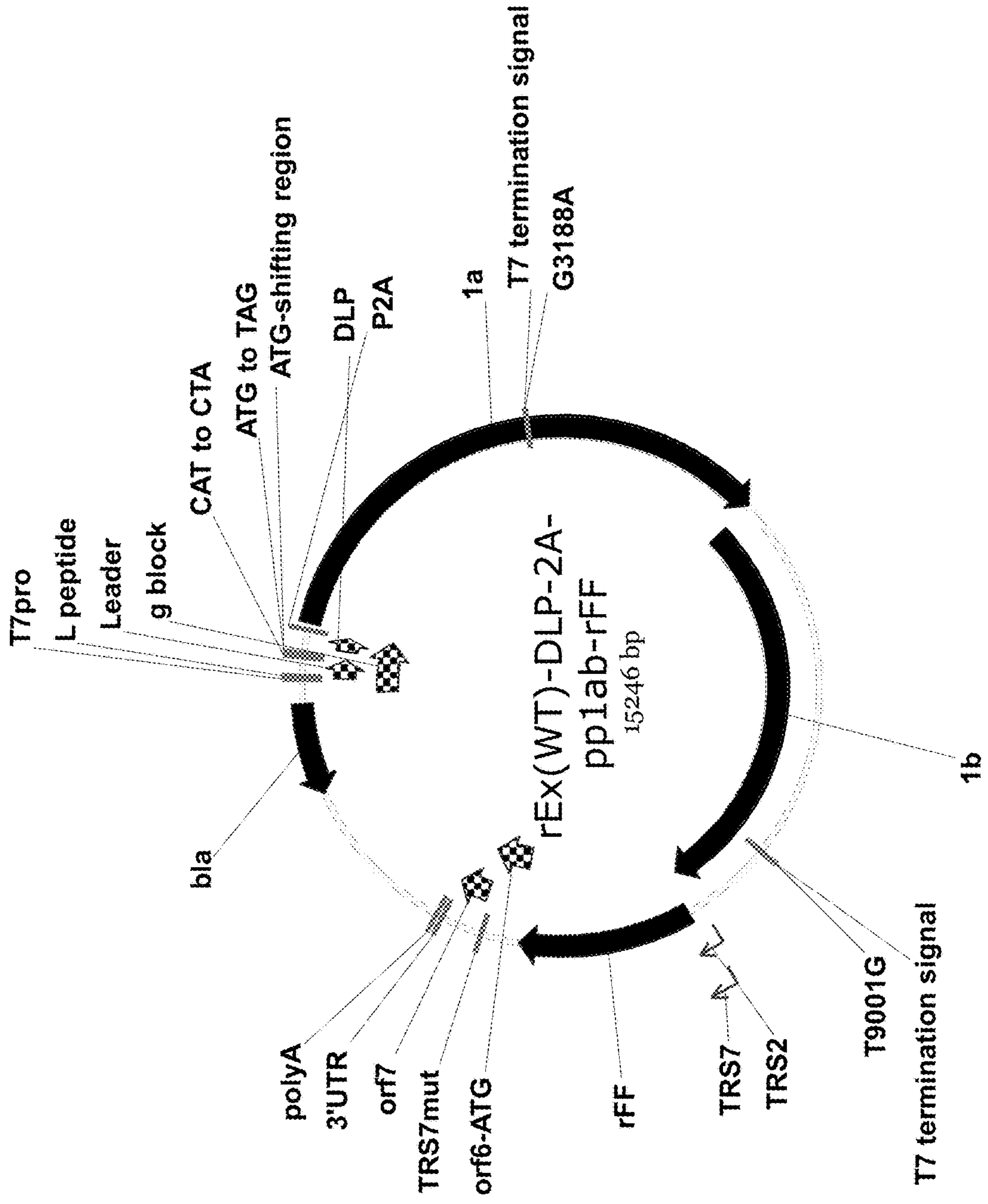
Figure 2D:
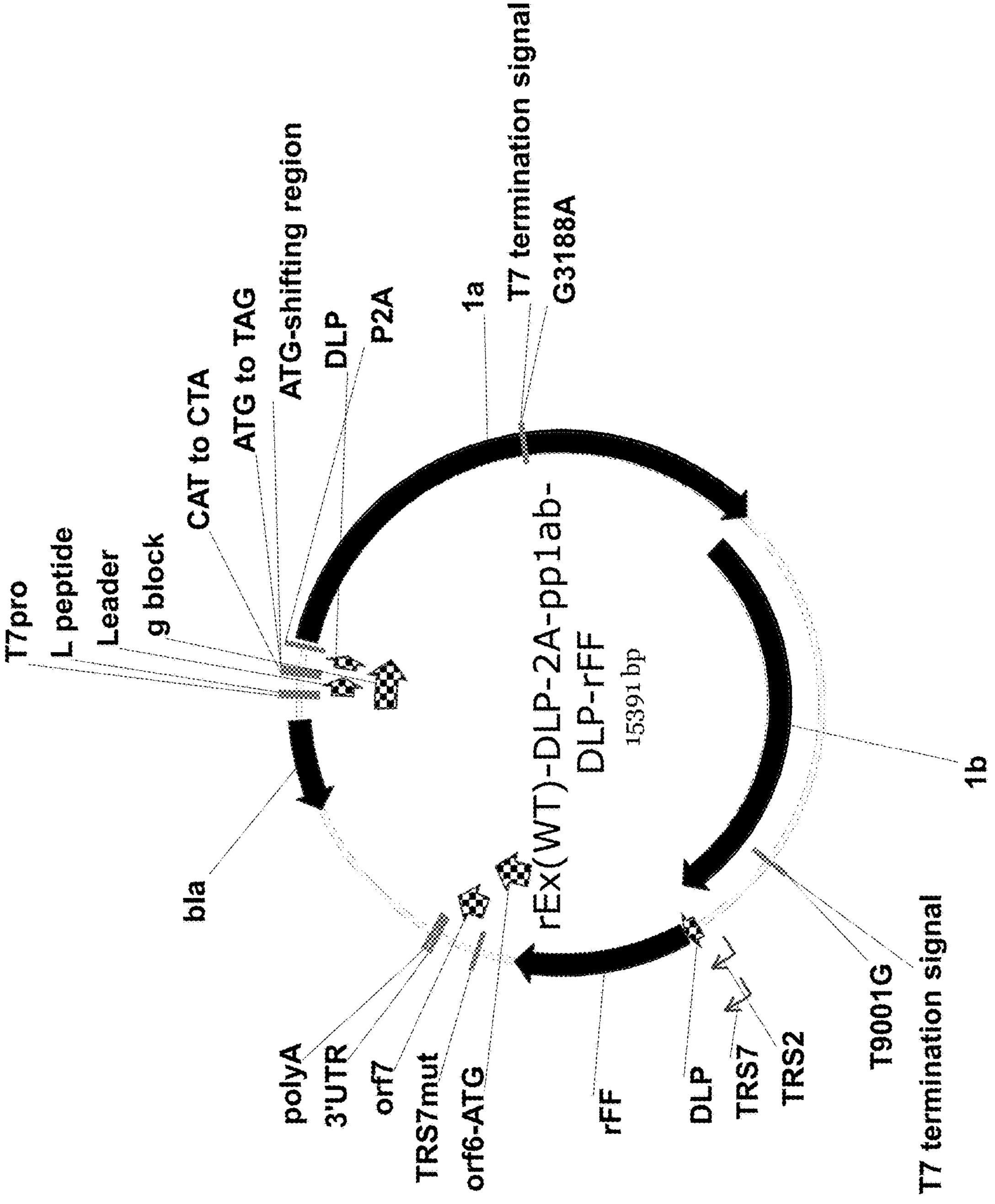
Figure 3A:
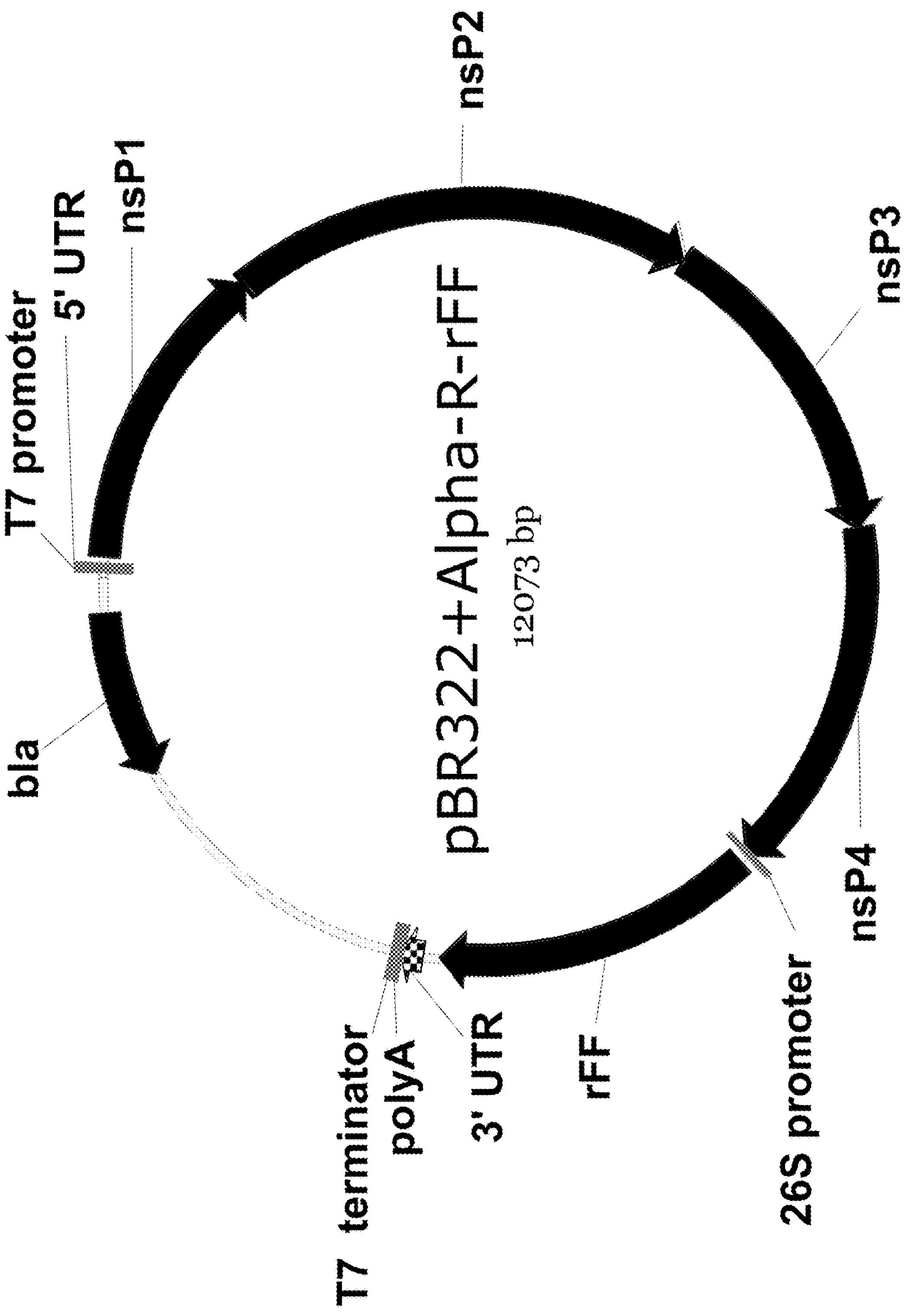
FIGS. 3A-3D are graphical illustrations of four non-limiting exemplary nucleic acid molecules of the present disclosure, where each of the nucleic acid molecules comprises a coding sequence for an alphavirus capsid enhancer (e.g., a DLP motif) and a coding sequence for a gene of interest (GOI), e.g., a red Firefly (rFF) reporter gene.
Figure 3B:
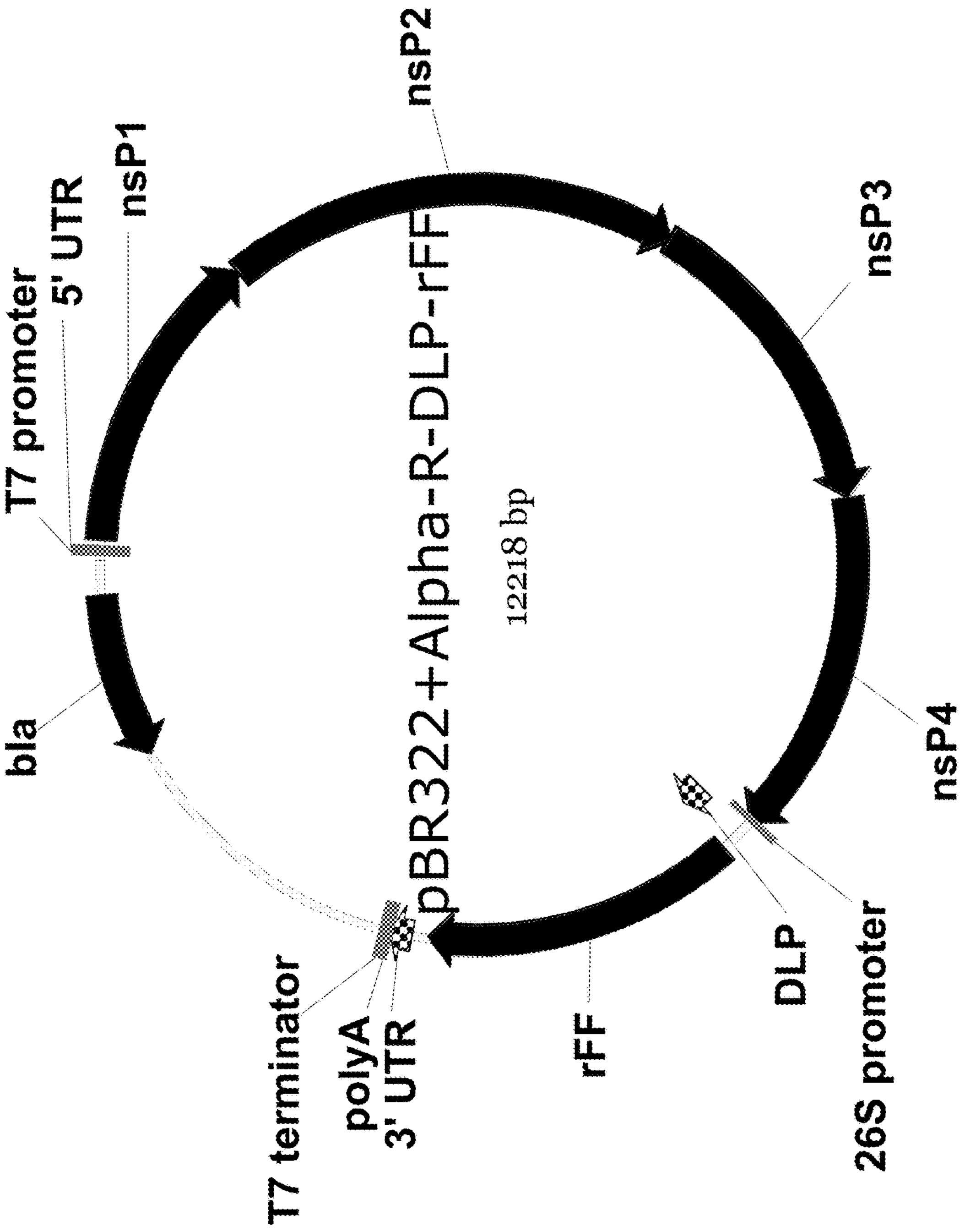
Figure 3C:
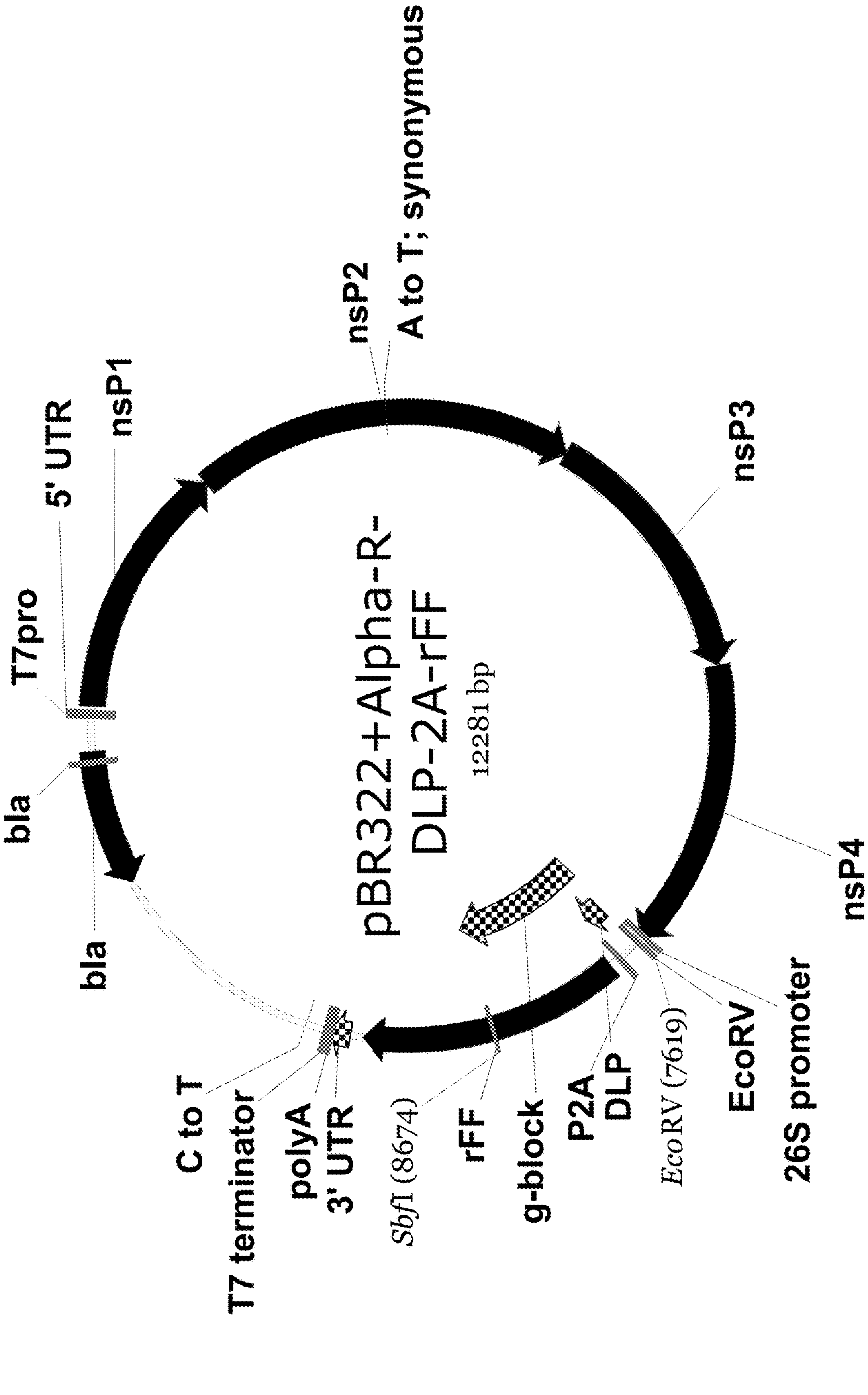
Figure 3D:
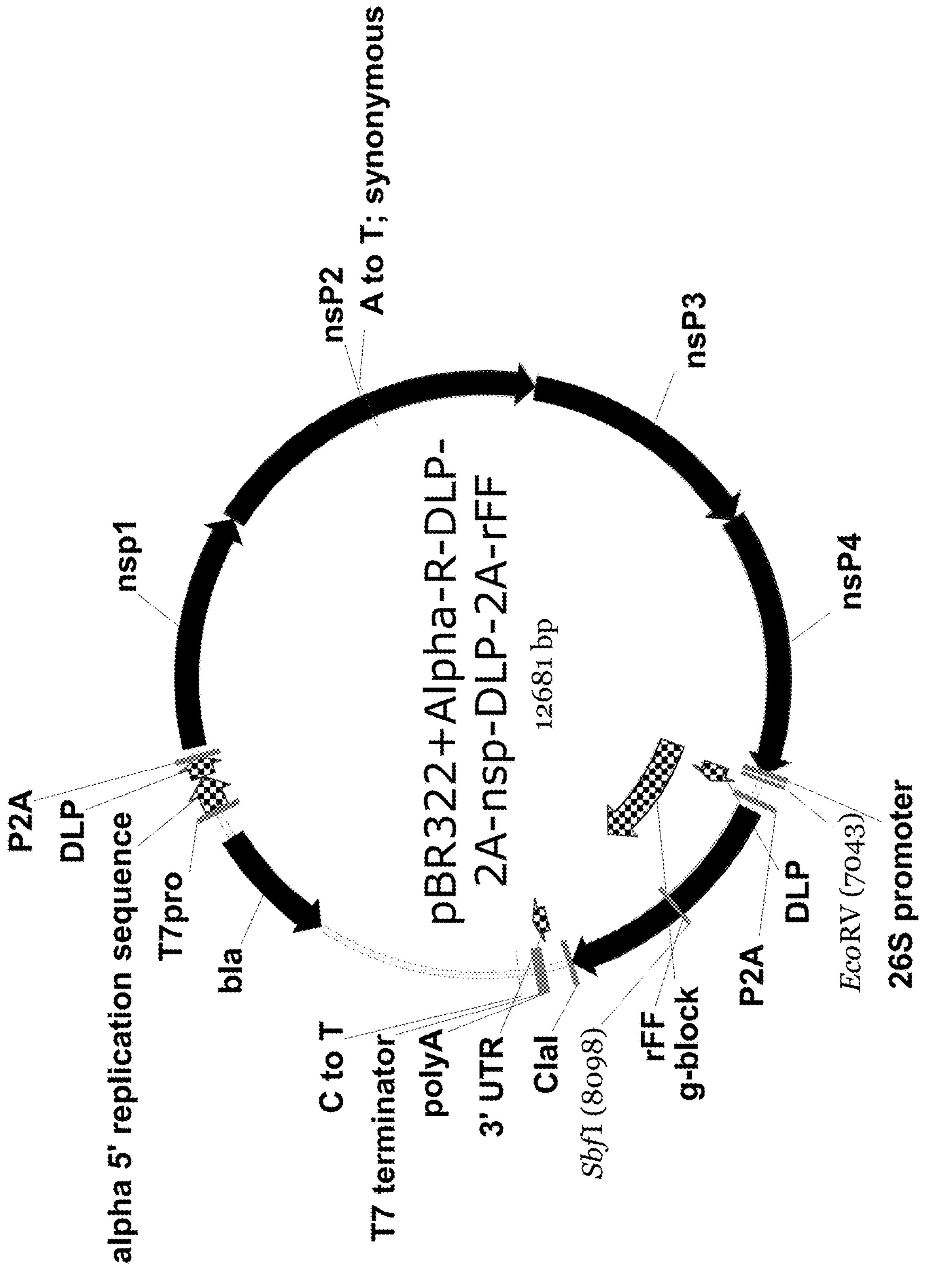

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope; the disclosure will be described with additional specificity and detail through use of the accompanying drawings.

DETAILED DESCRIPTION OF THE DISCLOSURE

The present disclosure generally relates to compositions and methods for use in regulating gene expression in cells. Some embodiments of the disclosure relate to expression systems, such as viral-based expression systems, with superior expression potential which are suitable for expressing heterologous molecules such as, for example, vaccines and therapeutic polypeptides, in recombinant cells. For example, some embodiments of the disclosure relate to nucleic acid molecules containing one or more structural elements of a viral capsid enhancer or a variant thereof. In some embodiments, at least one of the one or more structural elements comprises a RNA stem-loop. In some embodiments, at least one of the one or more structural elements is operably linked to a coding sequence of a gene of interest. Some embodiments of the disclosure relate to nucleic acid molecules such as transcription and/or expression constructs and vectors, containing a nucleic acid sequence encoding one or more structural elements of a viral capsid enhancer. Also disclosed herein in some embodiments are transcription vectors and expression vectors, such as viral-based vectors, comprising a coding sequence of a gene of interest. In some embodiments, the nucleic acid molecules of the present disclosure, e.g., messenger (mRNA) and RNA replicon, are generated via de novo synthesis and/or in vitro transcription. Recombinant cells that are genetically modified to include one or more of the nucleic acid molecules disclosed herein, as well as biomaterials and recombinant products derived from such cells are also within the scope of the application. Further provided herein are compositions and kits that include one or more of the nucleic acid molecules and/or recombinant cells disclosed herein, as well as methods for conferring a resistance to the innate immune system in a host cell.

In the following detailed description, reference is made to the accompanying drawings, which form a part hereof. In the drawings, similar symbols typically identify similar components, unless context dictates otherwise. The illustrative alternatives described in the detailed description, drawings, and claims are not meant to be limiting. Other alternatives may be used, and other changes may be made, without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of the present application.

Unless otherwise defined, all terms of art, notations and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

Some Definitions

The singular form "a", "an", and "the" include plural references unless the context clearly dictates otherwise. For example, the term "a cell" includes one or more cells, comprising mixtures thereof.

The term "about", as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The terms, "cells", "cell cultures", "cell line", "recombinant host cells", "recipient cells" and "host cells" as used herein, include the primary subject cells and any progeny thereof, without regard to the number of transfers. In some situations, a progeny is not exactly identical to the parental cell (due to deliberate or inadvertent mutations or differences in environment); however, such altered progeny is included in these terms, so long as the progeny retain the same or substantially similar functionality as that of the originally transformed cell.

As used herein, the term "construct" is intended to mean any recombinant nucleic acid molecule such as an expression cassette, plasmid, cosmid, fosmid, viral replicon, shuttle vector, autonomously replicating polynucleotide molecule, bacteriophage, or linear or circular, single-stranded or double-stranded, DNA or RNA polynucleotide molecule, derived from any source, capable of genomic integration or autonomous replication, comprising a nucleic acid molecule where nucleic acid sequences are linked in a functionally operative manner, e.g. operably linked.

The term "derived from" used herein refers to an origin or source, and may include naturally-occurring, recombinant, unpurified or purified molecules. The molecules of the present disclosure may be derived from viral or non-viral molecules. A protein or polypeptide derived from an original protein or polypeptide may include the original protein or polypeptide, in part or in whole, and may be a fragment or variant of the original protein or polypeptide.

The term "gene" is used broadly to refer to any segment of nucleic acid molecule that encodes a protein or that can be transcribed into a functional RNA. Genes may include sequences that are transcribed but are not part of a final, mature, and/or functional RNA transcript, and genes that encode proteins may further comprise sequences that are transcribed but not translated, for example, 5' untranslated regions, 3' untranslated regions, introns, etc. Further, genes may optionally further comprise regulatory sequences required for their expression, and such sequences may be, for example, sequences that are not transcribed or translated. Genes can be obtained from a variety of sources, including cloning from a source of interest or synthesizing from known or predicted sequence information, and may include sequences designed to have desired parameters.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. A nucleic acid sequence or amino acid sequence that has been removed from a host cell, subjected to laboratory manipulation, and introduced or reintroduced into a host cell is considered "non-native." Synthetic genes or partially synthetic genes introduced into a host cell or organism are "non-native." Non-native genes further include genes endogenous to the host cell operably linked to one or more heterologous regulatory sequences that have been recombined into the host genome, or genes endogenous to the host cell or organism that are in a locus of the genome other than that where they naturally occur.

The terms "naturally-occurring" and "wild-type", as used herein, refer to a form found in nature. For example, a naturally-occurring or wild-type nucleic acid molecule, nucleic acid sequence or protein may be present in and isolated from a natural source, and is not intentionally modified by human manipulation. As described in detail below, the nucleic acid molecules according to some embodiments of the present disclosure are non-naturally occurring nucleic acid molecules.

The term "heterologous" when used in reference to a polynucleotide, a gene, or a nucleic acid molecule refers to a polynucleotide, gene, or a nucleic acid molecule that is not derived from the host species. For example, "heterologous gene" or "heterologous nucleic acid sequence" as used herein, refers to a gene or nucleic acid sequence from a different species than the species of the host organism it is introduced into. When referring to a gene regulatory sequence such as, for example, an enhancer sequence, or to an auxiliary nucleic acid sequence used for manipulating expression of a gene sequence (e.g. a 5' untranslated region, 3' untranslated region, poly A addition sequence, etc.) or to a nucleic acid sequence encoding a protein domain or protein localization sequence, "heterologous" means that the regulatory or auxiliary sequence or sequence encoding a protein domain or localization sequence is from a different source than the gene with which the regulatory or auxiliary nucleic acid sequence or nucleic acid sequence encoding a protein domain or localization sequence is juxtaposed in a genome. Thus, a promoter operably linked to a gene to which it is not operably linked to in its natural state (for example, in the genome of a non-genetically engineered organism) is referred to herein as a "heterologous promoter," even though the promoter may be derived from the same species (or, in some cases, the same organism) as the gene to which it is linked. For example, in some embodiments disclosed herein, a coding sequence of a heterologous gene of interest (GOI) is not linked to the recombinant RNA replicon sequence in its natural state. In some embodiments, the coding GOI sequence is derived from another organism, such as another virus, bacteria, fungi, human cell (tumor Ag), parasite (malaria), etc.)

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. Nucleic acid molecules can have any three-dimensional structure. A nucleic acid molecule can be double-stranded or single-stranded (e.g., a sense strand or an antisense strand). Non-limiting examples of nucleic acid molecules include genes, gene fragments, exons, introns, messenger RNA (mRNA), transfer RNA, ribosomal RNA, siRNA, micro-RNA, tracrRNAs, crRNAs, guide RNAs, ribozymes, cDNA, recombinant polynucleotides, branched polynucleotides, nucleic acid probes and nucleic acid primers. A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein. The nucleic acid molecules of the present disclosure can be synthesized ex vitro by any means known in the art, for example, using one or more chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination) of nucleic acid molecules. In some embodiments, the nucleic acid molecules of the present disclosure are generated from de novo synthesis. In some embodiments, nucleic acid molecules can be synthesized de novo in whole or in part, using known chemical methods, known enzymatic techniques, or any combination thereof. For example, the component nucleic acid sequences can be synthesized by solid phase techniques, removed from the resin, and purified by preparative high performance liquid chromatography followed by chemical linkage and/or enzymatic ligation to form a chimeric nucleic acid molecule. The composition of the synthetic nucleic acid molecules may be confirmed by nucleic acid analysis or sequencing. In some embodiments, the nucleic acid molecules of the present disclosure can be enzymatically assembled from chemically synthesized oligonucleotides using techniques known in the art.

Nucleic acid molecules of the present disclosure can be nucleic acid molecules of any length, for example between about 0.5 Kb and about 1000 Kb, between about 0.5 Kb and about 500 Kb, between about 1 Kb and about 100 Kb, between about 2 Kb and about 50 Kb, or between about 5 Kb and about 20 Kb. In some embodiments, the nucleic acid molecule is, or is about, 0.5 Kb, 1 Kb, 2 Kb, 3 Kb, 4 Kb, 5 Kb, 6 Kb, 7 Kb, 8 Kb, 9 Kb, 10 Kb, 15 Kb, 20 Kb, 25 Kb, 30 Kb, 40 Kb, 50 Kb, 100 Kb, 200 Kb, 500 Kb, 1 Mb, or more, or a range between any two of these values.

The polynucleotides of the present disclosure can be "biologically active" with respect to either a structural attribute, such as the capacity of a nucleic acid to hybridize to another nucleic acid, or the ability of a polynucleotide sequence to be recognized and bound by one or more of a transcription factor, a ribosome, and a nucleic acid polymerase.

The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by ex vitro polymerase reaction(s), or to which linkers have been attached, or that has been integrated into a vector, such as a cloning vector or expression vector. As non-limiting examples, a recombinant nucleic acid molecule: 1) has been synthesized or modified ex vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination) of nucleic acid molecules; 2) includes conjoined nucleotide sequences that are not conjoined in nature, 3) has been engineered using molecular cloning techniques such that it lacks one or more nucleotides with respect to the naturally-occurring nucleic acid molecule sequence, and/or 4) has been manipulated using molecular cloning techniques such that it has one or more sequence changes or rearrangements with respect to the naturally-occurring nucleic acid sequence. As non-limiting examples, a cDNA is a recombinant DNA molecule, as is any nucleic acid molecule that has been generated by ex vitro polymerase reaction(s), or to which linkers have been attached, or that has been integrated into a vector, such as a cloning vector or expression vector. In some embodiments disclosed herein, the recombinant nucleic acid molecules of the present application are generated from de novo synthesis.

The term "variant" of a protein used herein refers to a polypeptide having an amino acid sequence that is the same or essentially the same as that of the reference protein except having at least one amino acid modified, for example, deleted, inserted, or replaced, respectively. The amino acid replacement may be a conservative amino acid substitution, preferably at a non-essential amino acid residue in the protein. A "conservative amino acid substitution" is one in which the amino acid residue is replaced with an amino acid residue having a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A variant of a protein may have an amino acid sequence at least about 80%, 90%, 95%, or 99%, preferably at least about 90%, more preferably at least about 95%, identical to the amino acid sequence of the protein. Preferably, a variant is a functional variant of a protein that retains the same function as the protein. The terms "variant", when used in reference to a nucleic acid sequence, refer to a nucleic acid sequence that differs by one or more nucleotides from another, usually related nucleotide acid sequence. As such, the term "variant" can refer to a change of one or more nucleotides of a reference nucleic acid which includes the insertion of one or more new nucleotides, deletion of one or more nucleotides, and substitution of one or more existing nucleotides. A "variation" is a difference between two different nucleotide sequences; typically, one sequence is a reference sequence. Broadly, the term "nucleotide variation" as used herein includes point mutation, multiple mutation, single nucleotide polymorphism (SNP), deletion, insertion, and translocation. The term "reference nucleic acid" is used herein to describe a nucleotide sequence having a known reference sequence of interest.

As used herein, the terms, "identical" or percent "identity", in the context of two or more nucleic acids or polypeptide sequences, refer to two or more sequences or subsequences that are the same or have a specified percentage of amino acid residues or nucleotides that are the same, when compared and aligned for maximum correspondence over a comparison window. Unless otherwise specified, the comparison window for a selected sequence, e.g., "SEQ ID NO: X" is the entire length of SEQ ID NO: X, and, e.g., the comparison window for "100 bp of SEQ ID NO: X" is the stated 100 bp. The degree of amino acid or nucleic acid sequence identity can be determined by various computer programs for aligning the sequences to be compared based on designated program parameters. For example, sequences can be aligned and compared using the local homology algorithm of Smith & Waterman *Adv. Appl. Math.* 2:482-89, 1981, the homology alignment algorithm of Needleman & Wunsch *J. Mol. Biol.* 48:443-53, 1970, or the search for similarity method of Pearson & Lipman *Proc. Nat'l. Acad. Sci. USA* 85:2444-48, 1988, and can be aligned and compared based on visual inspection or can use computer programs for the analysis (for example, GAP, BESTFIT, FASTA, and TFASTA in the Wisconsin Genetics Software Package, Genetics Computer Group, 575 Science Dr., Madison, Wis.).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-87, 1993). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, preferably less than about 0.01, and more preferably less than about 0.001.

As used herein, the term "vector" refers to a recombinant polynucleotide construct designed for transfer to a host cell, or between host cells, and that may be used for the purpose of transformation, e.g. the introduction of heterologous DNA into a host cell. A vector can be, for example a replicon, such as a plasmid, bacteriophage, or cosmid, into which another DNA segment may be inserted so as to bring about the replication of the inserted segment. Generally, a vector is capable of replication when associated with the proper control elements. The term "vector" includes cloning vectors and expression vectors, as well as viral vectors and integrating vectors. An "expression vector" is a vector that includes a regulatory region, thereby capable of expressing DNA sequences and fragments, for example ex vitro, ex vivo, and in vivo. In some embodiments, the vector is a plasmid, a bacteriophage vector, a cosmid, a fosmid, a viral replicon, or a combination thereof. In some embodiments, the vector is a eukaryotic vector, a prokaryotic vector (e.g., a bacterial plasmid), or a shuttle vector. An expression system can be, for example, an expression vector or an expression cassette. In some embodiments, the vector is a transcription vector. The term "transcription vector" refers to a vector capable of being transcribed but not translated. For example, transcription vectors can be used to amplify their insert.

Virus-based "replicon" expression vectors can be used as, for example, vaccines and therapeutic compositions. Replicon vectors may be utilized in several formats, including DNA, RNA, and recombinant viral particles. A wide body of literature has now demonstrated efficacy of viral replicon vectors for applications such as vaccines. Moreover, these terms may be referred to collectively as vectors, vector constructs or gene delivery vectors.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Viral Capsid Enhancers

Some viruses have sequences capable of forming one or more stem-loop structures which regulate, for example increase, capsid gene expression. The term "viral capsid enhancer" is used herein to refer to a regulatory element comprising sequences capable of forming such stem-loop structures. In some examples, the stem-loop structures are formed by sequences within the coding sequence of a capsid protein and named Downstream Loop (DLP) sequence. As disclosed herein, these stem-loop structures or variants thereof can be used to regulate, for example increase, expression level of genes of interest. For example, these stem-loop structures or variants thereof can be used in a recombinant vector (e.g., in a heterologous viral genome) for enhancing transcription and/or translation of coding sequence operably linked downstream thereto. As an example, members of the Alphavirus genus can resist the activation of antiviral RNA-activated protein kinase (PKR) by means of a prominent RNA structure present within in viral 26S transcripts, which allows an eIF2-independent translation initiation of these mRNAs. This structure, called the downstream loop (DLP), is located downstream from the AUG in SINV 26S mRNA and in other members of the Alphavirus genus. In the case of Sindbis virus, the DLP motif is found in the first ~150 nt of the Sindbis subgenomic RNA. The hairpin is located downstream of the Sindbis capsid AUG initiation codon (AUG is collated at nt 50 of the Sindbis subgenomic RNA). Previous studies of sequence comparisons and structural RNA analysis revealed the evolutionary conservation of DLP in SINV and predicted the existence of equivalent DLP structures in many members of the Alphavirus genus (see e.g., Ventoso, *J. Virol.* 9484-9494, Vol. 86, September 2012).

PKR phosphorylates the eukaryotic translation initiation factor 2α (eIF2 α). Phosphorylation of eIF2 α blocks translation initiation of mRNA and in doing so keeps viruses from a completing a productive replication cycle. PKR is activated by interferon and double stranded RNA. Alphavirus replication in host cells is known to induce the double-stranded RNA-dependent protein kinase (PKR). For example, Sindbis virus infection of cells induces PKR that results in phosphorylation of eIF2 α yet the viral subgenomic mRNA is efficiently translated while translation of all other cellular mRNAs is restricted. The subgenomic mRNA of Sindbis virus has a stable RNA hairpin loop located downstream of the wild type AUG initiator codon for the virus capsid protein (e.g., capsid enhancer). This hairpin loop, also called stem-loop, RNA structure is often referred to as the Downstream LooP structure (or DLP motif). It has been reported that the DLP structure can stall a ribosome on the wild type AUG and this supports translation of the subgenomic mRNA without the requirement for functional eIF2 α. Thus, subgenomic mRNAs of Sindbis virus (SINV) as well as of other alphaviruses are efficiently translated even in cells that have highly active PKR resulting in complete phosphorylation of eIF2α.

Structure of Alphavirus DLPs

Figure 11A:
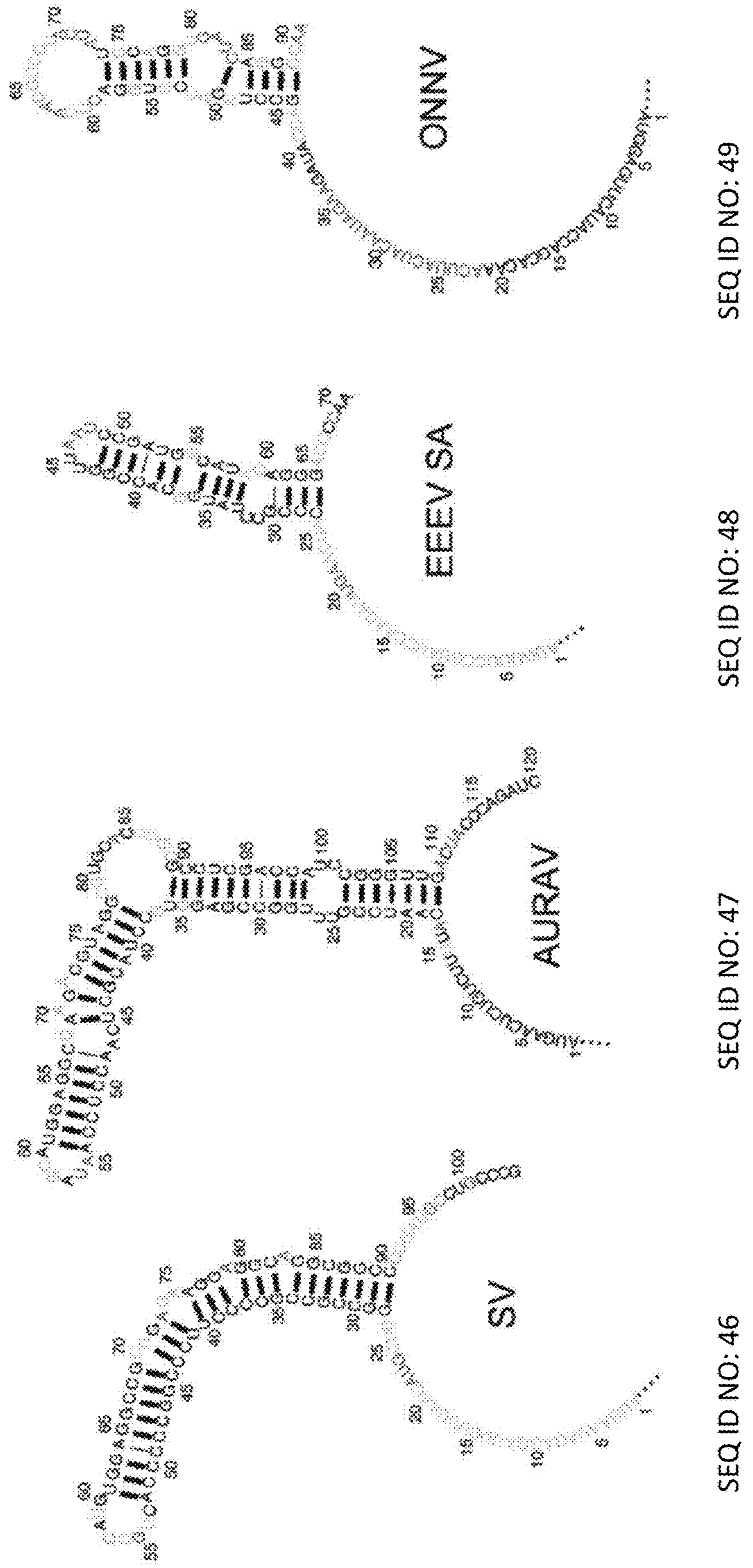
FIGS. 11A-B schematically show the predicted stem-loop RNA structure of the 5' CDS region of alphavirus mRNA 26S with a valley-peak topology. Two dimensional (2D) models of RNA structure based for the first 70-140 nucleotides of the CDS from seven representative Alphavirus mRNAs (SINV, SFV, RRV, SAGV, GETV, MIDV, UNAV, BEBV, MAYV and AURAV). The sequences were numbered from the initiation codon (AUGi), with A being the +1 position. The predicted structures are constructed based on SHAPE (selective 2'-hydroxyl acylation and primer extension) data (Toribio et al., 2016).
Figure 11B:
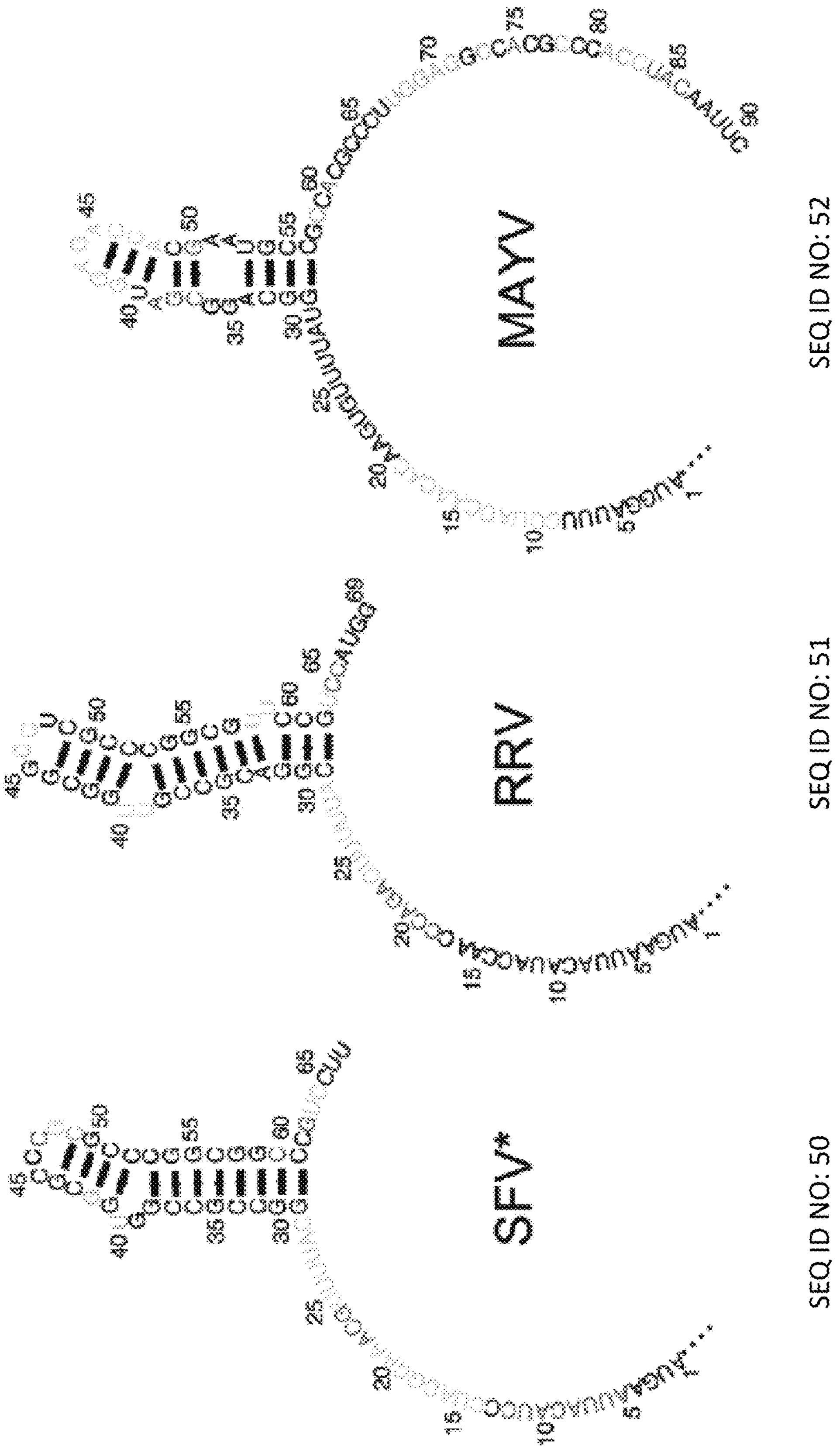

The DLP structure was first characterized in Sindbis virus (SINV) 26S mRNA and also detected in Semliki Forest virus (SFV). Similar DLP structures have been reported to be present in at least 14 other members of the Alphavirus genus including New World (for example, MAYV, UNAV, EEEV (NA), EEEV (SA), AURAV) and Old World (SV, SFV, BEBV, RRV, SAG, GETV, MIDV, CHIKV, and ONNV) members. The predicted structures of these Alphavirus 26S mRNAs were constructed based on SHAPE (selective 2'-hydroxyl acylation and primer extension) data (Toribio et al., *Nucleic Acids Res.* May 19; 44(9):4368-80, 2016), the content of which is hereby incorporated by reference). Stable stem-loop structures were detected in all cases except for CHIKV and ONNV, whereas MAYV and EEEV showed DLPs of lower stability (see FIGS. 11A-B and Toribio et al., 2016 supra). The highest DLP activities were reported for those Alphaviruses that contained the most stable DLP structures. In some instances, DLP activity depends on the distance between the DLP motif and the initiation codon AUG (AUGi). The AUG-DLP spacing in Alphavirus 26S mRNAs is tuned to the topology of the ES6S region of the ribosomal 18S rRNA in a way that allows the placement of the AUGi in the P site of the 40S subunit stalled by the DLP, allowing the incorporation of Met-tRNA without the participation of eIF2. Two main topologies were detected: a compact and stable structure in the SFV clade, and a more extended structure in the SINV group. In both cases, it was observed that DLP structures were preceded by a region of intense SHAPE reactivity, suggesting a single stranded conformation for the AUG-DLP stretch. Accordingly, this region showed a high content of A and a low content of G that resulted in a low propensity to form secondary structures when compared with equivalent positions in whole mouse mRNA transcriptome or in those Alphavirus mRNAs lacking DLPs. These results reported by Toribio et al. (2016, supra) suggest that the occurrence of DLPs in Alphavirus is probably linked to a flattening of the preceding region, resulting in a valley-peak topology for this region of mRNA.

In the case of Sindbis virus, the DLP motif is found in the first ~150 nt of the Sindbis subgenomic RNA. The hairpin is located downstream of the Sindbis capsid AUG initiation codon (AUG at nt 50 of the Sindbis subgenomic RNA) and results in stalling a ribosome such that the correct capsid gene AUG is used to initiate translation. This is because the hairpin causes ribosomes to pause eIF2α is not required to support translation initiation. Without being bound by any particular theory, it is believed that placing the DLP motif upstream of a coding sequence for any GOI typically results in a fusion-protein of N-terminal capsid amino acids that are encoded in the hairpin region to the GOI encoded protein because initiation occurs on the capsid AUG not the GOI AUG. In some embodiments disclosed herein, a porcine teschovirus-1 2A (P2A) peptide sequence was engineered in-frame immediately after the DLP sequence and in-frame immediately upstream of all GOI. The incorporation of the P2A peptide in the modified viral RNA replicons of the present disclosure allows release of a nearly pristine GOI protein from the capsid-GOI fusion; a single proline residue is added to all GOI proteins.

Without being bound by any particular theory, it is believed that the DLP allows translation to occur in an eIF2α independent manner, nucleic acid molecules and expression vectors (e.g., RNA replicon vectors) engineered to use it to initiate translation of non-structural proteins have increased functionality in cells that are innate immune system activated. Therefore, it is contemplated that DLP-engineered nucleic acid molecules and expression vectors (e.g., RNA replicon vectors) also function with more uniformity in different cells, individuals or populations of individuals because differences in the level of innate immune activation in each will naturally cause variability. In some embodiments, the DLP can assist in removing that variability because translation and replication of RNA replicon vectors (as well as GOI expression) can be less impacted by pre-existing innate immune responses. One of the significant values of the compositions and methods disclosed herein is that vaccine efficacy can be increased in individuals that are in a chronic or acute state of immune activation. Causes of chronic or acute immune activation could be found in individuals suffering from a subclinical or clinical infection or individuals undergoing medical treatments for cancer or other maladies (e.g., diabetes, malnutrition, high blood pressure, heart disease, Crohn's disease, muscular scleroses, etc.).

As described herein, DLP-containing nucleic acid molecules (for example, transcription and expression vectors (e.g., RNA viral replicons)) disclosed herein can be useful in conferring a resistance to the innate immune system in a subject. Unmodified RNA replicons are sensitive to the initial innate immune system state of cells they are introduced into. If the cells/individuals are in a highly active innate immune system state, the RNA replicon performance (e.g., replication and expression of a GOI) can be negatively impacted. By engineering a DLP to control initiation of protein translation, particularly of non-structural proteins, the impact of the pre-existing activation state of the innate immune system to influence efficient RNA replicon replication is removed or lessened. The result is more uniform and/or enhanced expression of a GOI that can impact vaccine efficacy or therapeutic impact of a treatment.

Arteriviruses

The arteriviruses (Family Arteriviridae, Genus Arterivirus) encompass an important group of enveloped, single-stranded, positive-sense RNA viruses which infect domestic and wild animals. Arteriviruses share a similar genome organization and replication strategy to that of members of the family Coronaviridae (genera Coronavirus and Torovirus), but differ considerably in their genetic complexity, genome length, biophysical properties, size, architecture, and structural protein composition of the viral particles (e.g., virion). Currently, the Arterivirus genus is considered to include equine arteritis virus (EAV), porcine reproductive and respiratory syndrome virus (PRRSV), lactate dehydrogenase-elevating virus (LDV) of mice, simian hemorrhagic fever virus (SHFV), and wobbly possum disease virus (WPDV).

Figure 10:
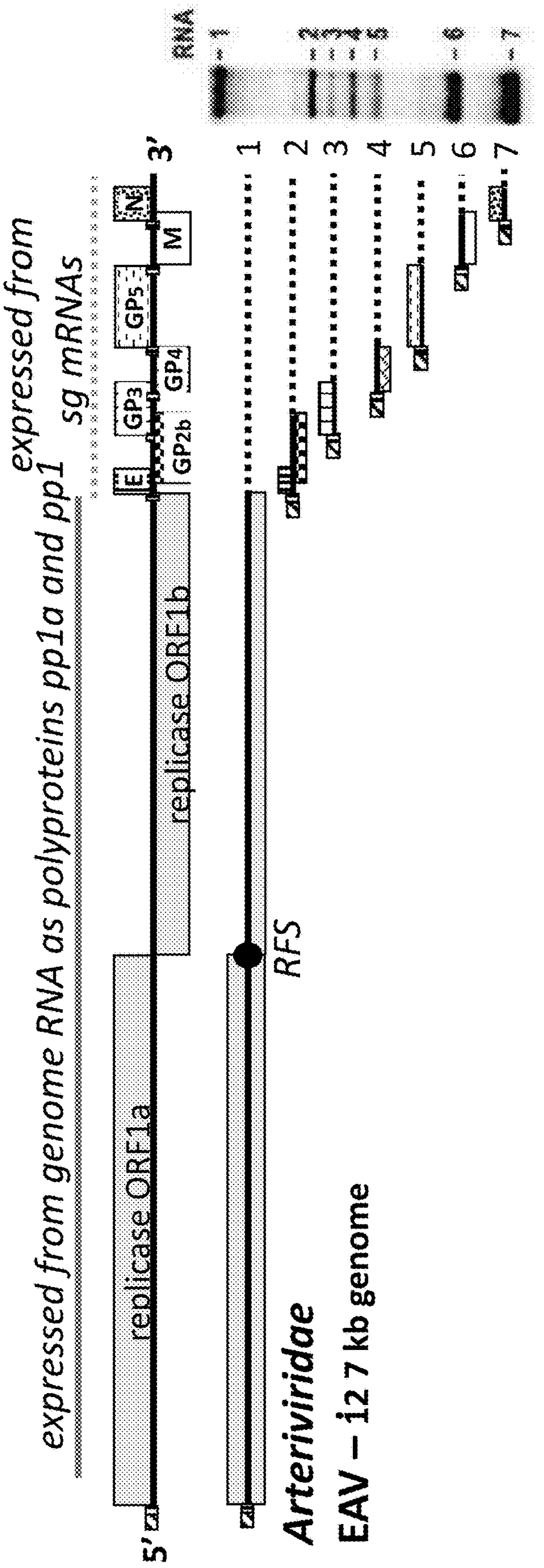
FIG. 10 schematically depicts EAV genomic structure and genome expression strategy. The names of the replicase gene and structural protein genes are given (references to the nomenclature of genes and proteins can be found in Snijder et al., 2005). Below the genome organization, the structural relationships of the genome and sg mRNAs are depicted. The leader sequence and TRSs found at the 5' end of the EAV mRNAs are indicated as blue and orange boxes, respectively. The ribosomal frameshifting element (RFS) found in the genome-length mRNA1 is indicated and the translated region of each mRNA is highlighted by a green line, whereas translationally silent regions are indicated by a red line. Only the translated open reading frames are indicated for each mRNA. The right-hand panels show a typical pattern of EAV mRNAs isolated from infected cells, visualized by hybridization to a probe complementary to the 3' end of the genome and therefore recognizing all viral mRNA species.

A typical arterivirus genome varies between 12.7 and 15.7 kb in length but their genome organization is relatively consistent with some minor variations. Exemplary genome organization and virion architecture of an arterivirus is shown in FIG. 10. The arterivirus genome is a polycistronic+ RNA, with 5' and 3' non-translated regions (NTRs) that flank an array of 10-15 known ORFs. The large replicase ORFs 1a and 1b occupy the 5'-proximal three-quarters of the genome, with the size of ORF1a being much more variable than that of ORF1b. Translation of ORF1a produces replicase polyprotein (pp) 1a, whereas ORF1b is expressed by −1 programmed ribosomal frameshifting (PRF), which C-terminally extends pp1a into pp1ab. In addition, a short transframe ORF has been reported to overlap the nsp2-coding region of ORF1a in the +1 frame and to be expressed by −2 PRF. The 3'-proximal genome part has a compact organization and contains 8 to 12 relatively small genes, most of which overlap with neighboring genes. These ORFs encode structural proteins and are expressed from a 3'-co-terminal nested set of sg mRNAs. The organization of these ORFs is conserved, but downstream of ORF1b, SHFV and all recently identified SHFV-like viruses contain three or four additional ORFs (~1.6 kb) that may be derived from an ancient duplication of ORFs 2-4. Together with the size variation in ORF1a, this presumed duplication explains the genome size differences among arteriviruses.

With regard to equine arteritis virus (EAV), the wild-type EAV genome is approximately 12.7 Kb in size. The 5' three fourths of the genome codes for two large replicase proteins 1a and 1ab; the amino acid sequences of the two proteins are N-terminally identical but due to a ribosomal frameshift the amino acid sequence of the C-terminal region of 1ab is unique. The 3' one quarter of the EAV genome codes for the virus's structural protein genes, all of which are expressed from subgenomic RNAs. The subgenomic RNAs form a nested set of 3' co-terminal RNAs that are generated via a discontinuous transcriptional mechanism. The subgenomic RNAs are made up of sequences that are not contiguous with the genomic RNA. All of the EAV subgenomic RNAs share a common 5' leader sequence (156 to 221 nt in length) that is identical to the genomic 5' sequence. The leader and body parts of the subgenomic RNAs are connected by a conserved sequence termed a transcriptional-regulatory sequence (TRS). The TRS is found on the 3' end of the leader (leader TRS) as well as in the subgenomic promoter regions located upstream of each structural protein gene (body TRS). Subgenomic RNAs are generated as the negative strand replication intermediate RNA is transcribed. As transcription occurs the replication complex pauses as it comes to each body TRS and then the nascent negative strand RNA become associated with the complementary positive strand leader TRS where negative strand RNA transcription continues. This discontinuous transcription mechanism results in subgenomic RNA with both 5' and 3' EAV conserved sequences. The negative strand subgenomic RNAs then become the template for production of the subgenomic positive sense mRNA.

Infectious cDNA clones, representing the entire genome of EAV, have been reported and they have been used to study EAV RNA replication and transcription for nearly two decades. In addition, infectious clones have been generated that contain the chloramphenicol acetyltransferase (CAT) gene inserted in place of ORF2 and ORF7, and CAT protein was shown to be expressed in cells electroporated with those RNAs. Modifications of the infectious clone via site directed mutagenesis and deletion of the structural protein gene regions has been used to determine the requirement for each structural gene in support of RNA replication (Molenkamp 2000). The study reported by Molenkamp 2000 concluded that the structural genes are not required to support RNA replication. Analysis of sequence homology requirements for TRS activity in subgenomic RNA production was conducted and used to better define how discontinuous transcription mechanistically occurs (van Marle 1999, Pasternak 2000, Pasternak 2001, Pasternak 2003, van den Born 2005) and defective interfering RNAs have been used to understand the minimal genomic sequences required for replication and packaging of RNA into virus particles (Molenkamp 2000a).

Alphaviruses

Alphavirus is a genus of genetically, structurally, and serologically related viruses of the group IV Togaviridae family which includes at least 30 members, each having single stranded RNA genomes of positive polarity enclosed in a nucleocapsid surrounded by an envelope containing viral spike proteins. Currently, the alphavirus genus comprises among others the Sindbis virus (SIN), the Semliki Forest virus (SFV), the Ross River virus (RRV), Venezuelan equine encephalitis virus (VEEV), and Eastern equine encephalitis virus (EEEV), which are all closely related and are able to infect various vertebrates such as mammal, rodents, fish, avian species, and larger mammals such as humans and horses as well as invertebrates such as insects. Transmission between species and individuals occurs mainly via mosquitoes making the alphaviruses a contributor to the collection of Arboviruses- or Arthropod-Borne Viruses. In particular, the Sindbis and the Semliki Forest viruses have been widely studied and, therefore, the life cycle, mode of replication, etc., of these viruses are well characterized. In particular, alphaviruses have been shown to replicate very efficiently in animal cells which makes them valuable as vectors for production of protein and nucleic acids in such cells.

Figure 9:
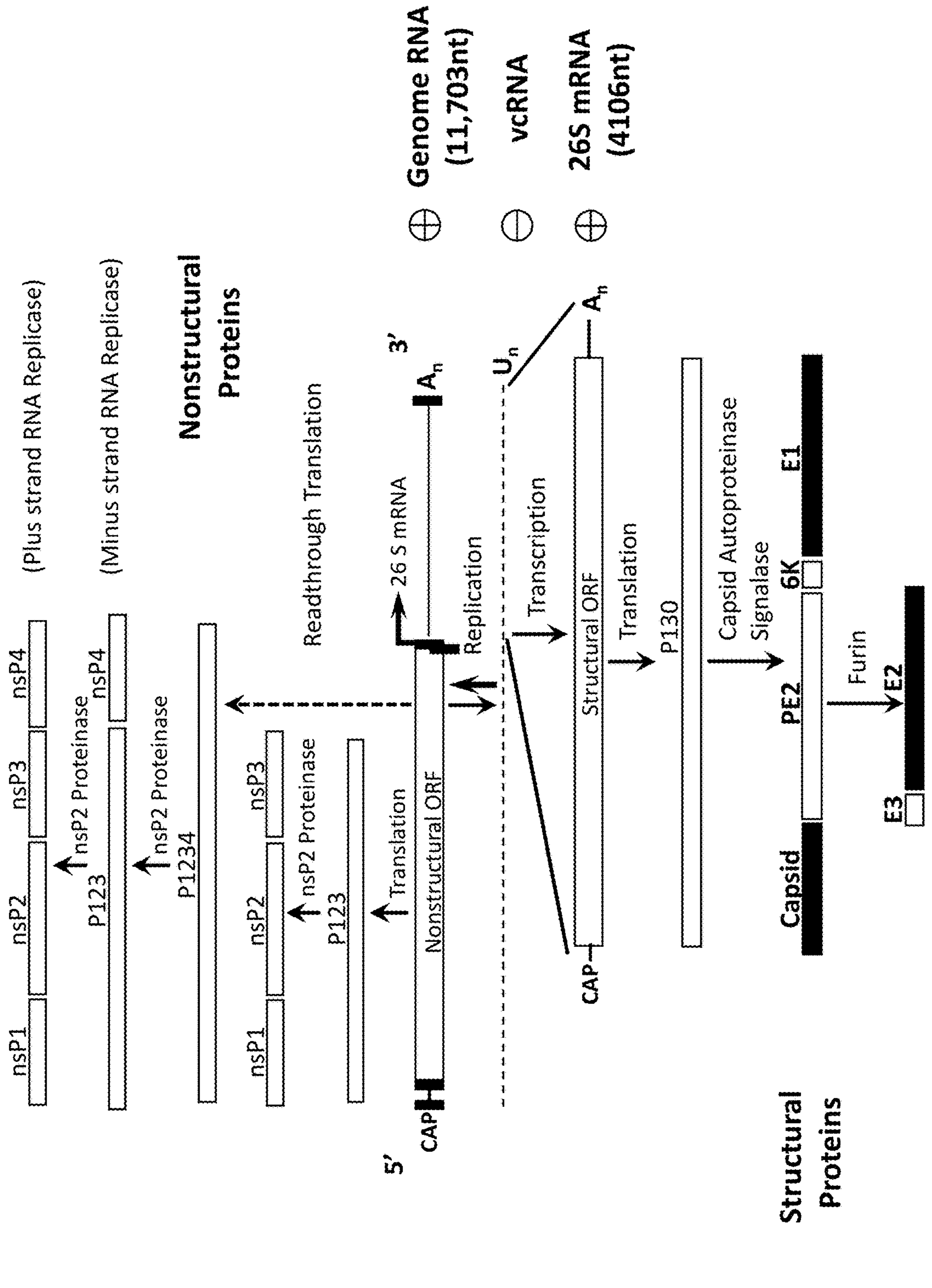
FIG. 9 schematically depicts a non-limiting exemplary alphavirus genomic structure and genome expression (adapted from Strauss et al., Microbiological Reviews, pp. 491-562, September 1994). Genome organization of a Sindbis virus (SINV) is shown. The names of the nonstructural genes and structural protein genes are given. Referenced to the nomenclature of the genes and proteins can be found in Strauss et al., supra, 1994. The 49S genomic RNA is illustrated schematically in the center, with its translated ORF shown as an open box. Small black boxes are conserved sequence elements; the open diamond denotes the leaky opal termination codon. The nonstructural polyproteins and their processed products are shown above. Termination at the opal codon produces P123, whose major function in replication is believed to be as a proteinase that acts in trans to process the polyproteins in active RNA replicases; this proteinase domain is found in the nsP2 region. Read-through of the opal stop codon produces P1234, which can form an active replicase. The 26S subgenomic mRNA is expanded below to show the structural ORF and its translation products. Polypeptides present in the virion are shaded. vcRNA is the minus-strand complement of the genomic RNA.

Alphavirus particles are enveloped, have a 70 nm diameter, tend to be spherical (although slightly pleomorphic), and have an approximately 40 nm isometric nucleocapsid. FIG. 9 depicts a typical alphavirus genomic structure and genome expression. Alphavirus genome is single-stranded RNA of positive polarity of approximately 11-12 kb in length, comprising a 5' cap, a 3' poly-A tail, and two open reading frames with a first frame encoding the nonstructural proteins with enzymatic function and a second frame encoding the viral structural proteins (e.g., the capsid protein C, E1 glycoprotein, E2 glycoprotein, E3 protein and 6K protein).

The 5' two-thirds of the alphavirus genome encodes a number of nonstructural proteins necessary for transcription and replication of viral RNA. These proteins are translated directly from the RNA and together with cellular proteins form the RNA-dependent RNA polymerase essential for viral genome replication and transcription of subgenomic RNA. Four nonstructural proteins (nsP1-4) are produced as a single polyprotein which constitutes the virus' replication machinery. The processing of the polyprotein occurs in a highly regulated manner, with cleavage at the P2/3 junction influencing RNA template use during genome replication. This site is located at the base of a narrow cleft and is not readily accessible. Once cleaved, nsP3 creates a ring structure that encircles nsP2. These two proteins have an extensive interface. Mutations in nsP2 that produce noncytopathic viruses or a temperature sensitive phenotypes cluster at the P2/P3 interface region. P3 mutations opposite the location of the nsP2 noncytopathic mutations prevent efficient cleavage of P2/3. This in turn can affect RNA infectivity altering viral RNA production levels.

The 3' one-third of the genome comprises subgenomic RNA which serves as a template for translation of all the structural proteins required for forming viral particles: the core nucleocapsid protein C, and the envelope proteins P62 and E1 that associate as a heterodimer. The viral membrane-anchored surface glycoproteins are responsible for receptor recognition and entry into target cells through membrane fusion. The subgenomic RNA is transcribed from the p26S subgenomic promoter present at the 3' end of the RNA sequence encoding the nsp4 protein. The proteolytic maturation of P62 into E2 and E3 causes a change in the viral surface. Together the E1, E2, and sometimes E3, glycoprotein "spikes" form an E1/E2 dimer or an E1/E2/E3 trimer, where E2 extends from the center to the vertices, E1 fills the space between the vertices, and E3, if present, is at the distal end of the spike. Upon exposure of the virus to the acidity of the endosome, E1 dissociates from E2 to form an E1 homotrimer, which is necessary for the fusion step to drive the cellular and viral membranes together. The alphaviral glycoprotein E1 is a class II viral fusion protein, which is structurally different from the class I fusion proteins found in influenza virus and HIV. The E2 glycoprotein functions to interact with the nucleocapsid through its cytoplasmic domain, while its ectodomain is responsible for binding a cellular receptor. Most alphaviruses lose the peripheral protein E3, while in Semliki viruses it remains associated with the viral surface.

Alphavirus replication has been reported to take place on membranous surface within the host cell. In the first step of the infectious cycle, the 5' end of the genomic RNA is translated into a polyprotein (nsP1-4) with RNA polymerase activity that produces a negative strand complementary to the genomic RNA. In a second step, the negative strand is used as a template for the production of two RNAs, respectively: (1) a positive genomic RNA corresponding to the genome of the secondary viruses producing, by translation, other nsp proteins and acting as a genome for the virus; and (2) subgenomic RNA encoding the structural proteins of the virus forming the infectious particles. The positive genomic RNA/subgenomic RNA ratio is regulated by proteolytic autocleavage of the polyprotein to nsp 1, nsp 2, nsp 3 and nsp 4. In practice, the viral gene expression takes place in two phases. In a first phase, there is main synthesis of positive genomic strands and of negative strands. During the second phase, the synthesis of subgenomic RNA is virtually exclusive, thus resulting in the production of large amount of structural protein.

Innate Immunity

Since innate immune activation can occur due to many different stimuli, vaccine approaches that rely on self-amplifying RNA replicons to express antigen or therapeutic GOI can be negatively impacted by the global host protein shutdown associated with PKR phosphorylation of eIF2$\alpha$. Engineering RNA replicons to function in a cellular environment where host protein translation is repressed would provide those systems with a significant advantage over standard RNA replicon systems.

Accordingly, RNA replicon systems that are negatively impacted by innate immune responses, such as systems derived from alphaviruses and arteriviruses, can be more effective at expressing their encoded GOI when engineered to contain a DLP motif. The DLP motif confers efficient mRNA translation in cellular environments where cellular mRNA translation is inhibited. When a DLP is linked with translation of a replicon vectors non-structural protein genes the replicase and transcriptase proteins are capable of initiating functional replication in PKR activated cellular environments. When a DLP is linked with translation of subgenomic mRNAs robust GOI expression is possible even when cellular mRNA is restricted due to innate immune activation.

Accordingly, engineering replicons that contain DLP structures to help drive translation of both non-structural protein genes and subgenomic mRNAs provides yet another powerful way to overcome innate immune activation.

Some embodiments of the disclosure relate to DLP structures that have been engineered to support translation of viral non-structural genes of replicon vectors derived from two different viruses, Venezuelan equine encephalitis virus (VEEV) and equine arteritis virus (EAV), thus conveying innate immune response evasion to the systems. As described in greater detail below, incorporation of the DLP structures into the replicon vectors made them both resistant to interferon (IFN) treatment and unexpectedly also resulted in an overall increase in GOI expression potential. The combination of IFN resistance and superior protein expression potential imparted by engineering a DLP into the RNA replicon systems make them suitable for use in individuals or populations where innate immune activation is acutely or chronically present.

Nucleic Acid Molecules of the Disclosure

Some aspects of the present disclosure relate to nucleic acid molecules, such as synthetic or recombinant nucleic acid molecules, that include one or more DLP motifs, a coding sequence for one or more DLP motifs, or a combination thereof. In some embodiments, the nucleic acid molecules of the disclosure can include a coding sequence for a gene of interest (GOI) operably linked to DLP motif(s) and/or the coding sequence for the DLP motifs.

In one aspect, disclosed herein is a nucleic acid molecule, comprising (i) a first nucleic acid sequence encoding one or more structural elements of a viral capsid enhancer or a variant thereof and (ii) a second nucleic acid sequence operably linked to the first nucleic acid sequence, wherein the second nucleic acid sequence comprises a coding sequence for a gene of interest (GOI). In some embodiments, at least one of the one or more structural elements of the viral capsid enhancer comprises one or more RNA stem-loops. In some embodiments, at least one of the one or more RNA stem-loops is comprised by a DLP motif present in the first nucleic acid sequence. In some embodiments, at least one of the one or more structural elements of the viral capsid enhancer does not comprise any RNA stem-loop.

As described above, a viral capsid enhancer comprises sequences within the 5' non-coding and/or 5' coding sequences (preferably, the 5' coding sequences) of that enhance expression (e.g., transcription and/or translation) of sequences operably linked therewith. In some embodiments of the present disclosure, the one or more structural elements of the viral capsid enhancer include one or two RNA stem-loops of the viral capsid enhancer. In some embodiments, the viral capsid enhancer of the present disclosure includes the sequences containing the 26S subgenomic promoter. In some embodiments, the viral capsid enhancer of the disclosure contains the 5' coding sequences at about nucleotides 20 to 250, about nucleotides 20 to 200, about nucleotides 20 to 150, about nucleotides 20 to 100, or about nucleotides 50 to 250, about nucleotides 100 to 250, about nucleotides 50 to 200, about nucleotides 75 to 250, about nucleotides 75 to 200, about nucleotides 75 to 150, about nucleotides 77 to 139, or about nucleotides 100 to 250, about nucleotides 150 to 250, about nucleotides 100 to 150, about nucleotides 100 to 200 of the viral 26S RNA, which is capable of forming a hairpin structure. In some embodiments, the first nucleic acid sequence encoding one or more structural elements of a viral capsid enhancer that are important for enhancing expression of a heterologous sequence operably linked thereto. In some embodiments, the first nucleic acid sequence includes encoding sequence for one or more RNA stem-loops of a viral capsid enhancer. In some embodiments, the first nucleic acid sequence encoding one or more structural elements of a viral capsid enhancer that are important for enhancing translation of a heterologous sequence operably linked thereto. In some embodiments, the first nucleic acid sequence encoding one or more structural elements of a viral capsid enhancer that are important for enhancing transcription of a heterologous sequence operably linked thereto.

In some embodiments, the first nucleic acid sequence of the nucleic acid molecule includes at least about 50, about 75, about 100, about 150, about 200, about 300, or more nucleotides from the 5' coding sequence for a viral capsid protein. In some embodiments, the first nucleic acid sequence of the nucleic acid molecule includes about 50, about 75, about 100, about 150, about 200, about 300, or more, or a range between any two of these values, nucleotides from the 5' coding sequence for a viral capsid protein. In some embodiments, the viral capsid enhancer is derived from a capsid gene of an alphavirus species selected from the group consisting of Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), and Buggy Creek virus. In some embodiments, the viral capsid enhancer is derived from a capsid gene of a Sindbis virus species or a Semliki Forest virus species. In some particular embodiments, the viral capsid enhancer is derived from a capsid gene of a Sindbis virus species. Additionally, one of ordinary skill in the art will appreciate that modifications may be made in the 5' coding sequences from the viral capsid protein without substantially reducing its enhancing activities. More information in this regard can be found in, e.g., Frolov et al., *J. Virology* 70:1182, 1994; Frolov et al., *J. Virology* 68:8111, 1994. In some embodiments, it can be advantage for such mutations to substantially preserve the RNA hairpin structure formed by the 5' capsid coding sequences.

In some embodiments, the viral capsid enhancer disclosed herein does not contain one or more, or all, of the 5' coding sequences of the capsid protein that are upstream of the hairpin structure. In some embodiments, the viral capsid enhancer disclosed herein does not contain all of the 5' coding sequences of the viral capsid protein that are upstream of the hairpin structure. In some embodiments, the viral capsid enhancer sequence may encode all or part of the capsid protein. Accordingly, in some embodiments disclosed herein, the capsid enhancer region will not encode the entire viral capsid protein. In some embodiments, the viral capsid enhancer sequence encodes an amino terminal fragment from the viral capsid protein. In those embodiments in which an otherwise functional capsid protein is encoded by the capsid enhancer sequence, it may be desirable to ablate the capsid autoprotease activity. Capsid mutations that reduce or ablate the autoprotease activity of the capsid protein are known in the art (see e.g., WO1996/37616). In addition or alternatively, one or more of amino acid residues in the capsid protein may be altered to reduce capsid protease activity.

As indicated above, previous studies of sequence comparisons and structural RNA analysis revealed the evolutionary conservation of DLP motifs in many members of the Alphavirus genus (see e.g., Ventoso, 2012 supra). Accordingly, in some further embodiments, the viral capsid enhancer sequence of the present disclosure can be of any other variant sequence such as, for example, a synthetic sequence or a heterologous sequence, that can form an RNA hairpin functionally or structurally equivalent to one or more of the RNA stem-loops predicted for a viral capsid enhancer and which can act to enhance translation of RNA sequences operably linked downstream thereto (e.g., coding sequence for a gene of interest). Non-limiting examples of RNA stem-loops which can act as a transcriptional and/or translational enhancer include those shown in FIGS. 11A-B. In some embodiments, the nucleic acid molecule of the disclosure includes an alphavirus capsid enhancer as derived from Sindbis virus (SINV; NC 001547.1), Aura virus (AURAV; AF126284), Chikungunya virus (CHIKV; NC 004162), O'Nyong-Nyong virus (ONNV; NC 001512), Eastern Equine Encephalitis virus (EEEV(SA); AF159559 and EEEV (NA); U01558), Mayaro virus (MAYV; DQ001069), Semliki Forest virus (SFV; NC 003215), Ross River virus (RRV; DQ226993 and Sagiyama virus (SAGV; AB032553), Getah virus (GETV; NC 006558), Middelburg virus (MIDV; EF536323), Una virus (UNAV; AF33948), or Bebaru virus (BEBV; AF339480) as described in Toribio et al., 2016 supra, the content of which is hereby incorporated by reference in its entirety, or a variant thereof.

Nucleic acid molecules having a high degree of sequence identity (e.g., at least 85%, at least 90%, at least 95%, at least 96%, at least 97%, at least 98%, at least 99%, or 100% sequence identity) to the coding sequence for a viral capsid enhancer disclosed herein can be identified and/or isolated by using the sequence described herein (e.g., SEQ ID NO: 1) or any others alphavirus capsid protein as they are known in the art, for example, by using the sequences of Sindbis virus (SINV; NC 001547.1), Aura virus (AURAV; AF126284), Chikungunya virus (CHIKV; NC 004162), O'Nyong-Nyong virus (ONNV; NC 001512), Eastern Equine Encephalitis virus (EEEV(SA); AF159559 and EEEV (NA); U01558), Mayaro virus (MAYV; DQ001069), Semliki Forest virus (SFV; NC 003215), Ross River virus (RRV; DQ226993 and Sagiyama virus (SAGV; AB032553), Getah virus (GETV; NC 006558), Middelburg virus (MIDV; EF536323), Una virus (UNAV; AF33948), and Bebaru virus (BEBV; AF339480), by genome sequence analysis, hybridization, and/or PCR with degenerate primers or gene-specific primers from sequences identified in the respective alphavirus genome. For example, the viral capsid enhancer can comprise, or consist of, a DLP motif from a virus species belonging to the Togaviridae family, for example an alphavirus species or a rubivirus species. In some embodiments, the nucleic acid molecule of the disclosure includes a viral capsid enhancer having a nucleic acid sequence that exhibits at least 80%, at least 85%, at least 90%, at least 95%, at least 96%, at least 97%, at least 98%, at least 99%, or 100% sequence identity to the 5' CDS portion of an alphavirus capsid protein. In some embodiments, the 5' CDS portion of an alphavirus capsid protein comprises at least the first 25, 50, 75, 80, 100, 150, or 200 nucleotides of the coding sequence for the alphavirus capsid protein. In some embodiments, the nucleic acid molecule of the disclosure includes a viral capsid enhancer having a nucleic acid sequence that exhibits at least 80%, at least 85%, at least 90%, at least 95%, at least 96%, at least 97%, at least 98%, at least 99%, or 100% sequence identity to the nucleic acid sequence of any one of SEQ ID NOs: 1 and 46-52. In some embodiments, the nucleic acid molecule comprises a viral capsid enhancer having a nucleic acid sequence that exhibits 80%, 85%, 90%, 91%, 92%, 93%, 94%, 95%, 96%, 97%, 98%, 99%, 100%, or a range between any two of these values, sequence identity to the nucleic acid sequence of any one of SEQ ID NOs: 1 and 46-52. In some embodiments, the nucleic acid molecule of the disclosure includes a viral capsid enhancer having a nucleic acid sequence that exhibits at least 80%, at least 85%, at least 90%, at least 95%, at least 96%, at least 97%, at least 98%, at least 99%, or 100% sequence identity to the sequence of SEQ ID NO: 1 disclosed herein. In some embodiments, the nucleic acid molecule of the disclosure includes a viral capsid enhancer having a nucleic acid sequence that exhibits at least 80%, at least 85%, at least 90%, at least 95%, at least 96%, at least 97%, at least 98%, at least 99%, or 100% sequence identity to any one of the sequences described in FIGS. 11A-B and/or FIG. 1A in the publication by Toribio et al. (2016 supra), the content of which is hereby incorporated by reference in its entirety.

Accordingly, in some embodiments, the nucleic acid molecule of the disclosure includes a viral capsid enhancer having a nucleic acid sequence that exhibits at least 80%, at least 85%, at least 90%, at least 95%, at least 96%, at least 97%, at least 98%, at least 99%, or 100% sequence identity to the sequence of any one of SEQ ID NOS: 46-52 disclosed herein. In some embodiments, the nucleic acid molecule of the disclosure includes a viral capsid enhancer having a nucleic acid sequence that exhibits at least 80%, at least 85%, at least 90%, at least 95%, at least 96%, at least 97%, at least 98%, at least 99%, or 100% sequence identity to the sequence set forth at SEQ ID NO: 46 disclosed herein. In some embodiments, the nucleic acid molecule of the disclosure includes a viral capsid enhancer having a nucleic acid sequence that exhibits at least 80%, at least 85%, at least 90%, at least 95%, at least 96%, at least 97%, at least 98%, at least 99%, or 100% sequence identity to the sequence set forth at SEQ ID NO: 47 disclosed herein. In some embodiments, the nucleic acid molecule of the disclosure includes a viral capsid enhancer having a nucleic acid sequence that exhibits at least 80%, at least 85%, at least 90%, at least 95%, at least 96%, at least 97%, at least 98%, at least 99%, or 100% sequence identity to the sequence set forth at SEQ ID NO: 48 disclosed herein. In some embodiments, the nucleic acid molecule of the disclosure includes a viral capsid enhancer having a nucleic acid sequence that exhibits at least 80%, at least 85%, at least 90%, at least 95%, at least 96%, at least 97%, at least 98%, at least 99%, or 100% sequence identity to the sequence set forth at SEQ ID NO: 49 disclosed herein. In some embodiments, the nucleic acid molecule of the disclosure includes a viral capsid enhancer having a nucleic acid sequence that exhibits at least 80%, at least 85%, at least 90%, at least 95%, at least 96%, at least 97%, at least 98%, at least 99%, or 100% sequence identity to the sequence set forth at SEQ ID NO: 50 disclosed herein. In some embodiments, the nucleic acid molecule of the disclosure includes a viral capsid enhancer having a nucleic acid sequence that exhibits at least 80%, at least 85%, at least 90%, at least 95%, at least 96%, at least 97%, at least 98%, at least 99%, or 100% sequence identity to the sequence set forth at SEQ ID NO: 51 disclosed herein. In some embodiments, the nucleic acid molecule of the disclosure includes a viral capsid enhancer having a nucleic acid sequence that exhibits at least 80%, at least 85%, at least 90%, at least 95%, at least 96%, at least 97%, at least 98%, at least 99%, or 100% sequence identity to the sequence set forth at SEQ ID NO: 52 disclosed herein.

In the nucleic acid molecule according to some embodiments of the present disclosure, the one or more RNA stem-loops are operably positioned upstream of the coding sequence for the GOI of the second nucleic acid sequence. In some embodiments, the one or more RNA stem-loops are operably positioned from about 1 to about 50 nucleotides, from about 10 to about 75 nucleotides, from about 30 to about 100 nucleotides, from about 40 to about 150 nucleotides, from about 50 to about 200 nucleotides, from about 60 to about 250 nucleotides, from about 100 to about 300 nucleotides, or from about 150 to about 500 nucleotides upstream of the coding sequence for the GOI. In some embodiments, the one or more RNA stem-loops are operably positioned from about 1, about 2, about 5, about 10, about 15, about 20, about 25, about 30, about 40, about 50, about 60, about 70, about 80, about 90, about 100, about 200, about 300, about 400, about 500, or a range between any two of these values, nucleotides upstream of the coding sequence for the GOI. In some embodiments, the one or more RNA stem-loops are operably positioned immediately upstream of the coding sequence for the GOI.

In some embodiments, the nucleic acid molecule further includes a 5'-unstranslated region (5'-UTR) sequence operably positioned upstream to the first nucleic acid sequence. In some embodiments, the 5'-UTR sequence is operably positioned from about 1 to about 50, from about 10 to about 75, from about 30 to about 100, from about 40 to about 150, from about 50 to about 200, from about 60 to about 250, from about 100 to about 300, or from about 150 to about 500 nucleotides upstream of the first nucleic acid sequence.

In some embodiments, the 5'-UTR sequence is operably positioned from about 1, about 2, about 5, about 10, about 15, about 20, about 25, about 30, about 40, about 50, about 60, about 70, about 80, about 90, or 100 nucleotides upstream of the first nucleic acid sequence. In some embodiments, the 5'-UTR sequence is operably positioned immediately upstream of the first nucleic acid sequence.

In some embodiments, the 5' UTR sequence is operably positioned downstream to the promoter. In some embodiments, the 5'-UTR sequence is operably positioned from about 1 to about 50, from about 10 to about 75, from about 30 to about 100, from about 40 to about 150, from about 50 to about 200, from about 60 to about 250, from about 100 to about 300, or from about 150 to about 500 nucleotides downstream of the promoter sequence. In some embodiments, the 5' UTR sequence is operably positioned from about 1, about 2, about 5, about 10, about 15, about 20, about 25, about 30, about 40, about 50, about 60, about 70, about 80, about 90, or 100 nucleotides downstream of the promoter sequence. In some embodiments, the 5' UTR sequence is operably positioned immediately downstream to the promoter sequence. In some embodiments, the 5' UTR sequence is operably positioned downstream to the promoter and upstream to the first nucleic acid sequence.

In some embodiments, the nucleic acid molecule comprises a 3' unstranslated region (3' UTR) sequence operably positioned downstream of the second nucleic acid sequence. In some embodiments, the 3' UTR sequence is operably positioned from about 1 to about 50 nucleotides, from about 10 to about 75 nucleotides, from about 30 to about 100 nucleotides, from about 40 to about 150 nucleotides, from about 50 to about 200 nucleotides, from about 60 to about 250 nucleotides, from about 100 to about 300 nucleotides, or from about 150 to about 500 nucleotides downstream of the second sequence nucleic acid sequence. In some embodiments, the 3' UTR sequence is operably positioned from about 1, about 2, about 5, about 10, about 15, about 20, about 25, about 30, about 40, about 50, about 60, about 70, about 80, about 90, about 100, about 200, about 300, about 400, about 500, or a range between any two of these values, nucleotides downstream of the second nucleic acid sequence. In some embodiments, the 3' UTR sequence is operably positioned immediately downstream of the second nucleic acid sequence.

In some embodiments disclosed herein, the coding sequence for the GOI is transcribed into a messenger RNA (mRNA) or part of an mRNA. As used herein, the term "mRNA" or "messenger RNA" refers to a single stranded RNA molecule that is synthesized during transcription, is complementary to one of the strands of double-stranded DNA, and serves to transmit the genetic information contained in DNA to the ribosomes for protein synthesis. The mRNA may be spliced, partially spliced or unspliced, and may be eukaryotic or prokaryotic mRNA. As discussed above, mRNA molecules according to some embodiments of the disclosure can be produced via de novo synthesis. In some embodiments disclosed herein, the coding sequence for the GOI encodes a polypeptide. In some embodiments, the polypeptide is a therapeutic polypeptide, a prophylactic polypeptide, a diagnostic polypeptide, a nutraceutical polypeptide, an industrial enzyme, a reporter polypeptide, or any combination thereof. In some embodiments, the polypeptide is an antibody, an antigen, an immune modulator, a cytokine, an enzyme, or any combination thereof.

In some embodiments, the nucleic acid molecule of the disclosure further includes a coding sequence for an autoprotease peptide (e.g., autocatalytic self-cleaving peptide), where the coding sequence for the autoprotease is optionally operably linked upstream to the second nucleic acid sequence. Generally, any proteolytic cleavage site known in the art can be incorporated into the nucleic acid molecules of the disclosure and can be, for example, proteolytic cleavage sequences that are cleaved post-production by a protease. Further suitable proteolytic cleavage sites also include proteolytic cleavage sequences that can be cleaved following addition of an external protease. As used herein the term "autoprotease" refers to a "self-cleaving" peptide that possesses autoproteolytic activity and is capable of cleaving itself from a larger polypeptide moiety. First identified in the foot-and-mouth disease virus (FMDV), a member of the picornavirus group, several autoproteases have been subsequently identified such as, for example, "2A like" peptides from equine rhinitis A virus (E2A), porcine teschovirus-1 (P2A) and Thosea asigna virus (T2A), and their activities in proteolytic cleavage have been shown in various ex vitro and in vivo eukaryotic systems. As such, the concept of autoproteases is available to one of skill in the art with many naturally-occurring autoprotease systems have been identified. Well studied autoprotease systems are e.g. viral proteases, developmental proteins (e.g. HetR, Hedgehog proteins), RumA autoprotease domain, UmuD, etc.). Non-limiting examples of autoprotease peptides suitable for the compositions and methods of the present disclosure include the peptide sequences from porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), or a combination thereof.

In some embodiments, the coding sequence for an autoprotease peptide is operably linked downstream to the first nucleic acid sequence and upstream to the second nucleic acid sequence. In some embodiments, the autoprotease peptide comprises, or consists of, a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof. In some embodiments, the autoprotease peptide includes a peptide sequence of porcine teschovirus-1 2A (P2A).

One of skill in the art will appreciate that different configurations of the viral capsid enhancer sequence, the sequence encoding the autoprotease peptide, and the sequence encoding the gene of interest can be employed as long as the capsid enhancer sequence enhances expression of the heterologous nucleic acid sequence(s), e.g. a coding sequence for a GOI, as compared with the level seen in the absence of the capsid enhancer sequence. These sequences will typically be configured so that the polypeptide encoded by the gene of interest can be released from the protease and any capsid protein sequence after cleavage by the autoprotease.

A non-limiting list of exemplary combinations of autoprotease peptides described herein (such as P2A, F2A, E2A, T2A, BmCPV2A, and BmIFV2A) with one or more viral capsid enhancer sequences described herein are provided in Tables 1 and 2. Table 1 provides a shorthand name for each viral capsid enhancer (e.g., “CE01”) and a shorthand name for each autoprotease peptide (e.g., “AP01”). Each numbered ‘X’ peptide in Table 2 has a corresponding autoprotease peptide provided in Table 1. Likewise, each numbered ‘Y’ enhancer in Table 2 has a corresponding viral capsid enhancer provided in Table 1. Therefore, each “X:Y” entry in Table 2 provides an example of a combination of a viral capsid enhancer and an autoprotease peptide that can be used in the molecules, compositions, and methods of the present disclosure. For example, the combination designated as “AP01:CE16” in Table 2 provides a combination of viral capsid enhancer derived from Sindbis virus (SINV) and an autoprotease peptide from porcine teschovirus-1 2A (P2A).

TABLE 1

Exemplary viral capsid enhancers and autoprotease peptides of the disclosure

| Viral Capsid Enhancer (Y) | | Autoprotease Peptide (X) | |
|---|---|---|---|
| Eastern equine encephalitis virus (EEEV) | (CE01) | porcine teschovirus-1 2A (P2A) | (AP01) |
| Venezuelan equine encephalitis virus (VEEV) | (CE02) | foot-and-mouth disease virus (FMDV) 2A (F2A) | (AP02) |
| Everglades virus (EVEV) | (CE03) | Equine Rhinitis A Virus (ERAV) 2A (E2A) | (AP03) |
| Mucambo virus (MUCV) | | Thosea asigna virus 2A (T2A) | (AP04) |
| Semliki forest virus (SFV) | (CE04) | cytoplasmic polyhedrosis virus 2A (BmCPV2A) | (AP05) |
| Pixuna virus (PIXV) | (CE05) | Flacherie Virus 2A (BmIFV2A) | (AP06) |
| Middleburg virus (MIDV) | (CE06) | | |
| Chikungunya virus (CHIKV) | (CE07) | | |
| O’Nyong-Nyong virus (ONNV) | (CE08) | | |
| Ross River virus (RRV) | (CE09) | | |
| Barmah Forest virus (BF) | (CE10) | | |
| Getah virus (GET) | (CE11) | | |
| Sagiyama virus (SAGV) | (CE12) | | |
| Bebaru virus (BEBV) | (CE13) | | |
| Mayaro virus (MAYV) | (CE14) | | |
| Una virus (UNAV) | (CE15) | | |
| Sindbis virus (SINV) | (CE16) | | |
| Aura virus (AURAV) | (CE17) | | |
| Whataroa virus (WHAV) | (CE18) | | |
| Babanki virus (BABV) | (CE19) | | |
| Kyzylagach virus (KYZV) | (CE20) | | |
| Western equine encephalitis virus (WEEV) | (CE21) | | |
| Highland J virus (HJV) | (CE22) | | |
| Fort Morgan virus (FMV) | (CE23) | | |
| Ndumu (NDUV) | (CE24) | | |
| Salmonid alphavirus (SAV) | (CE25) | | |
| Buggy Creek virus | (CE26) | | |

TABLE 2

| X:Y |
|---|
| AP01:CE01 |
| AP01:CE02 |
| AP01:CE03 |
| AP01:CE04 |
| AP01:CE05 |
| AP01:CE06 |
| AP01:CE07 |
| AP01:CE08 |
| AP01:CE09 |
| AP01:CE10 |
| AP01:CE11 |
| AP01:CE12 |
| AP01:CE13 |
| AP01:CE14 |
| AP01:CE15 |
| AP01:CE16 |
| AP01:CE17 |
| AP01:CE18 |
| AP01:CE19 |
| AP01:CE20 |
| AP01:CE21 |
| AP01:CE22 |
| AP01:CE23 |
| AP01:CE24 |
| AP01:CE25 |
| AP01:CE26 |
| AP02:CE01 |
| AP02:CE02 |

TABLE 2-continued

| X:Y |
| --- |
| AP02:CE03 |
| AP02:CE04 |
| AP02:CE05 |
| AP02:CE06 |
| AP02:CE07 |
| AP02:CE08 |
| AP02:CE09 |
| AP02:CE10 |
| AP02:CE11 |
| AP02:CE12 |
| AP02:CE13 |
| AP02:CE14 |
| AP02:CE15 |
| AP02:CE16 |
| AP02:CE17 |
| AP02:CE18 |
| AP02:CE19 |
| AP02:CE20 |
| AP02:CE21 |
| AP02:CE22 |
| AP02:CE23 |
| AP02:CE24 |
| AP02:CE25 |
| AP02:CE26 |
| AP03:CE01 |
| AP03:CE02 |
| AP03:CE03 |
| AP03:CE04 |
| AP03:CE05 |
| AP03:CE06 |
| AP03:CE07 |
| AP03:CE08 |
| AP03:CE09 |
| AP03:CE10 |
| AP03:CE11 |
| AP03:CE12 |
| AP03:CE13 |
| AP03:CE14 |
| AP03:CE15 |
| AP03:CE16 |
| AP03:CE17 |
| AP03:CE18 |
| AP03:CE19 |
| AP03:CE20 |
| AP03:CE21 |
| AP03:CE22 |
| AP03:CE23 |
| AP03:CE24 |
| AP03:CE25 |
| AP03:CE26 |
| AP04:CE01 |
| AP04:CE02 |
| AP04:CE03 |
| AP04:CE04 |
| AP04:CE05 |
| AP04:CE06 |
| AP04:CE07 |
| AP04:CE08 |
| AP04:CE09 |
| AP04:CE10 |
| AP04:CE11 |
| AP04:CE12 |
| AP04:CE13 |
| AP04:CE14 |
| AP04:CE15 |
| AP04:CE16 |
| AP04:CE17 |
| AP04:CE18 |
| AP04:CE19 |
| AP04:CE20 |
| AP04:CE21 |
| AP04:CE22 |
| AP04:CE23 |
| AP04:CE24 |
| AP04:CE25 |
| AP04:CE26 |
| AP05:CE01 |
| AP05:CE02 |

TABLE 2-continued

| X:Y |
| --- |
| AP05:CE03 |
| AP05:CE04 |
| AP05:CE05 |
| AP05:CE06 |
| AP05:CE07 |
| AP05:CE08 |
| AP05:CE09 |
| AP05:CE10 |
| AP05:CE11 |
| AP05:CE12 |
| AP05:CE13 |
| AP05:CE14 |
| AP05:CE15 |
| AP05:CE16 |
| AP05:CE17 |
| AP05:CE18 |
| AP05:CE19 |
| AP05:CE20 |
| AP05:CE21 |
| AP05:CE22 |
| AP05:CE23 |
| AP05:CE24 |
| AP05:CE25 |
| AP05:CE26 |
| AP06:CE01 |
| AP06:CE02 |
| AP06:CE03 |
| AP06:CE04 |
| AP06:CE05 |
| AP06:CE06 |
| AP06:CE07 |
| AP06:CE08 |
| AP06:CE09 |
| AP06:CE10 |
| AP06:CE11 |
| AP06:CE12 |
| AP06:CE13 |
| AP06:CE14 |
| AP06:CE15 |
| AP06:CE16 |
| AP06:CE17 |
| AP06:CE18 |
| AP06:CE19 |
| AP06:CE20 |
| AP06:CE21 |
| AP06:CE22 |
| AP06:CE23 |
| AP06:CE24 |
| AP06:CE25 |
| AP06:CE26 |

In one aspect, disclosed herein are novel nucleic acid molecules which include a nucleic acid sequence encoding a modified viral RNA replicon, wherein the modified viral RNA replicon includes a first nucleic acid sequence encoding one or more structural elements of a viral capsid enhancer (e.g., a DLP motif) or a variant thereof, wherein the viral capsid enhancer is heterologous to the viral RNA replicon, and a second nucleic acid sequence encoding at least one nonstructural viral protein or a portion thereof, wherein the first nucleic acid sequence is operably linked upstream to the second nucleic acid sequence.

The terms "replicon RNA" and "RNA replicon" used interchangeably herein, refers to RNA which contains all of the genetic information required for directing its own amplification or self-replication within a permissive cell. To direct its own replication, the RNA molecule 1) encodes polymerase, replicase, or other proteins which may interact with viral or host cell-derived proteins, nucleic acids or ribonucleoproteins to catalyze the RNA amplification process; and 2) contain cis-acting RNA sequences required for replication and transcription of the subgenomic replicon-encoded RNA. These sequences may be bound during the process of replication to its self-encoded proteins, or non-self-encoded cell-derived proteins, nucleic acids or ribonucleoproteins, or complexes between any of these components. In some embodiments of the present disclosure, a modified viral replicon RNA molecule typically contains the following ordered elements: 5' viral or defective-interfering RNA sequence(s) required in cis for replication, sequences coding for biologically active nonstructural proteins, promoter for the subgenomic RNA, 3' viral sequences required in cis for replication, and a polyadenylate tract. Further, the term replicon RNA generally refers to a molecule of positive polarity, or "message" sense, and the replicon RNA may be of length different from that of any known, naturally-occurring RNA viruses. In some embodiments of the present disclosure, the replicon RNA does not contain coding sequences for at least one of the structural viral proteins. In these instances, the sequences encoding structural genes can be substituted with one or more heterologous sequences such as, for example, a coding sequence for a gene of interest (GOI). In those instances where the replicon RNA is to be packaged into a recombinant alphavirus particle, it must contain one or more sequences, so-called packaging signals, which serve to initiate interactions with alphavirus structural proteins that lead to particle formation.

As used herein, "subgenomic RNA" refers to a RNA molecule of a length or size which is smaller than the genomic RNA from which it was derived. The viral subgenomic RNA should be transcribed from an internal promoter, whose sequences reside within the genomic RNA or its complement. Transcription of a subgenomic RNA may be mediated by viral-encoded polymerase(s) associated with host cell-encoded proteins, ribonucleoprotein(s), or a combination thereof. In some embodiments of the present disclosure, the subgenomic RNA is produced from a modified replicon RNA as disclosed herein and encodes or expresses one or more gene of interest (GOI). Instead of the native subgenomic promoter, the subgenomic RNA can be placed under control of internal ribosome entry site (IRES) derived from encephalomyocarditis viruses (EMCV), Bovine Viral Diarrhea Viruses (BVDV), polioviruses, Foot-and-mouth disease viruses (FMD), enterovirus 71, or hepatitis C viruses.

In some embodiments, the second nucleic acid sequence of the modified viral RNA replicon includes the coding sequence for at least one, at least two, at least three, or at least four nonstructural viral proteins. In some embodiments, the second nucleic acid sequence of the modified viral RNA replicon includes the coding sequence for a portion of the at least one nonstructural viral protein. For example, the second nucleic acid sequence of the modified viral RNA replicon can include about 10%, 20%, 30%, 40%, 50%, 60%, 70%, 80%, 90%, 95%, 100%, or a range between any two of these values, of the encoding sequence for the at least one nonstructural viral protein. In some embodiments, the second nucleic acid sequence of the modified viral RNA replicon can include the coding sequence for a substantial portion of the at least one nonstructural viral protein. As used herein, a "substantial portion" of a nucleic acid sequence encoding a nonstructural viral protein comprises enough of the nucleic acid sequence encoding the nonstructural viral protein to afford putative identification of that protein, either by manual evaluation of the sequence by one skilled in the art, or by computer-automated sequence comparison and identification using algorithms such as BLAST (see, for example, in "Basic Local Alignment Search Tool"; Altschul S F et al., J. Mol. Biol. 215:403-410, 1993). In some embodiments, the second nucleic acid sequence of the modified viral RNA replicon can include the entire coding sequence for the at least one nonstructural protein. In some embodiments, the second nucleic acid sequence comprises substantially all the coding sequence for the native viral nonstructural proteins.

The molecular techniques and methods by which these new nucleic acid molecules were constructed and characterized are described more fully in the Examples herein of the present application. As non-limiting examples, in the Examples section, the Venezuelan equine encephalitis virus (VEEV) and Equine arteritis virus (EAV) have been used to illustrate the compositions and methods disclosed herein.

In some embodiments, the nucleic acid molecules disclosed herein are recombinant nucleic acid molecules. As used herein, the term recombinant means any molecule (e.g. DNA, RNA, etc.), that is, or results, however indirect, from human manipulation of a polynucleotide. As non-limiting examples, a cDNA is a recombinant DNA molecule, as is any nucleic acid molecule that has been generated by ex vitro polymerase reaction(s), or to which linkers have been attached, or that has been integrated into a vector, such as a cloning vector or expression vector. As non-limiting examples, a recombinant nucleic acid molecule: 1) has been synthesized or modified ex vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination) of nucleic acid molecules; 2) includes conjoined nucleotide sequences that are not conjoined in nature; 3) has been engineered using molecular cloning techniques such that it lacks one or more nucleotides with respect to the naturally-occurring nucleic acid sequence; and/or 4) has been manipulated using molecular cloning techniques such that it has one or more sequence changes or rearrangements with respect to the naturally-occurring nucleic acid sequence.

A nucleic acid molecule, including a variant of a naturally-occurring nucleic acid sequence, can be produced using a number of methods known to those skilled in the art. The sequence of a nucleic acid molecule can be modified with respect to a naturally-occurring sequence from which it is derived using a variety of techniques including, but not limited to, classic mutagenesis techniques and recombinant DNA techniques, such as but not limited to site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, recombinational cloning, and chemical synthesis, including chemical synthesis of oligonucleotide mixtures and ligation of mixture groups to "build" a mixture of nucleic acid molecules, and combinations thereof. Nucleic acid molecule homologs can be selected from a mixture of modified nucleic acid molecules by screening for the function of the protein or the replicon encoded by the nucleic acid molecule and/or by hybridization with a wild-type gene or fragment thereof, or by PCR using primers having homology to a target or wild-type nucleic acid molecule or sequence.

In various embodiments disclosed herein, the nucleic acid molecule disclosed herein can include one or more of the following features.

In some embodiments, the modified viral RNA replicon includes a modified RNA replicon derived from a virus species belonging to the Alphavirus genus of the Togaviridae family or to the Arterivirus genus of the Arteriviridae family. Suitable arterivirus species includes Equine arteritis virus (EAV), Porcine respiratory and reproductive syndrome virus (PRRSV), Lactate dehydrogenase elevating virus (LDV), Simian hemorrhagic fever virus (SHFV), and wobbly possum disease virus (WPDV). Virulent and avirulent arterivirus strains are both suitable. Non-limiting examples of preferred arterivirus strains include, but not limited to, EAV-virulent Bucyrus strain (VBS), LDV-Plagemann, LDV-C, PRRSV-type 1, and PRRSV-type 2. Exemplary preferred EAV strains include, but not limited to, EAV VB53, EAV ATCC VR-796, EAV HK25, EAV HK116, EAV ARVAC MLV, EAV Bucyrus strain (Ohio), modified EAV Bucyrus, avirulant strain CA95, Red Mile (Kentucky), 84KY-A1 (Kentucky), Wroclaw-2 (Poland), Bibuna (Switzerland), and Vienna (Australia). Non-limiting preferred examples of PRRSV strains include PRRSV LV4.2.1, PRRSV 16244B, PRRSV HB-1(sh)/2002, PRRSV HB-2(sh)/2002, PRRSV HN1, PRRSV SD 01-08, PRRSV SD0802, PRRSV SD0803, PRRSV, and VR2332. Non-limiting preferred examples of SHFV strains and variants include SHFV variants SHFV-krtg1a and -krtg1b (SHFV-krtg1a/b), SHFVkrtg2a/b (GenBank accession # JX473847 to JX473850), SHFV-LVR, the SHFV prototype variant LVR 42-0/M6941 (NC_003092); SHFV-krc1 and SHFVkrc2 from Kibale red colobus (HQ845737 and HQ845738, respectively). Other non-limiting examples of preferred arteriviruses include PRRSV-Lelystad, the European (type 1) type strain (M96262); PRRSVVR2332, the North American (type 2) type strain (U87392); EAV-Bucyrus (NC_002532); EAV-s3685 (GQ903794); LDV-P, the Plagemann strain (U15146); and LDV-C, the neurovirulent type C strain (L13298).

In some embodiments, the first nucleic acid sequence is positioned upstream to a nucleic acid sequence encoding a portion or the entire pp1ab nonstructural protein of the modified arterivirus RNA replicon. In some embodiments, the first nucleic acid sequence is operably positioned within a region of about 1 to 1000 nucleotides downstream of the 5'-terminus of the modified viral RNA replicon. In some embodiments, the first nucleic acid sequence is operably positioned within a region of about 1 to 25, about 1 to 40, about 10 to 25, 10 to 50, about 10 to 100, about 20 to 50, about 20 to 75, about 25 to 100, about 25 to 100 nucleotides downstream of the 5'-terminus of the modified viral RNA replicon. In some embodiments, the first nucleic acid sequence is operably positioned within a region of about 1, 2, 5, 10, 15, 20, 25, 30, 40, 50, 75, 100, 125, 150, 200, 250, 300, or more, or a range between any two of these values, nucleotides downstream of the 5'-terminus of the modified viral RNA replicon. In some embodiments, the first nucleic acid sequence is operably positioned within a region of about 1 to 100, about 1 to 500, about 25 to 800, about 50 to 900, about 50 to 300, about 25 to 200, about 25 to 100, about 50 to 400, about 100 to 500, about 100 to 300, about 100 to 200, about 200 to 500, about 200 to 600, about 200 to 400, about 150 to 700, about 150 to 400, or about 500 to 1000 nucleotides downstream of the 5'-terminus of the modified viral RNA replicon.

Without being bound by any particular theory, it is believed that translational enhancing activity of a viral DLP motif can depend, in some embodiments, on the distance between the viral DLP motif and the initiation AUGi codon (Toribio et al., 2016 supra). Accordingly, in some embodiments, the first nucleic acid sequence is operably positioned a region of about 10 to 100 nucleotides downstream of the initiation codon AUGi of the modified viral RNA replicon. In some embodiments, the first nucleic acid sequence is operably positioned within a region of about 10 to 75, about 10 to 50, about 10 to 25, 15 to 75, about 15 to 50, about 15 to 25, about 25 to 75, about 25 to 50, about 25 to 100 nucleotides downstream of the initiation codon AUGi of the modified viral RNA replicon. In some embodiments, the first nucleic acid sequence is operably positioned within a region of about 25, 28, 31, 34, 37, 37, 40, 43, 46, 49, 50, or a range between any two of these values, nucleotides downstream of the initiation codon AUGi of the modified viral RNA replicon.

In some embodiments, the sequence encoding the modified viral RNA replicon further comprising one or more expression cassettes, wherein each of the expression cassettes comprises a promoter operably linked to a coding sequence for a gene of interest (GOI). As used herein, the term "expression cassette" refers to a construct of genetic material that contains coding sequences and enough regulatory information to direct proper transcription and/or translation of the coding sequences in a recipient cell, in vivo and/or ex vivo. The expression cassette may be inserted into a vector for targeting to a desired host cell and/or into a subject. Further, the term expression cassette may be used interchangeably with the term "expression construct". The term "expression cassette" as used herein, refers to a nucleic acid construct that encodes a protein or functional RNA operably linked to expression control elements, such as a promoter, and optionally, any or a combination of other nucleic acid sequences that affect the transcription or translation of the gene.

The term "operably linked", as used herein, denotes a functional linkage between two or more sequences. For example, an operably linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous.

The basic techniques for operably linking two or more sequences of DNA together are familiar to one of ordinary skill in the art, and such methods have been described in many books for standard molecular biological manipulation (see, for example, Maniatis et al., "*Molecular Cloning: A Laboratory Manual*" 2nd ed. Cold Spring Harbor Laboratory Press, Cold Spring Harbor, N.Y.; and Gibson et al., *Nature Methods* 6:343-45, 2009).

In some embodiments disclosed herein, the nucleic acid molecules disclosed herein can include more than one expression cassette. In principle, the nucleic acid molecules disclosed herein can generally include any number of expression cassettes. In some particular embodiments, the modified viral RNA replicon comprises at least two, three, four, five, or six expression cassettes. In some embodiments, at least one of the one or more expression cassettes is operably positioned downstream to a transcriptional regulatory sequence (TRS) of the modified arterivirus RNA replicon, wherein the TRS can be TRS1, TRS2, TRS3, TRS4, TRS5, TRS6, TRS7, or a combination thereof. In some particular embodiments, at least one of the one or more expression cassettes is operably positioned downstream of the TRS7 of the modified arterivirus RNA replicon.

The nucleic acid molecules as provided herein can find use, for example, as an expression or transcription vector that, when operably linked to a heterologous nucleic acid sequence such as, for example, a coding sequence of a gene of interest (GOI), can affect expression of the GOI. In some embodiments, the coding sequence of the GOI is optimized for expression at a level higher than the expression level of a reference coding sequence. In some embodiments, the reference coding sequence is a not codon-optimized. In some embodiments, the GOI coding sequence comprises codon optimization. With respect to codon-optimization of nucleic acid sequences, degeneracy of the genetic code provides the possibility to substitute at least one base of the protein encoding sequence of a gene with a different base without causing the amino acid sequence of the polypeptide produced from the gene to be changed. Hence, the nucleic acid molecules of the present disclosure may also have one or more nucleotide substitutions in accordance with degeneracy of the genetic code. References describing codon usage are readily publicly available. In some further embodiments of the disclosure, polynucleotide sequence variants can be produced for a variety of reasons, e.g., to optimize codon expression for a particular host (e.g., changing codons in the arterivirus mRNA to those preferred by other organisms such as human, hamster, mice, or monkey).

In some embodiments disclosed herein, the sequence of the GOI encode a polypeptide. The type of the polypeptide can vary depending on specific applications. For example, the polypeptide can be a therapeutic polypeptide, a prophylactic polypeptide, a diagnostic polypeptide, a nutraceutical polypeptide, an industrial enzyme, a reporter polypeptide, or any combination thereof. In some embodiments, the polypeptide is an antibody, an antigen, an immune modulator, a cytokine, an enzyme, or a combination thereof.

In some embodiments, the nucleic acid molecule as disclosed herein can further comprise a third nucleic acid sequence encoding one or more structural elements of a second viral capsid enhancer (e.g., a DLP motif), wherein the third nucleic acid sequence is operably linked upstream to the coding sequence for the GOI. The second DLP motif may be the same or may be different from the first DLP motif positioned upstream of the coding sequence for the nonstructural proteins. Accordingly, in some embodiments, the second DLP motif is the same as the first DLP motif positioned upstream of the coding sequence for the nonstructural proteins. In some embodiments, the second DLP motif is different from the first DLP motif positioned upstream of the coding sequence for the nonstructural proteins.

In some embodiments, the sequence encoding the modified viral RNA replicon further comprising a coding sequence for a proteolytic cleavage site operably linked downstream to the third nucleic acid sequence and upstream to the coding sequence for the GOI. Generally, any proteolytic cleavage site known in the art can be incorporated into the nucleic acid molecules of the disclosure and can be, for example, proteolytic cleavage sequences that are cleaved post-production by a protease. Further suitable proteolytic cleavage sites also include proteolytic cleavage sequences that can be cleaved following addition of an external protease. In some embodiments, the sequence encoding the modified viral RNA replicon further comprising a coding sequence for an autoprotease peptide operably linked downstream to the third nucleic acid sequence and upstream to the coding sequence for the GOI. In some embodiments, the autoprotease peptide includes a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof. In some embodiments, the autoprotease peptide includes a peptide sequence from porcine teschovirus-1 2A (P2A).

One of skill in the art will appreciate that different configurations of the viral capsid enhancer sequence, the coding sequence for the nonstructural proteins, the sequence encoding the autoprotease peptide, and the sequence encoding the gene of interest can be employed as long as the capsid enhancer sequence augments expression of the heterologous nucleic acid sequence(s), as compared with the level seen in the absence of the capsid enhancer sequence. These sequences will typically be configured so that the polypeptide encoded by the gene of interest can be released from the protease and any capsid protein sequence after cleavage by the autoprotease.

In some embodiments, the sequence of the nucleic acid molecule as disclosed herein includes a modified RNA replicon of an alphavirus virus species. In some embodiments, the modified alphavirus RNA replicon is of an alphavirus belonging to the VEEV/EEEV group, or the SF group, or the SIN group. Non-limiting examples of SF group alphaviruses include Semliki Forest virus, O'Nyong-Nyong virus, Ross River virus, Middelburg virus, Chikungunya virus, Barmah Forest virus, Getah virus, Mayaro virus, Sagiyama virus, Bebaru virus, and Una virus. Non-limiting examples of SIN group alphaviruses include Sindbis virus, Girdwood S. A. virus, South African Arbovirus No. 86, Ockelbo virus, Aura virus, Babanki virus, Whataroa virus, and Kyzylagach virus. Non-limiting examples of VEEV/EEEV group alphaviruses include Eastern equine encephalitis virus (EEEV), Venezuelan equine encephalitis virus (VEEV), Everglades virus (EVEV), Mucambo virus (MUCV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), and Una virus (UNAV).

Non-limiting examples of alphavirus species include Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), and Buggy Creek virus. Virulent and avirulent alphavirus strains are both suitable. In some embodiments, the modified alphavirus RNA replicon is of a Sindbis virus (SIN), a Semliki Forest virus (SFV), a Ross River virus (RRV), a Venezuelan equine encephalitis virus (VEEV), or an Eastern equine encephalitis virus (EEEV). In some embodiments, the modified alphavirus RNA replicon is of a Venezuelan equine encephalitis virus (VEEV).

In some instances where the nucleic acid molecule as disclosed herein includes a modified RNA replicon of an alphavirus virus species, the first nucleic acid sequence is positioned upstream to a nucleic acid sequence encoding one or more nonstructural proteins nsp1-4 or a portion thereof of the modified alphavirus RNA replicon. Accordingly, in some embodiments, the first nucleic acid sequence is positioned upstream to a nucleic acid sequence encoding the nonstructural proteins nsp1, nsp1-2, nsp1-3, nsp1-4, nsp2-4, nsp3-4, nsp2-3, nsp2, nsp3, nsp4, or a portion thereof of the modified alphavirus RNA replicon. In some embodiments, the sequence encoding the modified alphavirus RNA replicon further includes one or more expression cassettes, wherein each of the expression cassettes includes a promoter operably linked to a coding sequence for a gene of interest (GOI). In some embodiments, the modified alphavirus RNA replicon comprises at least two, three, four, five, or six expression cassettes. In some embodiments, at least one of the one or more expression cassettes is operably linked downstream of a nucleic acid sequence encoding one or more nonstructural proteins nsp1-4 or a portion thereof of the modified alphavirus RNA replicon. Accordingly, in some embodiments, at least one of the one or more expression cassettes is operably linked downstream of a nucleic acid sequence encoding the nonstructural proteins nsp1, nsp1-2, nsp1-3, nsp1-4, nsp2-4, nsp3-4, nsp2-3, nsp2, nsp3, nsp4, or a portion thereof, of the modified alphavirus RNA replicon.

In some embodiments, at least one of the one or more expression cassettes further comprises a third nucleic acid sequence encoding one or more structural elements of a second viral capsid enhancer (e.g., a DLP motif), wherein the third nucleic acid sequence is operably linked upstream to the coding sequence for the GOI. The second DLP motif may be the same or may be different from the first DLP motif positioned upstream of the coding sequence for at least of the nonstructural proteins nsp1-4 or a portion thereof. Accordingly, in some embodiments, the second DLP motif is the same as the first DLP motif positioned upstream of the coding sequence for the nonstructural proteins. In some embodiments, the second DLP motif is different from the first DLP motif positioned upstream of the coding sequence for the nonstructural proteins.

In some embodiments, the nucleic acid sequence of the present disclosure further comprises a coding sequence for an autoprotease peptide operably linked downstream to the third nucleic acid sequence and upstream to the coding sequence for the GOI. The autoprotease peptide can generally be any autoprotease peptide known in the art. Non-limiting examples of auprotease peptides include the peptide sequences from porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and any combinations thereof.

In a further aspect, some embodiments disclosed herein relate to a nucleic acid molecule including a nucleic acid sequence encoding a modified non-alphavirus RNA replicon, wherein the modified non-alphavirus RNA replicon comprising a first nucleic acid sequence encoding a viral capsid enhancer (e.g., a DLP motif). In some embodiments, the modified non-alphavirus RNA replicon further comprising a second nucleic acid sequence encoding at least one nonstructural viral protein or a portion thereof, wherein the first nucleic acid sequence is operably linked upstream to the second nucleic acid sequence.

In some embodiments, the modified non-alphavirus RNA replicon further comprising a coding sequence for an autoprotease peptide operably linked downstream to the first nucleic acid sequence and upstream to the second nucleic acid sequence. In some embodiments, the modified non-alphavirus RNA replicon includes a modified RNA replicon of a positive-strand RNA virus. In some embodiments, the modified non-alphavirus RNA replicon includes a modified RNA replicon of a negative-strand RNA virus.

Non-limiting examples of modified non-alphavirus RNA replicons include modified RNA replicons of virus species belonging to Togaviridae family, Flaviviridae family, Orthomyxoviridae family, Rhabdoviridae family, or Paramyxoviridae family. Accordingly, in some embodiments, the modified non-alphavirus RNA replicon includes a modified RNA replicon of a negative-strand RNA virus. Suitable negative-strand RNA virus species include, but are not limited to viral species of the families Orthomyxoviridae, Rhabdoviridae, and Paramyxoviridae. In some embodiments, the modified non-alphavirus RNA replicon includes a modified RNA replicon of a positive-strand virus species belonging to the Togaviridae family or Flaviviridae family. In some embodiments, the modified non-alphavirus RNA replicon includes a modified RNA replicon of a positive-strand virus species belonging to the Arterivirus genus of the Arteriviridae family. Suitable arterivirus species include, but are not limited to, species of Equine arteritis virus (EAV), Porcine respiratory and reproductive syndrome virus (PRRSV), Lactate dehydrogenase elevating virus (LDV), Simian hemorrhagic fever virus (SHFV), and wobbly possum disease virus (WPDV).

In some embodiments, the sequence encoding the non-alphavirus modified RNA replicon further includes one or more expression cassettes, wherein each of the expression cassettes comprises a promoter operably linked to a coding sequence for a gene of interest (GOD. In some embodiments, the modified non-alphavirus RNA replicon comprises at least two, three, four, five, or six expression cassettes. In some embodiments, at least one of the one or more expression cassettes is operably linked downstream of the second nucleic acid sequence encoding the at least one nonstructural viral protein or a portion thereof. In some embodiments, at least one of the one or more expression cassettes further comprises a third nucleic acid sequence encoding one or more structural elements of a viral capsid enhancer, wherein the third nucleic acid sequence is operably linked upstream to the coding sequence for the GOI. In some embodiments, the modified non-alphavirus RNA replicon further includes a coding sequence for an autoprotease peptide operably linked downstream to the third nucleic acid sequence and upstream to the coding sequence for the GOI.

Some embodiments of the disclosure relate to a nucleic acid molecule including a nucleic acid sequence encoding a modified viral RNA replicon which includes in 5'→3'direction a first nucleic acid sequence encoding a capsid enhancer from a Sindbis virus, a second nucleic acid sequence encoding an autoprotease peptide, and a third nucleic acid sequence encoding all of the viral nonstructural proteins. Some embodiments of the disclosure relate to a nucleic acid molecule including a nucleic acid sequence which encodes a modified viral RNA replicon, wherein the modified viral RNA replicon comprises a viral capsid enhancer and wherein the sequence of the modified viral RNA replicon exhibits at least 80% sequence identity to the sequence of at least one of SEQ ID NOs: 15-18 and 27-29.

Contemplated within the scope of the present disclosure are variants of the polynucleotides provided herein. Such variants may be naturally-occurring, including homologous polynucleotides from the same or a different species, or may be non-natural variants, for example polynucleotides synthesized using chemical synthesis methods, or generated using recombinant DNA techniques. With respect to nucleic acid sequences, degeneracy of the genetic code provides the possibility to substitute at least one base of the protein encoding sequence of a gene with a different base without causing the amino acid sequence of the polypeptide produced from the gene to be changed. Hence, the nucleic acid molecules of the present disclosure may also have any base sequence that has been changed from any polynucleotide sequence disclosed herein by substitution in accordance with degeneracy of the genetic code. References describing codon usage are readily publicly available. In further embodiments, polynucleotide sequence variants can be produced for a variety of reasons, e.g., to optimize codon expression for a particular host (e.g., changing codons in the viral mRNA to those preferred by other organisms such as mammals or fish species).

In some embodiments, the nucleic acid molecules of the present disclosure comprises in 5'→3'direction a nucleic acid sequence encoding a capsid enhancer from a Sindbis virus, a nucleic acid sequence encoding an autoprotease peptide, and a nucleic acid sequence encoding all of the viral nonstructural proteins of a modified viral RNA replicon. In some embodiments, the nucleic acid molecule comprises in 5'→3'direction a 5-UTR sequence, a first capsid enhancer from a Sindbis virus, an autoprotease peptide, a sequence encoding all of the viral nonstructural proteins of a modified viral RNA replicon, one or more expression cassettes, and a 3'UTR sequence, wherein at least one of the one or more expression cassettes comprises a second capsid enhancer from a Sindbis virus operably linked upstream of a coding sequence for a gene of interest (GOI).

Accordingly, in some embodiments, the nucleic acid molecule of the present disclosure includes a nucleic acid sequence which encodes a modified viral RNA replicon, wherein the sequence exhibits at least 90%, at least 95%, at least 96%, at least 97%, at least 98%, at least 99%, or 100% sequence identity to the sequence of at least one of SEQ ID NOs: 15-18 and 27-29.

In some embodiments, the nucleic acid molecule of the disclosure is an expression vector. In some embodiments, the expression vector further includes one or more additional regulatory sequences, which can be a transcriptional regulatory element or a translational regulatory element. The terms "regulatory element" and "regulatory region", as used interchangeably in the present disclosure, refer to a nucleic acid sequence that influences transcription or translation initiation and rate, and stability and/or mobility of a transcription or translation product. Such regulatory elements need not be of naturally-occurring sequences. Regulatory sequences include but are not limited to promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. In some embodiments, the expression vector of the disclosure further includes one or more of the following: an origin of replication, one or more sequences for promoting integration of the expression cassette into the host genome, a terminator sequence.

In some embodiments, the expression vector comprises at least one origin of replication ("ORI") sequence for replication in a cell. The vectors may further optionally comprise one or more selectable markers under the control of one or more eukaryotic promoters, one or more selectable markers under the control of one or more prokaryotic promoters, and/or one or more sequences that mediate recombination of an exogenous nucleic acid sequence into the target cell's genome.

An ORI is the sequence in a DNA molecule at which replication begins. The ORI serves as a base of assembly for the pre-replication complex. Depending on the ORI, such replication can proceed uni-directionally or bi-directionally. An expression vector as provided herein can include an ORI for replication of the expression vector in a cloning host, such as *E. coli* or yeast, and/or can include an ORI for replication of the expression vector in a target cell, which can be, for example, a mammalian cell. The structural biology of ORIs is widely conserved among prokaryotes, eukaryotes, and viruses. Most ORIs possess simple tri-, tetra-, or higher nucleotide repetition patterns. Most are AT-rich and contain inverted repeats. Those skilled in the art will be familiar with the more common ORIs, such as P15A and the pUC's ORI.

The expression vector can also, in some embodiments, carry a selectable marker. By way of example, a vector that includes an expression cassette may include, as a selectable marker, a gene conferring resistance to a poisonous substance, such as an antibiotic, a herbicide, or some other toxin, so that transformants can be selected by exposing the cells to the poison and selecting those cells which survive the encounter. In some embodiments, the selectable marker may be under the control of a promoter. In some embodiments, the promoter regulating expression of the selectable marker may be conditional or inducible. In some embodiments, the promoter regulating expression of the selectable marker may be preferably constitutive, and can be, for example, any promoter described herein or another promoter.

In some embodiments, the expression vector is a plasmid, a bacteriophage vector, a cosmid, a fosmid, a viral replicon, a shuttle vector, or a combination thereof. In some embodiments, the expression vector is an RNA replicon. In some embodiments, the expression vector is a prokaryotic expression vector. In some embodiments, the expression vector is a eukaryotic expression vector. In some embodiments, the nucleic acid molecule of the disclosure is produced via de novo synthesis. In some embodiments of the disclosure, de novo synthesis can be used to generate a synthetic mRNA molecule.

Recombinant Cells

In one aspect, some embodiments disclosed herein relate to a method of transforming a cell that includes introducing into a host cell, such as an animal cell, a nucleic acid molecule as provided herein, and selecting or screening for a transformed cell. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. In some embodiments, the nucleic acid molecule is introduced into a host cell by an electroporation procedure or a biolistic procedure.

In a related aspect, some embodiments relate to recombinant host cells, for example, recombinant animal cells that include a nucleic acid molecule described herein. The nucleic acid molecule can be stably integrated in the host genome, or can be episomally replicating, or present in the recombinant host cell as a mini-circle expression vector for a stable or transient expression. Accordingly, in some embodiments disclosed herein, the nucleic acid molecule is maintained and replicated in the recombinant host cell as an episomal unit. In some embodiments, the nucleic acid molecule is stably integrated into the genome of the recombinant cell. Stable integration can be completed using classical random genomic recombination techniques or with more precise genome editing techniques such as using guide RNA directed CRISPR/Cas9, or DNA-guided endonuclease genome editing NgAgo (*Natronobacterium gregoryi* Argonaute), or TALEN genome editing (transcription activator-like effector nucleases). In some embodiments, the nucleic acid molecule present in the recombinant host cell as a mini-circle expression vector for a stable or transient expression.

In some embodiments, host cells can be genetically engineered (e.g. transduced or transformed or transfected) with, for example, a vector construct of the present application that can be, for example, a vector for homologous recombination that includes nucleic acid sequences homologous to a portion of the genome of the host cell, or can be an expression vector for the expression of any or a combination of the genes of interest. The vector can be, for example, in the form of a plasmid, a viral particle, a phage, etc. In some embodiments, a vector for expression of a polypeptide of interest can also be designed for integration into the host, e.g., by homologous recombination. The vector containing a polynucleotide sequence as described herein, e.g., nucleic acid molecule comprising a modified alphavirus genome or replicon RNA, as well as, optionally, a selectable marker or reporter gene, can be employed to transform an appropriate host cell.

The methods and compositions disclosed herein may be deployed for genetic engineering of any species, including, but not limited to, prokaryotic and eukaryotic species. Suitable host cells to be modified using the compositions and methods according to the present disclosure can include, but not limited to, algal cells, bacterial cells, heterokonts, fungal cells, chytrid cells, microfungi, microalgae, and animal cells. In some embodiments, the animal cells are invertebrate animal cells. In some embodiments, the vertebrate animal cells are mammalians cells. Host cells can be either untransformed cells or cells that have already been transfected with at least one nucleic acid molecule.

The methods and compositions disclosed herein can be used, for example, with subject and/or host cells that are important or interesting for aquaculture, agriculture, animal husbandry, and/or for therapeutic and medical applications, including production of polypeptides used in the manufacturing of vaccines, pharmaceutical products, industrial products, chemicals, and the like. In some embodiments, the compositions and methods disclosed herein can be used with host cells from species that are natural hosts of alphaviruses, such as rodents, mice, fish, birds, and larger mammals such as humans, horses, pig, monkey, and apes as well as invertebrates. Particularly preferred species, in some embodiments of the application, are vertebrate animal species and invertebrate animal species. In principle, any animal species can be generally used and can be, for example, human, dog, bird, fish, horse, pig, primate, mouse, cotton rat, ferret, cattle, swine, sheep, rabbit, cat, goat, donkey, hamster, or buffalo. Non-limiting examples of suitable bird species include chicken, duck, goose, turkey, ostrich, emu, swan, peafowl, pheasant, partridge, and guinea fowl. In some particular embodiments, the fish is any species in the Salmonidae family. Primary mammalian cells and continuous/immortalized cells types are also suitable. Non-limiting examples of suitable animal host cells include, but not limited to, pulmonary equine artery endothelial cell, equine dermis cell, baby hamster kidney (BHK) cell, rabbit kidney cell, mouse muscle cell, mouse connective tissue cell, human cervix cell, human epidermoid larynx cell, Chinese hamster ovary cell (CHO), human HEK-293 cell, mouse 3T3 cell, Vero cell, Madin-Darby Canine Kidney Epithelial Cell (MDCK), primary chicken fibroblast cell, a HuT78 cell, A549 lung cell, HeLa cell, PER.C6® cell, WI-38 cell, MRC-5 cell, FRhL-2, and CEM T-cell. In some embodiments, the host cell is baby hamster kidney cell. In some embodiments, the baby hamster kidney cell is a BHK-21 cell.

Techniques for transforming a wide variety of the above-mentioned host cells and species are known in the art and described in the technical and scientific literature. Accordingly, cell cultures including at least one recombinant cell as disclosed herein are also within the scope of this application. Methods and systems suitable for generating and maintaining cell cultures are known in the art.

Heterologous Nucleic Acid Sequences

In accordance of some embodiments of the present disclosure, a wide variety of nucleic acid sequences can be carried by the nucleic acid molecules of the present disclosure. In some embodiments, nucleic acid molecules as described herein does not contain any additional heterologous nucleic acid sequence. In some embodiments, the nucleic acid molecules of the present disclosure contains one or more additional heterologous or foreign nucleic acid sequences. In some embodiments, the one or more additional heterologous or foreign nucleic acid sequences include a coding sequence for a gene of interest (GOI). In some embodiments disclosed herein, the coding sequence for the GOI encodes a polypeptide or a functional RNA. In some embodiments, the coding sequence for the GOI encodes a functional RNA selected from a ribosomal RNA, a tRNA, a ribozyme, a transactivating (tr) RNA of a CRISPR system, a crispr (cr) RNA of a CRISPR system, a chimeric guide RNA of a CRISPR system, a micro RNA, an interfering RNA (RNAi) molecule, a short hairpin (sh) RNA, or an antisense RNA molecule. In some embodiments, the coding sequence for the GOI encodes a polypeptide selected from the group consisting of a therapeutic polypeptide, a prophylactic polypeptide, a diagnostic polypeptide, a nutraceutical polypeptide, an industrial enzyme, a reporter polypeptide, or any combination thereof. In some embodiments, the coding sequence for the GOI encodes a polypeptide is selected from the group consisting of an antibody, an antigen, an immune modulator, and a cytokine.

In some embodiments, the heterologous nucleic acid sequence comprises a heterologous nucleic acid sequence of at least about 100 bases, 2 kb, 3.5 kb, 5 kb, 7 kb, or 8 kb. The heterologous RNA or heterologous nucleic acid sequence can be chosen from a wide variety of sequences derived from viruses, prokaryotes or eukaryotes. Examples of categories of heterologous sequences include, but are not limited to, immunogens (including native, modified or synthetic antigenic proteins, peptides, epitopes or immunogenic fragments), cytokines, toxins, therapeutic proteins, enzymes, antisense sequences, and immune response modulators.

A wide variety of GOI can be included in the nucleic acid molecules of the present disclosure to express a polypeptide of the GOI, including but not limited to, cytokines, toxins, prodrugs, antigens which stimulate an immune response, ribozymes, and proteins which assist or inhibit an immune response, as well as antisense sequences (or sense sequences for "antisense applications"). As noted above, within various embodiments of the disclosure the modified RNA replicon provided herein may contain the coding region of (and express, in some embodiments) two or more polypeptides of interest.

1) Cytokines

In some embodiments disclosed herein, the GOI encodes a cytokine. Generally, cytokines act to proliferate, activate, and/or differentiate immune effectors cells. Examples of cytokines include, but are not limited to macrophages, B lymphocytes, T lymphocytes, endothelial cells, fibroblasts, lymphokines likes gamma interferon, tumor necrosis factor, interleukin, IL-1, IL-2, IL-3, IL-4, IL-5, IL-6, IL-7, IL-8, IL-9, IL-10, IL-1, IL-12, IL-13, IL-14, IL-15, GM-CSF, CSF-1 and G-CSF.

In some related embodiments, the GOI encodes an immunomodulatory cofactor. As utilized within the context of the present disclosure, "immunomodulatory cofactor" refers to factors which, when manufactured by one or more of the cells involved in an immune response, or when added exogenously to the cells, cause the immune response to be different in quality or potency from that which would have occurred in the absence of the cofactor. The quality or potency of a response may be measured by a variety of assays known to one of skill in the art including, for example, ex vitro assays which measure cellular proliferation (e.g., 3 H thymidine uptake), and ex vitro cytotoxic assays (e.g., which measure 51 Cr release) (see Warner et al., AIDS Res. and Human Retroviruses 7:645-655, 1991).

Examples of immunomodulatory co-factors include, but are not limited, alpha interferon, gamma interferons, G-CSF, GM-CSF, TNFs, Interleukin-2 (IL-2), IL-4, IL-6, IL-12, IL-15, ICAM-1, ICAM-2, LFA-1, LFA-3, MHC class I molecules, MHC class II molecules, 2-microglobulin, chaperones, CD3, B7/BB 1, MHC linked transporter proteins, and analogues thereof.

The choice of which immunomodulatory cofactor to include within the nucleic acid molecules of the present disclosure may be based upon known therapeutic effects of the cofactor, or experimentally determined. For example, in chronic hepatitis B infections alpha interferon has been found to be efficacious in compensating a patient's immunological deficit and thereby assisting recovery from the disease. In some situations, a suitable immunomodulatory cofactor may be experimentally determined. Briefly, blood samples are first taken from patients with a hepatic disease. Peripheral blood lymphocytes (PBLs) are restimulated ex vitro with autologous or HLA-matched cells (e.g., EBV transformed cells), and transduced with modified arterivirus genome or replicon RNA of the present disclosure which directs the expression of an immunogenic portion of a hepatitis antigen and the immunomodulatory cofactor. Stimulated PBLs are used as effectors in a CTL assay with the BLA-matched transduced cells as targets. An increase in CTL response over that seen in the same assay performed using HLA-matched stimulator and target cells transduced with a vector encoding the antigen alone, indicates a useful immunomodulatory cofactor. In some embodiments, the immunomodulatory cofactor gamma interferon is particularly preferred.

Another non-limiting example of an immunomodulatory cofactor is the B7/BB1 costimulatory factor. Activation of the full functional activity of T cells requires two signals. One signal is provided by interaction of the antigen-specific T cell receptor with peptides which are bound to major histocompatibility complex (MEW) molecules, and the second signal, referred to as costimulation, is delivered to the T cell by antigen-presenting cells. The second signal is required for interleukin-2 (IL-2) production by T cells and appears to involve interaction of the B7/BB 1 molecule on antigen-presenting cells with CD28 and CTLA-4 receptors on T lymphocytes. In some embodiments, B7/BB 1 may be introduced into tumor cells in order to cause costimulation of CD8+ T cells, such that the CD8+ T cells produce enough IL-2 to expand and become fully activated. These CD8+ T cells can kill tumor cells that are not expressing B7 because costimulation is no longer required for further CTL function. Vectors that express both the costimulatory B7/BB1 factor and, for example, an immunogenic HBV core protein, may be constructed utilizing methods which are described herein. Cells transduced with these vectors will become more effective antigen-presenting cells. The HBV core-specific CTL response will be augmented from the fully activated CD8+ T cell via the costimulatory ligand B7/BB 1.

2) Toxins

In some embodiments disclosed herein, the GOI encodes a toxin. In some embodiments, toxins act to directly inhibit the growth of a cell. Examples of toxins include, but are not limited to, ricin, abrin, diphtheria toxin, cholera toxin, gelonin, pokeweed, antiviral protein, tritin, *Shigella* toxin, *Pseudomonas* exotoxin A, herpes simplex virus thymidine kinase (HSVTK), and *E. coli*. guanine phosphoribosyl transferase.

3) Pro-Drugs

In some embodiments disclosed herein, the GOI encodes a "pro-drug". As utilized within the context of the present disclosure, "pro-drug" refers to a gene product that activates a compound with little or no cytotoxicity into a toxic product. Representative examples of such gene products include HSVTK and VZVTK (as well as analogues and derivatives thereof), which selectively monophosphorylate certain purine arabinosides and substituted pyrimidine compounds, converting them to cytotoxic or cytostatic metabolites. More specifically, exposure of the drugs ganciclovir, acyclovir, or any of their analogues (e.g., FIAU, FIAC, and DHPG) to HSVTK phosphorylates the drug into its corresponding active nucleotide triphosphate form.

Non-limiting examples of pro-drugs which may be utilized within the context of the present disclosure include: *E. coli* guanine phosphoribosyl transferase which converts thioxanthine into toxic thioxanthine monophosphate; alkaline phosphatase, which will convert inactive phosphorylated compounds such as mitomycin phosphate and doxorubicin-phosphate to toxic dephosphorylated compounds; fungal (e.g., *Fusarium oxysporum*) and bacterial cytosine deaminase, which can convert 5-fluorocytosine to the toxic compound 5-fluorouracil; carboxypeptidase G2, which will cleave the glutamic acid from para-N-bis (2-chloroethyl) aminobenzoyl glutamic acid, thereby creating a toxic benzoic acid mustard; and Penicillin-V amidase, which will convert phenoxyacetabide derivatives of doxorubicin and melphalan to toxic compounds.

4) Antisense Sequence

In some embodiments disclosed herein, the coding sequence for the GOI is an antisense sequence. Antisense sequences are designed to bind to RNA transcripts, and thereby prevent cellular synthesis of a particular protein or prevent use of that RNA sequence by the cell. Non-limiting examples of such sequences include antisense thymidine kinase, antisense dihydrofolate reductase, antisense HER2, antisense ABL, antisense Myc, antisense ras, as well as antisense sequences which block any of the enzymes in the nucleotide biosynthetic pathway. In addition, in accordance with some embodiments disclosed herein, antisense sequences to interferon and 2 microglobulin may be utilized in order to decrease immune response.

In some embodiments, antisense RNA may be utilized as an anti-tumor agent in order to induce a potent Class I restricted response. In addition to binding RNA and thereby preventing translation of a specific mRNA, high levels of specific antisense sequences are believed to induce the increased expression of interferons (including gamma-interferon) due to the formation of large quantities of double-stranded RNA. The increased expression of gamma interferon, in turn, boosts the expression of MHC Class I antigens. Preferred antisense sequences for use in this regard include actin RNA, myosin RNA, and histone RNA. Antisense RNA which forms a mismatch with actin RNA is particularly preferred.

5) Ribozymes

In some embodiments disclosed herein, nucleic acid molecules comprising one or more RNA stem-loop structures are provided which produce ribozymes upon infection of a host cell. Ribozymes are used to cleave specific RNAs and are designed such that it can only affect one specific RNA sequence. Generally, the substrate binding sequence of a ribozyme is between 10 and 20 nucleotides long. The length of this sequence is sufficient to allow a hybridization with target RNA and disassociation of the ribozyme from the cleaved RNA. Representative examples for creating ribozymes include those described in U.S. Pat. Nos. 5,116,742; 5,225,337 and 5,246,921.

6) Proteins and Other Cellular Constituents

In some embodiments disclosed herein, a wide variety of proteins or other cellular constituents can be carried by the nucleic acid molecules of the present disclosure. Non-limiting examples of such proteins include native or altered cellular components, as well as foreign proteins or cellular constituents, found in for example, viruses, bacteria, parasites, fungus or animal such as mammalian.

Methods for Producing Polypeptides

The host cells of the present disclosure, such as a prokaryotic or eukaryotic host cell, can be used to produce (e.g., express) a molecule of interest such as, e.g., a polypeptide, encoded in an open reading frame of a gene of interest (GOI) as disclosed herein. Thus, the present application further provides methods for producing a molecule of interest such as, e.g., a polypeptide, using the host cells and/or the nucleic acid molecules of the present disclosure. The host cells can be, for example, isolated cells, cells in cell culture, cells in a living body, or a combination thereof.

Some embodiments disclosed herein provides methods for producing a polypeptide of interest. The method can include the introduction of a nucleic acid molecule according to any one of the aspects and embodiments of the present disclosure into a host cell, thereby producing a polypeptide encoded by the GOI in the host cell. In some embodiments where the introduced nucleic acid molecule is a RNA molecule, for example an mRNA molecule or a RNA replicon. The RNA molecule can be generated by any method known in the art, for example by de novo synthesis in whole or in part. For example, the RNA molecules, including but not limited to mRNA molecules and RNA replicons, can be produced using chemical methods, enzymatic techniques, or any combination thereof, for example, by chemical synthesis through de novo assembly (such as with oligonucleotides) or in vitro transcription reactions (using appropriate enzymes, buffers, nucleotides, etc.). In some instances where the introduced nucleic acid molecule is an mRNA, the mRNA can be directly delivered to cells in vivo for producing a polypeptide of interest (e.g., drug, antigen, etc.) in cells. The cells can be isolated cells; cells in cell cultures; cells in an tissue, an organ, and/or a subject; or any combination thereof. In some embodiments, no new mRNA copies are made in the cells, As disclosed herein, the incorporation of one or more RNA stem-loops from a viral capsid enhancer (e.g., DLP motifs) into the chemically synthesized RNA can confer the intended enhancement of gene expression once the DLP-containing mRNA is introduced into the cells.

In some embodiments where the introduced nucleic acid molecule is a vector such as, for example, an RNA replicon, new mRNA copies may be generated which includes coding sequence for a gene of interest operably linked to one or more DLP motifs. The incorporation the one or more DLP motifs into the vector, e.g., RNA replicon, can then confer the intended enhancement of gene expression once the DLP-containing vector or replicon is introduced into the cells Some embodiments disclosed herein provides methods for producing a polypeptide of interest in a host cell. Such method includes the cultivation of a recombinant host cell, including a nucleic acid molecule according to any one of the aspects and embodiments of the present disclosure. In some embodiments, the methods include culturing the host cell of present disclosure (into which a recombinant expression vector encoding the molecule of interest has been introduced) in a suitable medium such that the molecule of interest is produced. In some embodiments, the methods further include isolating the molecule of interest from the medium or the host cell.

Also disclosed are methods for producing a polypeptide of interest in a subject, including administering to the subject a nucleic acid molecule according to any one of the aspects and embodiments.

Suitable host cells and/or subjects for use in the methods and compositions disclosed herein include, but are not limited to, prokaryotic and eukaryotic species. Suitable host cells to be modified using the compositions and methods according to the present disclosure can include, but not limited to, algal cells, bacterial cells, heterokonts, fungal cells, chytrid cells, microfungi, microalgae, and animal cells. In some embodiments, the animal cells are invertebrate animal cells. In some embodiments, the vertebrate animal cells are mammalians cells. Host cells can be either untransformed cells or cells that have already been transfected with at least one nucleic acid molecule. Accordingly, biological samples, biomass, and progeny of a recombinant cell according to any one of the aspects and embodiments are also within the scope of the present application. Thus, as discussed in more detail below, polypeptides produced by a method according to this aspect of the application are also within the scope of this application.

In some embodiments, the recombinant cell is an animal cell. Therapeutic protein production in small and large scale is important field of development in pharmaceutical industry, because proteins produced in animal cells are believe to generally have proper processing, post-translational modification and therefore have adequate activity for treatment of the physiological condition. In principle, any animal species can be generally used and can be, for example, human, dog, bird, fish, horse, pig, primate, mouse, cotton rat, ferret, cattle, swine, sheep, rabbit, cat, goat, donkey, hamster, or buffalo. Non-limiting examples of suitable bird species include chicken, duck, goose, turkey, ostrich, emu, swan, peafowl, pheasant, partridge, and guinea fowl. In some particular embodiments, the fish is any species in the Salmonidae family. Primary mammalian cells and continuous/immortalized cells types are also suitable. Non-limiting examples of suitable animal host cells include, but not limited to, pulmonary equine artery endothelial cell, equine dermis cell, baby hamster kidney (BHK) cell, rabbit kidney cell, mouse muscle cell, mouse connective tissue cell, human cervix cell, human epidermoid larynx cell, Chinese hamster ovary cell (CHO), human HEK-293 cell, mouse 3T3 cell, Vero cell, Madin-Darby Canine Kidney Epithelial Cell (MDCK), primary chicken fibroblast cell, a HuT78 cell, A549 lung cell, HeLa cell, PER.C6® cell, WI-38 cell, MRC-5 cell, FRhL-2, and CEM T-cell. In some embodiments, the host cell is baby hamster kidney cell. In some embodiments, the baby hamster kidney cell is a BHK-21 cell.

Recombinant Polypeptides

Some embodiments disclosed herein relate to recombinant polypeptides produced by a method in accordance with one or more embodiments described herein. The recombinant polypeptides of the present application generally can be any recombinant polypeptides and can be, for example, one or more of therapeutic polypeptides, prophylactic polypeptides, diagnostic polypeptides, nutraceutical polypeptides, industrial enzymes, and reporter polypeptides. In some embodiments, the recombinant polypeptides can be one or more of antibodies, antigens, immune modulators, and cytokines. In some embodiments, the polypeptide of interest may have therapeutic or prophylactic activity.

Compositions and Formulations

Some embodiments disclosed herein relate to a composition comprising any of the recombinant polypeptides described herein. The composition can be, for example, a nutraceutical composition, a prophylactic composition, a pharmaceutical composition comprising a pharmaceutically acceptable carrier, or a mixture thereof. In some embodiments, the compositions of the present application can be used as a vaccine.

Some embodiments disclosed herein relate to a composition including any of the nucleic acid molecules (e.g., expression vectors) described herein. The composition can be, for example, a nutraceutical composition, a prophylactic composition, a pharmaceutical composition comprising a pharmaceutically acceptable carrier, or a mixture thereof. In some embodiments, the compositions of the present application can be used as a vaccine.

Some embodiments disclosed herein relate to a composition including any of the recombinant cells described herein. The composition can be, for example, a nutraceutical composition, a prophylactic composition, a pharmaceutical composition comprising a pharmaceutically acceptable carrier, or a mixture thereof. In some embodiments, the compositions of the present application can be used as a vaccine.

As used herein, the term "pharmaceutically-acceptable carrier" means a carrier that is useful in preparing a pharmaceutical composition or formulation that is generally safe, non-toxic, and neither biologically nor otherwise undesirable, and includes a carrier that is acceptable for veterinary use as well as human pharmaceutical use. In some embodiments, a pharmaceutically acceptable carrier is as simple as water, but it can also include, for example, a solution of physiological salt concentration. In some embodiments, a pharmaceutically acceptable carrier can be, or may include, stabilizers, diluents and buffers. Suitable stabilizers are for example SPGA, carbohydrates (such as dried milk, serum albumin or casein) or degradation products thereof. Suitable buffers are for example alkali metal phosphates. Diluents include water, aqueous buffers (such as buffered saline), alcohols and polyols (such as glycerol). For administration to animals or humans, the composition according to the present application can be given by any enteral or parenteral route, which includes inter alia intranasally, by spraying, intradermally, subcutaneously, orally, by aerosol, intramuscularly, or any combination thereof.

In some embodiments, the nucleic acid molecules (e.g., mRNAs and/or expression vectors), protein molecules, and/or compositions of the disclosure are in suitable formulations, for example pharmaceutical formulations. Provided herein include pharmaceutical formulations containing one or more of the molecules and/or compositions disclosed herein in a pharmaceutically acceptable vehicle. Some embodiments of the disclosure relate to pharmaceutical formulations comprising one or more of the expression vectors disclosed herein. Some embodiments of the disclosure relate to pharmaceutical formulations containing one or more of the nucleic acid molecules disclosed herein. Some embodiments of the disclosure relate to pharmaceutical formulations containing one or more of the polypeptides disclosed herein. Some embodiments of the disclosure relate to pharmaceutical formulations containing one or more of the recombinant cells disclosed herein.

The molecules (e.g., protein and nucleic acid molecules) and compositions disclosed herein can be in various formulations, for example pharmaceutical formulations. For example, the nucleic acid molecules (e.g., replicons, mRNAs and expression vectors), protein molecules, and/or compositions of the disclosure can be formulated, for example into a pharmaceutical formulation, with one or more covalent compounds (e.g., via direct linkage), non-covalent compounds (e.g., via charged based associations from LNPs or cationic nano-emulsions), physical compositions (e.g., vault proteins, non-charged lipid encapsulations), pharmaceutically acceptable buffers (e.g., saline, lactated Ringer's), and any combinations thereof. Many methods, reagents, and systems suitable for generating the foregoing pharmaceutical formulations are known in the art.

In some embodiments, molecules and/or compositions disclosed herein is formulated in a saline or a lipid formulation. The lipid formulation can be selected from, but is not limited to, liposomes, lipoplexes, copolymers such as PLGA, and lipid nanoparticles.

Particles and Nanoparticles

In some embodiments, one or more of the nucleic acid molecules, polypeptide molecules, and/or compositions disclosed herein can be incorporated into particles or nanoparticles. Particles comprising one or more of the molecules and compositions disclosed herein can be polymeric particles, lipid particles, solid lipid particles, self-assembled particles, composite nanoparticles of conjugate phospholipids, surfactants, proteins, polyaminoacids, inorganic particles, or combinations thereof (e.g., lipid stabilized polymeric particles). In some embodiments, the molecules and/or compositions disclosed herein are substantially encapsulated or partially encapsulated in the particles. In some embodiments, the molecules and/or compositions disclosed herein are deposited and/or absorbed on the surface of the particles. In some embodiments, the molecules and/or compositions disclosed herein are incorporated in the particles. In some embodiments, the molecules and/or compositions disclosed herein are part of or a component of the particle. The molecules and/or compositions of the disclosure can be, in some embodiments, attached to the surface of the particles with covalent bonds, or non-covalent interactions. In some embodiments, the molecules and/or compositions of the disclosure self-assemble into a particle.

As used herein, the term "encapsulate" means to enclose, surround or encase. As it relates to the formulation of the molecules and/or compositions of the present disclosure, encapsulation may be substantial, complete or partial. The term "substantially encapsulated" means that at least greater than 50%, 60%, 70%, 80%, 85%, 90%, 95%, 96%, 97%, 98%, 99%, 99.9%, 99.99%, or 99.999% of the molecules and/or compositions of the present disclosure may be enclosed, surrounded or encased within the particle. "Partially encapsulation" means that less than 10%, 15%, 20%, 30%, 40%, 50% of the molecules and/or compositions of the present disclosure may be enclosed, surrounded or encased within the particle. For example, at least 1%, 5%, 10%, 20%, 30%, 40%, 50%, 60%, 70%, 80%, 85%, 90%, 95%, 96%, 97%, 98%, 99%, 99.9%, 99.99%, or 99.999% of the molecules and/or compositions of the present disclosure are encapsulated in the particle. Encapsulation may be determined by any known method.

In some embodiments, the particles are polymeric particles or contain a polymeric matrix. The particles can generally contain any of the polymers known in the art. The particles will generally contain one or more biocompatible polymers. The polymers can be biodegradable polymers. The polymers can be hydrophobic polymers, hydrophilic polymers, or amphiphilic polymers. In some embodiments, the particles contain one or more polymers having an additional targeting moiety attached thereto. In some embodiments, the particles are inorganic particles, such as but not limited to, gold nanoparticles and iron oxide nanoparticles.

The size of the particles can be adjusted for the intended application. The particles can be nanoparticles or microparticles. The particle can have a diameter of about 10 nm to about 10 microns, about 10 nm to about 1 micron, about 10 nm to about 500 nm, about 20 nm to about 500 nm, or about 25 nm to about 250 nm. In some embodiments the particle is a nanoparticle having a diameter from about 25 nm to about 250 nm. In some embodiments, the particle is a nanoparticle having a diameter from about 50 nm to about 150 nm. In some embodiments, the particle is a nanoparticle having a diameter from about 70 nm to about 130 nm. In some embodiments, the particle is a nanoparticle having a diameter of about 100 nm. It is understood by those in the art that a plurality of particles will have a range of sizes and the diameter is understood to be the median diameter of the particle size distribution.

In some embodiments, the molecules and/or compositions disclosed herein may be incorporated into particles that are responsive to temperature, pH, and ionic conditions. For example, the particles may comprise an ionizable network of covalently cross-linked homopolymeric ionizable monomers wherein the ionizable network is covalently attached to a single terminal region of an amphiphilic copolymer to form a plurality of "dangling chains" and wherein the "dangling chains" of amphiphilic copolymer form immobile intra-network aggregates in aqueous solution, as disclosed in U.S. Pat. No. 7,204,997.

Liposomes, Lipoplexes, and Lipid Nanoparticles (LNPs)

The molecules and/or compositions of the disclosure can be formulated using one or more liposomes, lipoplexes, and/or lipid nanoparticles. In one embodiment, pharmaceutical formulations of the molecules and/or compositions of the disclosure include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In some embodiments, the molecules and/or compositions of the disclosure may be formulated in a lipid vesicle which may have crosslinks between functionalized lipid bilayers. In some embodiments, the molecules and/or compositions of the disclosure may be formulated in a lipid-polycation complex. The formation of the lipid-polycation complex may be accomplished by methods known in the art. As a non-limiting example, the polycation may include a cationic peptide or a polypeptide such as, but not limited to, polylysine, polyornithine and/or polyarginine and the cationic peptides. In some embodiments, the nucleic acid molecules and/or compositions disclosed herein may be formulated in a lipid-polycation complex which may further include a neutral lipid such as, but not limited to, cholesterol or dioleoyl phosphatidylethanolamine (DOPE). The liposome formulation may be influenced by, but not limited to, the selection of the cationic lipid component, the degree of cationic lipid saturation, the nature of the PEGylation, ratio of all components and biophysical parameters such as size.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain 1-5% of the lipid molar ratio of PEG-c-DOMG as compared to the cationic lipid, DSPC and cholesterol. In another embodiment, the PEG-c-DOMG may be replaced with a PEG lipid such as, but not limited to, PEG-DSG (1,2-Distearoyl-sn-glycerol, methoxypolyethylene glycol) or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200, and DLin-KC2-DMA.

In some embodiments, LNP formulations described herein may comprise a polycationic composition. In some embodiments, the LNP formulations comprising a polycationic composition may be used for the delivery of the modified RNA described herein in vivo and/or ex vitro. In some embodiments, the LNP formulations described herein may additionally comprise a permeability enhancer molecule. The nanoparticle formulations may be a carbohydrate nanoparticle comprising a carbohydrate carrier and a modified nucleic acid molecule (e.g., mRNA). As a non-limiting example, the carbohydrate carrier may include, but is not limited to, an anhydride-modified phytoglycogen or glycogen-type material, phtoglycogen octenyl succinate, phytoglycogen beta-dextrin, and anhydride-modified phytoglycogen beta-dextrin.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

Additional information regarding cationic lipids suitable for LNP formulations can be found in, for example, U.S. Publication No. US2017/0151339, which is herein incorporated by reference in its entirety.

The molecules and/or compositions of the disclosure can also be formulated as a nanoparticle using a combination of polymers, lipids, and/or other biodegradable agents, such as, but not limited to, calcium phosphate. Components may be combined in a core-shell, hybrid, and/or layer-by-layer architecture, to allow for fine-tuning of the nanoparticle so that delivery of the molecules and/or compositions of the disclosure may be enhanced.

Pharmaceutical formulations of the present disclosure may additionally comprise one or more pharmaceutically acceptable excipients, which, as used herein, includes any and all solvents, dispersion media, diluents, or other liquid vehicles, dispersion or suspension aids, surface active agents, isotonic agents, thickening and emulsifying agents, preservatives, solid binders, lubricants, and the like, as suited to the particular dosage form desired. More information in this regard can be found in Remington's The Science and Practice of Pharmacy, 21st Edition, A. R. Gennaro (Lippincott, Williams & Wilkins, Baltimore, Md., 2006) which discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

EXAMPLES

Additional alternatives are disclosed in further detail in the following examples, which are not in any way intended to limit the scope of the claims.

Example 1

General Experimental Procedure

DNA Template Preparation

Plasmid DNA templates were purified (Qiagen Cat. no. 12163) from 300 mL of saturated *E. coli* TransforMax Epi300 (Epicentre Cat. no. EC300105) cultures grown in LB broth media (Teknova Cat. no. L8000 06) supplemented with 50 ng/ml carbamicilin (Teknova Cat. no. NC9730116). Plasmid DNA was linearized by Not-I digestion (New England Biolabs NEB cat. no. R3189S) for one hour at 37° C. Linearized template DNA was then re-purified (Zymo Cat. no. D4003), and analyzed by 0.8% agarose gel (Life Technologies Cat. no. G5018-08) against a commercial 2-log DNA ladder (New England Biolabs, NEB Cat. no. N3200S). The presence of a single band was confirmed in each sample, corresponding to the expected fragment size of the linear DNA template, prior to proceeding with ex vitro transcription.

Ex Vitro Transcription

Ex vitro transcription (IVT) reactions were performed using 1 μg of DNA template prepared as described above, in a 20 μl reaction over a one hour incubation at 37° C. (NEB cat. no. E2065 S). 1 Unit of DNase I, provided by the supplier was then added directly to the IVT reaction, and incubated at 37° C. for an additional 15 mins. Reactions were then placed on ice, and purified using the manufactures suggested method (Qiagen Cat. no. 74104). Purified RNA was then quantified using a NanoDrop 2000c UV-Vis Spectrophotometer. RNA was visualized by electrophoresis through 0.8% Agarose gels (Life Technologies Cat. no. G5018-08) and compared with Millennium RNA Marker (Ambion Cat. No. AM7150), prior to proceeding with electroporation.

Transfection and Analysis

In a typical cell transfection experiment, replicon RNA was introduced into BHK-21 cells by electroporation using the SF Cell Line Nucleofector™ kit for the 4D-Nucleofector™ System (Lonza). BHK-21 cells were harvested using 0.25% trypsin and washed once with cold PBS. Cells were resuspended in SF Buffer at a cell density of $1\times10^6$ cells per 20 μL electroporation reaction. Three micrograms of RNA was electroporated into cells in triplicate in a 16-well cuvette strip and incubated at room temperature for 10 minutes. Electroporated cells were recovered into plates containing Dulbecco's Modified Eagle Medium containing 10% fetal bovine serum, followed by incubation for 16-18 h at standard cell culture conditions.

Intracellular analyses of replicon transfection efficiency and protein production were performed by flow cytometry. In these assays, transfected BHK-21 cells were fixed and permeabilized using fix/perm concentrate and permeabilization buffer (eBioscience). Cells were then incubated with antibodies for double-stranded RNA production (J2 anti-dsRNA IgG2A monoclonal antibody, English & Scientific Company) conjugated with R-Phycoerythrin (Innova Biosciences). Antigen production was assessed by additional incubation with antigen-specific antibodies conjugated with PE-Cy5 (Innova Biosciences) (e.g. antibodies for red Firefly, green *Renilla*, HA, or RSV-F0 (Abcam)). Cells were then washed once and analyzed using a FACSAria™ Fusion Cell Sorter (BD Biosciences) or FACSAria™ II Cell Sorter (BD Biosciences). Transfected BHK-21 cells stained with single colors for compensation controls were run prior to sample collection. Data was collected using FACSDiva (BD Biosciences) and further analyzed using FlowJo software. Initial gating was performed to exclude dead cells and debris using forward and side scatter plots. Further gating was conducted to identify cell populations that were positive for both dsRNA (R-PE-positive) and protein expression (PE-Cy5-positive or FITC-positive for GFP expression). Frequencies and mean fluorescence intensities were collected and utilized for construct comparison and optimization.

Example 2

Construction of DLP-Containing EAV Replicon Designs

This Example describes the generation of a number of arterivirus RNA replicon-based expression vectors with a DLP motif operably positioned upstream of the polyprotein/non-structural protein genes and/or a reporter gene. These arterivirus RNA replicon-based expression vectors were subsequently characterized and analyzed in the flow cytometry analysis and bulk luciferase analyses described in EXAMPLE 4.

A. Design

The respective design features of four EAV-based DLP replicon constructs are described below.

(1) rEX-DLP-rFF

In this construct, a DLP motif as placed immediately upstream of rFF and downstream of the TRS7 driving the transcription of rFF.

(2) rEX-DLP-pp1ab-rFF

In this construct, a DLP motif was placed immediately upstream of the pp1ab genes with a few careful design modifications described below to maintain the stem loop structure in the 5'UTR of the replicon known to be essential for replication and subgenomic mRNA transcription.

(i) The first 79 nucleotides of the nonstructural viral gene 1a is duplicated with its start codon mutated from ATG to TAG, denoted as "ATG-shifting region" (bold in the sequence of SEQ ID NO: 2 below).

(ii) The corresponding nucleotides, located upstream of the 1a gene, base-pairing with its start codon ATG and forming the stem, were also changed accordingly from CAT to CTA (underlined in the sequence of SEQ ID NO: 2 below).

(iii) DLP (italicized in the sequence below) was placed immediately downstream of the "ATG-shifting region" and upstream of the polyprotein 1ab genes (start codon ATG shown in the sequence of SEQ ID NO: 2 below).

(partial sequence)

SEQ ID NO: 2

CGAAGTGTGTATGGTGCCATATACGGCTCACCACCATATACACTGCAA

GAATTACTATTCTTGTGGGCCCCTCTCGGTAAATCCTAGAGGGCTTTC

CTCTCGTTATTGCGAGATTCGTCGTTAGATAACGGCAAGTTCCCTTTC

TTACTATCCTATTTTCATCTTGTGGCTTGACGGGTCACTGCCTACGTC

GTCGATCTCTATCAACTACCCTTGCGACTTAGGCAACCTTCTCCGCTA

CTGGATTTGGAGGGAGTTTTGTTAGGGACTGGTCCCTGGACTTACCCG

ACGCTTGTGAGC*ATAGTCAGCATAGTACATTTCATCTGACTAATACTA*

*CAACACCACCACCATGAATAGAGGATTCTTTAACATGCTCGGCCGCCG*

*CCCCTTCCCGGCCCCCACTGCCATGTGGAGGCCGCGGAGAAGGAGGCA*

*GGCGGCCCCGATG*ATGGCAACCTTCTCCGCTACTGGATTTGGAGG . . .

This construct was essentially identical to the second construct, where DLP was placed following the same three design modifications, except that a 2A protease sequence (SEQ ID NO: 3) was added immediately at the 3' end of DLP such that, when translated, the polyproteins could be released from the DLP-derived peptide through a selective cleavage by the protease. A comparative analysis of performances by replicon Construct 2 (described above) and Construct 3 would provide information on whether the 2A protease was needed for a functional replicon (see EXAMPLE 4 below).

SEQ ID NO: 3

GGAAGCGGAGCTACTAACTTCAGCCTGCTGAAGCAGGCTGGAGACGTGG

AGGAGAACCCTGGACCT (4) rEX-DLP-2A-pp1ab-DLP-rFF

This construct was essentially identical to the third construct described above, except that another DLP was placed immediately upstream of the reporter rFF gene (the same way as a DLP motif was placed in construct 1). A comparative analysis of performances by replicon Construct 3 (described above) and Construct 4 would provide information on whether the additional DLP placed upstream of the reporter gene has an added value to the expression of the reporter gene.

B. Construction rEx-DLP-rFF was built according to a 3-piece Gibson Assembly® procedure described in Gibson et al. (Enzymatic assembly of DNA molecules up to several hundred kilobases. *Nat. Methods* 6, 343-345, 2009) with rEx-rFF (c4; SEQ ID NO: 34) digested with SphI and EcoRI as a vector and a DLP-containing g-block as an insert. The nucleic acid sequence of the g-block used for construction of rEx-DLP-rFF is set forth at SEQ ID NO: 4 in the Sequence Listing.

The following primers were designed to amplify the corresponding fragments required to build the 3 new EAV-based DLP replicon constructs described above.

TABLE 3

| Primer | Primers designed for construction DLP-(2A)-pp1ab-rFF/DLP-rFF replicons | |
|---|---|---|
| RP114 | pp1a-DLP-F | GCCATGTGGAGGCCGCGGAGAAGGAGGCAGGCGGCCCCGATGATGGCAACCTTCTCCGCTACTGGAT (SEQ ID NO: 5) |
| RP115 | pBR322-3'SrfI-R | ACAATGTTGCCTCCCACATCTGCAA (SEQ ID NO: 6) |
| RP116 | pBR322-3'SrfI-F | GGGTCACAAGGTAGTCGCCGTGGTT (SEQ ID NO: 7) |
| RP117 | pBR322-bla-R | ACGTCAGGTGGCACTTTTCGGGGAA (SEQ ID NO: 8) |
| RP118 | pp1a-DLP-2A-F | AGCCTGCTGAAGCAGGCTGGAGACGTGGAGGAGAACCCTGGACCTATGGCAACCTTCTCCGCTACTGGAT (SEQ ID NO: 9) |

Construction of rEx-DLP-pp1ab-rFF

For the construction of the rEx-DLP-pp1ab-rFF vector, three nucleic acid fragments were generated by using a 3-piece Gibson Assembly® procedure, as follows.

Fragment 1 was generated with primers RP114 and RP115 and the template backbone rEx-rFF.

Fragment 2 was generated with primers RP116 and RP117 and template backbone rEx-rFF.

Fragment 3 was a g-block for rEx-DLP-pp1ab-rFF with the nucleic acid sequence set forth at SEQ ID NO: 10 in the Sequence Listing.

Construction of rEx-DLP-2A-pp1ab-rFF

For the construction of rEx-DLP-2A-pp1ab-rFF vector, three nucleic acid fragments were generated by using a 3-piece Gibson Assembly® procedure, as follows.

Fragment 4 was generated with primers RP118 and RP115 and the template backbone rEx-rFF.

Fragment 5 was generated with primers RP116 and RP117 and template backbone rEx-rFF.

Fragment 6 was a g-block for rEx-DLP-2A-pp1ab-rFF with the nucleic acid sequence set forth at SEQ ID NO: 11 in the Sequence Listing.

Construction of rEx-DLP-2A-pp1ab-DLP-rFF

For the construction of rEx-DLP-2A-pp1ab-DLP-rFF vector, three nucleic acid fragments were generated by using a 3-piece Gibson Assembly® procedure, as follows.

Fragment 7 was generated with primers RP118 and RP115 and the template backbone rEx-DLP-rFF.

Fragment 8 was generated with primers RP116 and RP117 and template backbone rEx-DLP-rFF.

Fragment 9 was a g-block for rEx-DLP-2A-pp1ab-DLP-rFF with the nucleic acid sequence set forth at SEQ ID NO: 12 in the Sequence Listing.

Construct assembly was performed according to a 3-piece Gibson Assembly® procedure described in Gibson et al. (2009, supra). In particular, the rEx-DLP-pp1ab-rFF construct was built using fragments 1, 2, and 3; the rEx-DLP-2A-pp1ab-rFF construct was built using fragments 4, 5, and 6; and the rEx-DLP-2A-pp1ab-DLP-rFF construct was built using fragments 7, 8, and 9. Assembled products were subsequently transformed into EPI300 cells from Epicenter. A total of 144 colonies were screened using the primers RP126 (SEQ ID NO: 13) and RP127 (SEQ ID NO: 14) for each transformation, resulting in 4 PCR-positive clones for rEx-DLP-pp1ab-rFF, 3 PCR-positive clones for rEx-DLP-2A-pp1ab-rFF, and 2 PCR-positive clones for rEx-DLP-2A-pp1ab-DLP-rFF. Subsequent MiSeq results revealed that clone 4, clones 3 and 15, and clones 18 and 20 were completely sequence-correct for rEx-DLP-pp1ab-rFF, rEx-DLP-2A-pp1ab-rFF, and rEx-DLP-2A-pp1ab-DLP-rFF, respectively.

TABLE 4

| Primer | Primers designed for colony screening of the DLP-(2A)-pp1ab replicons | |
|---|---|---|
| RP126 | DLP-pp1ab-screen-F | CAGCATCTTTTACTT TCACCAGCGTTTCTG (SEQ ID NO: 13) |
| RP127 | DLP-pp1ab-screen-R | GGAACTGGCGAAGCC AGTTTTAACA (SEQ ID NO: 14) |

The maps of rEx-DLP-rFF, rEx-DLP-pp1ab-rFF, rEx-DLP-2A-pp1ab-rFF, and rEx-DLP-2A-pp1ab-DLP-rFF are also shown in FIGS. 2A-2D.

The sequences of the resulting replicons are disclosed in the Sequence Listing with a T7 promoter and a polyA tail of 65 A's, as follows: rEx-DLP-rFF (SEQ ID NO: 15), rEx-DLP-pp1ab-rFF (SEQ ID NO: 16), rEx-DLP-2A-pp1ab-rFF (SEQ ID NO: 17), and rEx-DLP-2A-pp1ab-DLP-rFF (SEQ ID NO: 18).

Example 3

Construction of DLP-Containing Alphavirus Replicon Designs

This Example describes the generation of a number of Alphavirus RNA replicon-based expression vectors with a DLP motif positioned upstream of the polyprotein/non-structural protein genes and/or a reporter gene. These Alphavirus RNA replicon-based expression vectors were subsequently characterized and analyzed in the flow cytometry analysis and bulk luciferase analyses described in EXAMPLE 5.

A. Design

The respective design features of three Alphavirus-based DLP replicon constructs are described below.

(1) Alpha-R-DLP-rFF

In this construct, In this construct, DLP was placed immediately upstream of the start codon of the reporter gene rFF.

(2) Alpha-R-DLP-2A-nsp-rFF

In this construct, the sequence encoding the DLP motif and the 2A peptide sequence (which was the same sequence used in the rEx-DLP-2A-pp1ab-rFF replicon described in Example 2 above) was placed within the 5' end of the replicon with a few careful design modifications described below, to potentially maintain the sequence-structure requirement for replication and subgenomic mRNA transcription.

(i) The first 195 nucleotides of the nsp1 gene was duplicated with its start codon mutated from ATG to TAG (bold in the sequence of SEQ ID NO: 19 below).

(ii) This 195-nucleotide duplicated sequence was placed immediately following the 5' UTR of the wild-type Alphavirus (underlined in the sequence of SEQ ID NO: 19 below) and is followed by the DLP-2A sequence (italicized in the sequence below).

(iii) The start codon of the nsp1 gene following the DLP-2A sequence was removed (strike-through in the sequence of SEQ ID NO: 19 below).

(partial sequence)

SEQ ID NO: 19

GATAGGCGGCGCATGAGAGAAGCCCAGACCAATTACCTACCCAAATAG

GAGAAAGTTCACGTTGACATCGAGGAAGACAGCCCATTCCTCAGAGCT

TTGCAGCGGAGCTTCCCGCAGTTTGAGGTAGAAGCCAAGCAGGTCACT

GATAATGACCATGCTAATGCCAGAGCGTTTTCGCATCTGGCTTCAAAA

CTGATCGAAACGGAGGTGGACCCATCCGACACGATCCTTGACATTGGA

*ATAGTCAGCATAGTACATTTCATCTGACTAATACTACAACACCACCAC*

*CATGAATAGAGGATTCTTTAACATGCTCGGCCGCCGCCCCTTCCCGGC*

*CCCCACTGCCATGTGGAGGCCGCGGAGAAGGAGGCAGGCGGCCCCGGG*

*AAGCGGAGCTACTAACTTCAGCCTGCTGAAGCAGGCTGGAGACGTGGA*

*GGAGAACCCTGGACCT*~~ATG~~GAGAAAGTTCACG . . .

(3) Alpha-R-DLP-2A-nsp-DLP-rFF

This construct is essentially identical to Construct 2 following the same three design modifications, except that another DLP motif was placed immediately upstream of the reporter rFF gene (the same way as a DLP motif was placed in Construct 1). A comparative analysis of performances by replicon Constructs 2 and 3 would provide information on whether the additional DLP placed upstream of the reporter gene has an added value to the expression of the reporter gene (see EXAMPLE 5 below).

B. Construction

Construction of Alpha-R-DLP-rFF

Alpha-R-DLP-rFF was built via Gibson Assembly® procedure, using Alpha-R-eGFP (c6; SEQ ID NO: 35) digested with EcoRI/SapI as a vector and DLP-rFF as an insert PCR-amplified from the template rEx-DLP-rFF (c2, SEQ ID NO: 15) using the primers RP112 (SEQ ID NO: 20) and RP113 (SEQ ID NO: 21) to replace eGFP with DLP-rFF. Clones 2 and 3 were sequence-confirmed to be completely correct via MiSeq sequencing.

TABLE 5

| Primer | Primers used to clone DLP-rFF into Alpha-R-GFP (EcoRV/SapI) | |
|---|---|---|
| RP112 | DLP-rFF-F | CCTGAATGGACTACGACATAGTCTAG TCCGCCAAGATATCGCACCATAGTCA GCATAGTACATTTCATCTGACTAATA CT (SEQ ID NO: 20) |
| RP113 | DLP-rFF-R | GCAGCTTGCCAATTGCTGCTGTATCG ATCAATTAATCACATCTTGGCCACGG GTTTCTTC (SEQ ID NO: 21) |

Construction of Alpha-R-DLP-2A-nsp-rFF and Alpha-R-DLP-2A-nsp-DLP-rFF

Alpha-R-DLP-2A-nsp-rFF (Construct 2) and Alpha-R-DLP-2A-nsp-DLP-rFF (Construct 3) were built via Gibson Assembly® procedure, using the respective g-blocks as inserts and the vectors that had been PCR-amplified from the respective templates, Alpha-R-rFF (c6; SEQ ID NO: 35) and Alpha-R-DLP-rFF (c2; SEQ ID NO: 26), using the primers RP124 (SEQ ID NO: 22) and RP125 (SEQ ID NO: 23). Clones 1 and 3 of Alpha-R-DLP-2A-nsp-rFF and clones 8 and 32 of Alpha-R-DLP-2A-nsp-DLP-rFF were sequence-confirmed to be completely correct via MiSeq.

TABLE 6

| Primer | Primers used for construction of Alpha-DLP-nsp-rFF/DLP-rFF | |
|---|---|---|
| RP124 | 5'Alpha-P2A-F | GAAGCAGGCTGGAGACGTGGAGGAGAACCC TGGACCTGAGAAAGTTCACGTTGACATCGA GGAAGAC (SEQ ID NO: 22) |
| RP125 | 5'ScaI-R | CACCAGTCACAGAAAAGCATCTTACGGATG (SEQ ID NO: 23) |

The sequence of g-block used for the construction of Alpha-R-DLP-2A-nsp-rFF is provided in the Sequence Listing as SEQ ID NO: 24. The sequence of g-block used for the construction of Alpha-R-DLP-2A-nsp-DLP-rFF is also provided in the Sequence Listing as SEQ ID NO: 25.

The maps of Alpha-R-rFF, Alpha-R-DLP-rFF, Alpha-R-DLP-2A-nsp-rFF, and Alpha-R-DLP-2A-nsp-DLP-rFF are shown in FIGS. 3A-3D.

The sequences of the resulting replicons are also provided in the Sequence Listing with a T7 promoter and a polyA tail of 40 A's, as follows: Alpha-R-rFF (SEQ ID NO: 26), Alpha-R-DLP-rFF (SEQ ID NO: 27), Alpha-R-DLP-2A-nsp-rFF (SEQ ID NO: 28), and Alpha-R-DLP-2A-nsp-DLP-rFF (SEQ ID NO: 29).

Construction of Alpha-R-DLP-2A-rFF and Alpha-R-DLP-2A-nsp-DLP-2A-rFF

Without being bound by any particular theory, it is believed that placing a DLP motif immediately upstream of the reporter gene rFF without the inclusion of the 2A protease in between them may negatively impact protein expression of the GOI; this negative impact could be due to the fact that rFF now became a "fusion" protein, resulting from the presence of the DLP sequence translated into a peptide at the 5' end of rFF. Therefore, 2 new constructs were designed and built, including the 2A protease sequence between the DLP motif and the rFF gene for the two Alphavirus-replicon constructs, Alpha-R-DLP-rFF and Alpha-R-DLP-2A-nsp-DLP-rFF, to generate Alpha-R-DLP-2A-rFF and Alpha-R-DLP-2A-nsp-DLP-2A-rFF, respectively. The inclusion of the 2A protease peptide sequence would enable cleavage of the peptide encoded by the DLP sequence from rFF (see Example 5 below).

For this purpose, two g-block fragments were synthesized (SEQ ID NOS: 30 and 31) and cloned into their respective vectors digested with EcoRV/SbfI via Gibson Assembly. Clone 1 of Alpha-R-DLP-2A-rFF and clones 8 and 9 of Alpha-R-DLP-2A-nsp-DLP-2A-rFF were sequence-confirmed to be completely correct via Sanger sequencing using RP123 (SEQ ID NO: 32) and RP96 (P89; SEQ ID NO: 96).

TABLE 7

| Primer | Primers used to sequence Alpha-R-(DLP-2A-nsp)-DLP-2A-rFF constructs | |
|---|---|---|
| RP123 | Alpha-3'nsp4-F | GGCTGTTTAAGCTTGGCAAACCTCT (SEQ ID NO: 32) |
| RP96 | rFF-seq1 | AGCGAGAACTGCGAGGAATTCTT (SEQ ID NO: 33) |

Figure 4A:
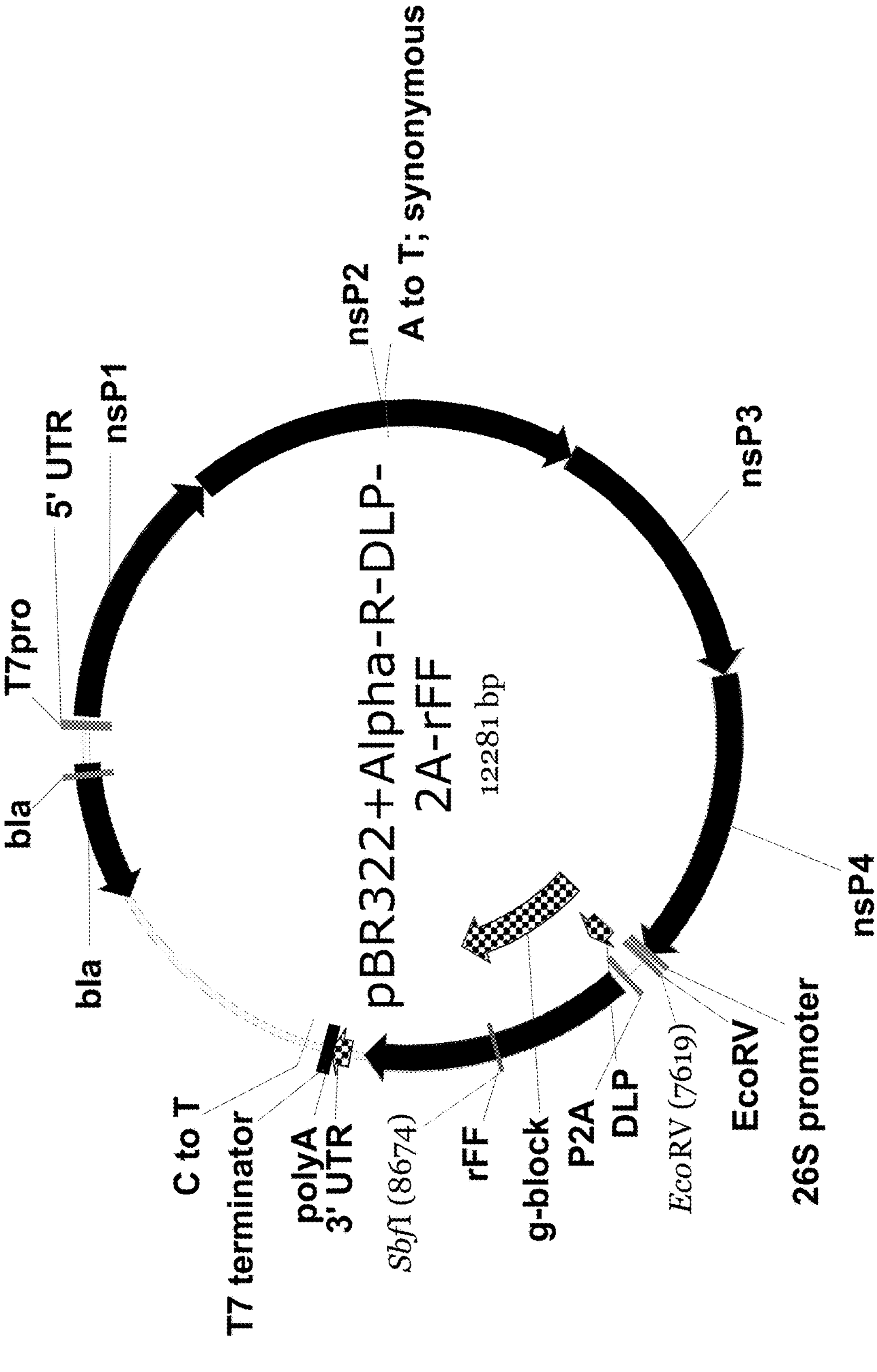
FIGS. 4A-4B are graphical illustrations of two other non-limiting exemplary nucleic acid molecules of the present disclosure, where each of the nucleic acid molecules comprises encoding coding sequence for an alphavirus capsid enhancer (e.g., a DLP motif) and a coding sequence for a gene of interest (GOI), e.g., a red Firefly (rFF) reporter gene.
Figure 4B:
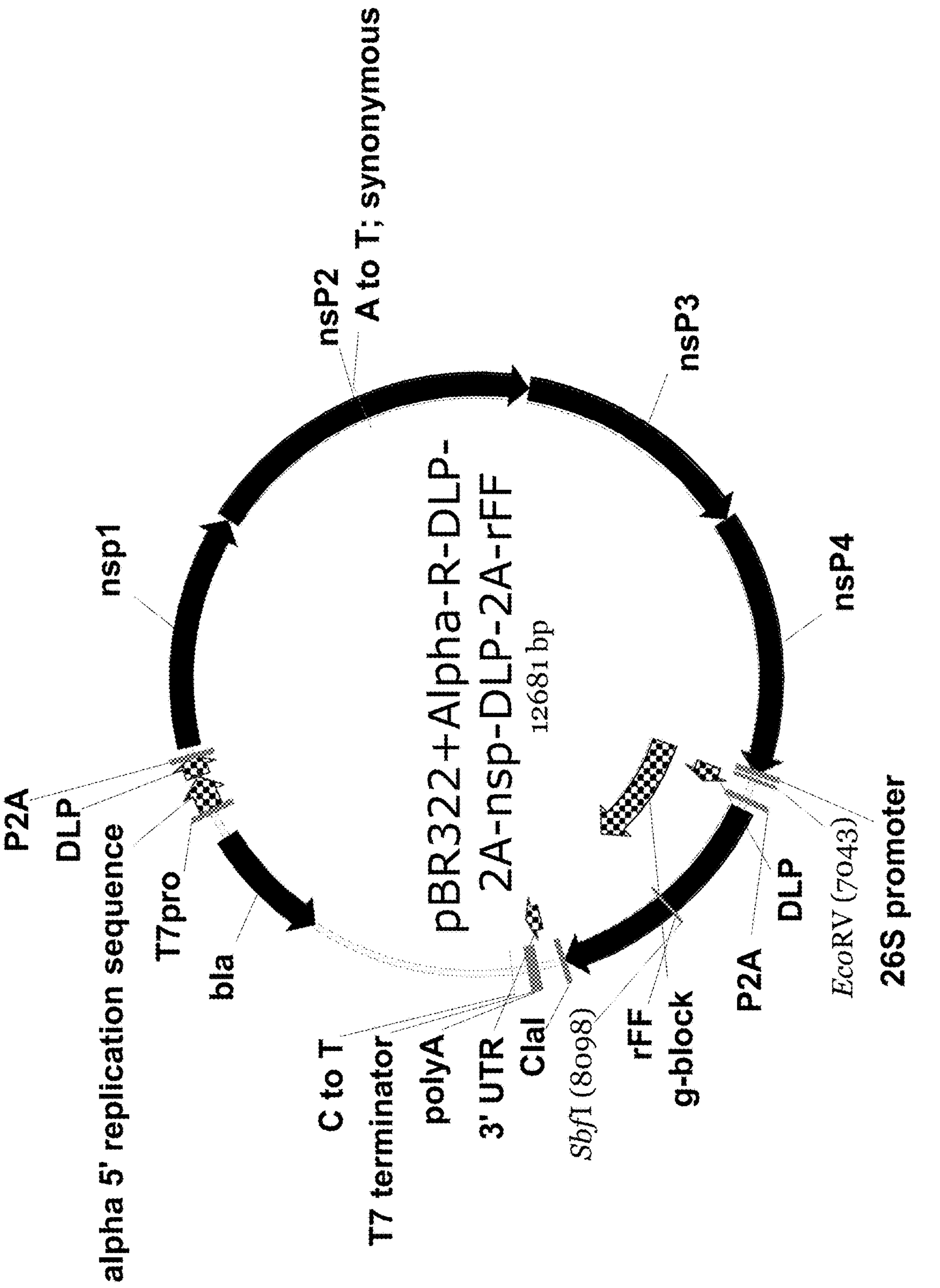

Schematic maps of Alpha-R-DLP-2A-rFF and Alpha-R-DLP-2A-nsp-DLP-2A-rFF are provided in FIGS. 4A-4B.

Example 4

Expression Analysis of EAV-Based DLP Containing Replicons

As presented in Examples 2 and 3 above, a number of EAV-based DLP containing replicons were constructed to determine the impact of engineering a DLP motif positioned upstream of either the replicon nonstructural protein genes or the GOI gene on a subgenomic mRNA (TABLE 8).

TABLE 8

| Listing of DLP-containing EAV Replicons and DLP-containing VEEV replicons. |
|---|
| EAV DLP Replicons |
| rEx-DLP-rFF |
| rEx-DLP-2A-rFF |
| rEx-DLP-pp1ab-rFF |
| rEx-DLP-2A-pp1ab-rFF |
| rEx-DLP-2A-pp1ab-DLP-rFF |
| rEx-DLP-2A-pp1ab-DLP-2A-rFF |
| VEEV DLP replicons |
| alpha-R-DLP-rFF |
| alpha-R-DLP-2A-rFF |
| alpha-R-DLP-2A-nsp-rFF |
| alpha-R-DLP-2A-nsp-DLP-rFF |
| alpha-R-DLP-2A-nsp-DLP-2A-rFF |

Initial characterization of the DLP replicon constructs was carried out ex vitro. RNA was produced and used to electroporate BHK cells as described in EXAMPLE 1 above. After electroporation cells were analyzed for protein expression by FACs analysis, Western blot or bulk luciferase assay.

A graphical summary of the results of experiments performed to measure the expression level of an exemplary gene of interest (GOI), rFF luciferase reporter, from EAV-based DLP replicons is shown in FIG. 5. Both FACs analysis and bulk luciferase data are presented. In these experiments, four different EAV DLP replicons were analyzed as follows:

1) rEx-DLP-rFF: an EAV-based replicon with a DLP motif positioned upstream to the subgenomic mRNA rFF transcript);

2) rEx-DLP-pp1ab-rFF: an EAV-based replicon with DLP positioned upstream to the non-structural pp1ab genes);

3) rEx-DLP-2A-pp1ab-rFF: an EAV-based replicon with a DLP motif positioned upstream to the nonstructural proteins and a 2A protease peptide positioned between the DLP and the pp1ab region); and 4) rEx-DLP-2A-pp1ab-DLP-rFF: an EAV-based replicon with a first DLP motif positioned upstream to the nonstructural proteins and a 2A protease peptide positioned between the DLP and the pp1ab region as well as a second DLP motif positioned upstream to the rFF subgenomic mRNA transcript).

Figure 5A:
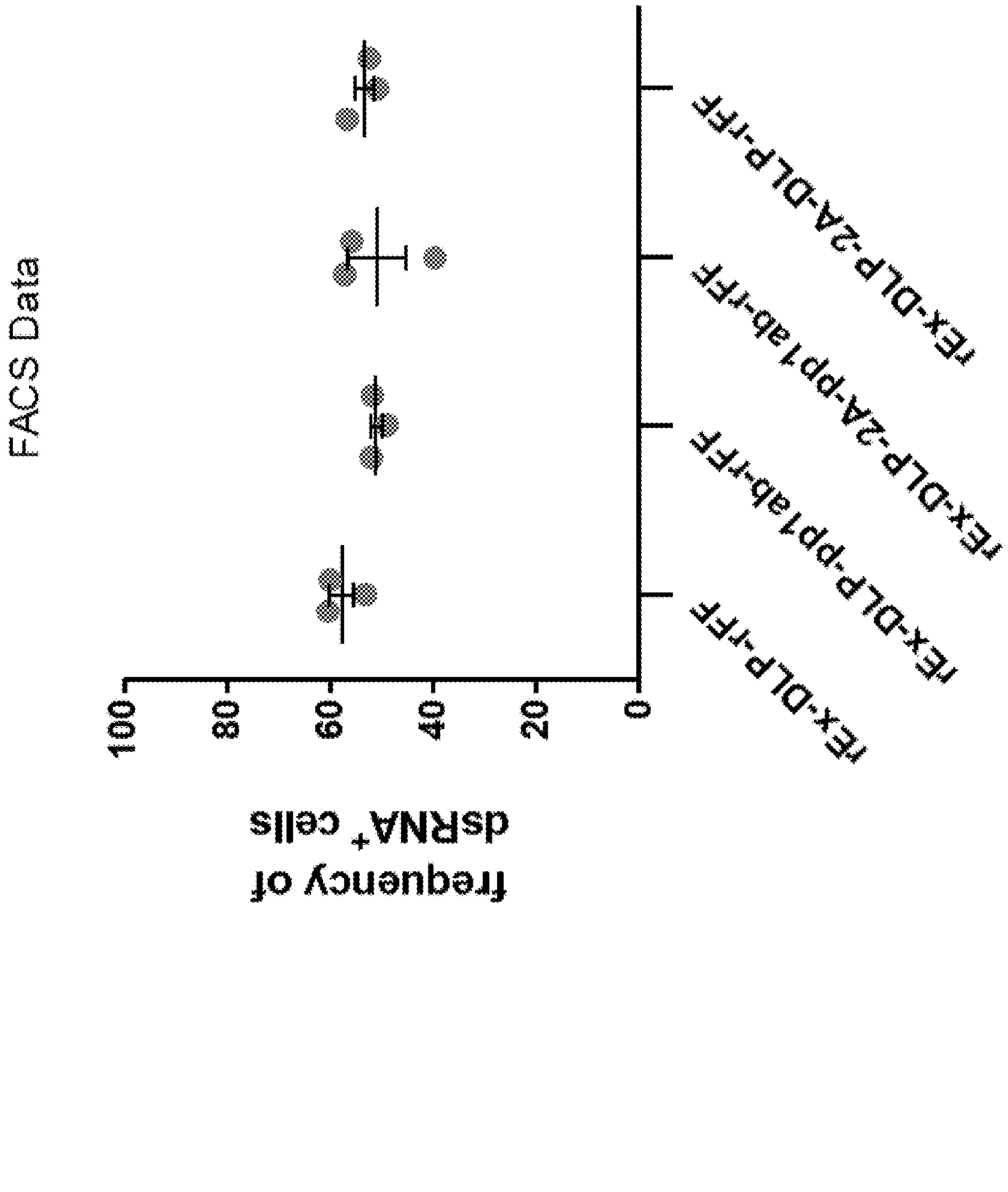
FIGS. 5A-5B graphically summarizes the results of flow cytometry analysis and bulk luciferase analyses performed to demonstrate that incorporating a DLP motif upstream of nucleic acid sequence encoding either EAV nonstructural protein genes or a gene of interest positioned in the subgenomic RNA, i.e. rFF reporter gene, did not negatively impact genomic RNA replication. In these experiments, FACS analysis (FIG. 5A) and bulk-cell luciferase assays (FIG. 5B) were carried out on electroporated cells.
Figure 5B:
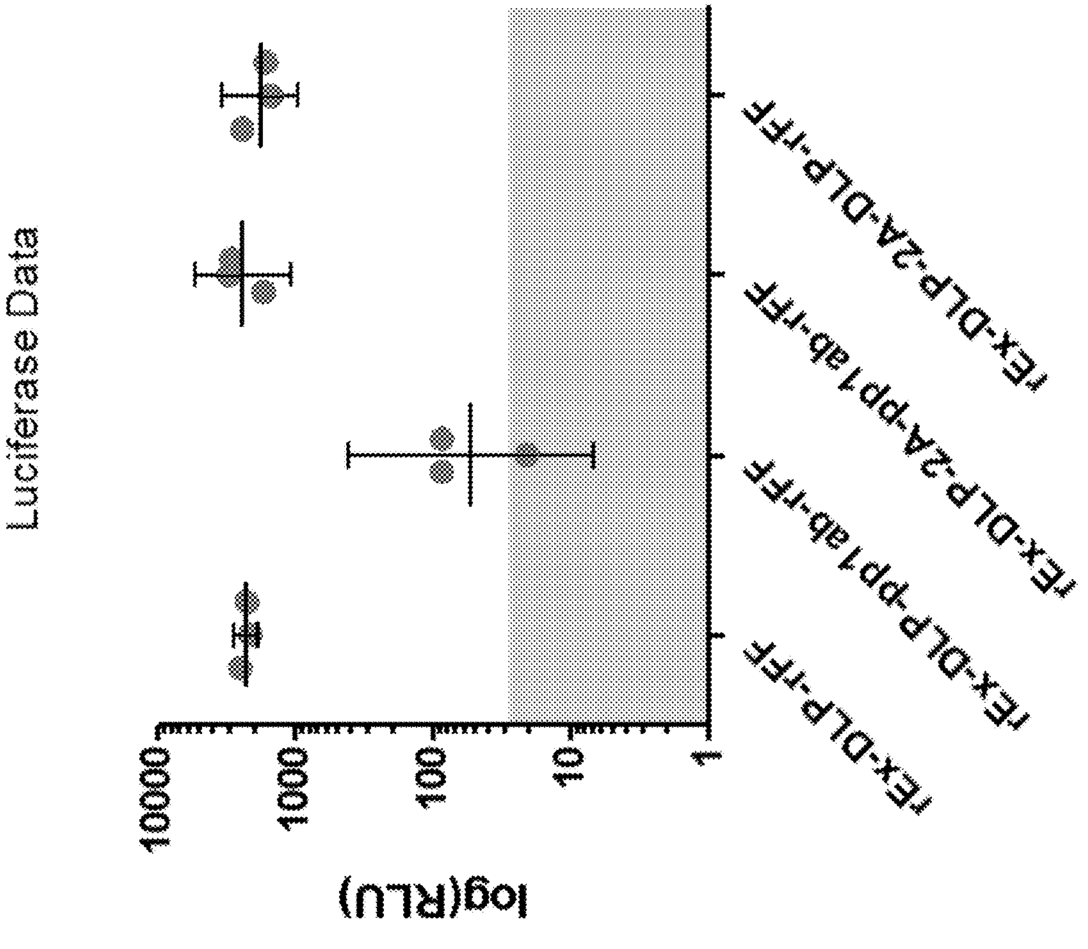

The results presented in FIGS. 5A-5B demonstrated that engineering a DLP motif upstream to either the EAV nonstructural protein genes (e.g., rEx-DLP-pp1ab-rFF, rEx-DLP-2A-pp1ab-rFF or rEx-DLP-2A-pp1ab-DLP-rFF) or the rFF reporter gene subgenomic RNA (e.g., rEx-DLP-rFF and rEx-DLP-2A-pp1ab-DLP-rFF) did not negatively impact genomic RNA replication as all four constructs demonstrated nearly identical electroporation efficiencies (FIG. 5A). Interestingly, bulk luciferase activity analysis demonstrated that the rEx-DLP-pp1ab-rFF replicon expressed significantly less luciferase than the other three replicon designs (FIG. 5B). As stated above, incorporation of a DLP motif upstream of any GOI would result in an N terminal fusion of Sindbis capsid amino acids encoded in the in-frame codons found in the DLP sequence. The fusion protein generated with the amino acids encoding DLP and the EAV nsP1 protein is believed to impact the EAV replication complex from efficiently producing subgenomic RNAs and result in the reduced rFF GOI expression levels noted. One of the most remarkable results from this study was that EAV replicon constructs with a DLP controlling translation of the nonstructural protein genes (rEx-DLP-pp1ab-rFF, rEx-DLP-2A-pp1ab-rFF and rEx-DLP-2A-pp1ab-DLP-rFF) were as efficiently translated as the replicon RNA that did not have a DLP in this position (rEx-DLP-rFF). This result would not be predicted based on work conducted by other researchers. It has been previously reported that incorporation 5' Sindbis virus subgenomic RNA sequences (including the DLP region) were only efficiently translated in cells infected with the virus. Stated differently, mRNA that contains a DLP motif associated with a reporter gene was reported to be poorly translated in cells that were not infected with Sindbis virus. The absence of innate immune activation in these cells rendered the DLP modified mRNA at a distinct translation disadvantage relative to translation of mRNAs that lack the DLP modification (all cellular mRNAs). The innate immune system was not activated in these cells at the time the DLP-containing replicon vectors were introduced so these DLP-containing mRNAs (capable of self-amplification) should be very inefficiently translated. Unexpectedly, that was not borne out in the experiments presented herein.

Figure 6A:
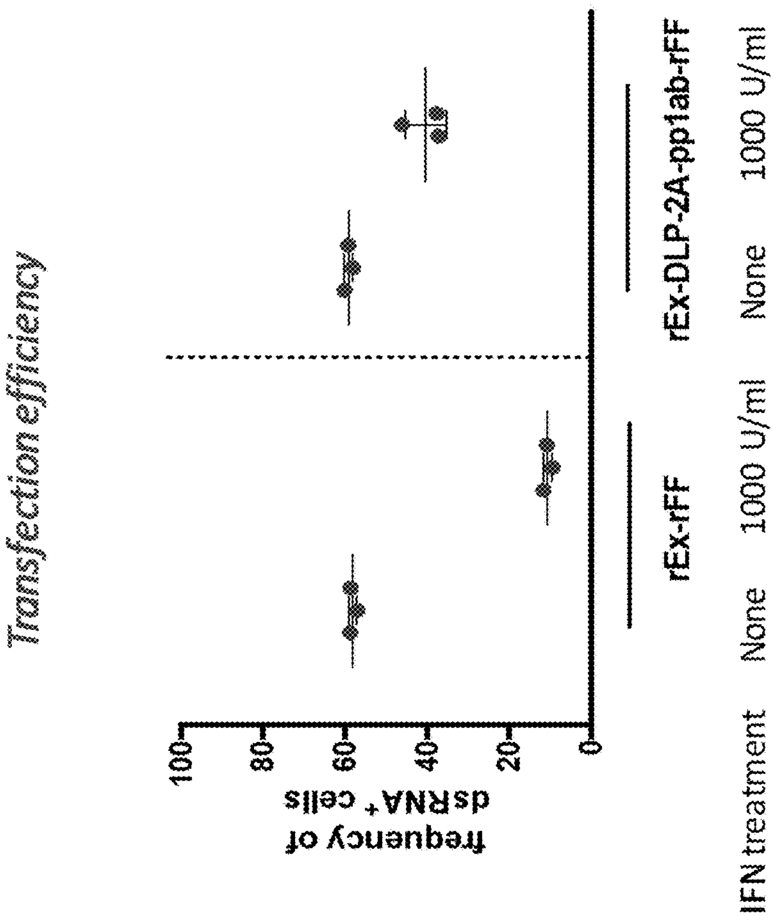
FIGS. 6A-B graphically summarize the results of another exemplary flow cytometry analysis and bulk luciferase analysis performed to demonstrate that modified arterivirus replicon RNAs with a DLP motif incorporated upstream of the sequence encoding nonstructural protein genes can replicate and express efficiently in host cells that had been treated with IFN to induce the cellular innate immune system. In these experiments, FACS analysis (FIG. 6A) and bulk-cell luciferase assays (FIG. 6B) were carried out on electroporated cells. IFN was added to cell culture media five hours post electroporation. Samples were collected in triplicate eighteen hours post electroporation for analysis.
Figure 6B:
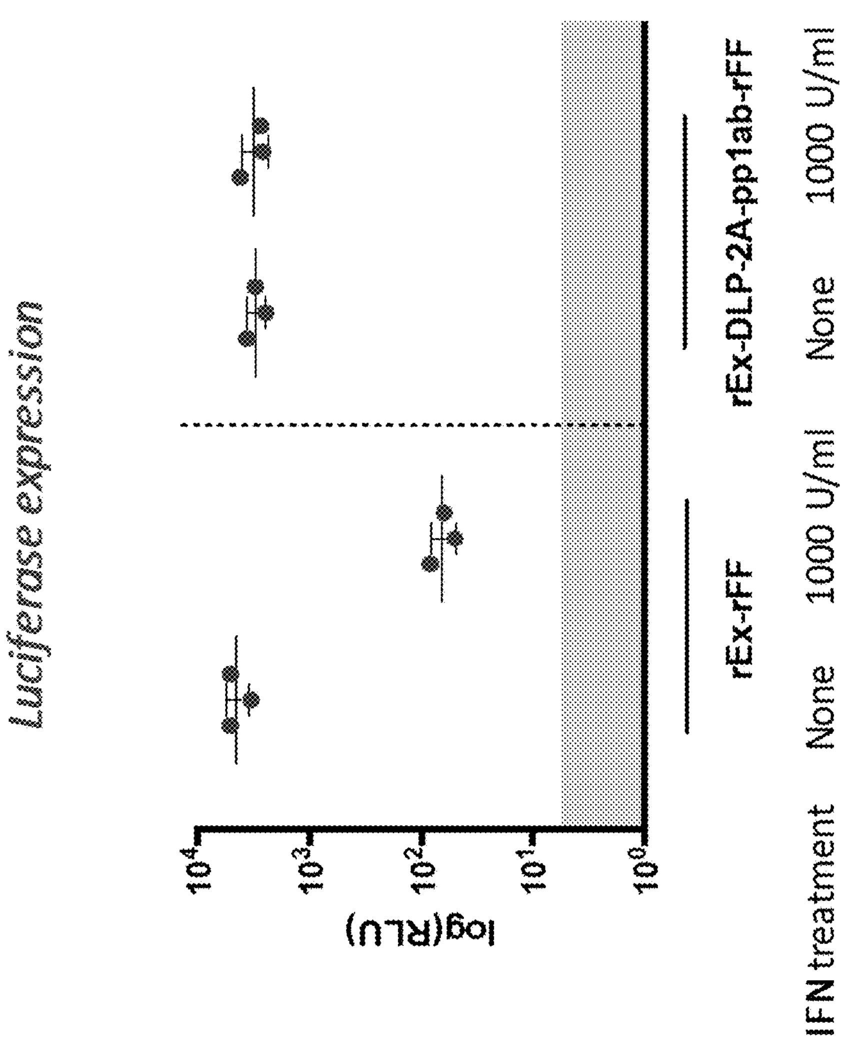

Subsequently, the rEx-DLP-2A-pp1ab-rFF EAV replicon was examined in cells that had been treated with IFN to induce the cellular innate immune system. IFN treatment of BHK cells will induce PKR activation and phosphorylation of eIF2α which in-turn results in shut-down of global cellular mRNA translation. It has been reported previously that arteriviruses are sensitive to IFN treatment (Luo et al. *Antiviral Res.* August; 91(2):99-101, 2011), therefore the IFN treatment of BHK cells, which are capable of responding to IFN exposure and induce the innate immune system, would result in shut-down of arterivirus replication. A representative example of the expression capacity of the DLP modified EAV replicon in the presence of innate immune system activation is shown in FIG. 6. The rEx-DLP-2A-pp1ab-rFF replicon demonstrated significant resistance to innate immune system activation when compared to an EAV replicon that was not modified to contain the DLP motif, i.e. rEx-rFF. Both replication (FIG. 6A) and expression (FIG. 6B) of the rEx-DLP-2A-pp1ab-rFF replicon were significantly higher in IFN treated cells when compared to the control rEx-rFF replicon. These data demonstrate that DLP modified EAV replicons are capable of overcoming innate immune system shut-down and that this replicon vector represents a significant advance in self-amplifying RNA technology.

Example 5

Expression Analysis of DLP-Containing VEEV Replicons

As presented in Examples 2 and 3 above, a number of VEEV-based DLP containing replicons were constructed to determine the impact of engineering a DLP motif positioned upstream of either the replicon nonstructural protein genes or the GOI gene on a subgenomic mRNA.

VEEV alphavirus replicon vectors were engineered to contain one or more DLP motifs by using a strategy similar to the construction of EAV-based replicon vectors. Importantly, unlike other members of the Alphavirus genus (mostly Old World virus members), the genome of VEEV does not contain a DLP motif associated with translation of its subgenomic mRNA. Initial analysis of the VEEV DLP replicons was carried out in BHK-21 cells as described in EXAMPLE 1 above. BHK-21 cells do not secrete IFN in response to RNA replication but these cells are able to respond to exogenous IFN to induce innate immune activation. In this experiment, four different alphavirus replicon constructs were tested. The experimental data presented in FIG. 7 shows DLP-containing alphavirus replicon replication and expression of the rFF luciferase gene in BHK cells that had been treated either at the time of electroporation (0 hr) or at 3 hr post electroporation with 1000 U/ml of exogenous IFN. The replicon RNAs tested were:

1) Alpha-R-rFF: a control VEEV-based replicon with no DLP present;

2) Alpha-R-DLP-rFF: a VEEV-based replicon with a DLP motif positioned upstream to the subgenomic mRNA rFF transcript;

3) Alpha-R-DLP-2A-nsp-rFF: a VEEV-based replicon with a DLP motif positioned upstream to the nonstructural proteins with a 2A protease between the DLP and the nsp region; and 4) Alpha-R-DLP-2A-nsp-DLP-rFF: VEEV-based replicon with a first DLP motif positioned upstream to the nonstructural proteins with a 2A protease between the DLP and the nsp region as well as with a second DLP motif positioned upstream to the rFF subgenomic mRNA transcript.

Figure 7A:
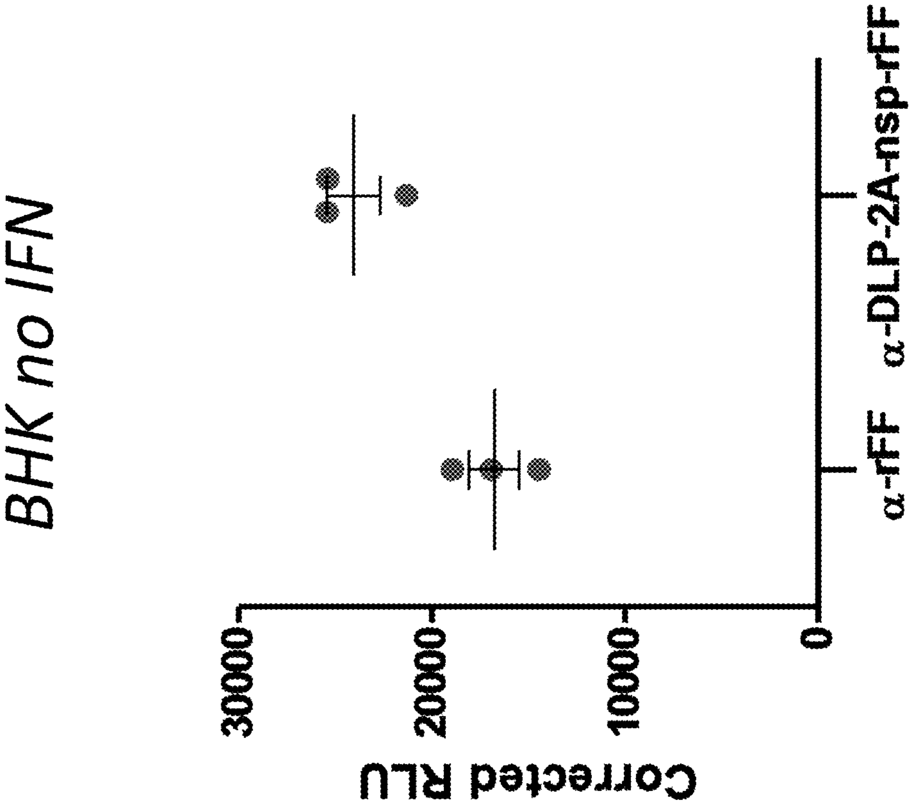
FIGS. 7A-C graphically summarizes the results of another exemplary bulk luciferase analysis performed to demonstrate that modified alphavirus replicon RNAs with a DLP motif incorporated upstream of the sequence encoding nonstructural protein genes can replicate and express efficiently in host cells that had been treated with IFN to induce the cellular innate immune system. In these experiments, bulk-cell luciferase assays were carried out on electroporated cells. IFN was added to cell culture media immediately after electroporation or three hours post electroporation. Samples were collected in triplicate eighteen hours post electroporation for analysis.
Figure 7B:
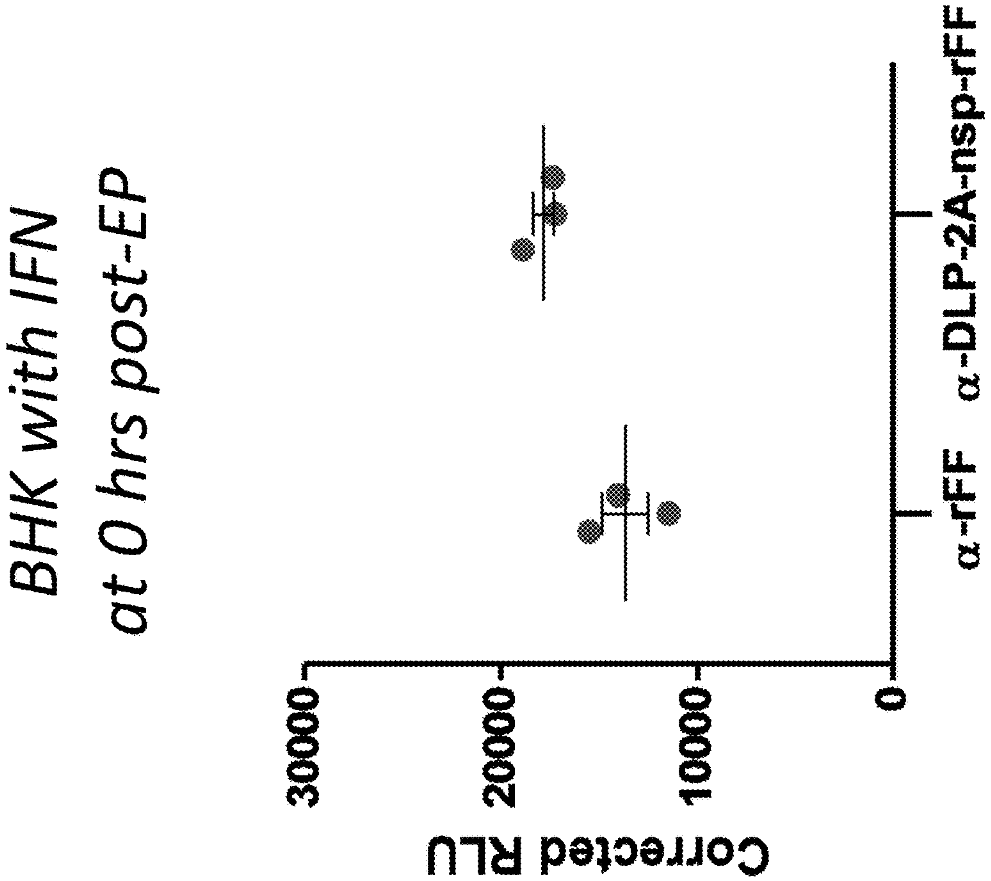
Figure 7C:
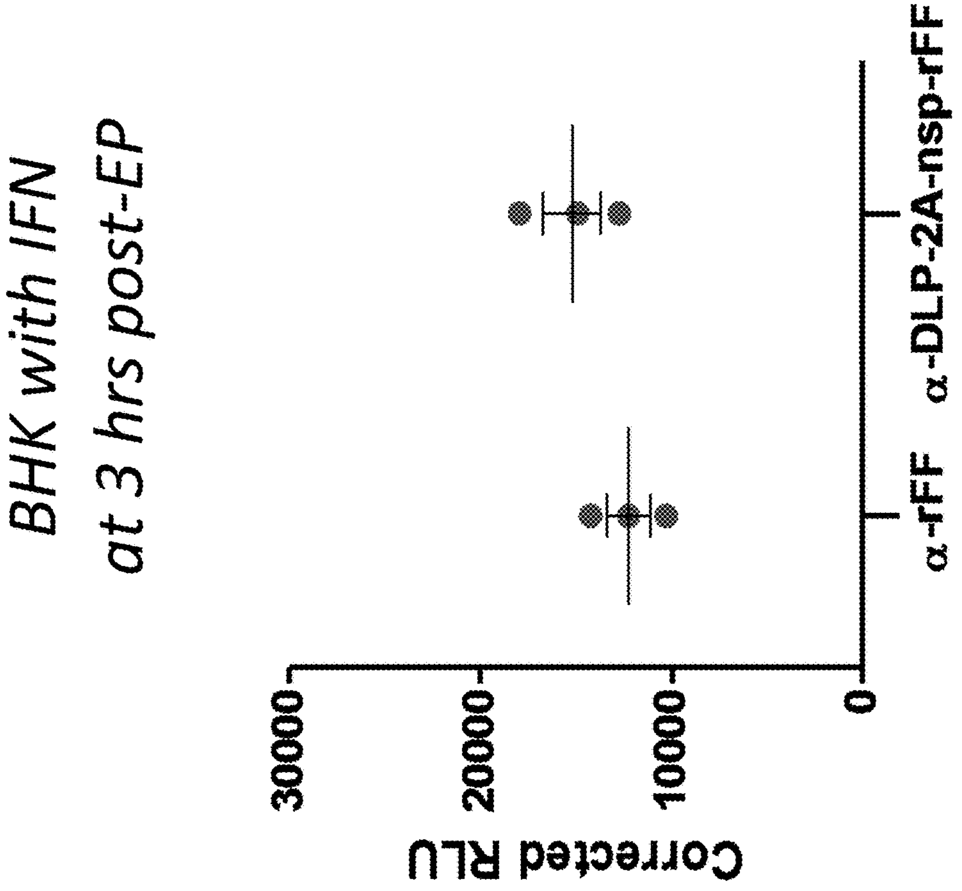

The results of luciferase expression normalized to the number of positive cells detected by FACs analysis are shown in FIG. 7. It was observed that the presence of a DLP motif controlling the translation of the VEEV non-structural protein genes resulted in higher reporter gene expression both in the absence and the presence of IFN treatment post electroporation (FIG. 7A-7C). Although the increase in rFF expression may have been considered statistically insignificant, the trend in all conditions was for increased protein expression. As stated above in EXAMPLE 4 with respect to DLP-containing EAV replicons, one may have expected that a DLP motif would have a negative impact on mRNA translation in cells that are not in an innate immune response activated state. In direct contrast to that expectation, the BHK cells that had not been treated with IFN (FIG. 7A) in these experiments represent the sample with the largest benefit to incorporation of a DLP motif.

Figure 8:
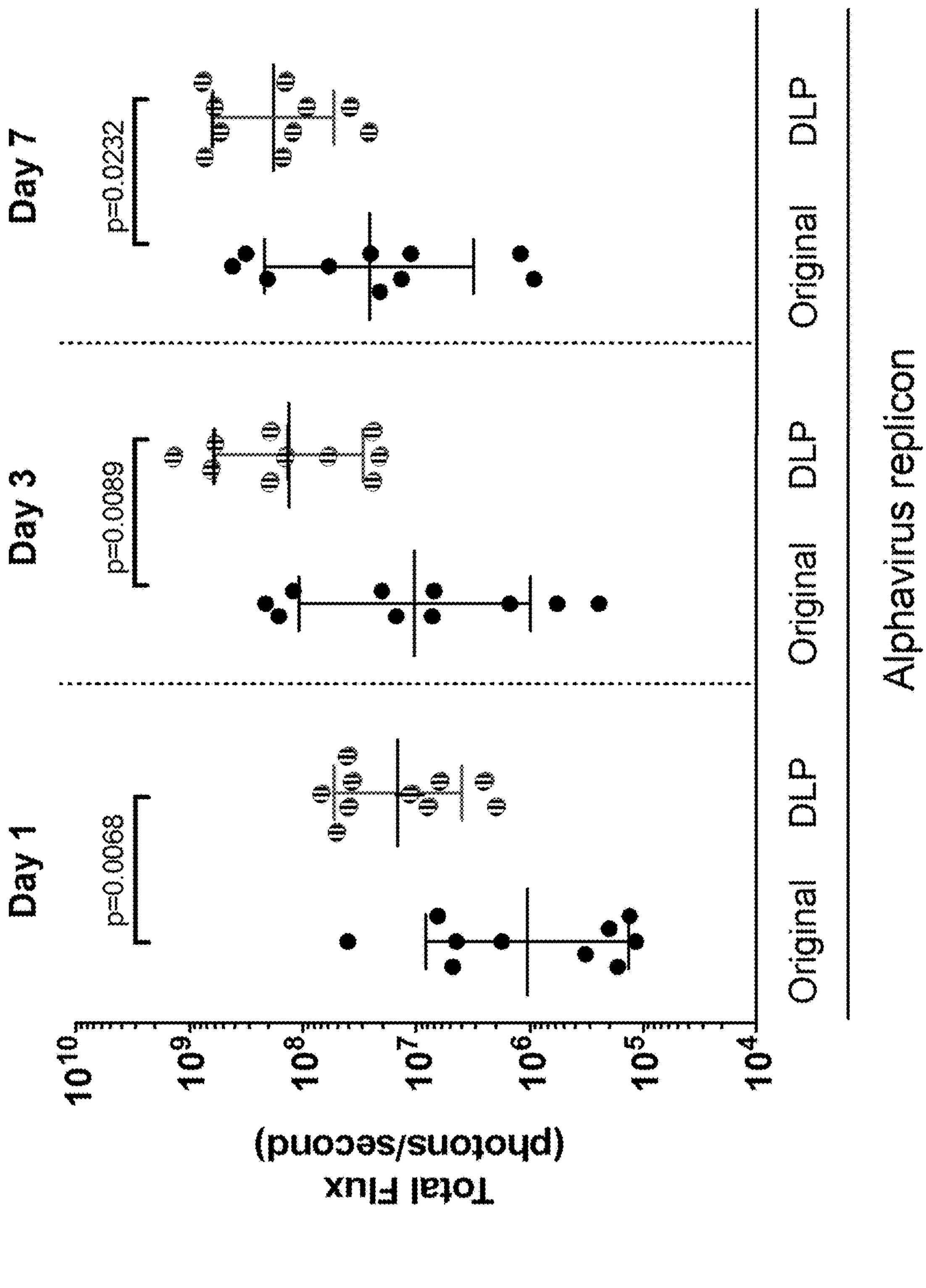
FIG. 8 graphically summarizes the results of exemplary in vivo experiments performed to demonstrate that modified alphavirus replicon RNAs with a DLP motif incorporated upstream of the sequence encoding nonstructural protein genes can replicate and express efficiently in Balb/c mice. In these experiments, whole body imaging of animals that had been injected with a modified alphavirus replicon RNA was conducted. Each animal received 7.5 μg of replicon RNA injected intramuscularly. Individual animals were imaged on day 1, day 3, and day 7. Original: mice injected with the alpha-R-rFF construct; DLP: mice injected with the alpha-R-DLP-2A-nsp-rFF construct.

Subsequently, the two RNA replicons alpha-R-rFF and alpha-DLP-2A-nsp-rFF were tested in vivo in Balb/c mice. In this experiment, mice were tested in groups of 10 animals. In these experiments, equal doses of RNA were injected intramuscularly into mice and whole body IVIS (In vivo Imaging System) analysis was carried out over course of one week. Whole body imaging was performed at day 1, day 3 and day 7 post injection. The total flux measured at the injection site is shown in FIG. 8. Although only modest increases in protein expression were noted ex vitro (FIG. 8) from the DLP modified VEEV replicon, statistically significantly higher protein expression was detected at all time points measured from the DLP modified VEEV replicon RNA (FIG. 8). This observation represents a significant advantage, because as unmodified VEEV replicon vectors are capable of very high protein expression that can reach up to 20% of the total cellular protein (Pushko et al 1997). The DLP modified VEEV replicon surpassed even this expression potential and demonstrated superior protein expression; for this reason, the DLP modified alphavirus replicon vector represents a significant advance over existing alphavirus replicon RNA technology.

There are at least three unexpected results that can be drawn from the experimental data presented in the Examples above. First, the DLP motif has been shown to negatively impact translation of mRNAs when a cell is not in an innate immune system activated state. The DLP-containing replicon RNAs disclosed herein were found to have not been negatively impacted in cells at a basal state of innate activation. Second, expression levels, especially for the DLP-containing VEEV replicons, were found to have been even higher than unmodified replicons in vivo; this observation demonstrated that expression levels even from an alphavirus replicon can be increased from previously high historic expression levels. Third, all positive strand RNA viruses have considerable sequence conservation in both the 5' and 3' ends of their genomes. The fact that both the VEEV replicon and the EAV replicon are flexible enough to accept incorporation of a stem loop structure (the DLP) in the 5' end of their RNAs is unexpected.

Example 6

In Vivo Immunogenicity Response Using DLP Replicon Expression Systems

Figure 12A:
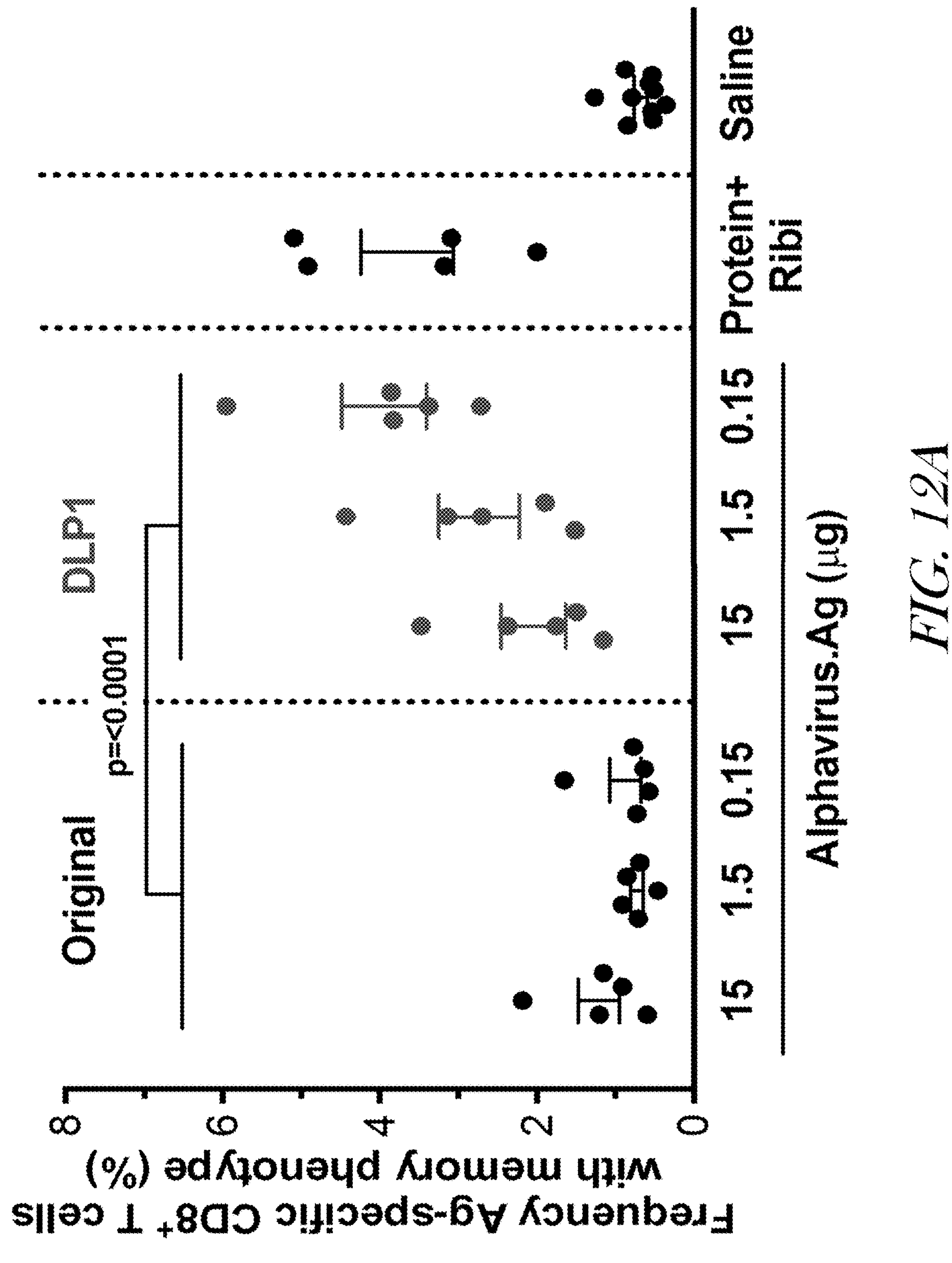
FIGS. 12A-C graphically summarize the results of exemplary in vivo experiments performed to demonstrate that modified alphavirus replicon RNAs with a DLP motif effect on immunogenicity in Balb/c mice. In this experiment, 6-8 week old BALB/c animals were primed at Days 0 and 42 using varying doses of the replicon RNA. Spleens and serum were collected on Day 56, and (a) flow cytometry for HA-specific T cell memory ($CD8^{+}CD44^{+}CD62L^{Lo}KLRG\text{-}1^{Lo}IL\text{-}7Ra^{Hi}CXCR3^{Hi}$) using Dextramers for detection (H-2 Kd [IYSTVASSL; SEQ ID NO: 44]) and (b,c) IFN-γ ELISpot to quantify $CD8^{+}$ and $CD4^{+}$ T cell effector responses. Statistics were one using multiple comparisons between matched doses using an ordinary one-way analysis of variance (ANOVA).
Figure 12B:
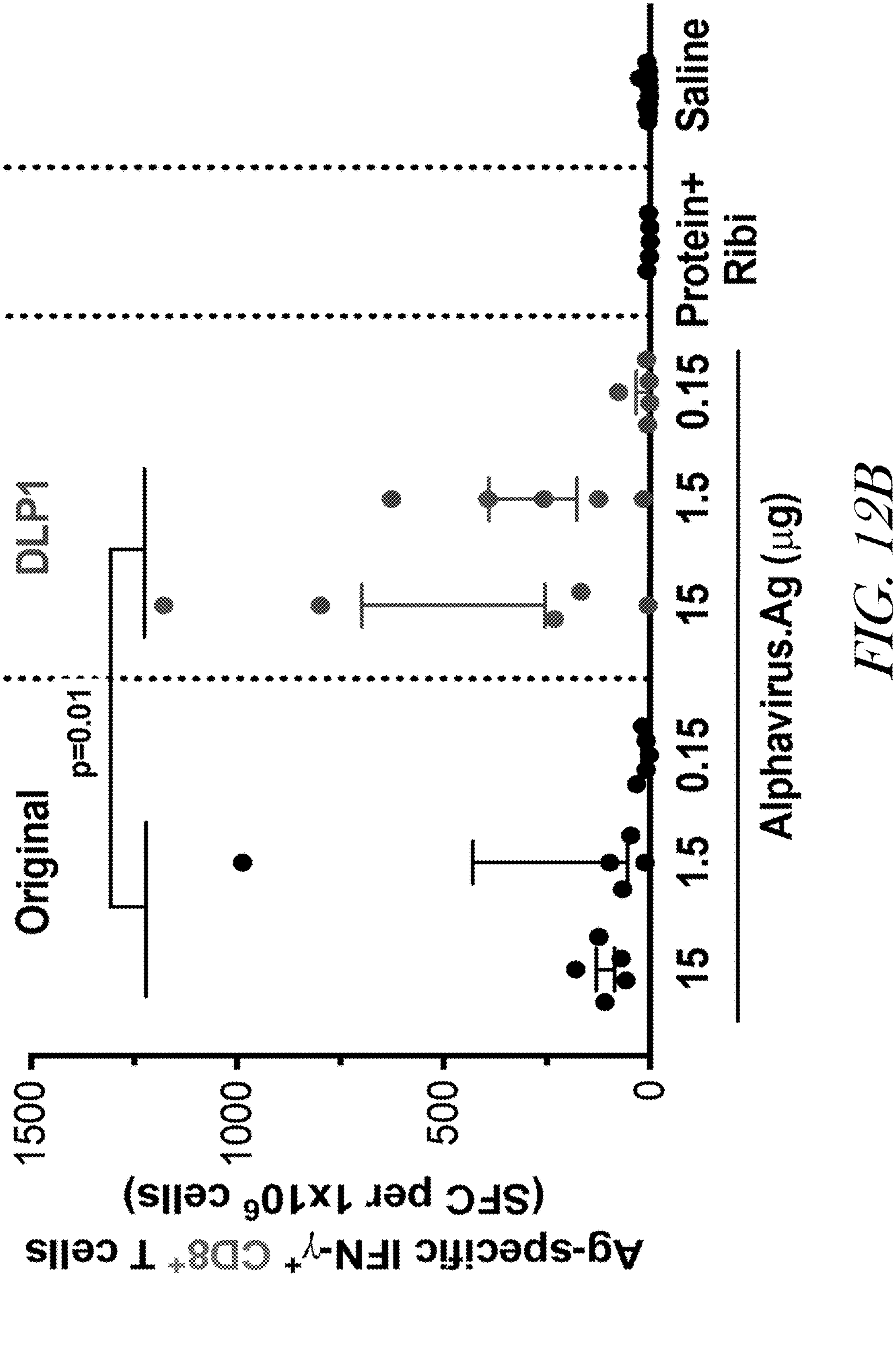
Figure 12C:
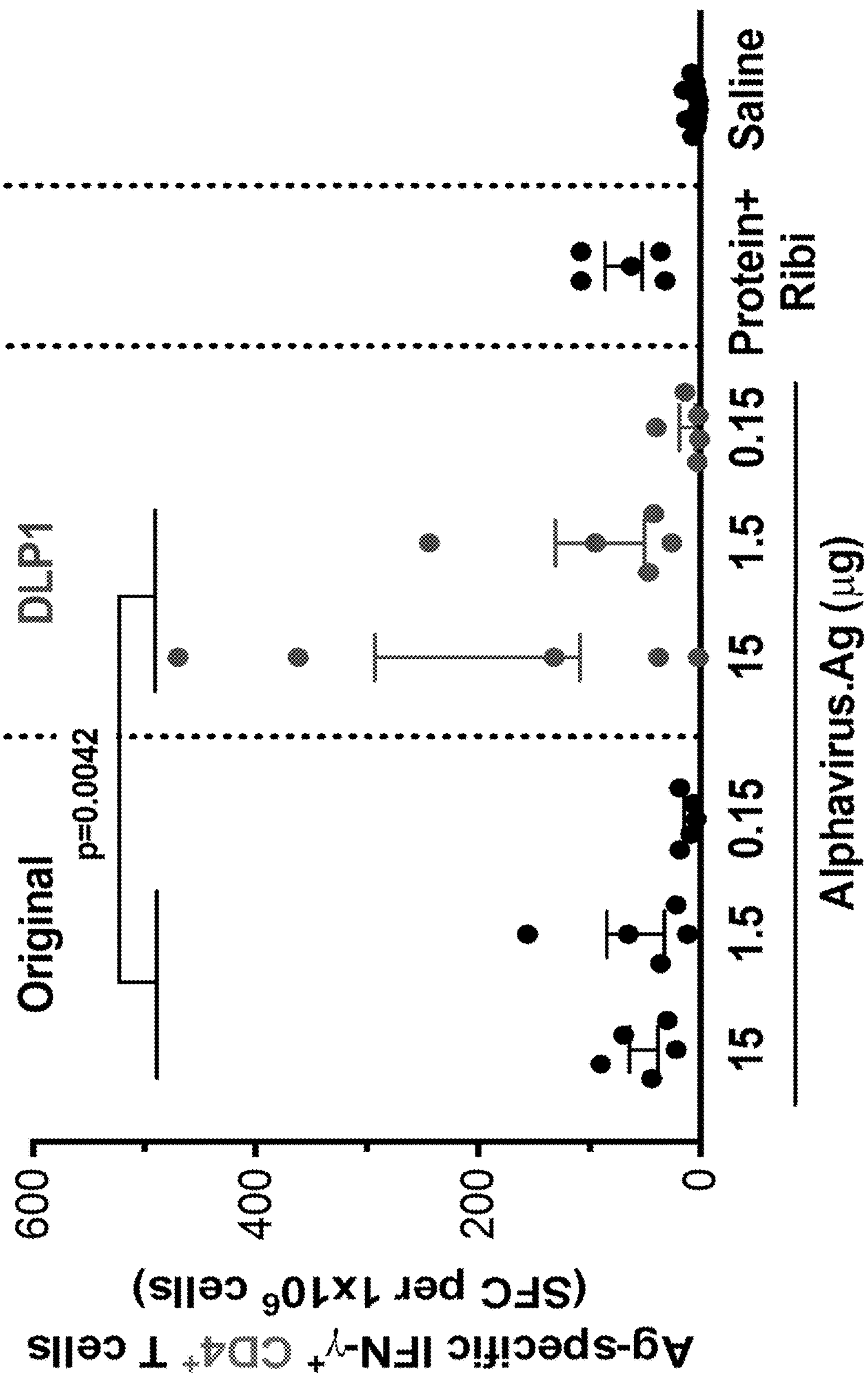

Alphavirus replicon vectors were engineered to contain one or more DLP motifs, as described above. The RNA replicon, Alpha-R-gDLP-HA, containing the DLP sequence was further analyzed in vivo in Balb/c mice. In this experiment, 15 μg, 1.5 μg, or 0.15 μg of RNA encoding Hemagglutinin from Influenza A/Vietnam/1203/2004 (H5N1) was injected into mice at intervals 6 weeks apart. Fourteen days following the final boost, spleens and serum were collected to analyze the immune responses to HA. A summary of the results of these experiments is presented in FIGS. 12A-12C. In FIG. 12A, a significant increase in memory precursor effector cells (MPECs) was observed in constructs containing the DLP motif compared with each comparable dose of an unmodified replicon. HA-specific MPECs were detected using dextramers (H-2 Kd (IYSTVASSL; SEQ ID NO: 44)) along with other population-specific markers ($CD8^{+}CD44^{+}$ $CD62L^{Lo}KLRG\text{-}1^{Lo}IL\text{-}7Ra^{Hi}CXCR3^{Hi}$). Of note, this benefit was also observable at low doses. In FIGS. 12B and 12C, effector T cell responses were measured by the number of antigen-specific HA cells that were secreting IFN-γ following stimulation with a $CD4^{+}$ T cell or $CD8^{+}$ T cell peptide. Animals immunized with replicons containing the DLP motif had a significantly higher frequency of cytokine-expressing $CD4^{+}$ and $CD8^{+}$ T cells are the 15 ug and 1.5 ug doses. Taken together, these data indicate a significant increase in both effector and memory T cell responses in response to immunization with antigen expressed by replicons containing the DLP motif as compared to the unmodified version.

Figure 14A:
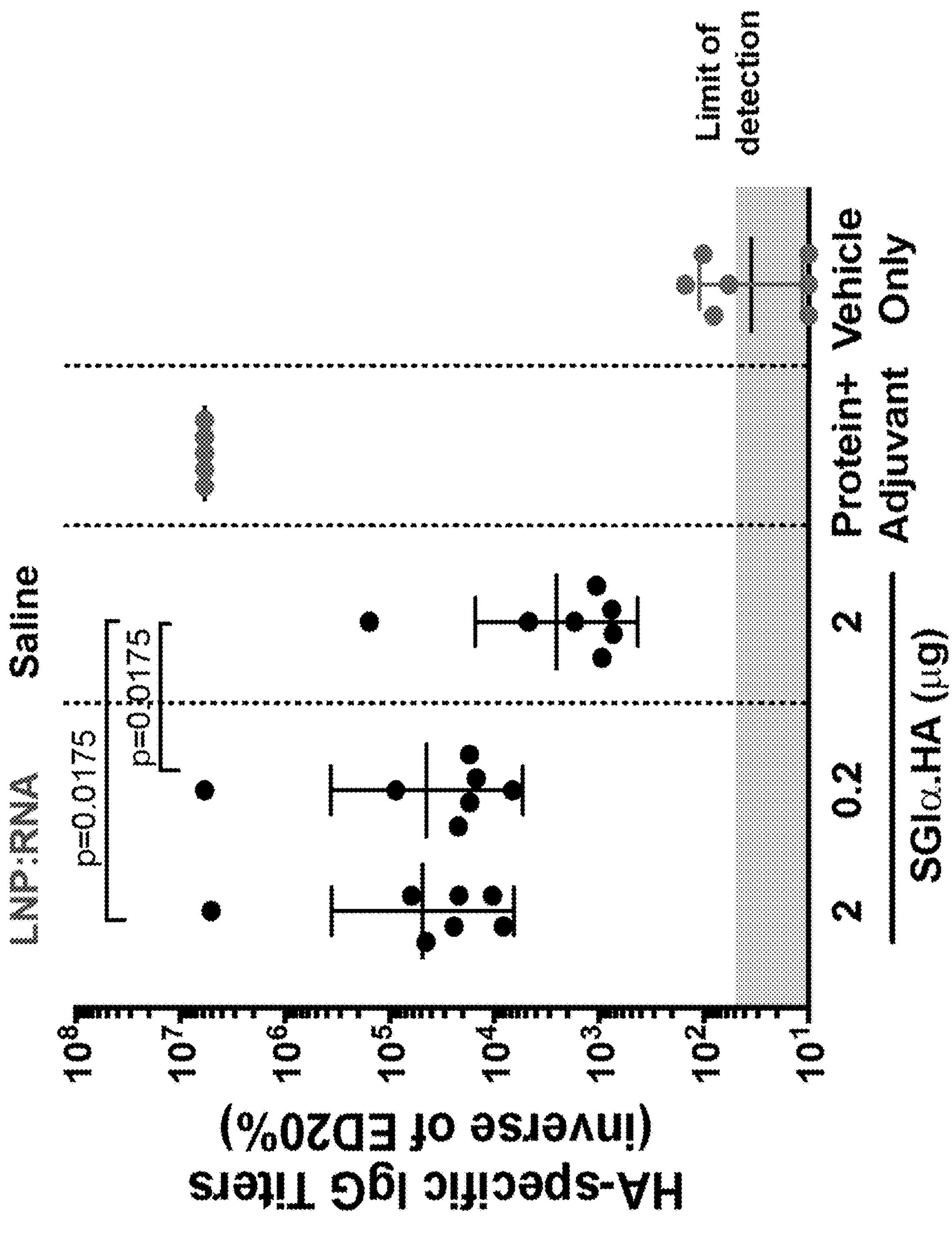
FIGS. 14A-14C graphically summarize the results of in vivo experiments performed to demonstrate that the DLP-containing replicons according to the present disclosure are compatible with LNP (cationic lipid nanoparticle) formulations. In this experiment, 6-8 week old BALB/c animals were primed at Days 0 and boosted at Day 28 using varying doses of an RNA replicon encoding HA. Spleens and serum were collected on Day 42.
Figure 14B:
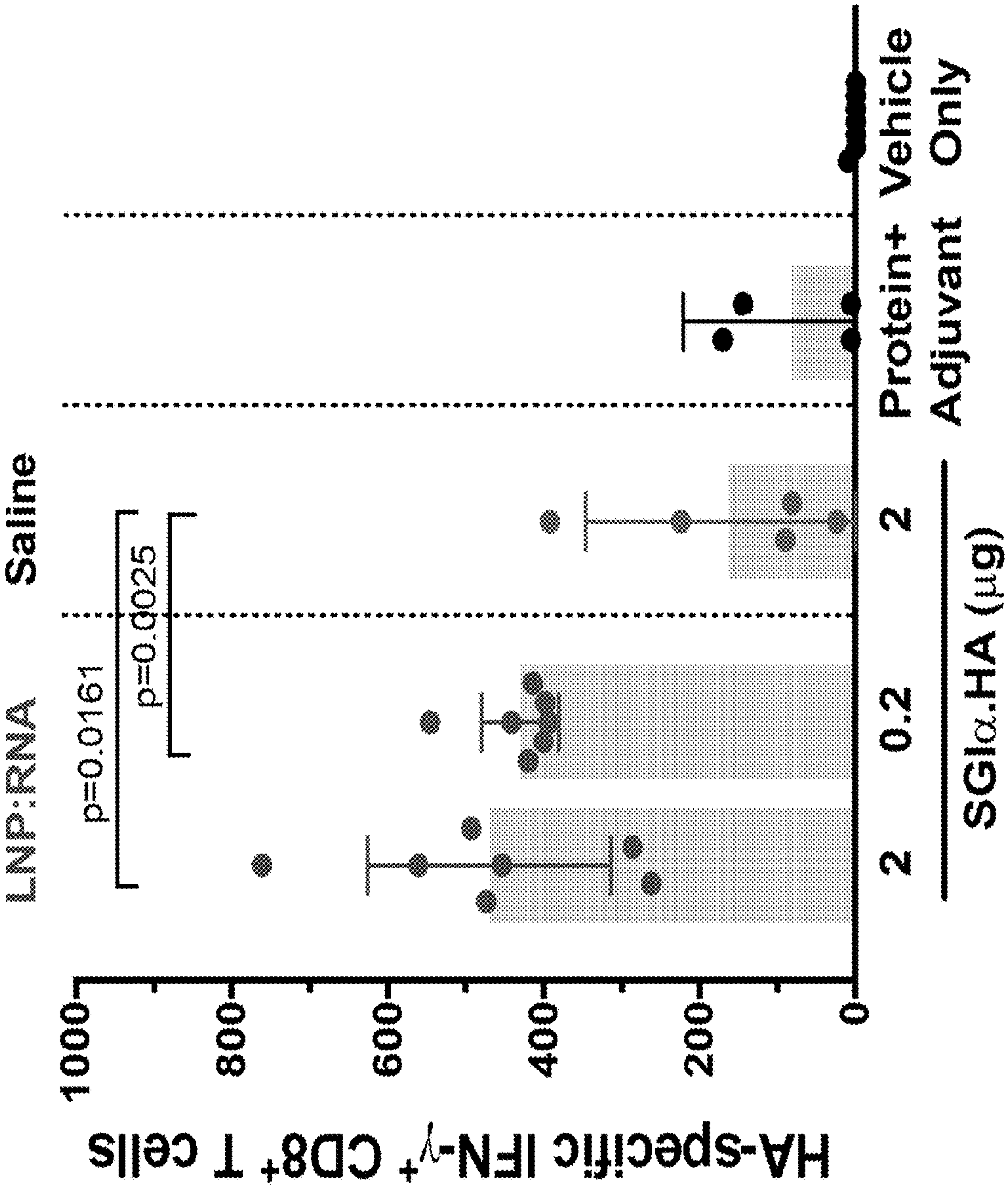
Figure 14C:
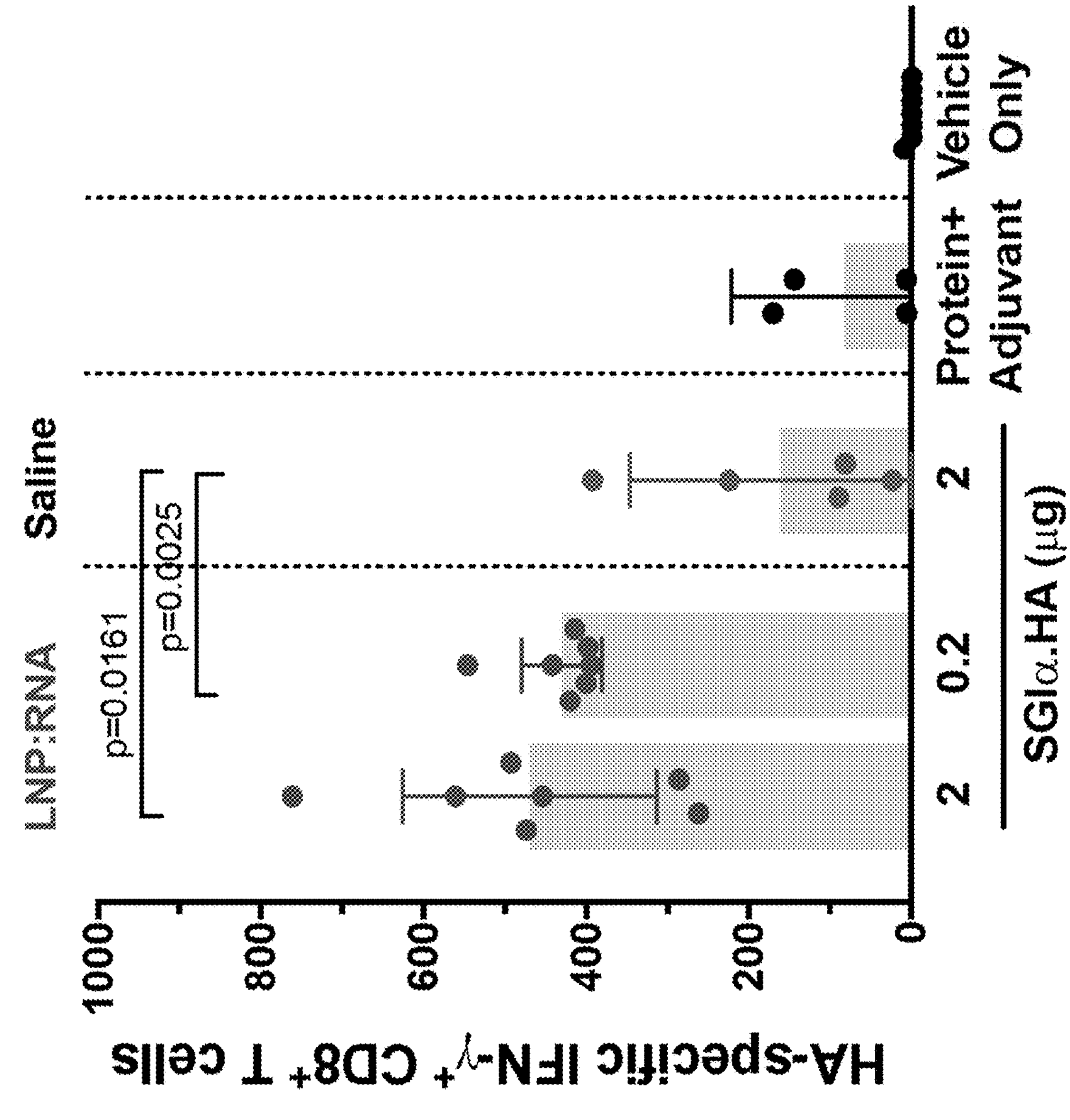

The above DLP-containing replicons were further analyzed in vivo in Balb/c mice for compatibility with LNP formulations. In this experiment, 2 μg or 0.2 μg of RNA encoding Hemagglutinin from Influenza A/Vietnam/1203/2004 (H5N1) was injected into mice at intervals 4 weeks apart. Fourteen days following the final boost, spleens and serum were collected to analyze the immune response to HA. A summary of these experiments is presented in FIG. 14A-14C. In FIGS. 14A-14C, an increase in T-cell and B-cell responses was observed using constructs containing the DLP motif when combined with LNP (cationic lipid nanoparticles) formulations. In FIG. 14A, HA-specific total IgG titers were significantly higher in all dose groups using LNP formulations compared to the group with replicon administered in saline. Furthermore, in FIGS. 14B and 14C, it was observed that HA-specific CD8+ and CD4+ T cells were also significantly higher in all dose groups using LNP formulations compared to the group with replicon administered in saline. Taken together, this data demonstrates that replicon constructs containing the DLP motif are compatible with representative formulations.

Example 7

Preventing Suppression of Immune Response Using DLP-Containing Replicons

Figure 13:
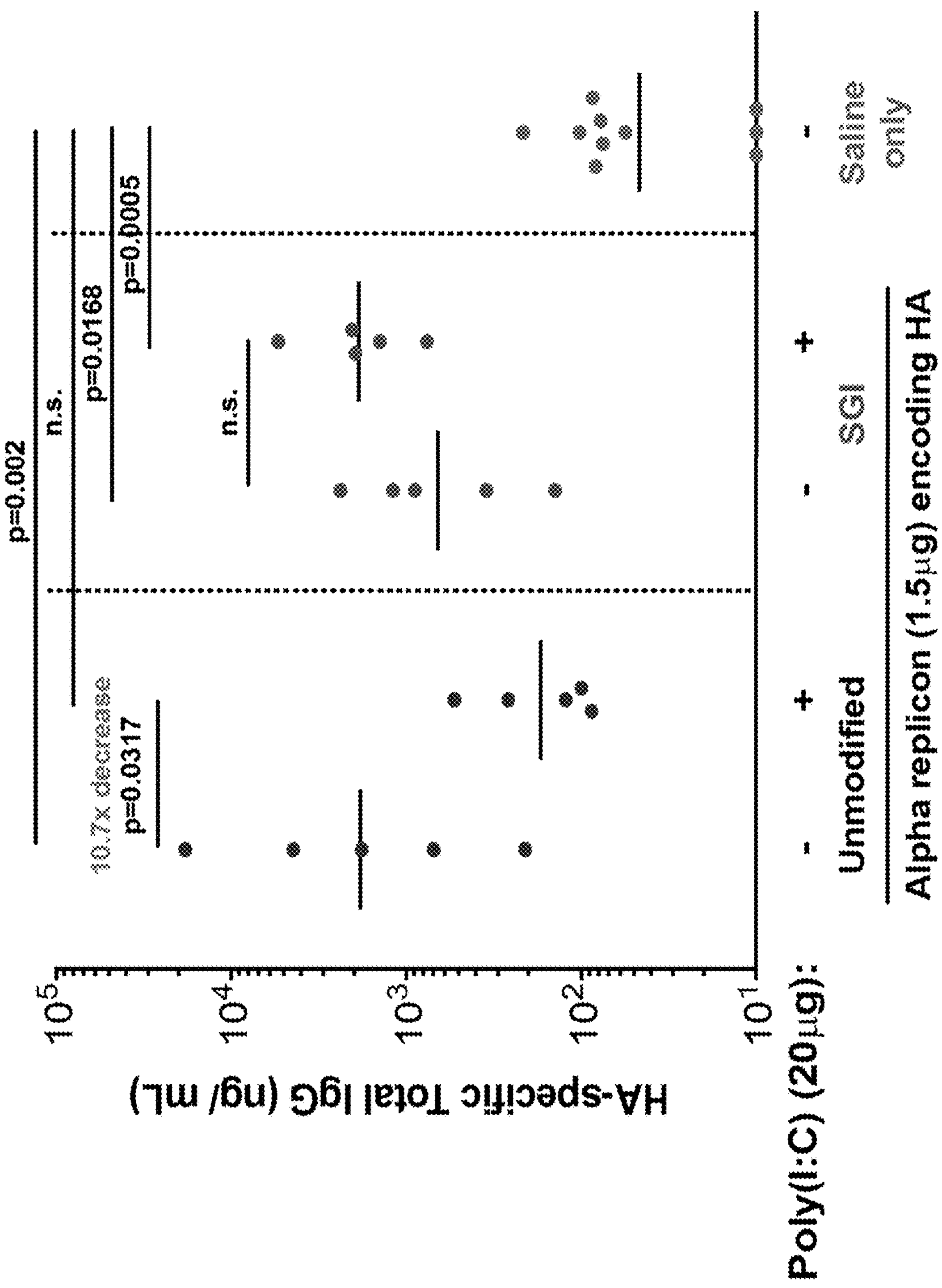
FIG. 13 graphically summarizes the results of exemplary in vivo experiments performed to demonstrate that modified alphavirus replicon RNAs with a DLP motif incorporated upstream of the sequence encoding nonstructural protein genes effectively prevent suppression of immune response upon pre-treatment with agents that simulate viral infection in Balb/c mic. 6-8 week old BALB/c animals were pre-treated with 20 μg of Poly(I:C) or saline administered via hydrodynamic tail vein injection 24 hours before vaccination to simulate an ongoing viral infection. Mice were then primed at Day 0 and boosted at Day 28 using a 1.5 μg dose of RNA replicon encoding HA. Serum was collected on Day 42, and HA-specific antibodies were measured in the serum. Serum antibody concentrations were calculated by interpolation of dilution versus optical density on a four-parametic logistic regression and using the 8D2 HA-specific monoclonal antibody as a standard. Statistics between individual groups were conducted using a Mann-Whitney (non-parametric) test.

DLP-containing replicons constructed as described above were further evaluated in vivo for the ability to prevent suppression of immune response in Balb/c mice. In these experiments, 1.5 μg of mRNA, with or without DLP motif, and carrying a coding sequence for Hemagglutinin derived from Influenza A/Vietnam/1203/2004 (H5N1) is injected into mice at intervals 4 weeks apart. Approximately 24 hours prior to injection, 6-8 week old BALB/c mice are pre-treated with 20 μg of Poly(I:C) or saline by hydrodynamic tail vein injection to simulate a viral infection. Fourteen days following the final boost, serum from these mice are collected to analyze the immune response to Hemagglutinin (HA). A summary of these experiments is presented in FIG. 13. In FIG. 13, a significant decrease is observed in the serum concentration of HA-specific antibodies in mice who were pre-treated with Poly(I:C) and received a doses of unmodified replicons. The levels in the Poly(I:C) group were not significantly above background. In contrast, animals pre-treated with Poly(I:C) and dosed with a construct containing the DLP motif showed no significant reductions in serum antigen-specific total IgG concentration. Taken together, these data show that the DLP motif protects against suppression of serum antibody levels in response to vaccination following a simulated viral infection compared to the unmodified version.

Example 8

Construction of DLP-Containing Expression Cassettes

Figure 15:
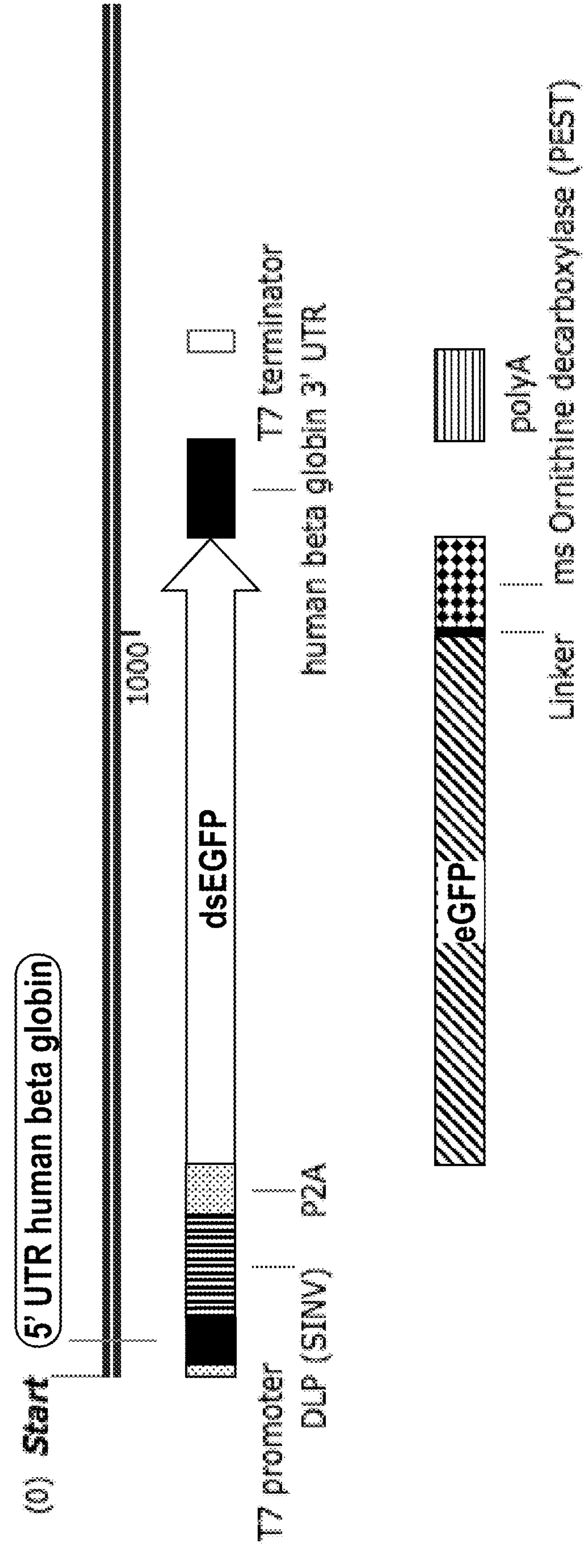
FIG. 15 graphically illustrates of a non-limiting exemplary configuration of DLP-containing mRNA, in which a Sindbis virus DLP element is placed upstream of a coding sequence for a gene of interest (GOI; dsGFP), and a 5' UTR sequence is placed immediately downstream of a T7 promoter and upstream of the Sindbis virus DLP sequence. The coding sequence for dsGFP is linked to the DLP element via a P2A signal, which is an autocatalytic self-cleaving peptide (e.g., autoprotease peptide) derived from the porcine teschovirus-1. Also shown at the bottom portion of the figure is another non-limiting exemplary configuration of DLP-containing mRNA, in which a coding sequence for a destabilized form of EGFP reporter gene (dsGFP) used as a GOI is operably linked to the proteolytic PEST degradation signal derived from a mouse ornithine decarboxylase gene (MODC).

This Example describes the generation of a plasmid vector for ex vitro transcription of an mRNA containing a Sindbis virus DLP element upstream of a gene of interest, e.g., a reporter gene, in accordance with some embodiments of the disclosure. The 5' and 3' untranslated regions (UTR) used in these experiments (SEQ ID NO: 36 and SEQ ID NO: 41, respectively) were derived from the human beta globin gene. The 5' UTR sequence was placed immediately downstream of a T7 promoter (SEQ ID NO: 37) and upstream of the Sindbis virus DLP sequence (SEQ ID NO: 38). In some experiments, the coding sequence for a gene of interest (GOI) was linked to the DLP via a P2A signal, which is an autocatalytic self-cleaving peptide (e.g., autoprotease peptide) derived from the porcine teschovirus-1. In some experiments, a coding sequence for a destabilized form of EGFP reporter gene (dsGFP) which, in this case used as a GOI, was operably linked to the proteolytic PEST degradation signal derived from a mouse ornithine decarboxylase gene (MODC). In some other experiments, a coding sequence of the Red firefly luciferase reported gene was used as the gene of interest (also see, Example 9 below). However, it is contemplated that coding sequences for any gene of interest could be deployed in this configuration. In addition, as illustrated in FIG. 15, a 3' UTR sequence derived from human beta globin, a polyA tail consisting of 120 adenine residues, and a T7 terminator were inserted downstream and adjacent to the stop codon of dsGFP. The nucleic acid sequences of each of the components described above are as follows:

TABLE 9

| Components of DLP dsGFP mRNAs | |
|---|---|
| 5' human beta globin UTR | 5'-ACATTTGCTTCTGACACAACTGTGTT<br>CACTAGCAACCTCAAACAGACACCGCCGC<br>CACC-3' (SEQ ID NO 36) |
| T7 Promoter | 5'-TAATACGACTCACTATAG-3'<br>(SEQ ID NO 37) |
| DLP Motif | 5'-ATAGTCAGCATAGTACATTTCATCTG<br>ACTAATACTACAACACCACCACCATGAAT<br>AGAGGATTCTTTAACATGCTCGGCCGCCG<br>CCCCTTCCCGGCCCCCACTGCCATGTGGA<br>GGCCGCGGAGAAGGAGGCAGGCGGCCCC<br>G-3' (SEQ ID NO 38) |
| P2A peptide | 5'-GGAAGCGGAGCTACTAACTTCAGCCT<br>GCTGAAGCAGGCTGGAGACGTGGAGGAGA<br>ACCCTGGACCT-3' (SEQ ID NO 39) |

TABLE 9-continued

| Components of DLP dsGFP mRNAs | |
|---|---|
| DsGFP | 5'-ATGGTGAGCAAGGGCGAGGAGCTGTT<br>CACCGGGGTGGTGCCCATCCTGGTCGAGC<br>TGGACGGCGACGTAAACGGCCACAAGTTC<br>AGCGTGTCCGGCGAGGGCGAGGGCGATGC<br>CACCTACGGCAAGCTGACCCTGAAGTTCA<br>TCTGCACCACCGGCAAGCTGCCCGTGCCC<br>TGGCCCACCCTCGTGACCACCCTGACCTA<br>CGGCGTGCAGTGCTTCAGCCGCTACCCCG<br>ACCACATGAAGCAGCACGACTTCTTCAAG<br>TCCGCCATGCCCGAAGGCTACGTCCAGGA<br>GCGCACCATCTTCTTCAAGGACGACGGCA<br>ACTACAAGACCCGCGCCGAGGTGAAGTTC<br>GAGGGCGACACCCTGGTGAACCGCATCGA<br>GCTGAAGGGCATCGACTTCAAGGAGGACG<br>GCAACATCCTGGGGCACAAGCTGGAGTAC<br>AACTACAACAGCCACAACGTCTATATCAT<br>GGCCGACAAGCAGAAGAACGGCATCAAGG<br>TGAACTTCAAGATCCGCCACAACATCGAG<br>GACGGCAGCGTGCAGCTCGCCGACCACTA<br>CCAGCAGAACACCCCCATCGGCGACGGCC<br>CCGTGCTGCTGCCCGACAACCACTACCTG<br>AGCACCCAGTCCGCCCTGAGCAAAGACCC<br>CAACGAGAAGCGCGATCACATGGTCCTGC<br>TGGAGTTCGTGACCGCCGCCGGGATCACT<br>CTCGGCATGGACGAGCTGTACAAGAAGCT<br>TAGCCATGGCTTCCCGCCGGAGGTGGAGG<br>AGCAGGATGATGGCACGCTGCCCATGTCT<br>TGTGCCCAGGAGAGCGGGATGGACCGTCA<br>CCCTGCAGCCTGTGCTTCTGCTAGGATCA<br>ATGTGTAG-3' (SEQ ID NO 40) |
| 3' Human beta globin UTR | 5'-GCTCGCTTTCTTGCTGTCCAATTTCT<br>ATTAAAGGTTCCTTTGTTCCCTAAGTCCA<br>ACTACTAAACTGGGGGATATTATGAAGGG<br>CCTTGAGCATCTGGATTCTGCCTAATAAA<br>AAACATTTATTTTCATTGCAA-3'<br>(SEQ ID NO: 41) |
| T7 Terminator | 5'-AACCCCTCTCTAAACGGAGGGGTTTT<br>TTT-3' (SEQ ID NO: 42) |
| Sequence of DLP dsGFP Mrna | 5'-TAATACGACTCACTATAGACATTTGC<br>TTCTGACACAACTGTGTTCACTAGCAACC<br>TCAAACAGACACCGCCGCCACCATAGTCA<br>GCATAGTACATTTCATCTGACTAATACTA<br>CAACACCACCACCATGAATAGAGGATTCT<br>TTAACATGCTCGGCCGCCGCCCCTTCCCG<br>GCCCCCACTGCCATGTGGAGGCCGCGGAG<br>AAGGAGGCAGGCGGCCCCGGGAAGCGGAG<br>CTACTAACTTCAGCCTGCTGAAGCAGGCT<br>GGAGACGTGGAGGAGAACCCTGGACCTAT<br>GGTGAGCAAGGGCGAGGAGCTGTTCACCG<br>GGGTGGTGCCCATCCTGGTCGAGCTGGAC<br>GGCGACGTAAACGGCCACAAGTTCAGCGT<br>GTCCGGCGAGGGCGAGGGCGATGCCACCT<br>ACGGCAAGCTGACCCTGAAGTTCATCTGC<br>ACCACCGGCAAGCTGCCCGTGCCCTGGCC<br>CACCCTCGTGACCACCCTGACCTACGGCG<br>TGCAGTGCTTCAGCCGCTACCCCGACCAC<br>ATGAAGCAGCACGACTTCTTCAAGTCCGC<br>CATGCCCGAAGGCTACGTCCAGGAGCGCA<br>CCATCTTCTTCAAGGACGACGGCAACTAC<br>AAGACCCGCGCCGAGGTGAAGTTCGAGGG<br>CGACACCCTGGTGAACCGCATCGAGCTGA<br>AGGGCATCGACTTCAAGGAGGACGGCAAC<br>ATCCTGGGGCACAAGCTGGAGTACAACTA<br>CAACAGCCACAACGTCTATATCATGGCCG<br>ACAAGCAGAAGAACGGCATCAAGGTGAAC<br>TTCAAGATCCGCCACAACATCGAGGACGG<br>CAGCGTGCAGCTCGCCGACCACTACCAGC<br>AGAACACCCCCATCGGCGACGGCCCCGTG<br>CTGCTGCCCGACAACCACTACCTGAGCAC<br>CCAGTCCGCCCTGAGCAAAGACCCCAACG<br>AGAAGCGCGATCACATGGTCCTGCTGGAG<br>TTCGTGACCGCCGCCGGGATCACTCTCGG<br>CATGGACGAGCTGTACAAGAAGCTTAGCC<br>ATGGCTTCCCGCCGGAGGTGGAGGAGCAG<br>GATGATGGCACGCTGCCCATGTCTTGTGC |

TABLE 9-continued

| Components of DLP dsGFP mRNAs |
|---|
| CCAGGAGAGCGGGATGGACCGTCACCCTG CAGCCTGTGCTTCTGCTAGGATCAATGTG TAGGCTCGCTTTCTTGCTGTCCAATTTCT ATTAAAGGTTCCTTTGTTCCCTAAGTCCA ACTACTAAACTGGGGGATATTATGAAGGG CCTTGAGCATCTGGATTCTGCCTAATAAA AAACATTTATTTTCATTGCAAAAAAAAAA AAAAAAAAAAAAAAAAAAAAAAAAAAAAA AAAAAAAAAAAAAAAAAAAAAAAAAAAAA AAAAAAAAAAAAAAAAAAAAAAAAAAAAA AAAAAAAAAAAAAAAAAAAAAAAAAACCCC TCTCTAAACGGAGGGGTTTTTTT-3' (SEQ ID NO: 43) |

In the above experiments, a DLP sequence from Sindbis virus was used. Additional experiments are performed to incorporate DLP sequences from other Old World alphavirus members such as SV, SFV, BEBV, RRV, SAG, GETV, MIDV, CHIKV, and ONNV, into the nucleic acid molecules of the present disclosure. The linkage of the DLP to the gene of interest can be configured with or without a self-cleaving peptide such as P2A. Without bound to any particular theory, it is believed that the requirement for a 2A sequence or other self-cleaving peptide is dependent on the individual gene being inserted into the gene cassette and on whether the additional amino acids added by the inclusion of DLP would affect the translated proteins function. It is further contemplated that the 5' and 3' UTR sequences used here may also be changed for any other set of functional UTRs regardless of origin.

Example 9

Figure 16A:
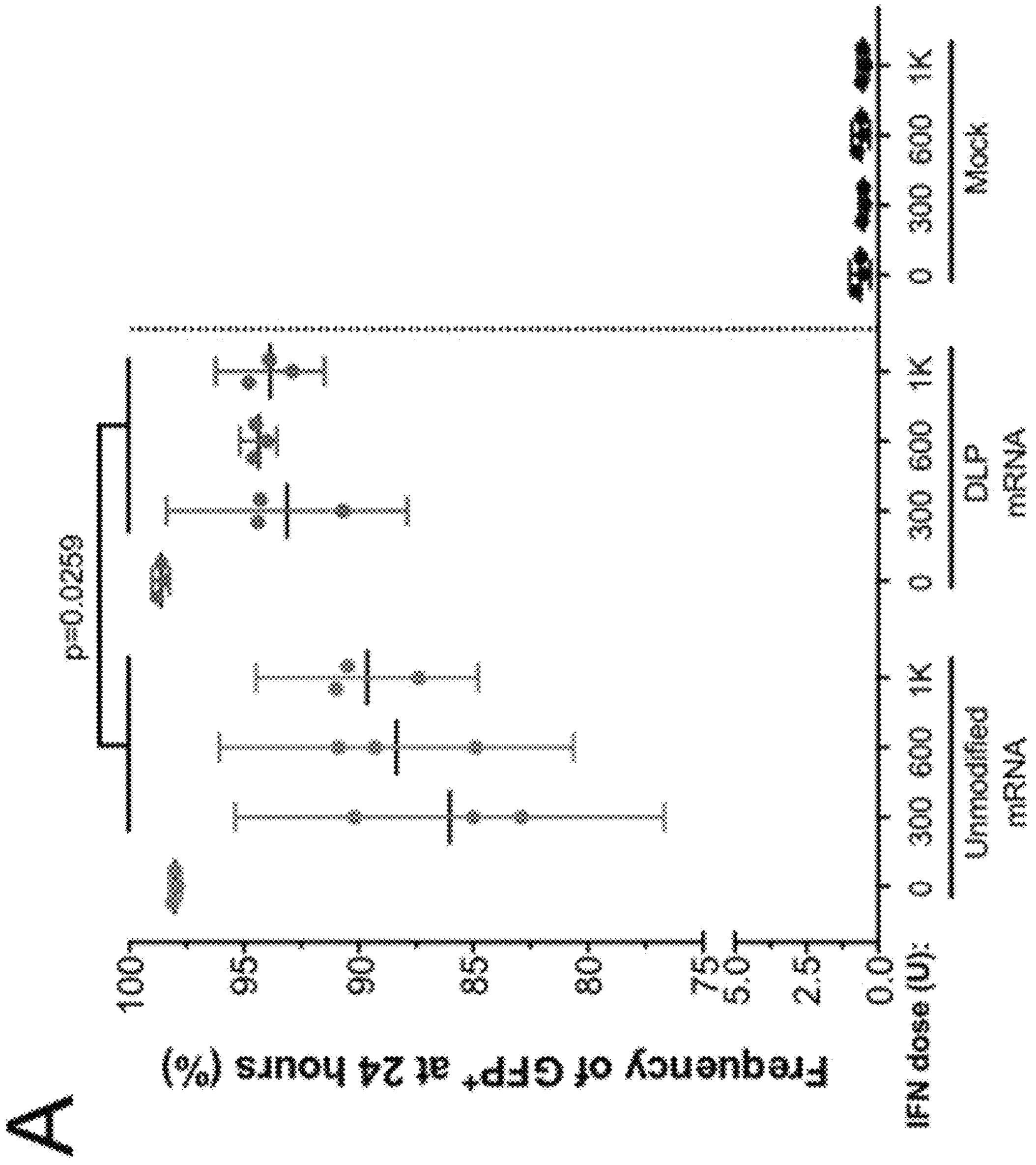
FIGS. 16A-D graphically summarize the results of experiments performed to demonstrate that DLP-containing modified mRNAs can confer interferon resistance.

Ex Vivo Evaluation of Gene Expression in DLP-Containing Expression Cassettes mRNAs derived from DLP-containing expression cassettes engineered to contain one or more DLP motifs, as described above, were evaluated ex vivo for the ability to enhance expression of the gene of interest in BHK-21 cells. As control, mRNA samples lacking the DLP sequence but otherwise identical to the DLP-containing mRNAs described above were assayed in parallel under the same conditions. In these experiments, BHK-21 cells were pre-treated with 300, 600 or 1000 U/mL of universal type I interferon or vehicle control for 2 hours. Following pre-treatment the cells were electroporated, in triplicate, with 2.5 μg of mRNA containing or lacking DLP motifs. The cells were placed back into media containing the same concentrations of interferon used during the pretreatment. The frequency of GFP positive cells and Mean Fluorescence Intensity (MFI) was assayed at 2, 4 and 24 hours post electroporation by flow cytometry. It was observed that DLP-containing mRNA yields significantly higher frequency of GFP positive cells compared to the non-DLP mRNA in the presence of interferon (FIG. 16A).

Figure 16B:
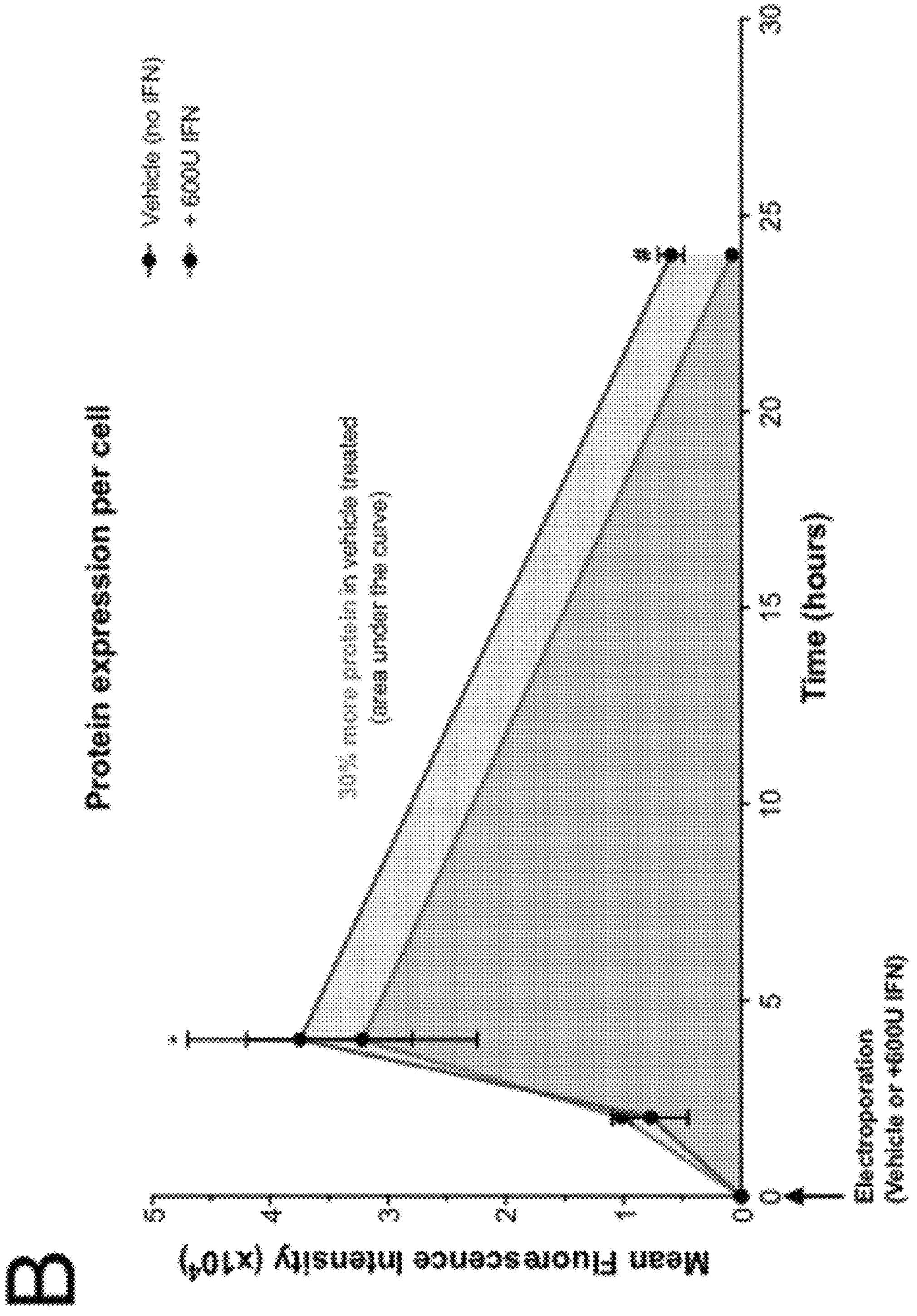
Figure 16C:
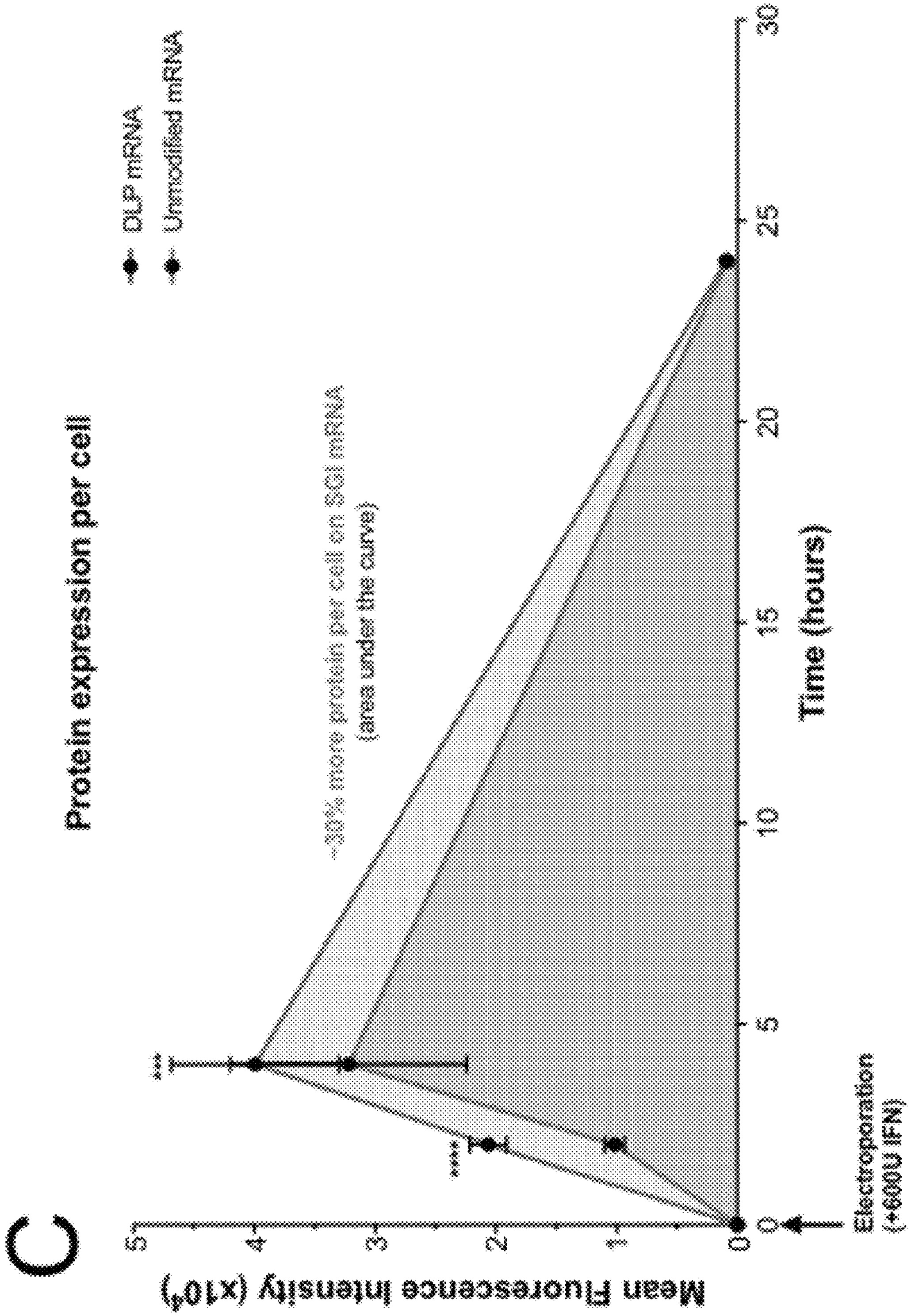
Figure 16D:
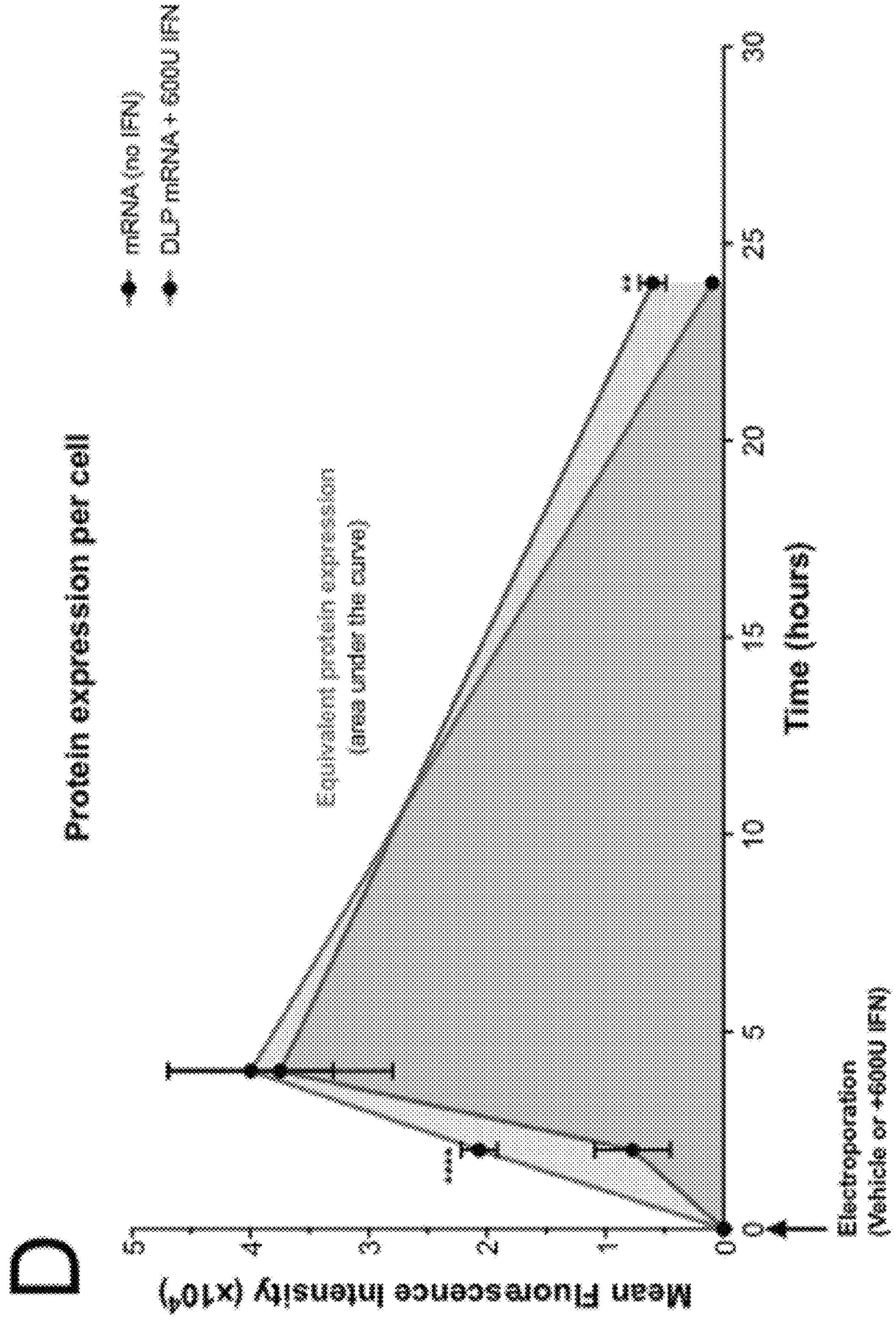

Furthermore, when the MFI of GFP was normalized to the frequency of GFP positive cells and plotted versus time, it was observed that the unmodified mRNA was sensitive to interferon treatment as exhibited by a statistically significant reduction of 30% in overall protein produced during the 24-hour time course (FIG. 16B). In contrast, the DLP-containing modified mRNA demonstrated resistance to interferon treatment as exhibited by a statistically significant increase of 30% in overall protein production over the control unmodified mRNA during the same 24-hour time course (FIG. 16C). The resistance to interferon treatment conferred by the presence of the DLP motifs was further strengthened by the finding that cells treated with interferon and electroporated with a DLP-containing mRNA produced as much protein as untreated cells electroporated with an unmodified mRNA (FIG. 16C).

Example 10

In Vivo Evaluation of Gene Expression in DLP-Containing Expression Cassettes mRNAs derived from DLP-containing expression cassettes engineered to contain one or more DLP motifs, as described above, are further evaluated in vivo for the ability to enhance expression of the gene of interest in Balb/c mice. In this experiment, 30 μg, 15 μg, or 1.5 μg of DLP-containing mRNA encoding red firefly luciferase is injected into mice at interval of 6 weeks apart. Red firefly luciferase expression is subsequently monitored by IVIS (In vivo Imaging System) analysis at 1, 3, 7, 10, 14, 21 and 28 days post injection. A significant increase in luciferase expression is observed in mice that receive DLP-containing mRNAs when compared to control animals that receive mRNA lacking the DLP motif.

Example 11

Preventing Suppression of Immune Response Using DLP-Containing mRNAs

DLP-containing mRNAs as described above are further evaluated in vivo for the ability to enhance expression of the gene of interest in Balb/c mice. In this experiment, 30 μg, 15 μg, or 1.5 μg of mRNA, with or without DLP motif, and carrying a coding sequence for Hemagglutinin derived from Influenza A/Vietnam/1203/2004 (H5N1) is injected into mice at intervals 4 weeks apart. Approximately 24 hours prior to injection, mice are pre-treated with 20 μg of Poly (I:C) or saline by hydrodynamic tail vein injection to simulate a viral infection. Fourteen days following the final boost, serum from these mice are collected to analyze the immune response to Hemagglutinin (HA). A significant decrease in the serum concentration of HA-specific antibodies is expected to be observed in mice that are pre-treated with Poly(I:C) and receive a dose of mRNA lacking the DLP sequence. In contrast, animals pre-treated with Poly(I:C) and dosed with mRNA containing the DLP motif are expected to not show significant reductions in serum antigen-specific total IgG concentration.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

All of the references disclosed herein, including but not limited to journal articles, textbooks, publications, patents and patent applications are hereby incorporated by reference in their entireties to the same extent as if each reference was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; any discussion and comment in a specific information source should no way be considered as an admission that such comment was widely accepted as the general opinion in the field.

The discussion of the general compositions and methods given herein is intended for illustrative purposes only. It is not intended to be exhaustive or to limit the disclosure. Individual aspects or features of a particular embodiment are generally not limited to that particular embodiment, but, where applicable, are interchangeable and can be used in a selected embodiment, even if not specifically shown or described. It is expressly contemplated that any aspect or feature of the present disclosure can be combined with any other aspect, features, or combination of aspects and features disclosed herein. Other alternative compositions, methods, and embodiments will be apparent to those of skill in the art upon review of this disclosure, and are to be included within the spirit and purview of this application.

What is claimed is:

1. A nucleic acid molecule, comprising a modified viral RNA replicon, wherein the modified viral RNA replicon comprises:

a first nucleic acid sequence encoding one or more structural elements of a viral capsid enhancer comprising one or more RNA stem-loops, wherein the viral capsid enhancer is heterologous to the viral RNA replicon; and a second nucleic acid sequence comprising a sequence encoding for at least one viral nonstructural protein of a corresponding unmodified viral RNA replicon, wherein the first nucleic acid sequence is operably linked upstream to the second nucleic acid sequence, wherein the nucleic acid molecule comprises a 5' UTR comprising a corresponding RNA for nucleotides 1-45 of SEQ ID NO: 19.

2. The nucleic acid molecule of claim 1, wherein the modified viral RNA replicon further comprises a coding sequence for an autoprotease peptide operably linked upstream to the second nucleic acid sequence.

3. The nucleic acid molecule of claim 2, wherein the coding sequence for the autoprotease peptide is operably linked downstream to the first nucleic acid sequence and upstream to the second nucleic acid sequence.

4. The nucleic acid molecule of claim 2, wherein the autoprotease peptide comprises a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof.

5. The nucleic acid molecule of claim 1, wherein the viral capsid enhancer is derived from a capsid gene of a virus species belonging to the alphavirus genus of Togaviridae family.

6. The nucleic acid molecule of claim 5, wherein the viral capsid enhancer comprises a downstream loop (DLP) motif of the virus species, and wherein the DLP motif comprises at least one of the one or more RNA stem-loops.

7. The nucleic acid molecule of claim 1, wherein the viral capsid enhancer comprises a nucleic acid sequence exhibiting at least 80% sequence identity to the RNA corresponding to at least one of SEQ ID NOs: 1 and 46-52.

8. The nucleic acid molecule of claim 1, wherein the modified viral RNA replicon further comprises one or more expression cassettes, wherein at least one of the one or more expression cassettes comprises a promoter operably linked to a sequence for a gene of interest (GOI).

9. The nucleic acid molecule of claim 8, wherein the modified viral RNA replicon further comprises:

a third nucleic acid sequence encoding one or more RNA stem-loops of a second viral capsid enhancer or a variant thereof, and a fourth nucleic acid sequence operably linked to the third nucleic acid sequence, wherein the fourth nucleic acid sequence comprises a sequence for a second gene of interest (GOI).

10. The nucleic acid molecule of claim 8, wherein the GOI encodes an antigen.

11. The nucleic acid molecule of claim 1, wherein the native viral nonstructural proteins of the corresponding unmodified viral RNA replicon is from an alphavirus or arterivirus.

12. The nucleic acid molecule of claim 1, wherein the nucleic acid molecule is produced via de novo synthesis and/or in vitro transcription.

13. The nucleic acid molecule of claim 1, wherein the modified RNA replicon is derived from Venezuelan equine encephalitis virus (VEEV), wherein the viral capsid enhancer comprises a downstream loop (DLP) motif derived from Sindbis virus (SINV), wherein the DLP motif comprises at least one of the one or more RNA stem-loops, wherein the modified RNA replicon further comprises one or more expression cassettes, wherein at least one of the one or more expression cassettes comprises a promoter operably linked to a coding sequence for a gene of interest (GOI), the viral capsid enhancer is operably linked to the coding sequence of the gene of interest and the second sequence comprises a sequence encoding for substantially all nonstructural proteins of a corresponding unmodified viral RNA replicon.

14. The nucleic acid of claim 13, wherein the DLP motif derived from SINV is operably positioned within 500 nucleotides downstream of the 5' terminus.

15. The nucleic acid molecule of claim 1, wherein the viral capsid enhancer comprises a downstream loop (DLP) motif derived from Sindbis virus (SINV), wherein the DLP motif comprises at least one of the one or more RNA stem-loops.

16. The nucleic acid of claim 1, wherein the modified RNA replicon is derived from Venezuelan equine encephalitis virus (VEEV), wherein the viral capsid enhancer comprises a downstream loop (DLP) motif derived from Sindbis vims (SINV), wherein the DLP motif comprises at least one of the one or more RNA stem-loops, wherein the modified RNA replicon further comprises one or more expression cassettes, wherein at least one of the one or more expression cassettes comprises a promoter operably linked to a coding sequence for a gene of interest (GOI), the GOI encodes an antigen, the first nucleic is a operably positioned within 500 nucleotides downstream of the 5' terminus, the viral capsid enhancer is operably linked to the coding sequence of the gene of interest and the second sequence comprises a sequence encoding for substantially all nonstructural proteins of a corresponding unmodified viral RNA replicon.

17. An encoding nucleic acid molecule comprising a nucleic acid sequence encoding the modified viral RNA replicon of claim 1.

18. A recombinant cell comprising a nucleic acid molecule of claim 1.

19. A cell culture comprising a recombinant cell of claim 18.

20. A composition, comprising a recombinant cell of claim 18, and a pharmaceutically acceptable carrier.

21. A composition, comprising a nucleic acid molecule of claim 1, and a pharmaceutically acceptable carrier.

22. A method for producing a polypeptide of interest in vitro, comprising culturing a host cell comprising a nucleic acid molecule according to claim 1, wherein the modified viral RNA replicon further comprises one or more expression cassettes, wherein at least one of the one or more expression cassettes comprises a promoter operably linked to a coding sequence for a polypeptide of interest.

23. A nucleic acid molecule comprising a modified viral RNA replicon, wherein the modified viral RNA replicon comprises, ordered from the 5'- to 3'-end, (1) a 5' untranslated region (5'-UTR), (2) a nucleotide sequence encoding an amino-terminal fragment of the rispl of the VEEV, (3) a downstream loop (DLP) motif derived from Sindbis virus (SINV), (4) a nucleotide sequence encoding a 2A protease sequence (P2A), and (5) a nucleotide sequence encoding a polyprotein comprising the sequences of the non-structural proteins nsp1, nsp2, nsp3 and nsp4 of the VEEV.

24. The nucleic acid molecule of claim 23, wherein the modified viral RNA replicon comprises, ordered from the 5'- to 3'-end, (1) a 5'-UTR comprising nucleotides 1 to 45 of a corresponding RNA for SEQ ID NO: 19, (2) a nucleotide sequence consisting of nucleotides 46-240 of a corresponding RNA for SEQ ID NO: 19, (3) a DLP motif comprising the nucleotide sequence of a corresponding RNA for SEQ ID NO: 38, (4) a nucleotide sequence encoding a P2A having the nucleotide sequence of a corresponding RNA for SEQ ID NO: 3, and (5) a nucleotide sequence encoding a polyprotein comprising the sequences of the non-structural proteins nsp1, nsp2, nsp3 and nsp4 of the VEEV.

25. A nucleic acid molecule encoding the nucleic acid molecule of claim 23.

26. The nucleic acid molecule of claim 23, wherein the modified RNA replicon further comprises one or more expression cassettes, wherein at least one of the one or more expression cassettes comprises a promoter operably linked to a coding sequence for a polypeptide of interest.

27. The nucleic acid molecule of claim 26, wherein the polypeptide of interest is selected from the group consisting of an antibody, an antigen, an immune modulator, a cytokine, an enzyme, and any combination thereof.

28. A composition, comprising the nucleic acid molecule of claim 26 and a pharmaceutically acceptable carrier.

29. A method for producing a polypeptide of interest in a subject, comprising administering to the subject the nucleic acid molecule of claim 26.

30. A recombinant cell comprising the nucleic acid molecule of claim 23.

31. A nucleic acid molecule comprising the nucleotide sequence of SEQ ID NO: 19.

32. A nucleic acid molecule comprising a modified non-alphavirus RNA replicon, wherein the modified non-alphavirus RNA replicon comprises a first nucleic acid sequence encoding one or more structural elements of a viral capsid enhancer or a variant thereof comprising one or more RNA stem-loops, and a second nucleic acid sequence comprising a sequence encoding for at least one viral nonstructural protein of a corresponding unmodified viral RNA replicon, wherein the first nucleic acid sequence is operably linked upstream to the second nucleic acid sequence, wherein the nucleic acid molecule comprises a 5' UTR comprising a corresponding RNA for nucleotides 1-45 of SEQ ID NO: 19.

33. A method for producing a polypeptide of interest in a cell, comprising introducing a modified viral RNA replicon into the cell, wherein the modified viral RNA replicon comprises:

a first nucleic acid sequence encoding one or more structural elements of a viral capsid enhancer comprising one or more RNA stem-loops, wherein the viral capsid enhancer is heterologous to the viral RNA replicon, and a second nucleic acid sequence comprising a sequence encoding for at least one nonstructural protein of a corresponding unmodified viral RNA replicon, wherein the first nucleic acid sequence is operably linked upstream to the second nucleic acid sequence, and further wherein the nucleic acid molecule comprises a 5' UTR comprising a corresponding RNA for nucleotides 1-45 of SEQ ID NO: 19; and the modified RNA replicon further comprises one or more expression cassettes, wherein at least one of the one or more expression cassettes comprises a promoter operably linked to a coding sequence for the polypeptide of interest, thereby producing the polypeptide of interest in the cell.

34. The method of claim 33, wherein the modified viral RNA replicon is produced via de novo synthesis and/or in vitro transcription before being introduced into the cell.

35. The method of claim 33, wherein the modified viral RNA replicon comprises a downstream loop (DLP) motif of a virus species, and wherein the DLP motif comprises at least one of the one or more RNA stem-loops of the viral capsid enhancer, the first nucleic acid is operably positioned within 500 nucleotides downstream of the 5' terminus, the viral capsid enhancer is operably linked to the coding sequence of the polypeptide of interest and the second sequence comprises a sequence encoding for substantially all nonstructural proteins of the corresponding unmodified viral RNA replicon.

36. The method of claim 33, wherein the cell is present in a tissue, an organ, or a subject, and wherein the subject is a vertebrate or invertebrate.

37. A method for conferring a resistance to the innate immune system in a subject, comprising administering to the subject a nucleic acid molecule comprising a nucleic acid sequence which encodes a modified viral RNA replicon, wherein the modified viral RNA replicon comprises:

a first nucleic acid sequence encoding one or more structural elements of a viral capsid enhancer comprising one or more RNA stem-loops, wherein the viral capsid enhancer is heterologous to the viral RNA replicon, and a second nucleic acid sequence comprising a sequence encoding for at least one viral nonstructural protein of a corresponding unmodified viral RNA replicon and one or more expression cassettes, wherein at least one of the one or more expression cassettes comprises a promoter operably linked to a coding sequence for the polypeptide of interest, wherein the first nucleic acid sequence is operably linked upstream to the second nucleic acid sequence, and further wherein the nucleic acid molecule comprises a 5' UTR comprising a corresponding RNA for nucleotides 1-45 of SEQ ID NO: 19.

38. The method of claim 37, wherein the viral capsid enhancer is derived from a capsid gene of a virus species belonging to the Togaviridae family.

39. The method of claim 38, wherein the virus species belongs to the *Alphavirus* genus of the Togaviridae family.

40. The method of claim 37, wherein the viral capsid enhancer comprises a nucleic acid sequence exhibiting at least 80% sequence identity to a corresponding RNA for at least one of SEQ ID NOs: 1 and 46-52.

41. The method of claim 37, wherein the modified viral RNA replicon further comprises a coding sequence for an autoprotease peptide operably linked downstream to the first nucleic acid sequence and upstream to the second nucleic acid sequence.

42. The method of claim 37, wherein the modified viral RNA replicon comprises a modified RNA replicon derived from a virus species belonging to the *Alphavirus* genus of the Togaviridae family or to the *Arterivirus* genus of the Arteriviridae family.

43. The method of claim 42, wherein the nucleic acid sequence encoding a modified *arterivirus* RNA replicon comprises one or more expression cassettes, and wherein at least one of the expression cassettes comprises a promoter operably linked to a coding sequence for a gene of interest (GOI).

44. The method of claim 43, wherein at least one of the one or more expression cassettes is operably linked downstream of the second nucleic acid sequence encoding the nonstructural protein is the entire pp lab nonstructural protein of the modified *arterivirus* RNA replicon.

45. A method for producing a polypeptide of interest in a subject, comprising administering to the subject a nucleic acid molecule comprising a nucleic acid sequence encoding a modified non-*alphavirus* RNA replicon, wherein the modified non- *alphavirus* RNA replicon comprises a first nucleic acid sequence encoding one or more structural elements of an *alphavirus* capsid enhancer comprising one or more RNA stem-loops, a second nucleic acid sequence comprising a sequence encoding for at least one viral nonstructural protein of a corresponding unmodified viral RNA replicon and one or more expression cassettes, wherein the first nucleic acid sequence is operably linked upstream to the second nucleic acid sequence, wherein at least one of the one or more expression cassettes comprises a promoter operably linked to a coding sequence for the polypeptide of interest, and further wherein the nucleic acid molecule comprises a 5' UTR comprising a corresponding RNA for nucleotides 1-45 of SEQ ID NO: 19.

46. A method for producing a polypeptide of interest, comprising culturing a host cell comprising a nucleic acid molecule which comprises a nucleic acid sequence encoding a modified non-*alphavirus* RNA replicon, wherein the modified non-*alphavirus* RNA replicon comprises a first nucleic acid sequence encoding one or more structural elements of an *alphavirus* capsid enhancer comprising one or more RNA stem-loops, a second nucleic acid sequence comprising a sequence encoding for at least one viral nonstructural proteins of a corresponding unmodified viral RNA replicon and one or more expression cassettes, wherein the first nucleic acid sequence is operably linked upstream to the second nucleic acid sequence, wherein at least one of the one or more expression cassettes comprises a promoter operably linked to a coding sequence for the polypeptide of interest, and further wherein the nucleic acid molecule comprises a 5' UTR comprising a corresponding RNA for nucleotides 1-45 of SEQ ID NO: 19.

47. A method for producing a messenger RNA (mRNA) in a cell, comprising introducing into the cell a nucleic acid molecule comprising a modified viral RNA replicon, wherein the modified viral RNA replicon comprises a first nucleic acid sequence encoding one or more structural elements of a viral capsid enhancer comprising one or more RNA stem-loops, wherein the viral capsid enhancer is heterologous to the viral RNA replicon, and a second nucleic acid sequence comprising a sequence encoding for at least one viral nonstructural protein of a corresponding unmodified viral RNA replicon, wherein the first nucleic acid sequence is operably linked upstream to the second nucleic acid sequence, further wherein the nucleic acid molecule comprises a 5' UTR comprising a corresponding RNA for nucleotides 1-45 of SEQ ID NO: 19, and wherein the modified RNA replicon further comprises one or more expression cassettes, wherein at least one of the one or more expression cassettes comprises a promoter operably linked to a coding sequence for a gene of interest (GOI), thereby producing a mRNA of the GOI.

48. The method of claim 47, wherein the modified viral RNA replicon is derived from a virus species belonging to a family selected from the group consisting of *Togaviridae* family, *Arteriviridae* family, *Flaviviridae* family, *Orthomyxoviridae* family, *Rhabdoviridae* family, and *Paramyxoviridae* family.

49. A method for conferring a resistance to the innate immune system in a subject, comprising administering to the subject a nucleic acid molecule comprising a nucleic acid sequence encoding a modified non-*alphavirus* RNA replicon, wherein the modified non-*alphavirus* RNA replicon comprises a first nucleic acid sequence encoding one or more structural elements of an *alphavirus* capsid enhancer comprising one or more RNA stem-loops, and a second nucleic acid sequence comprising a sequence encoding for at least one viral nonstructural proteins of a corresponding unmodified viral RNA replicon, wherein the first nucleic acid sequence is operably linked upstream to the second nucleic acid sequence, wherein the nucleic acid molecule comprises a 5' UTR comprising a corresponding RNA for nucleotides 1-45 of SEQ ID NO: 19, and wherein expression of the modified non-*alphavirus* RNA replicon encoded by the nucleic acid molecule confers a resistance to innate immune response in the subject.

50. A method for conferring a resistance to the innate immune system in a subject, comprising administering to the subject a nucleic acid molecule comprising a nucleic acid sequence which encodes a modified viral RNA replicon, wherein the modified viral RNA replicon comprises:

a first nucleic acid sequence encoding one or more structural elements of a viral capsid enhancer comprising one or more RNA stem-loops, wherein the viral capsid enhancer is heterologous to the viral RNA replicon, and a second nucleic acid sequence comprising a sequence encoding for at least one viral nonstructural protein of a corresponding unmodified viral RNA replicon, wherein the first nucleic acid sequence is operably linked upstream to the second nucleic acid sequence, and wherein expression of the modified replicon RNA encoded by the nucleic acid molecule confers a resistance to innate immune response in the subject, and further wherein the nucleic acid molecule comprises a 5' UTR comprising a corresponding RNA for nucleotides 1-45 of SEQ ID NO: 19.

* * * * *